US011466062B2

(12) United States Patent
Amstutz et al.

(10) Patent No.: US 11,466,062 B2
(45) Date of Patent: Oct. 11, 2022

(54) ANKYRIN REPEAT BINDING PROTEINS AND THEIR USES

(71) Applicant: Molecular Partners AG, Zurich-Schlieren (CH)

(72) Inventors: Patrick Amstutz, Kilchberg (CH); Valerie Perrine Calabro, Bergdietikon (CH); Marcel Walser, Winterthur (CH)

(73) Assignee: MOLECULAR PARTNERS AG, Zurich-Schlieren (CH)

( * ) Notice: Subject to any disclaimer, the term of this patent is extended or adjusted under 35 U.S.C. 154(b) by 0 days.

(21) Appl. No.: 17/313,543

(22) Filed: May 6, 2021

(65) Prior Publication Data

US 2021/0347835 A1 Nov. 11, 2021

Related U.S. Application Data

(60) Provisional application No. 63/020,882, filed on May 6, 2020, provisional application No. 63/021,024, filed on May 6, 2020, provisional application No. 63/057,477, filed on Jul. 28, 2020, provisional application No. 63/069,174, filed on Aug. 24, 2020, provisional application No. 63/145,192, filed on Feb. 3, 2021.

(51) Int. Cl.

| | |
|---|---|
| ***C07K 14/47*** | (2006.01) |
| ***A61P 31/14*** | (2006.01) |
| ***A61K 38/00*** | (2006.01) |

(52) U.S. Cl.

CPC .............. *C07K 14/47* (2013.01); *A61P 31/14* (2018.01); *A61K 38/00* (2013.01)

(58) Field of Classification Search

CPC .......... C07K 14/47; A61P 31/14; A61K 38/00
See application file for complete search history.

(56) References Cited

U.S. PATENT DOCUMENTS

| | | | |
|---|---|---|---|
| 7,417,130 B2 | 8/2008 | Stumpp et al. | |
| 8,710,187 B2 | 4/2014 | Binz et al. | |
| 8,722,618 B2 | 5/2014 | Jacobs et al. | |
| 8,846,577 B2 | 9/2014 | Steiner et al. | |
| 8,901,076 B2 | 12/2014 | Binz et al. | |
| 9,163,070 B2 | 10/2015 | Baumann | |
| 9,221,892 B2 | 12/2015 | Binz | |
| 9,284,361 B2 | 3/2016 | Steiner et al. | |
| 9,365,629 B2 | 6/2016 | Parmeggiani et al. | |
| 9,458,211 B1 | 10/2016 | Bakker et al. | |
| 10,370,414 B2 | 8/2019 | Fiedler et al. | |
| 10,717,772 B2 | 7/2020 | Metz et al. | |
| 2008/0206201 A1 | 8/2008 | Beier et al. | |
| 2013/0296221 A1 | 11/2013 | Binz | |
| 2014/0005125 A1* | 1/2014 | Baumann .............. | C07K 14/71 514/20.8 |
| 2015/0284463 A1 | 10/2015 | Tamaskovic et al. | |
| 2016/0251404 A1 | 9/2016 | Tresch et al. | |
| 2020/0385488 A1 | 12/2020 | Reichen et al. | |

FOREIGN PATENT DOCUMENTS

| | | | |
|---|---|---|---|
| WO | WO 2002/020565 A2 | 3/2002 | |
| WO | WO 2005/063815 A2 | 7/2005 | |
| WO | WO 2009/040338 A1 | 4/2009 | |
| WO | WO 2010/060748 A1 | 6/2010 | |
| WO | WO 2011/135067 A1 | 11/2011 | |
| WO | WO 2012/069654 A1 | 5/2012 | |
| WO | WO 2012/069655 A2 | 5/2012 | |
| WO | WO 2014/001442 A1 | 1/2014 | |
| WO | WO 2014/083208 A1 | 6/2014 | |
| WO | WO 2014/191574 A1 | 12/2014 | |
| WO | WO 2016/156596 A1 | 10/2016 | |
| WO | WO 2018/054971 A1 | 3/2018 | |
| WO | WO 2020/245171 | 12/2020 | |
| WO | WO 2020/245173 | 12/2020 | |
| WO | WO 2020/245175 | 12/2020 | |
| WO | WO 2021/116462 | 6/2021 | |
| WO | WO 2021/116469 | 6/2021 | |
| WO | WO 2021/116470 | 6/2021 | |
| WO | WO-2021116462 A1 * | 6/2021 | ............ C07K 16/30 |

OTHER PUBLICATIONS

Amstutz et al., "Intracellular Kinase Inhibitors Selected from Combinatorial Libraries of Designed Ankyrin Repeat Proteins", JBC (2005) vol. 280 No. 26, 24715-24722.

Amstutz et al., "Rapid selection of specific MAP kinase-binders from designed ankyrin repeat protein libraries," Protein Engineering, Design & Selection (2006) 19(5), pp. 219-229.

Baum, Alina et al., "Antibody cocktail to SARS-CoV-2 spike protein prevents rapid mutational escape seen with individual antibodies," Science, vol. 369, pp. 1014-1018 (2020).

Binz, H. Kaspar et al., "Designing Repeat Proteins: Well-expressed, Soluble and Stable Proteins from Combinatorial Libraries of Consensus Ankyrin Repeat Proteins," J. Mol. Biol. vol. 332, pp. 489-503 (2003).

Binz, H. Kaspar et al., "High-affinity binders selected from designed ankyrin repeat protein libraries," Nature Biotechnology, vol. 22, No. 5, pp. 575-582 (2004).

Binz et al., "Designed Repeat Proteins—Molecules with Antibody-like Binding Properties," BIOforum Europe Apr. 2005, pp. 34-36, Git Verlag GmbH & Co. KG, Darmstadt.

Binz et al., "Engineered proteins as specific binding reagents," Current Opinion in Biotechnology (2005) 16, pp. 459-469.

Binz et al., "Engineering novel binding proteins from nonimmunoglobulin domains," Nature Biotechnology (2005) 23(10), pp. 1257-1268.

(Continued)

*Primary Examiner* — Larry D Riggs, II
*Assistant Examiner* — Joseph Fischer
(74) *Attorney, Agent, or Firm* — Finnegan, Henderson, Farabow, Garrett & Dunner LLP

(57) ABSTRACT

The present invention relates to recombinant binding proteins comprising one or more designed ankyrin repeat domains with binding specificity for coronavirus spike proteins, nucleic acids encoding such proteins, pharmaceutical compositions comprising such proteins or nucleic acids, and the use of such proteins, nucleic acids or pharmaceutical compositions in the treatment of coronavirus diseases, particularly diseases caused by SARS-CoV-2.

21 Claims, 57 Drawing Sheets

Specification includes a Sequence Listing.

(56) References Cited

OTHER PUBLICATIONS

Binz et al., "Design and characterization of MP0250, a tri-specific anti-HGF/anti-VEGF DARPin® drug candidate", mAbs (2017) vol. 9 No.8, pp. 1262-1269.
Binz et al., "Crystal Structure of a Consensus-Designed Ankyrin Repeat Protein: Implications for Stability," Proteins: Structure, Function, and Bioinformatics 65:280-84 (2006).
Boersma et al., "DARPins and other repeat protein scaffolds: advances in engineering and applications," CurrOpin Biotechnol (2011) 22(6), pp. 849-857.
Chichili, Vishnu Priyanka Reddy et al., "Linkers in the structural biology of protein-protein interactions," Protein Science, vol. 22, pp. 153-167 (2012).
Eggel et al., "DARPins as Bispecific Receptor Antagonists Analyzed for Immunoglobulin E Receptor Blockage", J Mol Biol (2009) 393, pp. 598-607.
Fiedler et al., "MP0250, a VEGF and HGF neutralizing DARPin® molecule shows high anti-tumor efficacy . . . patient-derieved tumor models", Oncotarget 2017, (incl. Supplement).
Forrer, Patrik et al., "A novel strategy to design binding molecules harnessing the modular nature of repeat proteins," FEBS Letters, vol. 539 pp. 2-6 (2003).
Forrer et al., "Consensus Design of Repeat Proteins," ChemBioChem (2004) 5, pp. 183-189.
Hanes, Jozef et al., "In vitro selection and evolution of functional proteins by using ribosome display," Proc. Natl. Acad. Sci. USA, vol. 94, pp. 4937-4942 (1997).
Hanes, Jozef et al., "Ribosome display efficiently selects and evolves high-affinity antibodies in vitro from immune libraries," Proc. Natl. Acad. Sci. USA, vol. 95, pp. 14130-14135 (1998).
He et al., "Ribosome display: cell-free protein display technology," Brief Fund Genomic Proteomic (2002) 1(2), pp. 204-212.
Interlandi, Gianluca et al., "Characterization and Further Stabilization of Designed Ankyrin Repeat Proteins by Combining Molecular Dynamics Simulations and Experiments," J. Mol. Biol., vol. 375, pp. 837-854 (2008).
Kawe et al., "Isolation of Intracellular Proteinase Inhibitors Derived from Designed Ankyrin Repeat Proteins by Genetic Screening," J Biol Chem (2006) 281, pp. 40252-63.
Kohl et al., "Designed to be stable: Crystal structure of a consensus ankyrin repeat protein", PNAS (2003) 100(4), pp. 1700-1705.
Kramer et al., "Structural Determinants for Improved Stability of Designed Ankyrin Repeat Proteins with a Redesigned C-Capping Module", J Mol Biol (2010) 404, pp. 381-391.
Ku, Zhiqiang et al., "Molecular determinants and mechanism for antibody cocktail preventing SARS-CoV-2 escape," Nature Communications, vol. 12, No. 469, pp. 1-13 (2021).
Main, Ewan R.G. et al., "Design of Stable a-Helical Arrays from an Idealized TPR Motif," Structure, vol. 11, pp. 497-508 (2003).
Munnink, Bas B. Oude et al., "Transmission of SARS-CoV-2 on mink farms between humans and mink and back to humans," Science, vol. 371, pp. 172-177 (2021).
Nguyen, Hoang Hiep et al., "Surface Plasmon Resonance: A Versatile Technique for Biosensor Applications," *Sensors*, vol. 15, pp. 10481-10510 (2015).
Niesen, Frank H. et al., "The use of differential scanning fluorimetry to detect ligand interactions that promote protein stability," Nature Protocols, vol. 2, No. 9, pp. 2212-2221 (2007).
Pluckthun, Andreas: "Designed Ankyri n Repeat Proteins (DARPins): Binding Proteins for Research, Diagnostics, and Therapy", Annual Review of Pharmacology and Toxicology, vol. 55, No. 1, (2015).
Roethenberber et al., "Multi-specific DARPin theraputices demonstrate very high potency against mutatet SARS-CoV-2 variants in vitro", bioRxiv. 2021.
Sennhauser et al., "Chaperone-Assisted Crystallography with DARPins", Structure (2008) 16, pp. 1443-1453.
Shibo, Jiang et al.: "Neutralizing Antibodies against SARS-CoV-2 and Other Human Coronaviruses", Trends in Immunology, vol. 41, No. 5 (2020).
Steiner et al., "Efficient Selection of DARPins with Sub-nanomolar Affinities using SRP Phage Display", J Mol Biol 2008, 382(5), pp. 1211-1227 (incl. Supplement).
Steiner et al., "Half-life extension using serum albumin-binding DARPin® domains", PEDS (2017), pp. 1-9.
Stumpp et al., "Designing Repeat Proteins: Modular Leucine-rich Repeat Protein Libraries Based on the Mammalian Ribonuclease Inhibitor Family", J Mol Biol, 332, pp. 471-487 (2003).
Stumpp, Michael T. et al., "DARPins: A True Alternative to Antibodies," Current Opinion in Drug Discovery & Development, vol. 10, No. 2, pp. 153-159 (2007).
Stumpp et al., "DARPins: A new generation of protein therapeutics", Drug Discovery Today (2008) 13(15-16), pp. 695-701.
Stumpp et al., "Beyond Antibodies: The DARPin(R) Drug Platform", BioDrugs, (2020).
Tanaka, Nobutada et al., "Structural basis for recognition of 2',5'-linked oligoadenylates by human ribonuclease L," The EMBO Journal, vol. 23, pp. 3929-3938 (2004).
Thomson, Emma C. et al., "The circulating SARS-CoV-2 spike variant N439K maintains fitness while evading antibody-mediated immunity," Cell, vol. 184, No. 5, pp. 1171-1187 (2021).
Theurillat et al., "Designed ankyrin repeat proteins: a novel tool fortesting epidermal growth factor receptor 2 expression in breast cancer", Modern Pathology (2010), pp. 1-9.
Torriani, Giulia et al., "Macropinocytosis contributes to hantavirus entry into human airway epithelial cells," Virology, vol. 531, pp. 57-68 (2019).
Trimpert, Jakob et al., "The Roborovski Dwarf Hamster Is A Highly Susceptible Model for a Rapid and Fatal Course of SARS-CoV-2 Infection," Cell Reports, vol. 33, pp. 1-9 (2020).
Veesler et al., "Crystal Structure and Function of a DARPin Neutralizing Inhibitor of Lactococcal Phage TP901-1", J Biol Chem (2009) 284(44), pp. 30718-30726.
Walser, Marcel et al.: "Highly potent anti-SARS-CoV-2 multi-DARPin therapeutic candidates", bioRxiv, pp. 1-39 (2020).
Walser, Marcel et al.: "Highly potent anti-SARS-CoV-2 multi-DARPin therapeutic candidates ", bioRxiv, pp. 1-146 (2020).
Wang, Chunyan et al.: "A human monoclonal antibody blocking SARS-CoV-2 infectiont 1 , Nature Communications," vol. 11, No. 1 (2020).
Wrapp, Daniel et al., "Cryo-EM structure of the 2019-nCoV spike in the prefusion conformation," Science, vol. 367, pp. 1260-1263 (2020).
Yan, Renhong et al., "Structural basis for the recognition of SARS-CoV-2 by full-length human ACE2," Science, vol. 367, pp. 1444-1448 (2020).
Yi, Chunyan et al., "Key residues of the receptor binding motif in the spike protein of SARS-CoV-2 that interact with ACE2 and neutralizing antibodies," Cellular & Molecular Immunology, vol. 17, No. 17, pp. 621-630 (2020).
Zahnd, Christian et al., "Ribosome display: selecting and evolving proteins in vitro that specifically bind to a target," Nature Methods, vol. 4, No. 3, pp. 269-279 (2007).
Zahnd et al., "Selection and Characterization of Her2 Binding-designed Ankyrin Repeat Proteins," J Biol Chem (2006) 281(46), pp. 35167-35175.
Zahnd et al., "Efficient Tumor Targeting with High-Affinity Designed Ankyrin Repeat Proteins: . . . and Molecular Size", Cancer Res (2010) 70(4), pp. 1595-1605 (incl. Supplement).
Zahnd et al., "A designed ankyrin repeat protein evolved to picomolar affinity to Her2," J Mol Biol., 369(4), pp. 1015-1028 (2007).
Zeng, Xin et al.: "Isolation of a human monoclonal antibody specific for the receptor binding domain of SARS-CoV-2 using a competitive phage biopanning strategy", Antibody Therapeutics, vol. 3, No. 2 (2020).

* cited by examiner

A

B.1.1.7 (Δ9)

C

B.1.351 (Δ5)

Figure 29
A
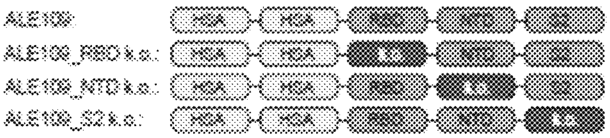
B
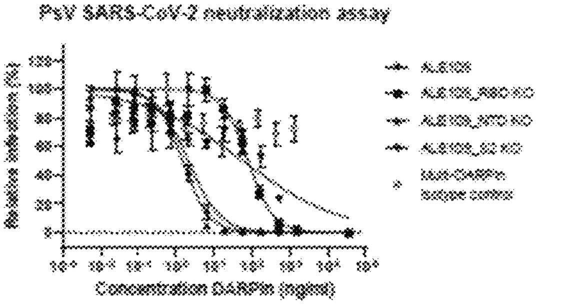
C
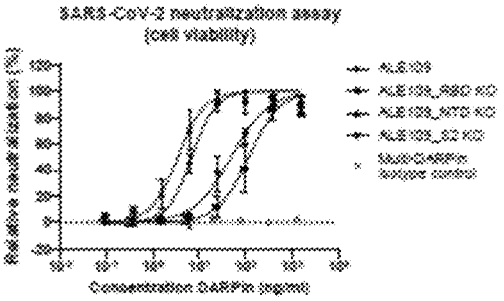
D
| | [illegible] | | |
|---|---|---|---|
| | [illegible] | [illegible] | [illegible] |
| ALE109 | 3.1 | 7 | 3.2 |
| ALE109_RBD k.o. | 80.5 | 137.5 | 28.8 |
| ALE109_NTD k.o. | 1.5 | 3.5 | 1.8 |
| ALE109_S2 k.o. | 38.8 | 48.1 | 28.8 |
Neutralization potency:
ALE109 ~ ALE109_NTD k.o. > ALE109_RBD k.o. ~ ALE109_S2 k.o.
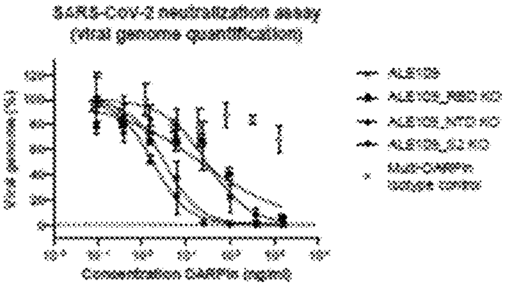

Figure 31

| Passage #1 | DARPin or Antibody Concentrations [μg/mL] | | | | | | |
|---|---|---|---|---|---|---|---|
| Constructs | 50 | 10 | 2 | 0.4 | 0.08 | 0.016 | no drug |
| DARPin Candidates | Cytopathic Effect [%] | | | | | | |
| RBD - 2 | 0% | 0% | 0% | 5% | ≥ 90% | ≥ 90% | ≥ 90% |
| ALE049 | 0% | 0% | 0% | 0% | ≥ 90% | ≥ 90% | ≥ 90% |
| ALE109 | 0% | 0% | 0% | 0% | ≥ 90% | ≥ 90% | ≥ 90% |
| ALE049 & ALE109 | 0% | 0% | 0% | 0% | ≥ 90% | ≥ 90% | ≥ 90% |
| Antibody Candidates | Cytopathic Effect [%] | | | | | | |
| S309 | 0% | 0% | 60% | ≥ 90% | ≥ 90% | ≥ 90% | ≥ 90% |
| RA1 | 0% | 0% | 0% | 5% | 80% | ≥ 90% | ≥ 90% |
| RA2 | 80% | ≥ 90% | ≥ 90% | ≥ 90% | ≥ 90% | ≥ 90% | ≥ 90% |
| RA1 & RA2 | 0% | 0% | 0% | 0% | ≥ 90% | ≥ 90% | ≥ 90% |
| IgG Negative Control | ≥ 90% | ≥ 90% | ≥ 90% | ≥ 90% | ≥ 90% | ≥ 90% | ≥ 90% |

| Passage #2 | DARPin or Antibody Concentrations [μg/mL] | | | | | | |
|---|---|---|---|---|---|---|---|
| Constructs | 50 | 10 | 2 | 0.4 | 0.08 | 0.016 | no drug |
| DARPin Candidates | Cytopathic Effect [%] | | | | | | |
| RBD - 2 | 0% | 60% | ≥ 90% | ≥ 90% | ≥ 90% | ≥ 90% | ≥ 90% |
| ALE049 | 0% | 0% | 0% | 0% | 0% | 50% | ≥ 90% |
| ALE109 | 0% | 0% | 0% | 0% | 0% | ≥ 90% | ≥ 90% |
| ALE049 & ALE109 | 0% | 0% | 0% | 0% | 0% | ≥ 90% | ≥ 90% |
| antibody Candidates | Cytopathic Effect [%] | | | | | | |
| S309 | ≥ 90% | ≥ 90% | ≥ 90% | ≥ 90% | ≥ 90% | ≥ 90% | ≥ 90% |
| RA1 | 0% | 0% | 80% | ≥ 90% | ≥ 90% | ≥ 90% | ≥ 90% |
| RA2 | ≥ 90% | ≥ 90% | ≥ 90% | ≥ 90% | ≥ 90% | ≥ 90% | ≥ 90% |
| RA1 & RA2 | 0% | 0% | 0% | 0% | 0% | ≥ 90% | ≥ 90% |
| IgG Negative Control | ≥ 90% | ≥ 90% | ≥ 90% | ≥ 90% | ≥ 90% | ≥ 90% | ≥ 90% |

| Passage #3 | DARPin or Antibody Concentrations [μg/mL] | | | | | | |
|---|---|---|---|---|---|---|---|
| Constructs | 50 | 10 | 2 | 0.4 | 0.08 | 0.016 | no drug |
| DARPin Candidates | Cytopathic Effect [%] | | | | | | |
| RBD - 2 | ≥ 90% | ≥ 90% | ≥ 90% | ≥ 90% | ≥ 90% | ≥ 90% | ≥ 90% |
| ALE049 | 0% | 0% | 0% | 0% | ≥ 90% | ≥ 90% | ≥ 90% |
| ALE109 | 0% | 0% | 0% | 40% | ≥ 90% | ≥ 90% | ≥ 90% |
| ALE049 & ALE109 | 0% | 0% | 0% | 0% | ≥ 90% | ≥ 90% | ≥ 90% |
| antibody Candidates | Cytopathic Effect [%] | | | | | | |
| S309 | ≥ 90% | ≥ 90% | ≥ 90% | ≥ 90% | ≥ 90% | ≥ 90% | ≥ 90% |
| RA1 | 0% | 0% | 5% | ≥ 90% | ≥ 90% | ≥ 90% | ≥ 90% |
| RA2 | ≥ 90% | ≥ 90% | ≥ 90% | ≥ 90% | ≥ 90% | ≥ 90% | ≥ 90% |
| RA1 & RA2 | 0% | 0% | 0% | 0% | ≥ 90% | ≥ 90% | ≥ 90% |
| IgG Negative Control | ≥ 90% | ≥ 90% | ≥ 90% | ≥ 90% | ≥ 90% | ≥ 90% | ≥ 90% |

| Passage #4 | DARPin or Antibody Concentrations [μg/mL] | | | | | | |
|---|---|---|---|---|---|---|---|
| Constructs | 50 | 10 | 2 | 0.4 | 0.08 | 0.016 | no drug |
| DARPin Candidates | Cytopathic Effect [%] | | | | | | |
| RBD - 2 | n.d. | n.d. | n.d. | n.d. | n.d. | n.d. | n.d. |
| ALE049 | 0% | 0% | 0% | 40% | ≥ 90% | ≥ 90% | ≥ 90% |
| ALE109 | 0% | 0% | ≥ 90% | ≥ 90% | ≥ 90% | ≥ 90% | ≥ 90% |
| ALE049 & ALE109 | 0% | 0% | 0% | 0% | 5% | ≥ 90% | ≥ 90% |
| antibody Candidates | Cytopathic Effect [%] | | | | | | |
| S309 | n.d. | n.d. | n.d. | n.d. | n.d. | n.d. | n.d. |
| RA1 | ≥ 90% | ≥ 90% | ≥ 90% | ≥ 90% | ≥ 90% | ≥ 90% | ≥ 90% |
| RA2 | n.d. | n.d. | n.d. | n.d. | n.d. | n.d. | n.d. |
| RA1 & RA2 | 0% | 0% | 0% | 0% | ≥ 90% | ≥ 90% | ≥ 90% |
| IgG Negative Control | n.d. | n.d. | n.d. | n.d. | n.d. | n.d. | n.d. |

n.d : not determined as virus acquired resistance in previous passage

| | EC50 |
|---|---|
| ALE049 | 0.03170 |
| ALE058 | 0.03065 |
| ALE109 | 0.02716 |
| ALE126 - std. linker | 0.03243 |
| ALE129 - 8aa linker ext | 0.03836 |
| ALE133 - 15aa linker ext | 0.04440 |

Figure 36

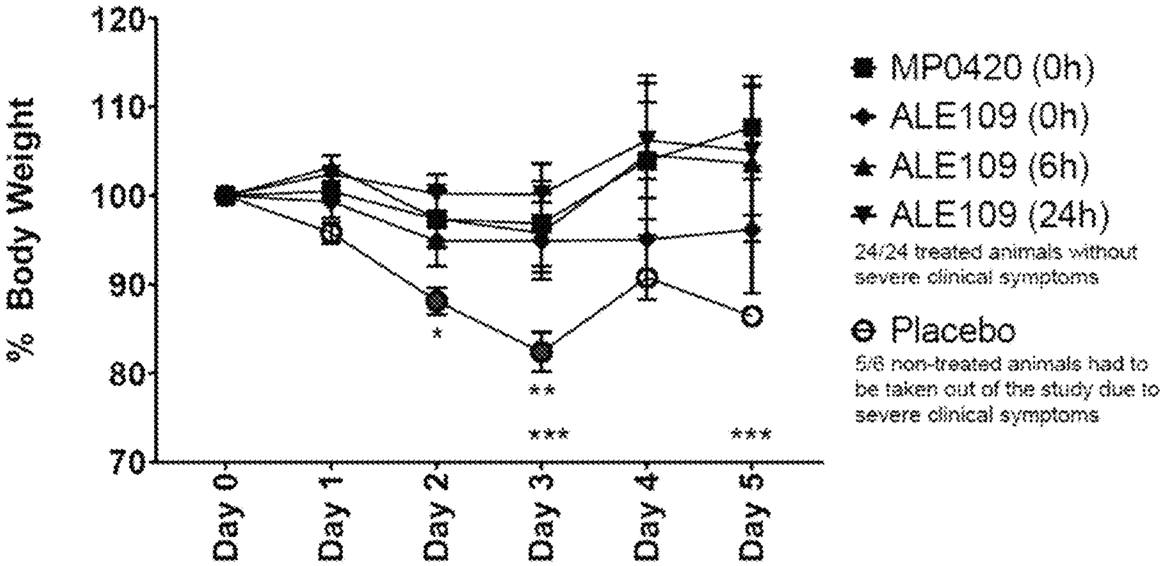

*Two hamsters were taken out of placebo group due to severe clinical symptoms and body weight loss at day 2.

**Three additional hamsters were taken out of placebo group due to severe clinical symptoms and body weight loss at day 3 with only one animal remaining until day 5.

***Three animals of the treated groups were sacrificed at day 3 and the other animals at day 5 for analytical purposes.

Figure 37 (A-B)
A
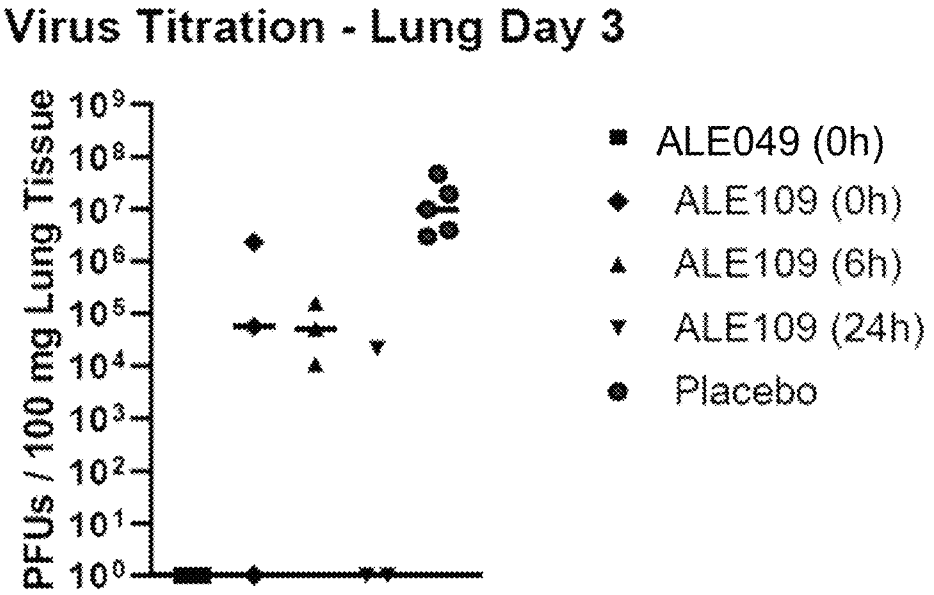
Placebo: animals taken out of the study (at day 2 and 3) due to severe clinical symtoms and body weight loss.
B
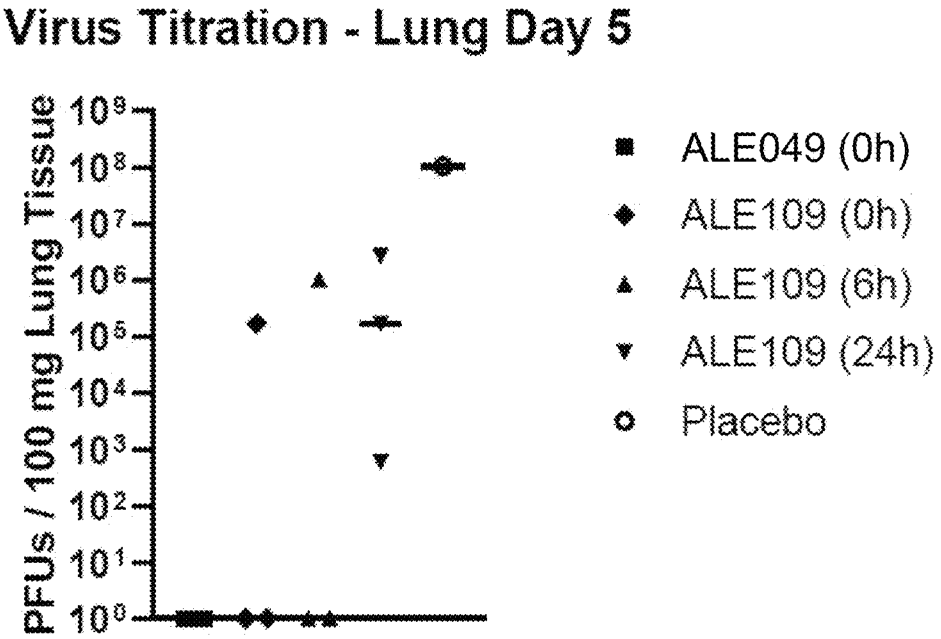

Figure 37 (C-D)
C
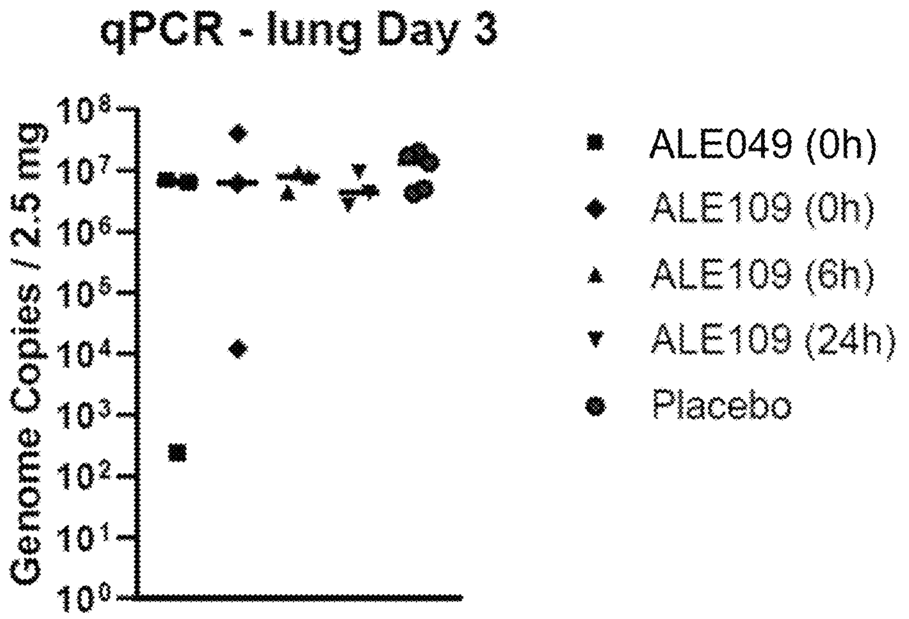
Placebo: animals taken out of the study (at day 2 and 3) due to severe clinical symtoms and body weight loss.
D
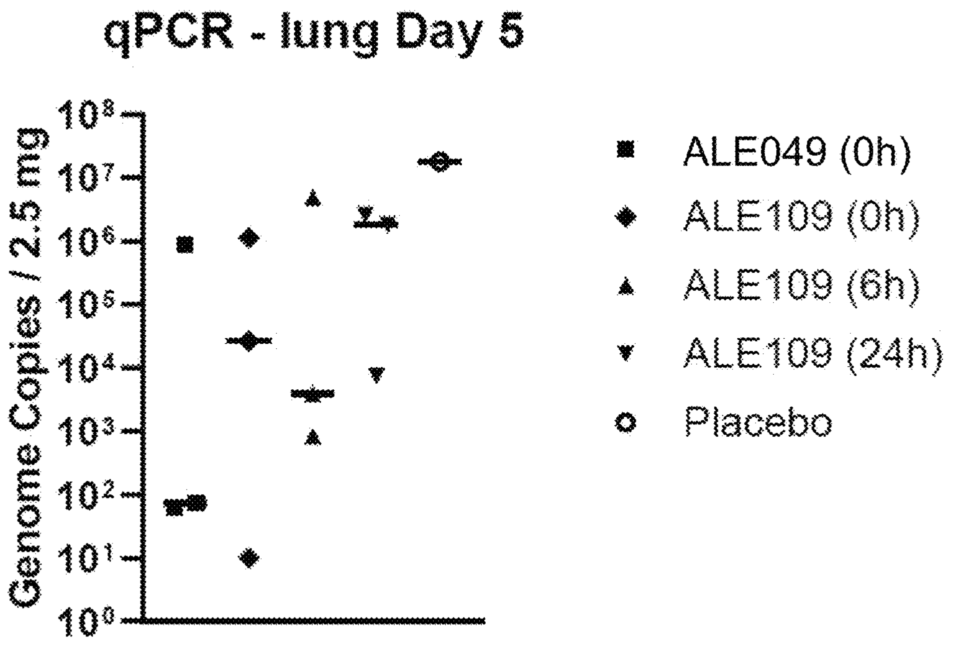

Figure 38 (A-B)
A
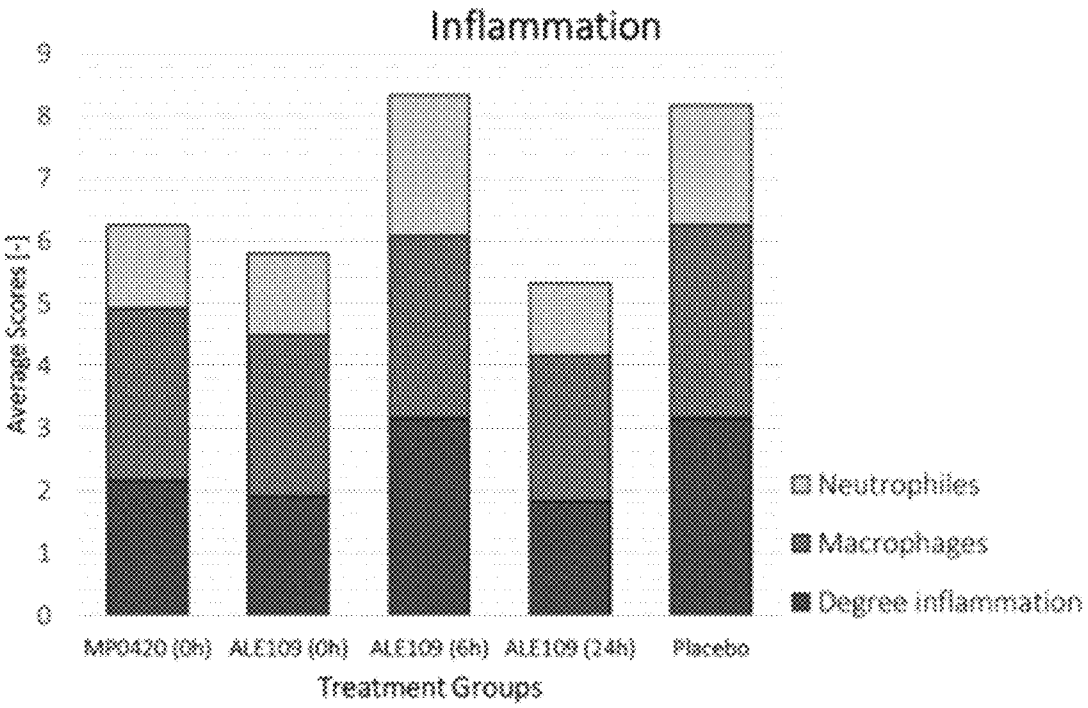
B
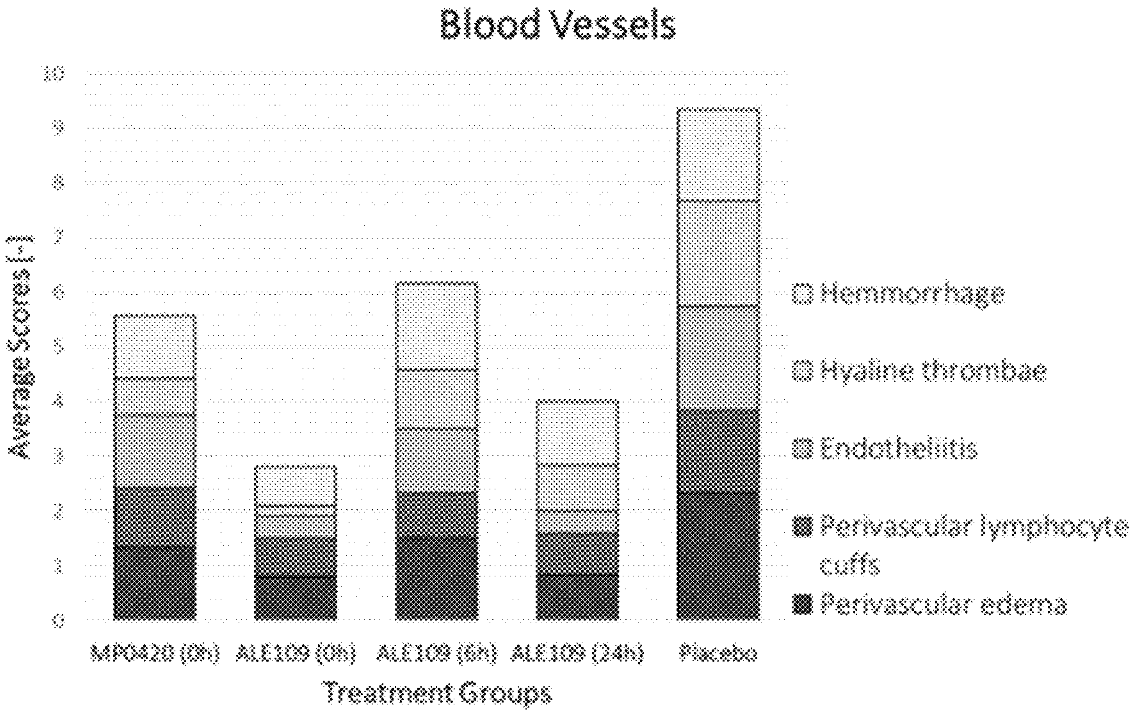

Figure 38 (C-D)
C
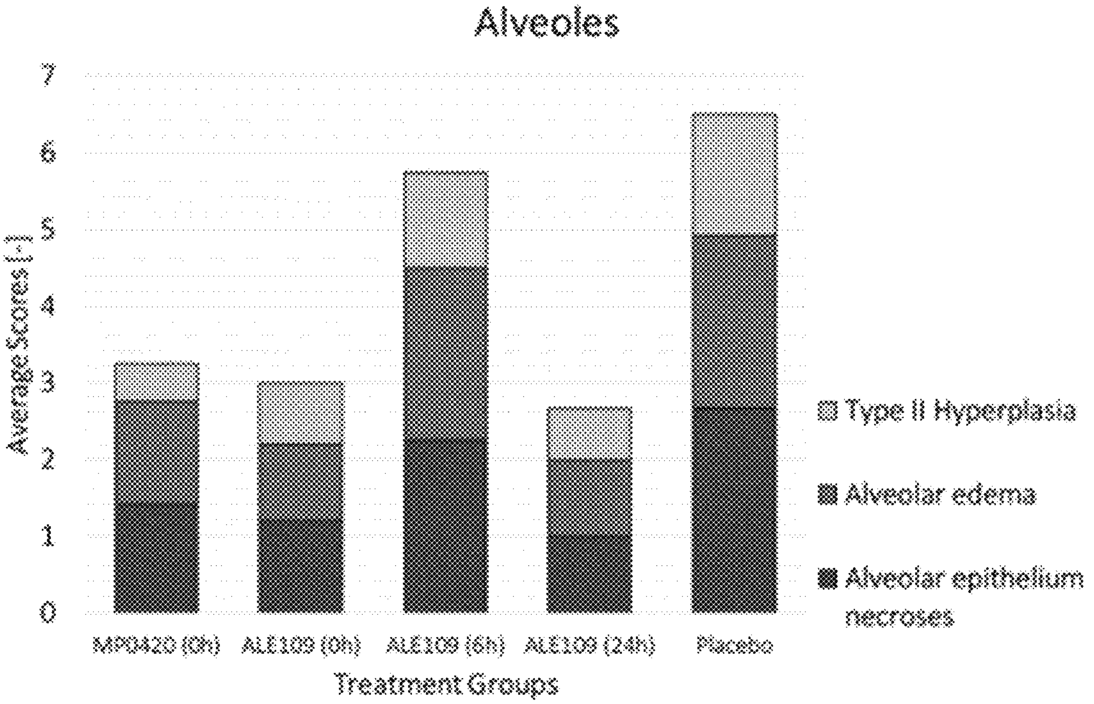
D
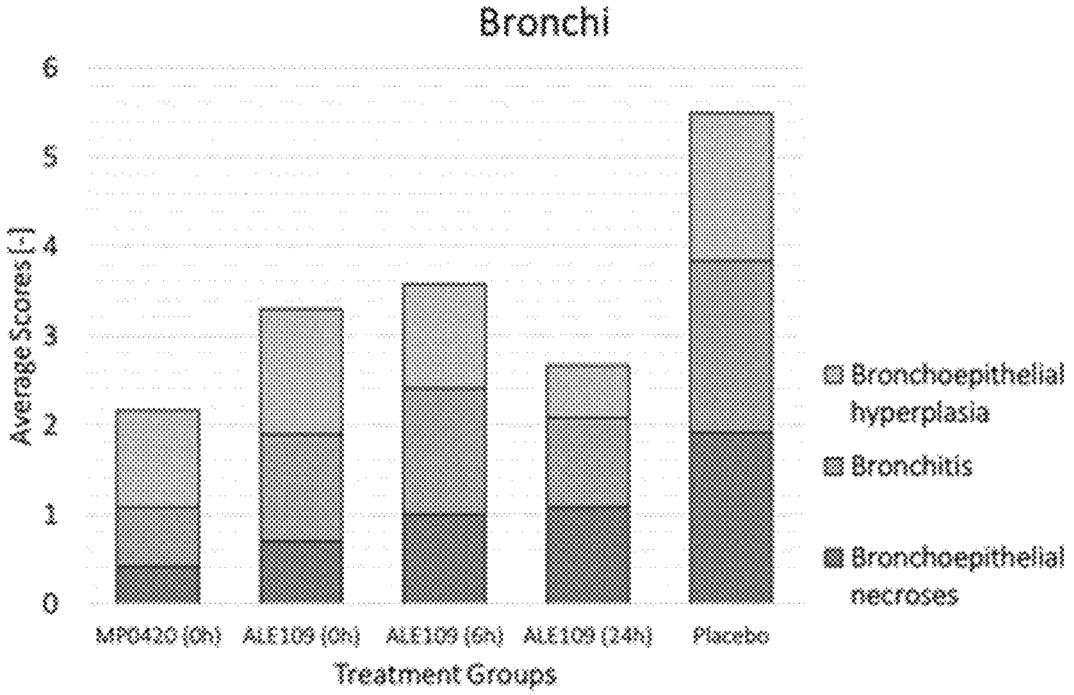

```
                    SEQUENCE LISTING


<160> NUMBER OF SEQ ID NOS: 95

<210> SEQ ID NO 1
<211> LENGTH: 126
<212> TYPE: PRT
<213> ORGANISM: Artificial Sequence
<220> FEATURE:
<223> OTHER INFORMATION: Spike protein binding domain
```

<400> SEQUENCE: 1

Gly Ser Asp Leu Gly Asn Lys Leu Leu Asp Ala Ala Trp Val Gly Gln
1 5 10 15

Asp Asp Glu Val Arg Ile Leu Leu Ala Ala Gly Ala Asp Val Asn Ala
20 25 30

Lys Asp Trp Gln Gly Glu Thr Pro Leu His Leu Ala Ala Thr Lys Gly
35 40 45

His Leu Glu Ile Val Glu Val Leu Leu Lys Ala Gly Ala Asp Val Asn
50 55 60

Ala Lys Asp Val Val Gly Tyr Thr Pro Leu His Val Ala Ala Ser Gln
65 70 75 80

Gly His Leu Glu Ile Val Glu Val Leu Leu Lys Ala Gly Ala Asp Val
85 90 95

Asn Ala Gln Asp Val His Gly Tyr Thr Pro Ala Asp Leu Ala Ala Gln
100 105 110

Ala Gly His Glu Asp Ile Ala Glu Val Leu Gln Lys Ala Ala
115 120 125

<210> SEQ ID NO 2
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 2

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Arg Glu Gly Trp Thr Pro Leu His Leu Ala Ala His Gln Gly
35 40 45

His Leu Glu Ile Val Glu Val Leu Leu Lys Ala Gly Ala Asp Val Asn
50 55 60

Ala Lys Asp Val Phe Gly Arg Thr Pro Leu His Leu Ala Ala Trp Val
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Pro Ala Ala Ile
100 105 110

Tyr Gly His Leu Glu Ile Val Glu Val Leu Leu Lys Ala Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala
145 150 155

<210> SEQ ID NO 3
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 3

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Arg Glu Gly Lys Thr Pro Leu His Val Ala Ala Gln Glu Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ile
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Ala Ala Ala Leu
100 105 110

His Gly His Leu Glu Ile Val Glu Val Leu Leu Asn Ala Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala
145 150 155

<210> SEQ ID NO 4
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 4

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Lys Ile Gly Val Thr Pro Leu His Ile Ala Ala Glu Val Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ser
65 70 75 80

Gly His Leu Glu Ile Val Glu Val Leu Val Lys Ala Gly Ala Asp Val
85 90 95

Asn Ala Lys Asp Ile Ala Gly Ala Thr Pro Leu His Ala Ala Ala Leu
100 105 110

Phe Gly His Leu Glu Ile Val Glu Val Leu Leu Lys Val Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala
145 150 155

<210> SEQ ID NO 5
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 5

Gly Ser Asp Leu Gly Lys Lys Leu Leu Gln Ala Ala Arg Ala Gly Gln

-continued

```
1               5                   10                  15

Leu Asp Glu Val Arg Glu Leu Leu Lys Ala Gly Ala Asp Val Asn Ala
            20                  25                  30

Lys Asp Gln Glu Gly Ile Thr Pro Leu His Val Ala Ala His Gln Gly
        35                  40                  45

His Leu Glu Ile Val Glu Val Leu Leu Lys Ala Gly Ala Asp Val Asn
    50                  55                  60

Ala Lys Asp Val Trp Gly Arg Thr Pro Leu His Leu Ala Ala Trp Arg
65                  70                  75                  80

Gly His Leu Glu Ile Val Glu Val Leu Leu Lys Ala Gly Ala Asp Val
                85                  90                  95

Asn Ala Lys Asp His Ala Gly Ala Thr Pro Leu His Ala Ala Ala Leu
            100                 105                 110

Ser Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155
```

<210> SEQ ID NO 6
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 6

```
Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Arg Glu Gly Ile Thr Pro Leu His Leu Ala Ala Gln His Gly
        35                  40                  45

His Leu Glu Ile Val Glu Val Leu Leu Lys Ala Gly Ala Asp Val Asn
    50                  55                  60

Ala Lys Asp Val Trp Gly Arg Thr Pro Leu His Leu Ala Ala Trp Gln
65                  70                  75                  80

Gly His Leu Glu Ile Val Glu Val Leu Leu Lys Ala Gly Ala Asp Val
                85                  90                  95

Asn Ala Lys Asp Leu Ala Gly Ala Thr Pro Leu His Val Ala Ala Leu
            100                 105                 110

Tyr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155
```

<210> SEQ ID NO 7
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 7

```
Gly Ser Asp Leu Gly Leu Lys Leu Leu Thr Ala Ala Lys Gln Gly Gln
1               5                   10                  15

Asp Asp Glu Val Arg Ile Leu Leu Ala Ala Gly Ala Asp Val Asn Ala
            20                  25                  30

Lys Asp Tyr Arg Gly Leu Thr Pro Leu His Tyr Ala Ala Ala Ile Gly
        35                  40                  45

His Leu Glu Ile Val Glu Val Leu Leu Lys Ala Gly Ala Asp Val Asn
    50                  55                  60

Ala Lys Asp Gln Tyr Gly Ala Thr Pro Leu His Val Ala Ala Tyr Ile
65                  70                  75                  80

Gly His Leu Glu Ile Val Glu Val Leu Leu Lys Ala Gly Ala Asp Val
                85                  90                  95

Asn Ala Gln Asp Phe Ser Gly Ser Thr Pro Ala Asp Leu Ala Ala Glu
            100                 105                 110

Glu Gly His Glu Asp Ile Ala Glu Val Leu Gln Lys Ala Ala
        115                 120                 125


<210> SEQ ID NO 8
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 8

Gly Ser Asp Leu Gly Trp Lys Leu Leu Trp Ala Ala Gln Val Gly Gln
1               5                   10                  15

Asp Asp Glu Val Arg Ile Leu Leu Ala Ala Gly Ala Asp Val Asn Ala
            20                  25                  30

Lys Asp Asp Leu Gly Trp Thr Pro Leu His Ile Ala Ala Trp Val Gly
        35                  40                  45

His Leu Glu Ile Val Glu Val Leu Leu Lys Ala Gly Ala Asp Val Asn
    50                  55                  60

Ala Lys Asp Phe Thr Gly Arg Thr Pro Leu His His Ala Ala Thr Glu
65                  70                  75                  80

Gly His Leu Glu Ile Val Lys Val Leu Leu Lys Ala Gly Ala Asp Val
                85                  90                  95

Asn Ala Gln Asp Asp Val Gly His Thr Pro Ala Asp Leu Ala Ala Leu
            100                 105                 110

Trp Gly His Glu Asp Ile Ala Glu Val Leu Gln Lys Ala Ala
        115                 120                 125


<210> SEQ ID NO 9
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 9

Gly Ser Asp Leu Gly His Lys Leu Leu Leu Ala Ala Gln Ala Gly Gln
1               5                   10                  15

Asp Asp Glu Val Arg Ile Leu Leu Ala Ala Gly Ala Asp Val Asn Ala
            20                  25                  30

Lys Asp Val Phe Gly Gln Thr Pro Leu His Val Ala Ala Val Ala Gly
        35                  40                  45

His Leu Glu Ile Val Glu Val Leu Leu Lys Ala Gly Ala Asp Val Asn
    50                  55                  60
```

```
Ala Lys Asp Ser Ile Gly Tyr Thr Pro Leu His His Ala Ala Arg Val
65                  70                  75                  80

Gly His Leu Glu Ile Val Glu Val Leu Leu Lys Ala Gly Ala Asp Val
                85                  90                  95

Asn Ala Gln Asp Trp Ile Gly Ile Thr Pro Ala Asp Leu Ala Ala Phe
            100                 105                 110

Glu Gly His Glu Asp Ile Ala Glu Val Leu Gln Lys Ala Ala
        115                 120                 125


<210> SEQ ID NO 10
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 10

Gly Ser Asp Leu Gly Gln Lys Leu Leu His Ala Ala Gln Tyr Gly Gln
1               5                   10                  15

Asp Asp Glu Val Arg Ile Leu Leu Ala Ala Gly Ala Asp Val Asn Ala
            20                  25                  30

Lys Asp Lys Gln Gly Asn Thr Pro Leu His Ile Ala Ala Phe His Gly
        35                  40                  45

His Leu Glu Ile Val Glu Val Leu Leu Lys Ala Gly Ala Asp Val Asn
    50                  55                  60

Ala Lys Asp Gln Trp Gly Leu Thr Pro Leu His Leu Ala Ala Ala Trp
65                  70                  75                  80

Gly His Leu Glu Ile Val Glu Val Leu Leu Lys Ala Gly Ala Asp Val
                85                  90                  95

Asn Ala Gln Asp Asn Tyr Gly Gln Thr Pro Ala Asp Leu Ala Ala Glu
            100                 105                 110

Ser Gly His Glu Asp Ile Ala Glu Val Leu Gln Lys Ala Ala
        115                 120                 125


<210> SEQ ID NO 11
<211> LENGTH: 159
<212> TYPE: PRT
<213> ORGANISM: Artificial Sequence
<220> FEATURE:
<223> OTHER INFORMATION: Spike protein binding domain

<400> SEQUENCE: 11

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Glu Thr Gly Phe Thr Pro Leu His Val Ala Ala Glu Lys Gly
        35                  40                  45

His Leu Glu Ile Val Glu Val Leu Leu Lys Ala Gly Ala Asp Val Asn
    50                  55                  60

Ala Lys Asp His Phe Gly Phe Thr Pro Leu His Leu Val Ser Glu Trp
65                  70                  75                  80

Gly His Leu Glu Ile Val Glu Val Leu Leu Lys Ala Gly Ala Asp Val
                85                  90                  95

Asn Ala Lys Asp Ser Tyr Gly Trp Thr Pro Leu His Val Ala Ala Ile
            100                 105                 110

Leu Gly His Leu Glu Ile Val Glu Val Leu Leu Lys Ala Gly Ala Asp
```

```
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155


<210> SEQ ID NO 12
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 12

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
```

-continued

```
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Asn Lys Leu Leu Asp Ala Ala Trp Val Gly Gln Asp Asp Glu
                485                 490                 495

Val Arg Ile Leu Leu Ala Ala Gly Ala Asp Val Asn Ala Lys Asp Trp
            500                 505                 510

Gln Gly Glu Thr Pro Leu His Leu Ala Ala Thr Lys Gly His Leu Glu
        515                 520                 525

Ile Val Glu Val Leu Leu Lys Ala Gly Ala Asp Val Asn Ala Lys Asp
    530                 535                 540

Val Val Gly Tyr Thr Pro Leu His Val Ala Ala Ser Gln Gly His Leu
545                 550                 555                 560

Glu Ile Val Glu Val Leu Leu Lys Ala Gly Ala Asp Val Asn Ala Gln
                565                 570                 575

Asp Val His Gly Tyr Thr Pro Ala Asp Leu Ala Ala Gln Ala Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Lys Thr Pro Leu His Val Ala Ala Gln Glu
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Ile Gly His Leu Glu Ile Val Glu Val Leu Leu Lys Ala Gly Ala Asp
705                 710                 715                 720

Val Asn Ala Lys Asp Val Ser Gly Ala Thr Pro Leu His Ala Ala Ala
                725                 730                 735

Leu His Gly His Leu Glu Ile Val Glu Val Leu Leu Asn Ala Gly Ala
            740                 745                 750
```

Asp Val Asn Ala Gln Asp Lys Ser Gly Lys Thr Pro Ala Asp Leu Ala
755 760 765

Ala Arg Ala Gly His Gln Asp Ile Ala Glu Val Leu Gln Lys Ala Ala
770 775 780

<210> SEQ ID NO 13
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 13

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

Asn Ala Gln Asp Ile Phe Gly Lys Thr Pro Ala Asp Ile Ala Ala Asp
100 105 110

Ala Gly His Glu Asp Ile Ala Glu Val Leu Gln Lys Ala Ala Gly Ser
115 120 125

Pro Thr Pro Thr Pro Thr Thr Pro Thr Pro Thr Pro Thr Thr Pro Thr
130 135 140

Pro Thr Pro Thr Gly Ser Asp Leu Gly Lys Lys Leu Leu Glu Ala Ala
145 150 155 160

Arg Ala Gly Gln Asp Asp Glu Val Arg Glu Leu Leu Lys Ala Gly Ala
165 170 175

Asp Val Asn Ala Lys Asp Tyr Phe Ser His Thr Pro Leu His Leu Ala
180 185 190

Ala Arg Asn Gly His Leu Lys Ile Val Glu Val Leu Leu Lys Ala Gly
195 200 205

Ala Asp Val Asn Ala Lys Asp Phe Ala Gly Lys Thr Pro Leu His Leu
210 215 220

Ala Ala Asn Glu Gly His Leu Glu Ile Val Glu Val Leu Leu Lys Ala
225 230 235 240

Gly Ala Asp Val Asn Ala Gln Asp Ile Phe Gly Lys Thr Pro Ala Asp
245 250 255

Ile Ala Ala Asp Ala Gly His Glu Asp Ile Ala Glu Val Leu Gln Lys
260 265 270

Ala Ala Gly Ser Pro Thr Pro Thr Pro Thr Thr Pro Thr Pro Thr Pro
275 280 285

Thr Thr Pro Thr Pro Thr Pro Thr Gly Ser Asp Leu Gly Lys Lys Leu
290 295 300

Leu Gln Ala Ala Arg Ala Gly Gln Leu Asp Glu Val Arg Glu Leu Leu
305 310 315 320

Lys Ala Gly Ala Asp Val Asn Ala Lys Asp Lys Ile Gly Val Thr Pro
325 330 335

-continued

```
Leu His Ile Ala Ala Glu Val Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ser Gly His Leu Glu Ile Val Glu Val
    370                 375                 380

Leu Val Lys Ala Gly Ala Asp Val Asn Ala Lys Asp Ile Ala Gly Ala
385                 390                 395                 400

Thr Pro Leu His Ala Ala Ala Leu Phe Gly His Leu Glu Ile Val Glu
                405                 410                 415

Val Leu Leu Lys Val Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510

Glu Gly Trp Thr Pro Leu His Leu Ala Ala His Gln Gly His Leu Glu
        515                 520                 525

Ile Val Glu Val Leu Leu Lys Ala Gly Ala Asp Val Asn Ala Lys Asp
    530                 535                 540

Val Phe Gly Arg Thr Pro Leu His Leu Ala Ala Trp Val Gly His Leu
545                 550                 555                 560

Glu Ile Val Glu Val Leu Leu Lys Ala Gly Ala Asp Val Asn Ala Lys
                565                 570                 575

Asp Val Ser Gly Ala Thr Pro Leu His Pro Ala Ala Ile Tyr Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Asn Lys Leu Leu Asp Ala Ala Trp Val
            660                 665                 670

Gly Gln Asp Asp Glu Val Arg Ile Leu Leu Ala Ala Gly Ala Asp Val
        675                 680                 685

Asn Ala Lys Asp Trp Gln Gly Glu Thr Pro Leu His Leu Ala Ala Thr
    690                 695                 700

Lys Gly His Leu Glu Ile Val Glu Val Leu Leu Lys Ala Gly Ala Asp
705                 710                 715                 720

Val Asn Ala Lys Asp Val Val Gly Tyr Thr Pro Leu His Val Ala Ala
                725                 730                 735

Ser Gln Gly His Leu Glu Ile Val Glu Val Leu Leu Lys Ala Gly Ala
            740                 745                 750
```

```
Asp Val Asn Ala Gln Asp Val His Gly Tyr Thr Pro Ala Asp Leu Ala
        755                 760                 765

Ala Gln Ala Gly His Glu Asp Ile Ala Glu Val Leu Gln Lys Ala Ala
    770                 775                 780


<210> SEQ ID NO 14
<211> LENGTH: 817
<212> TYPE: PRT
<213> ORGANISM: Artificial Sequence
<220> FEATURE:
<223> OTHER INFORMATION: Multi-specific binding protein

<400> SEQUENCE: 14

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Lys Ile Gly Val Thr Pro
                325                 330                 335
```

```
Leu His Ile Ala Ala Glu Val Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ser Gly His Leu Glu Ile Val Glu Val
    370                 375                 380

Leu Val Lys Ala Gly Ala Asp Val Asn Ala Lys Asp Ile Ala Gly Ala
385                 390                 395                 400

Thr Pro Leu His Ala Ala Ala Leu Phe Gly His Leu Glu Ile Val Glu
                405                 410                 415

Val Leu Leu Lys Val Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510

Glu Gly Ile Thr Pro Leu His Leu Ala Ala Gln His Gly His Leu Glu
        515                 520                 525

Ile Val Glu Val Leu Leu Lys Ala Gly Ala Asp Val Asn Ala Lys Asp
    530                 535                 540

Val Trp Gly Arg Thr Pro Leu His Leu Ala Ala Trp Gln Gly His Leu
545                 550                 555                 560

Glu Ile Val Glu Val Leu Leu Lys Ala Gly Ala Asp Val Asn Ala Lys
                565                 570                 575

Asp Leu Ala Gly Ala Thr Pro Leu His Val Ala Ala Leu Tyr Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Lys Lys Leu Leu Gln Ala Ala Arg Ala
            660                 665                 670

Gly Gln Leu Asp Glu Val Arg Glu Leu Leu Lys Ala Gly Ala Asp Val
        675                 680                 685

Asn Ala Lys Asp Arg Glu Gly Lys Thr Pro Leu His Val Ala Ala Gln
    690                 695                 700

Glu Gly His Leu Glu Ile Val Glu Val Leu Leu Lys Ala Gly Ala Asp
705                 710                 715                 720

Val Asn Ala Lys Asp Val Trp Gly Arg Thr Pro Leu His Leu Ala Ala
                725                 730                 735

Trp Ile Gly His Leu Glu Ile Val Glu Val Leu Leu Lys Ala Gly Ala
            740                 745                 750

Asp Val Asn Ala Lys Asp Val Ser Gly Ala Thr Pro Leu His Ala Ala
```

```
        755                 760                 765

Ala Leu His Gly His Leu Glu Ile Val Glu Val Leu Leu Asn Ala Gly
    770                 775                 780

Ala Asp Val Asn Ala Gln Asp Lys Ser Gly Lys Thr Pro Ala Asp Leu
785                 790                 795                 800

Ala Ala Arg Ala Gly His Gln Asp Ile Ala Glu Val Leu Gln Lys Ala
                805                 810                 815

Ala


<210> SEQ ID NO 15
<211> LENGTH: 817
<212> TYPE: PRT
<213> ORGANISM: Artificial Sequence
<220> FEATURE:
<223> OTHER INFORMATION: Multi-specific binding protein

<400> SEQUENCE: 15

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300
```

-continued

```
Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510

Glu Gly Lys Thr Pro Leu His Val Ala Ala Gln Glu Gly His Leu Glu
        515                 520                 525

Ile Val Glu Val Leu Leu Lys Ala Gly Ala Asp Val Asn Ala Lys Asp
    530                 535                 540

Val Trp Gly Arg Thr Pro Leu His Leu Ala Ala Trp Ile Gly His Leu
545                 550                 555                 560

Glu Ile Val Glu Val Leu Leu Lys Ala Gly Ala Asp Val Asn Ala Lys
                565                 570                 575

Asp Val Ser Gly Ala Thr Pro Leu His Ala Ala Ala Leu His Gly His
            580                 585                 590

Leu Glu Ile Val Glu Val Leu Leu Asn Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Lys Lys Leu Leu Gln Ala Ala Arg Ala
            660                 665                 670

Gly Gln Leu Asp Glu Val Arg Glu Leu Leu Lys Ala Gly Ala Asp Val
        675                 680                 685

Asn Ala Lys Asp Arg Glu Gly Ile Thr Pro Leu His Leu Ala Ala Gln
    690                 695                 700

His Gly His Leu Glu Ile Val Glu Val Leu Leu Lys Ala Gly Ala Asp
705                 710                 715                 720
```

```
Val Asn Ala Lys Asp Val Trp Gly Arg Thr Pro Leu His Leu Ala Ala
                725                 730                 735

Trp Gln Gly His Leu Glu Ile Val Glu Val Leu Leu Lys Ala Gly Ala
            740                 745                 750

Asp Val Asn Ala Lys Asp Leu Ala Gly Ala Thr Pro Leu His Val Ala
        755                 760                 765

Ala Leu Tyr Gly His Leu Glu Ile Val Glu Val Leu Leu Lys Ala Gly
    770                 775                 780

Ala Asp Val Asn Ala Gln Asp Lys Ser Gly Lys Thr Pro Ala Asp Leu
785                 790                 795                 800

Ala Ala Arg Ala Gly His Gln Asp Ile Ala Glu Val Leu Gln Lys Ala
                805                 810                 815

Ala


<210> SEQ ID NO 16
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 16

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
```

-continued

```
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Leu Lys Leu
    290                 295                 300

Leu Thr Ala Ala Lys Gln Gly Gln Asp Asp Glu Val Arg Ile Leu Leu
305                 310                 315                 320

Ala Ala Gly Ala Asp Val Asn Ala Lys Asp Tyr Arg Gly Leu Thr Pro
                325                 330                 335

Leu His Tyr Ala Ala Ala Ile Gly His Leu Glu Ile Val Glu Val Leu
            340                 345                 350

Leu Lys Ala Gly Ala Asp Val Asn Ala Lys Asp Gln Tyr Gly Ala Thr
        355                 360                 365

Pro Leu His Val Ala Ala Tyr Ile Gly His Leu Glu Ile Val Glu Val
    370                 375                 380

Leu Leu Lys Ala Gly Ala Asp Val Asn Ala Gln Asp Phe Ser Gly Ser
385                 390                 395                 400

Thr Pro Ala Asp Leu Ala Ala Glu Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Lys Thr Pro Leu His Val Ala Ala Gln Glu Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Ile Gly His Leu Glu
        515                 520                 525

Ile Val Glu Val Leu Leu Lys Ala Gly Ala Asp Val Asn Ala Lys Asp
    530                 535                 540

Val Ser Gly Ala Thr Pro Leu His Ala Ala Ala Leu His Gly His Leu
545                 550                 555                 560

Glu Ile Val Glu Val Leu Leu Asn Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Ile Thr Pro Leu His Leu Ala Ala Gln His
            660                 665                 670

Gly His Leu Glu Ile Val Glu Val Leu Leu Lys Ala Gly Ala Asp Val
        675                 680                 685
```

```
Asn Ala Lys Asp Val Trp Gly Arg Thr Pro Leu His Leu Ala Ala Trp
    690                 695                 700

Gln Gly His Leu Glu Ile Val Glu Val Leu Leu Lys Ala Gly Ala Asp
705                 710                 715                 720

Val Asn Ala Lys Asp Leu Ala Gly Ala Thr Pro Leu His Val Ala Ala
                725                 730                 735

Leu Tyr Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 17
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 17

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270
```

```
Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Trp Lys Leu
    290                 295                 300

Leu Trp Ala Ala Gln Val Gly Gln Asp Asp Glu Val Arg Ile Leu Leu
305                 310                 315                 320

Ala Ala Gly Ala Asp Val Asn Ala Lys Asp Asp Leu Gly Trp Thr Pro
                325                 330                 335

Leu His Ile Ala Ala Trp Val Gly His Leu Glu Ile Val Glu Val Leu
            340                 345                 350

Leu Lys Ala Gly Ala Asp Val Asn Ala Lys Asp Phe Thr Gly Arg Thr
        355                 360                 365

Pro Leu His His Ala Ala Thr Glu Gly His Leu Glu Ile Val Lys Val
    370                 375                 380

Leu Leu Lys Ala Gly Ala Asp Val Asn Ala Gln Asp Asp Val Gly His
385                 390                 395                 400

Thr Pro Ala Asp Leu Ala Ala Leu Trp Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Lys Ile
465                 470                 475                 480

Gly Val Thr Pro Leu His Ile Ala Ala Glu Val Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Ser Gly His Leu Glu
        515                 520                 525

Ile Val Glu Val Leu Val Lys Ala Gly Ala Asp Val Asn Ala Lys Asp
    530                 535                 540

Ile Ala Gly Ala Thr Pro Leu His Ala Ala Ala Leu Phe Gly His Leu
545                 550                 555                 560

Glu Ile Val Glu Val Leu Leu Lys Val Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Asn Lys Leu Leu Asp Ala Ala Trp Val Gly
625                 630                 635                 640

Gln Asp Asp Glu Val Arg Ile Leu Leu Ala Ala Gly Ala Asp Val Asn
                645                 650                 655

Ala Lys Asp Trp Gln Gly Glu Thr Pro Leu His Leu Ala Ala Thr Lys
            660                 665                 670

Gly His Leu Glu Ile Val Glu Val Leu Leu Lys Ala Gly Ala Asp Val
        675                 680                 685
```

```
Asn Ala Lys Asp Val Val Gly Tyr Thr Pro Leu His Val Ala Ala Ser
    690                 695                 700

Gln Gly His Leu Glu Ile Val Glu Val Leu Leu Lys Ala Gly Ala Asp
705                 710                 715                 720

Val Asn Ala Gln Asp Val His Gly Tyr Thr Pro Ala Asp Leu Ala Ala
                725                 730                 735

Gln Ala Gly His Glu Asp Ile Ala Glu Val Leu Gln Lys Ala Ala
            740                 745                 750


<210> SEQ ID NO 18
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 18

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300
```

-continued

```
Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510

Glu Gly Ile Thr Pro Leu His Leu Ala Ala Gln His Gly His Leu Glu
        515                 520                 525

Ile Val Glu Val Leu Leu Lys Ala Gly Ala Asp Val Asn Ala Lys Asp
    530                 535                 540

Val Trp Gly Arg Thr Pro Leu His Leu Ala Ala Trp Gln Gly His Leu
545                 550                 555                 560

Glu Ile Val Glu Val Leu Leu Lys Ala Gly Ala Asp Val Asn Ala Lys
                565                 570                 575

Asp Leu Ala Gly Ala Thr Pro Leu His Val Ala Ala Leu Tyr Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Leu Lys Leu Leu Thr Ala Ala Lys Gln
            660                 665                 670

Gly Gln Asp Asp Glu Val Arg Ile Leu Leu Ala Ala Gly Ala Asp Val
        675                 680                 685

Asn Ala Lys Asp Tyr Arg Gly Leu Thr Pro Leu His Tyr Ala Ala Ala
    690                 695                 700

Ile Gly His Leu Glu Ile Val Glu Val Leu Leu Lys Ala Gly Ala Asp
705                 710                 715                 720

Val Asn Ala Lys Asp Gln Tyr Gly Ala Thr Pro Leu His Val Ala Ala
```

```
                725                 730                 735

Tyr Ile Gly His Leu Glu Ile Val Glu Val Leu Leu Lys Ala Gly Ala
            740                 745                 750

Asp Val Asn Ala Gln Asp Phe Ser Gly Ser Thr Pro Ala Asp Leu Ala
        755                 760                 765

Ala Glu Glu Gly His Glu Asp Ile Ala Glu Val Leu Gln Lys Ala Ala
    770                 775                 780


<210> SEQ ID NO 19
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 19

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
```

-continued

```
305                 310                 315                 320

Lys Ala Gly Ala Asp Val Asn Ala Lys Asp Lys Ile Gly Val Thr Pro
                325                 330                 335

Leu His Ile Ala Ala Glu Val Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ser Gly His Leu Glu Ile Val Glu Val
    370                 375                 380

Leu Val Lys Ala Gly Ala Asp Val Asn Ala Lys Asp Ile Ala Gly Ala
385                 390                 395                 400

Thr Pro Leu His Ala Ala Ala Leu Phe Gly His Leu Glu Ile Val Glu
                405                 410                 415

Val Leu Leu Lys Val Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Asn Lys Leu Leu Asp Ala Ala Trp Val Gly Gln Asp Asp Glu
                485                 490                 495

Val Arg Ile Leu Leu Ala Ala Gly Ala Asp Val Asn Ala Lys Asp Trp
            500                 505                 510

Gln Gly Glu Thr Pro Leu His Leu Ala Ala Thr Lys Gly His Leu Glu
        515                 520                 525

Ile Val Glu Val Leu Leu Lys Ala Gly Ala Asp Val Asn Ala Lys Asp
    530                 535                 540

Val Val Gly Tyr Thr Pro Leu His Val Ala Ala Ser Gln Gly His Leu
545                 550                 555                 560

Glu Ile Val Glu Val Leu Leu Lys Ala Gly Ala Asp Val Asn Ala Gln
                565                 570                 575

Asp Val His Gly Tyr Thr Pro Ala Asp Leu Ala Ala Gln Ala Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Trp Lys Leu Leu Trp Ala Ala Gln Val Gly
625                 630                 635                 640

Gln Asp Asp Glu Val Arg Ile Leu Leu Ala Ala Gly Ala Asp Val Asn
                645                 650                 655

Ala Lys Asp Asp Leu Gly Trp Thr Pro Leu His Ile Ala Ala Trp Val
            660                 665                 670

Gly His Leu Glu Ile Val Glu Val Leu Leu Lys Ala Gly Ala Asp Val
        675                 680                 685

Asn Ala Lys Asp Phe Thr Gly Arg Thr Pro Leu His His Ala Ala Thr
    690                 695                 700

Glu Gly His Leu Glu Ile Val Lys Val Leu Leu Lys Ala Gly Ala Asp
705                 710                 715                 720

Val Asn Ala Gln Asp Asp Val Gly His Thr Pro Ala Asp Leu Ala Ala
                725                 730                 735
```

```
Leu Trp Gly His Glu Asp Ile Ala Glu Val Leu Gln Lys Ala Ala
            740                 745                 750


<210> SEQ ID NO 20
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 20

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350
```

-continued

```
Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510

Glu Gly Ile Thr Pro Leu His Leu Ala Ala Gln His Gly His Leu Glu
        515                 520                 525

Ile Val Glu Val Leu Leu Lys Ala Gly Ala Asp Val Asn Ala Lys Asp
    530                 535                 540

Val Trp Gly Arg Thr Pro Leu His Leu Ala Ala Trp Gln Gly His Leu
545                 550                 555                 560

Glu Ile Val Glu Val Leu Leu Lys Ala Gly Ala Asp Val Asn Ala Lys
                565                 570                 575

Asp Leu Ala Gly Ala Thr Pro Leu His Val Ala Ala Leu Tyr Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly His Lys Leu Leu Leu Ala Ala Gln Ala
            660                 665                 670

Gly Gln Asp Asp Glu Val Arg Ile Leu Leu Ala Ala Gly Ala Asp Val
        675                 680                 685

Asn Ala Lys Asp Val Phe Gly Gln Thr Pro Leu His Val Ala Ala Val
    690                 695                 700

Ala Gly His Leu Glu Ile Val Glu Val Leu Leu Lys Ala Gly Ala Asp
705                 710                 715                 720

Val Asn Ala Lys Asp Ser Ile Gly Tyr Thr Pro Leu His His Ala Ala
                725                 730                 735

Arg Val Gly His Leu Glu Ile Val Glu Val Leu Leu Lys Ala Gly Ala
            740                 745                 750

Asp Val Asn Ala Gln Asp Trp Ile Gly Ile Thr Pro Ala Asp Leu Ala
        755                 760                 765
```

Ala Phe Glu Gly His Glu Asp Ile Ala Glu Val Leu Gln Lys Ala Ala
    770                 775                 780

<210> SEQ ID NO 21
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 21

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly His Lys Leu
    290                 295                 300

Leu Leu Ala Ala Gln Ala Gly Gln Asp Asp Glu Val Arg Ile Leu Leu
305                 310                 315                 320

Ala Ala Gly Ala Asp Val Asn Ala Lys Asp Val Phe Gly Gln Thr Pro
                325                 330                 335

Leu His Val Ala Ala Val Ala Gly His Leu Glu Ile Val Glu Val Leu
            340                 345                 350

-continued

```
Leu Lys Ala Gly Ala Asp Val Asn Ala Lys Asp Ser Ile Gly Tyr Thr
        355                 360                 365

Pro Leu His His Ala Ala Arg Val Gly His Leu Glu Ile Val Glu Val
    370                 375                 380

Leu Leu Lys Ala Gly Ala Asp Val Asn Ala Gln Asp Trp Ile Gly Ile
385                 390                 395                 400

Thr Pro Ala Asp Leu Ala Ala Phe Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Lys Thr Pro Leu His Val Ala Ala Gln Glu Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Ile Gly His Leu Glu
        515                 520                 525

Ile Val Glu Val Leu Leu Lys Ala Gly Ala Asp Val Asn Ala Lys Asp
    530                 535                 540

Val Ser Gly Ala Thr Pro Leu His Ala Ala Ala Leu His Gly His Leu
545                 550                 555                 560

Glu Ile Val Glu Val Leu Leu Asn Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Ile Thr Pro Leu His Leu Ala Ala Gln His
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Gln Gly His Leu Glu Ile Val Glu Val Leu Leu Lys Ala Gly Ala Asp
705                 710                 715                 720

Val Asn Ala Lys Asp Leu Ala Gly Ala Thr Pro Leu His Val Ala Ala
                725                 730                 735

Leu Tyr Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
```

770 775 780

<210> SEQ ID NO 22
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 22

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

Asn Ala Gln Asp Ile Phe Gly Lys Thr Pro Ala Asp Ile Ala Ala Asp
100 105 110

Ala Gly His Glu Asp Ile Ala Glu Val Leu Gln Lys Ala Ala Gly Ser
115 120 125

Pro Thr Pro Thr Pro Thr Thr Pro Thr Pro Thr Pro Thr Thr Pro Thr
130 135 140

Pro Thr Pro Thr Gly Ser Asp Leu Gly Lys Lys Leu Leu Glu Ala Ala
145 150 155 160

Arg Ala Gly Gln Asp Asp Glu Val Arg Glu Leu Leu Lys Ala Gly Ala
165 170 175

Asp Val Asn Ala Lys Asp Tyr Phe Ser His Thr Pro Leu His Leu Ala
180 185 190

Ala Arg Asn Gly His Leu Lys Ile Val Glu Val Leu Leu Lys Ala Gly
195 200 205

Ala Asp Val Asn Ala Lys Asp Phe Ala Gly Lys Thr Pro Leu His Leu
210 215 220

Ala Ala Asn Glu Gly His Leu Glu Ile Val Glu Val Leu Leu Lys Ala
225 230 235 240

Gly Ala Asp Val Asn Ala Gln Asp Ile Phe Gly Lys Thr Pro Ala Asp
245 250 255

Ile Ala Ala Asp Ala Gly His Glu Asp Ile Ala Glu Val Leu Gln Lys
260 265 270

Ala Ala Gly Ser Pro Thr Pro Thr Pro Thr Thr Pro Thr Pro Thr Pro
275 280 285

Thr Thr Pro Thr Pro Thr Pro Thr Gly Ser Asp Leu Gly Asn Lys Leu
290 295 300

Leu Asp Ala Ala Trp Val Gly Gln Asp Asp Glu Val Arg Ile Leu Leu
305 310 315 320

Ala Ala Gly Ala Asp Val Asn Ala Lys Asp Trp Gln Gly Glu Thr Pro
325 330 335

Leu His Leu Ala Ala Thr Lys Gly His Leu Glu Ile Val Glu Val Leu
340 345 350

Leu Lys Ala Gly Ala Asp Val Asn Ala Lys Asp Val Val Gly Tyr Thr

```
        355                 360                 365

Pro Leu His Val Ala Ala Ser Gln Gly His Leu Glu Ile Val Glu Val
    370                 375                 380

Leu Leu Lys Ala Gly Ala Asp Val Asn Ala Gln Asp Val His Gly Tyr
385                 390                 395                 400

Thr Pro Ala Asp Leu Ala Ala Gln Ala Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Ile Thr Pro Leu His Leu Ala Ala Gln His Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Gln Gly His Leu Glu
        515                 520                 525

Ile Val Glu Val Leu Leu Lys Ala Gly Ala Asp Val Asn Ala Lys Asp
    530                 535                 540

Leu Ala Gly Ala Thr Pro Leu His Val Ala Ala Leu Tyr Gly His Leu
545                 550                 555                 560

Glu Ile Val Glu Val Leu Leu Lys Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly His Lys Leu Leu Leu Ala Ala Gln Ala Gly
625                 630                 635                 640

Gln Asp Asp Glu Val Arg Ile Leu Leu Ala Ala Gly Ala Asp Val Asn
                645                 650                 655

Ala Lys Asp Val Phe Gly Gln Thr Pro Leu His Val Ala Ala Val Ala
            660                 665                 670

Gly His Leu Glu Ile Val Glu Val Leu Leu Lys Ala Gly Ala Asp Val
        675                 680                 685

Asn Ala Lys Asp Ser Ile Gly Tyr Thr Pro Leu His His Ala Ala Arg
    690                 695                 700

Val Gly His Leu Glu Ile Val Glu Val Leu Leu Lys Ala Gly Ala Asp
705                 710                 715                 720

Val Asn Ala Gln Asp Trp Ile Gly Ile Thr Pro Ala Asp Leu Ala Ala
                725                 730                 735

Phe Glu Gly His Glu Asp Ile Ala Glu Val Leu Gln Lys Ala Ala
            740                 745                 750
```

<210> SEQ ID NO 23
<211> LENGTH: 751
<212> TYPE: PRT
<213> ORGANISM: Artificial Sequence -continued
<220> FEATURE:
<223> OTHER INFORMATION: Multi-specific binding protein

<400> SEQUENCE: 23

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly His Lys Leu
    290                 295                 300

Leu Leu Ala Ala Gln Ala Gly Gln Asp Asp Glu Val Arg Ile Leu Leu
305                 310                 315                 320

Ala Ala Gly Ala Asp Val Asn Ala Lys Asp Val Phe Gly Gln Thr Pro
                325                 330                 335

Leu His Val Ala Ala Val Ala Gly His Leu Glu Ile Val Glu Val Leu
            340                 345                 350

Leu Lys Ala Gly Ala Asp Val Asn Ala Lys Asp Ser Ile Gly Tyr Thr
        355                 360                 365

Pro Leu His His Ala Ala Arg Val Gly His Leu Glu Ile Val Glu Val
    370                 375                 380

Leu Leu Lys Ala Gly Ala Asp Val Asn Ala Gln Asp Trp Ile Gly Ile
385                 390                 395                 400
```

```
Thr Pro Ala Asp Leu Ala Ala Phe Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Ile Thr Pro Leu His Leu Ala Ala Gln His Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Gln Gly His Leu Glu
        515                 520                 525

Ile Val Glu Val Leu Leu Lys Ala Gly Ala Asp Val Asn Ala Lys Asp
    530                 535                 540

Leu Ala Gly Ala Thr Pro Leu His Val Ala Ala Leu Tyr Gly His Leu
545                 550                 555                 560

Glu Ile Val Glu Val Leu Leu Lys Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Asn Lys Leu Leu Asp Ala Ala Trp Val Gly
625                 630                 635                 640

Gln Asp Asp Glu Val Arg Ile Leu Leu Ala Ala Gly Ala Asp Val Asn
                645                 650                 655

Ala Lys Asp Trp Gln Gly Glu Thr Pro Leu His Leu Ala Ala Thr Lys
            660                 665                 670

Gly His Leu Glu Ile Val Glu Val Leu Leu Lys Ala Gly Ala Asp Val
        675                 680                 685

Asn Ala Lys Asp Val Val Gly Tyr Thr Pro Leu His Val Ala Ala Ser
    690                 695                 700

Gln Gly His Leu Glu Ile Val Glu Val Leu Leu Lys Ala Gly Ala Asp
705                 710                 715                 720

Val Asn Ala Gln Asp Val His Gly Tyr Thr Pro Ala Asp Leu Ala Ala
                725                 730                 735

Gln Ala Gly His Glu Asp Ile Ala Glu Val Leu Gln Lys Ala Ala
            740                 745                 750


<210> SEQ ID NO 24
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 24

Gly Ser Asp Leu Gly Lys Lys Leu Leu Glu Ala Ala Arg Ala Gly Gln
1               5                   10                  15
```

```
Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430
```

-continued

```
Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510

Phe Gly Gln Thr Pro Leu His Val Ala Ala Val Ala Gly His Leu Glu
        515                 520                 525

Ile Val Glu Val Leu Leu Lys Ala Gly Ala Asp Val Asn Ala Lys Asp
    530                 535                 540

Ser Ile Gly Tyr Thr Pro Leu His His Ala Ala Arg Val Gly His Leu
545                 550                 555                 560

Glu Ile Val Glu Val Leu Leu Lys Ala Gly Ala Asp Val Asn Ala Gln
                565                 570                 575

Asp Trp Ile Gly Ile Thr Pro Ala Asp Leu Ala Ala Phe Glu Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Gln Lys Leu Leu His Ala Ala Gln Tyr Gly
625                 630                 635                 640

Gln Asp Asp Glu Val Arg Ile Leu Leu Ala Ala Gly Ala Asp Val Asn
                645                 650                 655

Ala Lys Asp Lys Gln Gly Asn Thr Pro Leu His Ile Ala Ala Phe His
            660                 665                 670

Gly His Leu Glu Ile Val Glu Val Leu Leu Lys Ala Gly Ala Asp Val
        675                 680                 685

Asn Ala Lys Asp Gln Trp Gly Leu Thr Pro Leu His Leu Ala Ala Ala
    690                 695                 700

Trp Gly His Leu Glu Ile Val Glu Val Leu Leu Lys Ala Gly Ala Asp
705                 710                 715                 720

Val Asn Ala Gln Asp Asn Tyr Gly Gln Thr Pro Ala Asp Leu Ala Ala
                725                 730                 735

Glu Ser Gly His Glu Asp Ile Ala Glu Val Leu Gln Lys Ala Ala
            740                 745                 750


<210> SEQ ID NO 25
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 25

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45
```

```
His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
```

```
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510

Phe Gly Gln Thr Pro Leu His Val Ala Ala Val Ala Gly His Leu Glu
        515                 520                 525

Ile Val Glu Val Leu Leu Lys Ala Gly Ala Asp Val Asn Ala Lys Asp
    530                 535                 540

Ser Ile Gly Tyr Thr Pro Leu His His Ala Ala Arg Val Gly His Leu
545                 550                 555                 560

Glu Ile Val Glu Val Leu Leu Lys Ala Gly Ala Asp Val Asn Ala Gln
                565                 570                 575

Asp Trp Ile Gly Ile Thr Pro Ala Asp Leu Ala Ala Phe Glu Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Glu Thr Gly Phe Thr Pro Leu His Val Ala Ala Glu Lys
            660                 665                 670

Gly His Leu Glu Ile Val Glu Val Leu Leu Lys Ala Gly Ala Asp Val
        675                 680                 685

Asn Ala Lys Asp His Phe Gly Phe Thr Pro Leu His Leu Val Ser Glu
    690                 695                 700

Trp Gly His Leu Glu Ile Val Glu Val Leu Leu Lys Ala Gly Ala Asp
705                 710                 715                 720

Val Asn Ala Lys Asp Ser Tyr Gly Trp Thr Pro Leu His Val Ala Ala
                725                 730                 735

Ile Leu Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780
```

<210> SEQ ID NO 26
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 26

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
```

-continued

```
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Gln Lys Leu
    290                 295                 300

Leu His Ala Ala Gln Tyr Gly Gln Asp Asp Glu Val Arg Ile Leu Leu
305                 310                 315                 320

Ala Ala Gly Ala Asp Val Asn Ala Lys Asp Lys Gln Gly Asn Thr Pro
                325                 330                 335

Leu His Ile Ala Ala Phe His Gly His Leu Glu Ile Val Glu Val Leu
            340                 345                 350

Leu Lys Ala Gly Ala Asp Val Asn Ala Lys Asp Gln Trp Gly Leu Thr
        355                 360                 365

Pro Leu His Leu Ala Ala Ala Trp Gly His Leu Glu Ile Val Glu Val
    370                 375                 380

Leu Leu Lys Ala Gly Ala Asp Val Asn Ala Gln Asp Asn Tyr Gly Gln
385                 390                 395                 400

Thr Pro Ala Asp Leu Ala Ala Glu Ser Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly His Lys Leu Leu Leu Ala Ala Gln Ala Gly Gln Asp Asp Glu Val
    450                 455                 460

Arg Ile Leu Leu Ala Ala Gly Ala Asp Val Asn Ala Lys Asp Val Phe
465                 470                 475                 480
```

```
Gly Gln Thr Pro Leu His Val Ala Ala Val Ala Gly His Leu Glu Ile
                485                 490                 495

Val Glu Val Leu Leu Lys Ala Gly Ala Asp Val Asn Ala Lys Asp Ser
            500                 505                 510

Ile Gly Tyr Thr Pro Leu His His Ala Ala Arg Val Gly His Leu Glu
        515                 520                 525

Ile Val Glu Val Leu Leu Lys Ala Gly Ala Asp Val Asn Ala Gln Asp
    530                 535                 540

Trp Ile Gly Ile Thr Pro Ala Asp Leu Ala Ala Phe Glu Gly His Glu
545                 550                 555                 560

Asp Ile Ala Glu Val Leu Gln Lys Ala Ala Gly Ser Pro Thr Pro Thr
                565                 570                 575

Pro Thr Thr Pro Thr Pro Thr Pro Thr Thr Pro Thr Pro Thr Pro Thr
            580                 585                 590

Gly Ser Asp Leu Gly Lys Lys Leu Leu Gln Ala Ala Arg Ala Gly Gln
        595                 600                 605

Leu Asp Glu Val Arg Glu Leu Leu Lys Ala Gly Ala Asp Val Asn Ala
    610                 615                 620

Lys Asp Arg Glu Gly Ile Thr Pro Leu His Leu Ala Ala Gln His Gly
625                 630                 635                 640

His Leu Glu Ile Val Glu Val Leu Leu Lys Ala Gly Ala Asp Val Asn
                645                 650                 655

Ala Lys Asp Val Trp Gly Arg Thr Pro Leu His Leu Ala Ala Trp Gln
            660                 665                 670

Gly His Leu Glu Ile Val Glu Val Leu Leu Lys Ala Gly Ala Asp Val
        675                 680                 685

Asn Ala Lys Asp Leu Ala Gly Ala Thr Pro Leu His Val Ala Ala Leu
    690                 695                 700

Tyr Gly His Leu Glu Ile Val Glu Val Leu Leu Lys Ala Gly Ala Asp
705                 710                 715                 720

Val Asn Ala Gln Asp Lys Ser Gly Lys Thr Pro Ala Asp Leu Ala Ala
                725                 730                 735

Arg Ala Gly His Gln Asp Ile Ala Glu Val Leu Gln Lys Ala Ala
            740                 745                 750
```

<210> SEQ ID NO 27
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 27

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95
```

-continued

```
Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Glu Thr Gly Phe Thr Pro
                325                 330                 335

Leu His Val Ala Ala Glu Lys Gly His Leu Glu Ile Val Glu Val Leu
            340                 345                 350

Leu Lys Ala Gly Ala Asp Val Asn Ala Lys Asp His Phe Gly Phe Thr
        355                 360                 365

Pro Leu His Leu Val Ser Glu Trp Gly His Leu Glu Ile Val Glu Val
    370                 375                 380

Leu Leu Lys Ala Gly Ala Asp Val Asn Ala Lys Asp Ser Tyr Gly Trp
385                 390                 395                 400

Thr Pro Leu His Val Ala Ala Ile Leu Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510
```

Phe Gly Gln Thr Pro Leu His Val Ala Ala Val Ala Gly His Leu Glu
515 520 525

Ile Val Glu Val Leu Leu Lys Ala Gly Ala Asp Val Asn Ala Lys Asp
530 535 540

Ser Ile Gly Tyr Thr Pro Leu His His Ala Ala Arg Val Gly His Leu
545 550 555 560

Glu Ile Val Glu Val Leu Leu Lys Ala Gly Ala Asp Val Asn Ala Gln
565 570 575

Asp Trp Ile Gly Ile Thr Pro Ala Asp Leu Ala Ala Phe Glu Gly His
580 585 590

Glu Asp Ile Ala Glu Val Leu Gln Lys Ala Ala Gly Ser Pro Thr Pro
595 600 605

Thr Pro Thr Thr Pro Thr Pro Thr Pro Thr Thr Pro Thr Pro Thr Pro
610 615 620

Thr Gly Ser Asp Leu Gly Lys Lys Leu Leu Gln Ala Ala Arg Ala Gly
625 630 635 640

Gln Leu Asp Glu Val Arg Glu Leu Leu Lys Ala Gly Ala Asp Val Asn
645 650 655

Ala Lys Asp Arg Glu Gly Lys Thr Pro Leu His Val Ala Ala Gln Glu
660 665 670

Gly His Leu Glu Ile Val Glu Val Leu Leu Lys Ala Gly Ala Asp Val
675 680 685

Asn Ala Lys Asp Val Trp Gly Arg Thr Pro Leu His Leu Ala Ala Trp
690 695 700

Ile Gly His Leu Glu Ile Val Glu Val Leu Leu Lys Ala Gly Ala Asp
705 710 715 720

Val Asn Ala Lys Asp Val Ser Gly Ala Thr Pro Leu His Ala Ala Ala
725 730 735

Leu His Gly His Leu Glu Ile Val Glu Val Leu Leu Asn Ala Gly Ala
740 745 750

Asp Val Asn Ala Gln Asp Lys Ser Gly Lys Thr Pro Ala Asp Leu Ala
755 760 765

Ala Arg Ala Gly His Gln Asp Ile Ala Glu Val Leu Gln Lys Ala Ala
770 775 780

<210> SEQ ID NO 28
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 28

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

```
Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Gln Glu Gly Ile Thr Pro
                325                 330                 335

Leu His Val Ala Ala His Gln Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Arg Gly His Leu Glu Ile Val Glu Val
    370                 375                 380

Leu Leu Lys Ala Gly Ala Asp Val Asn Ala Lys Asp His Ala Gly Ala
385                 390                 395                 400

Thr Pro Leu His Ala Ala Ala Leu Ser Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Asn Lys Leu Leu Asp Ala Ala Trp Val Gly Gln Asp Asp Glu
                485                 490                 495

Val Arg Ile Leu Leu Ala Ala Gly Ala Asp Val Asn Ala Lys Asp Trp
            500                 505                 510

Gln Gly Glu Thr Pro Leu His Leu Ala Ala Thr Lys Gly His Leu Glu
```

```
        515                 520                 525

Ile Val Glu Val Leu Leu Lys Ala Gly Ala Asp Val Asn Ala Lys Asp
    530                 535                 540

Val Val Gly Tyr Thr Pro Leu His Val Ala Ala Ser Gln Gly His Leu
545                 550                 555                 560

Glu Ile Val Glu Val Leu Leu Lys Ala Gly Ala Asp Val Asn Ala Gln
                565                 570                 575

Asp Val His Gly Tyr Thr Pro Ala Asp Leu Ala Ala Gln Ala Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Lys Thr Pro Leu His Val Ala Ala Gln Glu
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Ile Gly His Leu Glu Ile Val Glu Val Leu Leu Lys Ala Gly Ala Asp
705                 710                 715                 720

Val Asn Ala Lys Asp Val Ser Gly Ala Thr Pro Leu His Ala Ala Ala
                725                 730                 735

Leu His Gly His Leu Glu Ile Val Glu Val Leu Leu Asn Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 29
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 29

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
```

-continued

```
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Asn Lys Leu
    290                 295                 300

Leu Asp Ala Ala Trp Val Gly Gln Asp Asp Glu Val Arg Ile Leu Leu
305                 310                 315                 320

Ala Ala Gly Ala Asp Val Asn Ala Lys Asp Trp Gln Gly Glu Thr Pro
                325                 330                 335

Leu His Leu Ala Ala Thr Lys Gly His Leu Glu Ile Val Glu Val Leu
            340                 345                 350

Leu Lys Ala Gly Ala Asp Val Asn Ala Lys Asp Val Val Gly Tyr Thr
        355                 360                 365

Pro Leu His Val Ala Ala Ser Gln Gly His Leu Glu Ile Val Glu Val
    370                 375                 380

Leu Leu Lys Ala Gly Ala Asp Val Asn Ala Gln Asp Val His Gly Tyr
385                 390                 395                 400

Thr Pro Ala Asp Leu Ala Ala Gln Ala Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Trp Thr Pro Leu His Leu Ala Ala His Gln Gly His Leu Glu Ile
                485                 490                 495

Val Glu Val Leu Leu Lys Ala Gly Ala Asp Val Asn Ala Lys Asp Val
            500                 505                 510

Phe Gly Arg Thr Pro Leu His Leu Ala Ala Trp Val Gly His Leu Glu
        515                 520                 525
```

```
Ile Val Glu Val Leu Leu Lys Ala Gly Ala Asp Val Asn Ala Lys Asp
    530                 535                 540

Val Ser Gly Ala Thr Pro Leu His Pro Ala Ala Ile Tyr Gly His Leu
545                 550                 555                 560

Glu Ile Val Glu Val Leu Leu Lys Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Gln Glu Gly Ile Thr Pro Leu His Val Ala Ala His Gln
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Arg Gly His Leu Glu Ile Val Glu Val Leu Leu Lys Ala Gly Ala Asp
705                 710                 715                 720

Val Asn Ala Lys Asp His Ala Gly Ala Thr Pro Leu His Ala Ala Ala
                725                 730                 735

Leu Ser Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 30
<211> LENGTH: 817
<212> TYPE: PRT
<213> ORGANISM: Artificial Sequence
<220> FEATURE:
<223> OTHER INFORMATION: Multi-specific binding protein

<400> SEQUENCE: 30

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110
```

-continued

```
Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Gln
            500                 505                 510

Glu Gly Ile Thr Pro Leu His Val Ala Ala His Gln Gly His Leu Glu
        515                 520                 525
```

-continued

```
Ile Val Glu Val Leu Leu Lys Ala Gly Ala Asp Val Asn Ala Lys Asp
    530                 535                 540

Val Trp Gly Arg Thr Pro Leu His Leu Ala Ala Trp Arg Gly His Leu
545                 550                 555                 560

Glu Ile Val Glu Val Leu Leu Lys Ala Gly Ala Asp Val Asn Ala Lys
                565                 570                 575

Asp His Ala Gly Ala Thr Pro Leu His Ala Ala Ala Leu Ser Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly Lys Lys Leu Leu Gln Ala Ala Arg Ala
            660                 665                 670

Gly Gln Leu Asp Glu Val Arg Glu Leu Leu Lys Ala Gly Ala Asp Val
        675                 680                 685

Asn Ala Lys Asp Arg Glu Gly Ile Thr Pro Leu His Leu Ala Ala Gln
    690                 695                 700

His Gly His Leu Glu Ile Val Glu Val Leu Leu Lys Ala Gly Ala Asp
705                 710                 715                 720

Val Asn Ala Lys Asp Val Trp Gly Arg Thr Pro Leu His Leu Ala Ala
                725                 730                 735

Trp Gln Gly His Leu Glu Ile Val Glu Val Leu Leu Lys Ala Gly Ala
            740                 745                 750

Asp Val Asn Ala Lys Asp Leu Ala Gly Ala Thr Pro Leu His Val Ala
        755                 760                 765

Ala Leu Tyr Gly His Leu Glu Ile Val Glu Val Leu Leu Lys Ala Gly
    770                 775                 780

Ala Asp Val Asn Ala Gln Asp Lys Ser Gly Lys Thr Pro Ala Asp Leu
785                 790                 795                 800

Ala Ala Arg Ala Gly His Gln Asp Ile Ala Glu Val Leu Gln Lys Ala
                805                 810                 815

Ala


<210> SEQ ID NO 31
<211> LENGTH: 817
<212> TYPE: PRT
<213> ORGANISM: Artificial Sequence
<220> FEATURE:
<223> OTHER INFORMATION: Multi-specific binding protein

<400> SEQUENCE: 31

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
```

```
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495
```

Val Arg Glu Leu Leu Lys Ala Gly Ala Asp Val Asn Ala Lys Asp Arg
500 505 510

Glu Gly Lys Thr Pro Leu His Val Ala Ala Gln Glu Gly His Leu Glu
515 520 525

Ile Val Glu Val Leu Leu Lys Ala Gly Ala Asp Val Asn Ala Lys Asp
530 535 540

Val Trp Gly Arg Thr Pro Leu His Leu Ala Ala Trp Ile Gly His Leu
545 550 555 560

Glu Ile Val Glu Val Leu Leu Lys Ala Gly Ala Asp Val Asn Ala Lys
565 570 575

Asp Val Ser Gly Ala Thr Pro Leu His Ala Ala Ala Leu His Gly His
580 585 590

Leu Glu Ile Val Glu Val Leu Leu Asn Ala Gly Ala Asp Val Asn Ala
595 600 605

Gln Asp Lys Ser Gly Lys Thr Pro Ala Asp Leu Ala Ala Arg Ala Gly
610 615 620

His Gln Asp Ile Ala Glu Val Leu Gln Lys Ala Ala Gly Ser Pro Thr
625 630 635 640

Pro Thr Pro Thr Thr Pro Thr Pro Thr Pro Thr Thr Pro Thr Pro Thr
645 650 655

Pro Thr Gly Ser Asp Leu Gly Lys Lys Leu Leu Gln Ala Ala Arg Ala
660 665 670

Gly Gln Leu Asp Glu Val Arg Glu Leu Leu Lys Ala Gly Ala Asp Val
675 680 685

Asn Ala Lys Asp Gln Glu Gly Ile Thr Pro Leu His Val Ala Ala His
690 695 700

Gln Gly His Leu Glu Ile Val Glu Val Leu Leu Lys Ala Gly Ala Asp
705 710 715 720

Val Asn Ala Lys Asp Val Trp Gly Arg Thr Pro Leu His Leu Ala Ala
725 730 735

Trp Arg Gly His Leu Glu Ile Val Glu Val Leu Leu Lys Ala Gly Ala
740 745 750

Asp Val Asn Ala Lys Asp His Ala Gly Ala Thr Pro Leu His Ala Ala
755 760 765

Ala Leu Ser Gly His Leu Glu Ile Val Glu Val Leu Leu Lys Ala Gly
770 775 780

Ala Asp Val Asn Ala Gln Asp Lys Ser Gly Lys Thr Pro Ala Asp Leu
785 790 795 800

Ala Ala Arg Ala Gly His Gln Asp Ile Ala Glu Val Leu Gln Lys Ala
805 810 815

Ala

<210> SEQ ID NO 32
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 32

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

-continued

```
Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Leu Lys Leu
    290                 295                 300

Leu Thr Ala Ala Lys Gln Gly Gln Asp Asp Glu Val Arg Ile Leu Leu
305                 310                 315                 320

Ala Ala Gly Ala Asp Val Asn Ala Lys Asp Tyr Arg Gly Leu Thr Pro
                325                 330                 335

Leu His Tyr Ala Ala Ala Ile Gly His Leu Glu Ile Val Glu Val Leu
            340                 345                 350

Leu Lys Ala Gly Ala Asp Val Asn Ala Lys Asp Gln Tyr Gly Ala Thr
        355                 360                 365

Pro Leu His Val Ala Ala Tyr Ile Gly His Leu Glu Ile Val Glu Val
    370                 375                 380

Leu Leu Lys Ala Gly Ala Asp Val Asn Ala Gln Asp Phe Ser Gly Ser
385                 390                 395                 400

Thr Pro Ala Asp Leu Ala Ala Glu Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
```

-continued

```
    450                 455                 460

Arg Glu Leu Leu Lys Ala Gly Ala Asp Val Asn Ala Lys Asp Arg Glu
465                 470                 475                 480

Gly Lys Thr Pro Leu His Val Ala Ala Gln Glu Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Ile Gly His Leu Glu
        515                 520                 525

Ile Val Glu Val Leu Leu Lys Ala Gly Ala Asp Val Asn Ala Lys Asp
    530                 535                 540

Val Ser Gly Ala Thr Pro Leu His Ala Ala Ala Leu His Gly His Leu
545                 550                 555                 560

Glu Ile Val Glu Val Leu Leu Asn Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Gln Glu Gly Ile Thr Pro Leu His Val Ala Ala His Gln
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Arg Gly His Leu Glu Ile Val Glu Val Leu Leu Lys Ala Gly Ala Asp
705                 710                 715                 720

Val Asn Ala Lys Asp His Ala Gly Ala Thr Pro Leu His Ala Ala Ala
                725                 730                 735

Leu Ser Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 33
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 33

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
```

-continued

```
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Trp Lys Leu
    290                 295                 300

Leu Trp Ala Ala Gln Val Gly Gln Asp Asp Glu Val Arg Ile Leu Leu
305                 310                 315                 320

Ala Ala Gly Ala Asp Val Asn Ala Lys Asp Asp Leu Gly Trp Thr Pro
                325                 330                 335

Leu His Ile Ala Ala Trp Val Gly His Leu Glu Ile Val Glu Val Leu
            340                 345                 350

Leu Lys Ala Gly Ala Asp Val Asn Ala Lys Asp Phe Thr Gly Arg Thr
        355                 360                 365

Pro Leu His His Ala Ala Thr Glu Gly His Leu Glu Ile Val Lys Val
    370                 375                 380

Leu Leu Lys Ala Gly Ala Asp Val Asn Ala Gln Asp Asp Val Gly His
385                 390                 395                 400

Thr Pro Ala Asp Leu Ala Ala Leu Trp Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460
```

```
Arg Glu Leu Leu Lys Ala Gly Ala Asp Val Asn Ala Lys Asp Gln Glu
465                 470                 475                 480

Gly Ile Thr Pro Leu His Val Ala Ala His Gln Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Arg Gly His Leu Glu
        515                 520                 525

Ile Val Glu Val Leu Leu Lys Ala Gly Ala Asp Val Asn Ala Lys Asp
    530                 535                 540

His Ala Gly Ala Thr Pro Leu His Ala Ala Ala Leu Ser Gly His Leu
545                 550                 555                 560

Glu Ile Val Glu Val Leu Leu Lys Ala Gly Ala Asp Val Asn Ala Gln
                565                 570                 575

Asp Lys Ser Gly Lys Thr Pro Ala Asp Leu Ala Ala Arg Ala Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Ile Thr Pro Leu His Leu Ala Ala Gln His
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Gln Gly His Leu Glu Ile Val Glu Val Leu Leu Lys Ala Gly Ala Asp
705                 710                 715                 720

Val Asn Ala Lys Asp Leu Ala Gly Ala Thr Pro Leu His Val Ala Ala
                725                 730                 735

Leu Tyr Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 34
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 34

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45
```

-continued

```
His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460
```

-continued

Pro Thr Pro Thr Pro Thr Thr Pro Thr Pro Thr Pro Thr Gly Ser Asp
465 470 475 480

Leu Gly Gln Lys Leu Leu His Ala Ala Gln Tyr Gly Gln Asp Asp Glu
485 490 495

Val Arg Ile Leu Leu Ala Ala Gly Ala Asp Val Asn Ala Lys Asp Lys
500 505 510

Gln Gly Asn Thr Pro Leu His Ile Ala Ala Phe His Gly His Leu Glu
515 520 525

Ile Val Glu Val Leu Leu Lys Ala Gly Ala Asp Val Asn Ala Lys Asp
530 535 540

Gln Trp Gly Leu Thr Pro Leu His Leu Ala Ala Ala Trp Gly His Leu
545 550 555 560

Glu Ile Val Glu Val Leu Leu Lys Ala Gly Ala Asp Val Asn Ala Gln
565 570 575

Asp Asn Tyr Gly Gln Thr Pro Ala Asp Leu Ala Ala Glu Ser Gly His
580 585 590

Glu Asp Ile Ala Glu Val Leu Gln Lys Ala Ala Gly Ser Pro Thr Pro
595 600 605

Thr Pro Thr Thr Pro Thr Pro Thr Pro Thr Thr Pro Thr Pro Thr Pro
610 615 620

Thr Gly Ser Asp Leu Gly Lys Lys Leu Leu Gln Ala Ala Arg Ala Gly
625 630 635 640

Gln Leu Asp Glu Val Arg Glu Leu Leu Lys Ala Gly Ala Asp Val Asn
645 650 655

Ala Lys Asp Glu Thr Gly Phe Thr Pro Leu His Val Ala Ala Glu Lys
660 665 670

Gly His Leu Glu Ile Val Glu Val Leu Leu Lys Ala Gly Ala Asp Val
675 680 685

Asn Ala Lys Asp His Phe Gly Phe Thr Pro Leu His Leu Val Ser Glu
690 695 700

Trp Gly His Leu Glu Ile Val Glu Val Leu Leu Lys Ala Gly Ala Asp
705 710 715 720

Val Asn Ala Lys Asp Ser Tyr Gly Trp Thr Pro Leu His Val Ala Ala
725 730 735

Ile Leu Gly His Leu Glu Ile Val Glu Val Leu Leu Lys Ala Gly Ala
740 745 750

Asp Val Asn Ala Gln Asp Lys Ser Gly Lys Thr Pro Ala Asp Leu Ala
755 760 765

Ala Arg Ala Gly His Gln Asp Ile Ala Glu Val Leu Gln Lys Ala Ala
770 775 780

<210> SEQ ID NO 35
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 35

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

```
His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
```

```
465                 470                 475                 480

Leu Gly Gln Lys Leu Leu His Ala Ala Gln Tyr Gly Gln Asp Asp Glu
                485                 490                 495

Val Arg Ile Leu Leu Ala Ala Gly Ala Asp Val Asn Ala Lys Asp Lys
            500                 505                 510

Gln Gly Asn Thr Pro Leu His Ile Ala Ala Phe His Gly His Leu Glu
        515                 520                 525

Ile Val Glu Val Leu Leu Lys Ala Gly Ala Asp Val Asn Ala Lys Asp
    530                 535                 540

Gln Trp Gly Leu Thr Pro Leu His Leu Ala Ala Ala Trp Gly His Leu
545                 550                 555                 560

Glu Ile Val Glu Val Leu Leu Lys Ala Gly Ala Asp Val Asn Ala Gln
                565                 570                 575

Asp Asn Tyr Gly Gln Thr Pro Ala Asp Leu Ala Ala Glu Ser Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Gln Lys Leu Leu His Ala Ala Gln Tyr Gly
625                 630                 635                 640

Gln Asp Asp Glu Val Arg Ile Leu Leu Ala Ala Gly Ala Asp Val Asn
                645                 650                 655

Ala Lys Asp Lys Gln Gly Asn Thr Pro Leu His Ile Ala Ala Phe His
            660                 665                 670

Gly His Leu Glu Ile Val Glu Val Leu Leu Lys Ala Gly Ala Asp Val
        675                 680                 685

Asn Ala Lys Asp Gln Trp Gly Leu Thr Pro Leu His Leu Ala Ala Ala
    690                 695                 700

Trp Gly His Leu Glu Ile Val Glu Val Leu Leu Lys Ala Gly Ala Asp
705                 710                 715                 720

Val Asn Ala Gln Asp Asn Tyr Gly Gln Thr Pro Ala Asp Leu Ala Ala
                725                 730                 735

Glu Ser Gly His Glu Asp Ile Ala Glu Val Leu Gln Lys Ala Ala
            740                 745                 750


<210> SEQ ID NO 36
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 36

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
```

-continued

```
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Gln Glu Gly Ile Thr Pro
                325                 330                 335

Leu His Val Ala Ala His Gln Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Arg Gly His Leu Glu Ile Val Glu Val
    370                 375                 380

Leu Leu Lys Ala Gly Ala Asp Val Asn Ala Lys Asp His Ala Gly Ala
385                 390                 395                 400

Thr Pro Leu His Ala Ala Ala Leu Ser Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Gln Ala Ala Arg Ala Gly Gln Leu Asp Glu
                485                 490                 495

Val Arg Glu Leu Leu Lys Ala Gly Ala Asp Val Asn Ala Lys Asp Arg
            500                 505                 510
```

```
Glu Gly Ile Thr Pro Leu His Leu Ala Ala Gln His Gly His Leu Glu
        515                 520                 525

Ile Val Glu Val Leu Leu Lys Ala Gly Ala Asp Val Asn Ala Lys Asp
    530                 535                 540

Val Trp Gly Arg Thr Pro Leu His Leu Ala Ala Trp Gln Gly His Leu
545                 550                 555                 560

Glu Ile Val Glu Val Leu Leu Lys Ala Gly Ala Asp Val Asn Ala Lys
                565                 570                 575

Asp Leu Ala Gly Ala Thr Pro Leu His Val Ala Ala Leu Tyr Gly His
            580                 585                 590

Leu Glu Ile Val Glu Val Leu Leu Lys Ala Gly Ala Asp Val Asn Ala
        595                 600                 605

Gln Asp Lys Ser Gly Lys Thr Pro Ala Asp Leu Ala Ala Arg Ala Gly
    610                 615                 620

His Gln Asp Ile Ala Glu Val Leu Gln Lys Ala Ala Gly Ser Pro Thr
625                 630                 635                 640

Pro Thr Pro Thr Thr Pro Thr Pro Thr Pro Thr Thr Pro Thr Pro Thr
                645                 650                 655

Pro Thr Gly Ser Asp Leu Gly His Lys Leu Leu Leu Ala Ala Gln Ala
            660                 665                 670

Gly Gln Asp Asp Glu Val Arg Ile Leu Leu Ala Ala Gly Ala Asp Val
        675                 680                 685

Asn Ala Lys Asp Val Phe Gly Gln Thr Pro Leu His Val Ala Ala Val
    690                 695                 700

Ala Gly His Leu Glu Ile Val Glu Val Leu Leu Lys Ala Gly Ala Asp
705                 710                 715                 720

Val Asn Ala Lys Asp Ser Ile Gly Tyr Thr Pro Leu His His Ala Ala
                725                 730                 735

Arg Val Gly His Leu Glu Ile Val Glu Val Leu Leu Lys Ala Gly Ala
            740                 745                 750

Asp Val Asn Ala Gln Asp Trp Ile Gly Ile Thr Pro Ala Asp Leu Ala
        755                 760                 765

Ala Phe Glu Gly His Glu Asp Ile Ala Glu Val Leu Gln Lys Ala Ala
    770                 775                 780
```

<210> SEQ ID NO 37
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 37

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95
```

-continued

```
Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly His Lys Leu
    290                 295                 300

Leu Leu Ala Ala Gln Ala Gly Gln Asp Asp Glu Val Arg Ile Leu Leu
305                 310                 315                 320

Ala Ala Gly Ala Asp Val Asn Ala Lys Asp Val Phe Gly Gln Thr Pro
                325                 330                 335

Leu His Val Ala Ala Val Ala Gly His Leu Glu Ile Val Glu Val Leu
            340                 345                 350

Leu Lys Ala Gly Ala Asp Val Asn Ala Lys Asp Ser Ile Gly Tyr Thr
        355                 360                 365

Pro Leu His His Ala Ala Arg Val Gly His Leu Glu Ile Val Glu Val
    370                 375                 380

Leu Leu Lys Ala Gly Ala Asp Val Asn Ala Gln Asp Trp Ile Gly Ile
385                 390                 395                 400

Thr Pro Ala Asp Leu Ala Ala Phe Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Lys Thr Pro Leu His Val Ala Ala Gln Glu Gly His Leu Glu Ile
                485                 490                 495

Val Glu Val Leu Leu Lys Ala Gly Ala Asp Val Asn Ala Lys Asp Val
            500                 505                 510
```

Trp Gly Arg Thr Pro Leu His Leu Ala Ala Trp Ile Gly His Leu Glu
515 520 525

Ile Val Glu Val Leu Leu Lys Ala Gly Ala Asp Val Asn Ala Lys Asp
530 535 540

Val Ser Gly Ala Thr Pro Leu His Ala Ala Ala Leu His Gly His Leu
545 550 555 560

Glu Ile Val Glu Val Leu Leu Asn Ala Gly Ala Asp Val Asn Ala Gln
565 570 575

Asp Lys Ser Gly Lys Thr Pro Ala Asp Leu Ala Ala Arg Ala Gly His
580 585 590

Gln Asp Ile Ala Glu Val Leu Gln Lys Ala Ala Gly Ser Pro Thr Pro
595 600 605

Thr Pro Thr Thr Pro Thr Pro Thr Pro Thr Thr Pro Thr Pro Thr Pro
610 615 620

Thr Gly Ser Asp Leu Gly Lys Lys Leu Leu Gln Ala Ala Arg Ala Gly
625 630 635 640

Gln Leu Asp Glu Val Arg Glu Leu Leu Lys Ala Gly Ala Asp Val Asn
645 650 655

Ala Lys Asp Gln Glu Gly Ile Thr Pro Leu His Val Ala Ala His Gln
660 665 670

Gly His Leu Glu Ile Val Glu Val Leu Leu Lys Ala Gly Ala Asp Val
675 680 685

Asn Ala Lys Asp Val Trp Gly Arg Thr Pro Leu His Leu Ala Ala Trp
690 695 700

Arg Gly His Leu Glu Ile Val Glu Val Leu Leu Lys Ala Gly Ala Asp
705 710 715 720

Val Asn Ala Lys Asp His Ala Gly Ala Thr Pro Leu His Ala Ala Ala
725 730 735

Leu Ser Gly His Leu Glu Ile Val Glu Val Leu Leu Lys Ala Gly Ala
740 745 750

Asp Val Asn Ala Gln Asp Lys Ser Gly Lys Thr Pro Ala Asp Leu Ala
755 760 765

Ala Arg Ala Gly His Gln Asp Ile Ala Glu Val Leu Gln Lys Ala Ala
770 775 780

<210> SEQ ID NO 38
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 38

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

```
Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly His Lys Leu
    290                 295                 300

Leu Leu Ala Ala Gln Ala Gly Gln Asp Asp Glu Val Arg Ile Leu Leu
305                 310                 315                 320

Ala Ala Gly Ala Asp Val Asn Ala Lys Asp Val Phe Gly Gln Thr Pro
                325                 330                 335

Leu His Val Ala Ala Val Ala Gly His Leu Glu Ile Val Glu Val Leu
            340                 345                 350

Leu Lys Ala Gly Ala Asp Val Asn Ala Lys Asp Ser Ile Gly Tyr Thr
        355                 360                 365

Pro Leu His His Ala Ala Arg Val Gly His Leu Glu Ile Val Glu Val
    370                 375                 380

Leu Leu Lys Ala Gly Ala Asp Val Asn Ala Gln Asp Trp Ile Gly Ile
385                 390                 395                 400

Thr Pro Ala Asp Leu Ala Ala Phe Glu Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly Lys Lys Leu Leu Gln Ala Ala Arg Ala Gly Gln Leu Asp Glu Val
    450                 455                 460

Arg Glu Leu Leu Lys Ala Gly Ala Asp Val Asn Ala Lys Asp Arg Glu
465                 470                 475                 480

Gly Ile Thr Pro Leu His Leu Ala Ala Gln His Gly His Leu Glu Ile
                485                 490                 495

Val Glu Val Leu Leu Lys Ala Gly Ala Asp Val Asn Ala Lys Asp Val
            500                 505                 510

Trp Gly Arg Thr Pro Leu His Leu Ala Ala Trp Gln Gly His Leu Glu
```

515 520 525

Ile Val Glu Val Leu Leu Lys Ala Gly Ala Asp Val Asn Ala Lys Asp
530 535 540

Leu Ala Gly Ala Thr Pro Leu His Val Ala Ala Leu Tyr Gly His Leu
545 550 555 560

Glu Ile Val Glu Val Leu Leu Lys Ala Gly Ala Asp Val Asn Ala Gln
565 570 575

Asp Lys Ser Gly Lys Thr Pro Ala Asp Leu Ala Ala Arg Ala Gly His
580 585 590

Gln Asp Ile Ala Glu Val Leu Gln Lys Ala Ala Gly Ser Pro Thr Pro
595 600 605

Thr Pro Thr Thr Pro Thr Pro Thr Pro Thr Thr Pro Thr Pro Thr Pro
610 615 620

Thr Gly Ser Asp Leu Gly Lys Lys Leu Leu Gln Ala Ala Arg Ala Gly
625 630 635 640

Gln Leu Asp Glu Val Arg Glu Leu Leu Lys Ala Gly Ala Asp Val Asn
645 650 655

Ala Lys Asp Gln Glu Gly Ile Thr Pro Leu His Val Ala Ala His Gln
660 665 670

Gly His Leu Glu Ile Val Glu Val Leu Leu Lys Ala Gly Ala Asp Val
675 680 685

Asn Ala Lys Asp Val Trp Gly Arg Thr Pro Leu His Leu Ala Ala Trp
690 695 700

Arg Gly His Leu Glu Ile Val Glu Val Leu Leu Lys Ala Gly Ala Asp
705 710 715 720

Val Asn Ala Lys Asp His Ala Gly Ala Thr Pro Leu His Ala Ala Ala
725 730 735

Leu Ser Gly His Leu Glu Ile Val Glu Val Leu Leu Lys Ala Gly Ala
740 745 750

Asp Val Asn Ala Gln Asp Lys Ser Gly Lys Thr Pro Ala Asp Leu Ala
755 760 765

Ala Arg Ala Gly His Gln Asp Ile Ala Glu Val Leu Gln Lys Ala Ala
770 775 780

<210> SEQ ID NO 39
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 39

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

Asn Ala Gln Asp Ile Phe Gly Lys Thr Pro Ala Asp Ile Ala Ala Asp

-continued

```
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Gln Glu Gly Ile Thr Pro
                325                 330                 335

Leu His Val Ala Ala His Gln Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Arg Gly His Leu Glu Ile Val Glu Val
    370                 375                 380

Leu Leu Lys Ala Gly Ala Asp Val Asn Ala Lys Asp His Ala Gly Ala
385                 390                 395                 400

Thr Pro Leu His Ala Ala Ala Leu Ser Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510

Phe Gly Gln Thr Pro Leu His Val Ala Ala Val Ala Gly His Leu Glu
        515                 520                 525
```

```
Ile Val Glu Val Leu Leu Lys Ala Gly Ala Asp Val Asn Ala Lys Asp
    530                 535                 540

Ser Ile Gly Tyr Thr Pro Leu His His Ala Ala Arg Val Gly His Leu
545                 550                 555                 560

Glu Ile Val Glu Val Leu Leu Lys Ala Gly Ala Asp Val Asn Ala Gln
                565                 570                 575

Asp Trp Ile Gly Ile Thr Pro Ala Asp Leu Ala Ala Phe Glu Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Gln Lys Leu Leu His Ala Ala Gln Tyr Gly
625                 630                 635                 640

Gln Asp Asp Glu Val Arg Ile Leu Leu Ala Ala Gly Ala Asp Val Asn
                645                 650                 655

Ala Lys Asp Lys Gln Gly Asn Thr Pro Leu His Ile Ala Ala Phe His
            660                 665                 670

Gly His Leu Glu Ile Val Glu Val Leu Leu Lys Ala Gly Ala Asp Val
        675                 680                 685

Asn Ala Lys Asp Gln Trp Gly Leu Thr Pro Leu His Leu Ala Ala Ala
    690                 695                 700

Trp Gly His Leu Glu Ile Val Glu Val Leu Leu Lys Ala Gly Ala Asp
705                 710                 715                 720

Val Asn Ala Gln Asp Asn Tyr Gly Gln Thr Pro Ala Asp Leu Ala Ala
                725                 730                 735

Glu Ser Gly His Glu Asp Ile Ala Glu Val Leu Gln Lys Ala Ala
            740                 745                 750
```

<210> SEQ ID NO 40
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 40

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140
```

-continued

```
Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Ile Thr Pro
                325                 330                 335

Leu His Leu Ala Ala Gln His Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Gln Gly His Leu Glu Ile Val Glu Val
    370                 375                 380

Leu Leu Lys Ala Gly Ala Asp Val Asn Ala Lys Asp Leu Ala Gly Ala
385                 390                 395                 400

Thr Pro Leu His Val Ala Ala Leu Tyr Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510

Phe Gly Gln Thr Pro Leu His Val Ala Ala Val Ala Gly His Leu Glu
        515                 520                 525

Ile Val Glu Val Leu Leu Lys Ala Gly Ala Asp Val Asn Ala Lys Asp
    530                 535                 540

Ser Ile Gly Tyr Thr Pro Leu His His Ala Ala Arg Val Gly His Leu
545                 550                 555                 560
```

-continued

```
Glu Ile Val Glu Val Leu Leu Lys Ala Gly Ala Asp Val Asn Ala Gln
                565                 570                 575

Asp Trp Ile Gly Ile Thr Pro Ala Asp Leu Ala Ala Phe Glu Gly His
            580                 585                 590

Glu Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Glu Thr Gly Phe Thr Pro Leu His Val Ala Ala Glu Lys
            660                 665                 670

Gly His Leu Glu Ile Val Glu Val Leu Leu Lys Ala Gly Ala Asp Val
        675                 680                 685

Asn Ala Lys Asp His Phe Gly Phe Thr Pro Leu His Leu Val Ser Glu
    690                 695                 700

Trp Gly His Leu Glu Ile Val Glu Val Leu Leu Lys Ala Gly Ala Asp
705                 710                 715                 720

Val Asn Ala Lys Asp Ser Tyr Gly Trp Thr Pro Leu His Val Ala Ala
                725                 730                 735

Ile Leu Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780
```

<210> SEQ ID NO 41
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 41

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140
```

-continued

```
Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Gln Lys Leu
    290                 295                 300

Leu His Ala Ala Gln Tyr Gly Gln Asp Asp Glu Val Arg Ile Leu Leu
305                 310                 315                 320

Ala Ala Gly Ala Asp Val Asn Ala Lys Asp Lys Gln Gly Asn Thr Pro
                325                 330                 335

Leu His Ile Ala Ala Phe His Gly His Leu Glu Ile Val Glu Val Leu
            340                 345                 350

Leu Lys Ala Gly Ala Asp Val Asn Ala Lys Asp Gln Trp Gly Leu Thr
        355                 360                 365

Pro Leu His Leu Ala Ala Ala Trp Gly His Leu Glu Ile Val Glu Val
    370                 375                 380

Leu Leu Lys Ala Gly Ala Asp Val Asn Ala Gln Asp Asn Tyr Gly Gln
385                 390                 395                 400

Thr Pro Ala Asp Leu Ala Ala Glu Ser Gly His Glu Asp Ile Ala Glu
                405                 410                 415

Val Leu Gln Lys Ala Ala Gly Ser Pro Thr Pro Thr Pro Thr Thr Pro
            420                 425                 430

Thr Pro Thr Pro Thr Thr Pro Thr Pro Thr Pro Thr Gly Ser Asp Leu
        435                 440                 445

Gly His Lys Leu Leu Leu Ala Ala Gln Ala Gly Gln Asp Asp Glu Val
    450                 455                 460

Arg Ile Leu Leu Ala Ala Gly Ala Asp Val Asn Ala Lys Asp Val Phe
465                 470                 475                 480

Gly Gln Thr Pro Leu His Val Ala Ala Val Ala Gly His Leu Glu Ile
                485                 490                 495

Val Glu Val Leu Leu Lys Ala Gly Ala Asp Val Asn Ala Lys Asp Ser
            500                 505                 510

Ile Gly Tyr Thr Pro Leu His His Ala Ala Arg Val Gly His Leu Glu
        515                 520                 525

Ile Val Glu Val Leu Leu Lys Ala Gly Ala Asp Val Asn Ala Gln Asp
    530                 535                 540

Trp Ile Gly Ile Thr Pro Ala Asp Leu Ala Ala Phe Glu Gly His Glu
545                 550                 555                 560

Asp Ile Ala Glu Val Leu Gln Lys Ala Ala Gly Ser Pro Thr Pro Thr
```

```
                565                 570                 575

Pro Thr Thr Pro Thr Pro Thr Pro Thr Thr Pro Thr Pro Thr Pro Thr
            580                 585                 590

Gly Ser Asp Leu Gly Lys Lys Leu Leu Gln Ala Ala Arg Ala Gly Gln
        595                 600                 605

Leu Asp Glu Val Arg Glu Leu Leu Lys Ala Gly Ala Asp Val Asn Ala
    610                 615                 620

Lys Asp Gln Glu Gly Ile Thr Pro Leu His Val Ala Ala His Gln Gly
625                 630                 635                 640

His Leu Glu Ile Val Glu Val Leu Leu Lys Ala Gly Ala Asp Val Asn
                645                 650                 655

Ala Lys Asp Val Trp Gly Arg Thr Pro Leu His Leu Ala Ala Trp Arg
            660                 665                 670

Gly His Leu Glu Ile Val Glu Val Leu Leu Lys Ala Gly Ala Asp Val
        675                 680                 685

Asn Ala Lys Asp His Ala Gly Ala Thr Pro Leu His Ala Ala Ala Leu
    690                 695                 700

Ser Gly His Leu Glu Ile Val Glu Val Leu Leu Lys Ala Gly Ala Asp
705                 710                 715                 720

Val Asn Ala Gln Asp Lys Ser Gly Lys Thr Pro Ala Asp Leu Ala Ala
                725                 730                 735

Arg Ala Gly His Gln Asp Ile Ala Glu Val Leu Gln Lys Ala Ala
            740                 745                 750


<210> SEQ ID NO 42
<211> LENGTH: 784
<212> TYPE: PRT
<213> ORGANISM: Artificial Sequence
<220> FEATURE:
<223> OTHER INFORMATION: Multi-specific binding protein

<400> SEQUENCE: 42

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
```

-continued

```
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Glu Thr Gly Phe Thr Pro
                325                 330                 335

Leu His Val Ala Ala Glu Lys Gly His Leu Glu Ile Val Glu Val Leu
            340                 345                 350

Leu Lys Ala Gly Ala Asp Val Asn Ala Lys Asp His Phe Gly Phe Thr
        355                 360                 365

Pro Leu His Leu Val Ser Glu Trp Gly His Leu Glu Ile Val Glu Val
    370                 375                 380

Leu Leu Lys Ala Gly Ala Asp Val Asn Ala Lys Asp Ser Tyr Gly Trp
385                 390                 395                 400

Thr Pro Leu His Val Ala Ala Ile Leu Gly His Leu Glu Ile Val Glu
                405                 410                 415

Val Leu Leu Lys Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly His Lys Leu Leu Leu Ala Ala Gln Ala Gly Gln Asp Asp Glu
                485                 490                 495

Val Arg Ile Leu Leu Ala Ala Gly Ala Asp Val Asn Ala Lys Asp Val
            500                 505                 510

Phe Gly Gln Thr Pro Leu His Val Ala Ala Val Ala Gly His Leu Glu
        515                 520                 525

Ile Val Glu Val Leu Leu Lys Ala Gly Ala Asp Val Asn Ala Lys Asp
    530                 535                 540

Ser Ile Gly Tyr Thr Pro Leu His His Ala Ala Arg Val Gly His Leu
545                 550                 555                 560

Glu Ile Val Glu Val Leu Leu Lys Ala Gly Ala Asp Val Asn Ala Gln
                565                 570                 575

Asp Trp Ile Gly Ile Thr Pro Ala Asp Leu Ala Ala Phe Glu Gly His
            580                 585                 590

Glu Asp Ile Ala Glu Val Leu Gln Lys Ala Ala Gly Ser Pro Thr Pro
        595                 600                 605
```

```
Thr Pro Thr Thr Pro Thr Pro Thr Pro Thr Thr Pro Thr Pro Thr Pro
    610                 615                 620

Thr Gly Ser Asp Leu Gly Lys Lys Leu Leu Gln Ala Ala Arg Ala Gly
625                 630                 635                 640

Gln Leu Asp Glu Val Arg Glu Leu Leu Lys Ala Gly Ala Asp Val Asn
                645                 650                 655

Ala Lys Asp Arg Glu Gly Ile Thr Pro Leu His Leu Ala Ala Gln His
            660                 665                 670

Gly His Leu Glu Ile Val Glu Val Leu Leu Lys Ala Gly Ala Asp Val
        675                 680                 685

Asn Ala Lys Asp Val Trp Gly Arg Thr Pro Leu His Leu Ala Ala Trp
    690                 695                 700

Gln Gly His Leu Glu Ile Val Glu Val Leu Leu Lys Ala Gly Ala Asp
705                 710                 715                 720

Val Asn Ala Lys Asp Leu Ala Gly Ala Thr Pro Leu His Val Ala Ala
                725                 730                 735

Leu Tyr Gly His Leu Glu Ile Val Glu Val Leu Leu Lys Ala Gly Ala
            740                 745                 750

Asp Val Asn Ala Gln Asp Lys Ser Gly Lys Thr Pro Ala Asp Leu Ala
        755                 760                 765

Ala Arg Ala Gly His Gln Asp Ile Ala Glu Val Leu Gln Lys Ala Ala
    770                 775                 780


<210> SEQ ID NO 43
<211> LENGTH: 703
<212> TYPE: PRT
<213> ORGANISM: Artificial Sequence
<220> FEATURE:
<223> OTHER INFORMATION: Target domain of spike protein

<400> SEQUENCE: 43

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190
```

-continued

Thr Pro Ile Asn Leu Val Arg Asp Leu Pro Gln Gly Phe Ser Ala Leu
195 200 205

Glu Pro Leu Val Asp Leu Pro Ile Gly Ile Asn Ile Thr Arg Phe Gln
210 215 220

Thr Leu Leu Ala Leu His Arg Ser Tyr Leu Thr Pro Gly Asp Ser Ser
225 230 235 240

Ser Gly Trp Thr Ala Gly Ala Ala Ala Tyr Tyr Val Gly Tyr Leu Gln
245 250 255

Pro Arg Thr Phe Leu Leu Lys Tyr Asn Glu Asn Gly Thr Ile Thr Asp
260 265 270

Ala Val Asp Cys Ala Leu Asp Pro Leu Ser Glu Thr Lys Cys Thr Leu
275 280 285

Lys Ser Phe Thr Val Glu Lys Gly Ile Tyr Gln Thr Ser Asn Phe Arg
290 295 300

Val Gln Pro Thr Glu Ser Ile Val Arg Phe Pro Asn Ile Thr Asn Leu
305 310 315 320

Cys Pro Phe Gly Glu Val Phe Asn Ala Thr Arg Phe Ala Ser Val Tyr
325 330 335

Ala Trp Asn Arg Lys Arg Ile Ser Asn Cys Val Ala Asp Tyr Ser Val
340 345 350

Leu Tyr Asn Ser Ala Ser Phe Ser Thr Phe Lys Cys Tyr Gly Val Ser
355 360 365

Pro Thr Lys Leu Asn Asp Leu Cys Phe Thr Asn Val Tyr Ala Asp Ser
370 375 380

Phe Val Ile Arg Gly Asp Glu Val Arg Gln Ile Ala Pro Gly Gln Thr
385 390 395 400

Gly Lys Ile Ala Asp Tyr Asn Tyr Lys Leu Pro Asp Asp Phe Thr Gly
405 410 415

Cys Val Ile Ala Trp Asn Ser Asn Asn Leu Asp Ser Lys Val Gly Gly
420 425 430

Asn Tyr Asn Tyr Leu Tyr Arg Leu Phe Arg Lys Ser Asn Leu Lys Pro
435 440 445

Phe Glu Arg Asp Ile Ser Thr Glu Ile Tyr Gln Ala Gly Ser Thr Pro
450 455 460

Cys Asn Gly Val Glu Gly Phe Asn Cys Tyr Phe Pro Leu Gln Ser Tyr
465 470 475 480

Gly Phe Gln Pro Thr Asn Gly Val Gly Tyr Gln Pro Tyr Arg Val Val
485 490 495

Val Leu Ser Phe Glu Leu Leu His Ala Pro Ala Thr Val Cys Gly Pro
500 505 510

Lys Lys Ser Thr Asn Leu Val Lys Asn Lys Cys Val Asn Phe Asn Phe
515 520 525

Asn Gly Leu Thr Gly Thr Gly Val Leu Thr Glu Ser Asn Lys Lys Phe
530 535 540

Leu Pro Phe Gln Gln Phe Gly Arg Asp Ile Ala Asp Thr Thr Asp Ala
545 550 555 560

Val Arg Asp Pro Gln Thr Leu Glu Ile Leu Asp Ile Thr Pro Cys Ser
565 570 575

Phe Gly Gly Val Ser Val Ile Thr Pro Gly Thr Asn Thr Ser Asn Gln
580 585 590

Val Ala Val Leu Tyr Gln Asp Val Asn Cys Thr Glu Val Pro Val Ala
595 600 605

```
Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Gly Gly
            660                 665                 670

Gly Ser Gly Gly Gly Ser His His His His His His His His His His
        675                 680                 685

Gly Leu Asn Asp Ile Phe Glu Ala Gln Lys Ile Glu Trp His Glu
    690                 695                 700


<210> SEQ ID NO 44
<211> LENGTH: 1209
<212> TYPE: PRT
<213> ORGANISM: Artificial Sequence
<220> FEATURE:
<223> OTHER INFORMATION: Target domain of spike protein

<400> SEQUENCE: 44

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270
```

-continued

```
Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Ser Val
            660                 665                 670

Ala Ser Gln Ser Ile Ile Ala Tyr Thr Met Ser Leu Gly Ala Glu Asn
        675                 680                 685

Ser Val Ala Tyr Ser Asn Asn Ser Ile Ala Ile Pro Thr Asn Phe Thr
```

```
    690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
        755                 760                 765

Gln Val Lys Gln Ile Tyr Lys Thr Pro Pro Ile Lys Asp Phe Gly Gly
    770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
        835                 840                 845

Leu Leu Thr Asp Glu Met Ile Ala Gln Tyr Thr Ser Ala Leu Leu Ala
    850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
        915                 920                 925

Ala Leu Gly Lys Leu Gln Asp Val Val Asn Gln Asn Ala Gln Ala Leu
    930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
        995                 1000                1005

Leu Ala Ala Thr Lys Met Ser Glu Cys Val Leu Gly Gln Ser Lys Arg
    1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055

Glu Lys Asn Phe Thr Thr Ala Pro Ala Ile Cys His Asp Gly Lys Ala
            1060                1065                1070

His Phe Pro Arg Glu Gly Val Phe Val Ser Asn Gly Thr His Trp Phe
        1075                1080                1085

Val Thr Gln Arg Asn Phe Tyr Glu Pro Gln Ile Ile Thr Thr Asp Asn
    1090                1095                1100

Thr Phe Val Ser Gly Asn Cys Asp Val Val Ile Gly Ile Val Asn Asn
1105                1110                1115                1120
```

```
Thr Val Tyr Asp Pro Leu Gln Pro Glu Leu Asp Ser Phe Lys Glu Glu
                1125                1130                1135

Leu Asp Lys Tyr Phe Lys Asn His Thr Ser Pro Asp Val Asp Leu Gly
            1140                1145                1150

Asp Ile Ser Gly Ile Asn Ala Ser Val Val Asn Ile Gln Lys Glu Ile
        1155                1160                1165

Asp Arg Leu Asn Glu Val Ala Lys Asn Leu Asn Glu Ser Leu Ile Asp
    1170                1175                1180

Leu Gln Glu Leu Gly Lys Tyr Glu Gln Tyr Ile Lys Trp Pro Ala His
1185                1190                1195                1200

His His His His His His His His His
                1205


<210> SEQ ID NO 45
<211> LENGTH: 462
<212> TYPE: PRT
<213> ORGANISM: Artificial Sequence
<220> FEATURE:
<223> OTHER INFORMATION: Target domain of spike protein

<400> SEQUENCE: 45

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Gly
    210                 215                 220

Gly Gly Ser Gly Gly Gly Ser Pro Lys Ser Ser Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 46
<211> LENGTH: 10
<212> TYPE: PRT
<213> ORGANISM: Artificial Sequence
<220> FEATURE:
<223> OTHER INFORMATION: His-tag

<400> SEQUENCE: 46

Met Arg Gly Ser His His His His His His
1               5                   10


<210> SEQ ID NO 47
<211> LENGTH: 126
<212> TYPE: PRT
<213> ORGANISM: Artificial Sequence
<220> FEATURE:
<223> OTHER INFORMATION: Human serum albumin binding domain

<400> SEQUENCE: 47

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
```

```
            100                 105                 110

Ala Gly His Glu Asp Ile Ala Glu Val Leu Gln Lys Ala Ala
        115                 120                 125


<210> SEQ ID NO 48
<211> LENGTH: 126
<212> TYPE: PRT
<213> ORGANISM: Artificial Sequence
<220> FEATURE:
<223> OTHER INFORMATION: Human serum albumin binding domain

<400> SEQUENCE: 48

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Ala Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala
        115                 120                 125


<210> SEQ ID NO 49
<211> LENGTH: 126
<212> TYPE: PRT
<213> ORGANISM: Artificial Sequence
<220> FEATURE:
<223> OTHER INFORMATION: Human serum albumin binding domain

<400> SEQUENCE: 49

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asp Ala
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala
        115                 120                 125


<210> SEQ ID NO 50
<211> LENGTH: 33
<212> TYPE: PRT
<213> ORGANISM: Artificial Sequence
<220> FEATURE:
```

```
<223> OTHER INFORMATION: Consensus sequence
<220> FEATURE:
<221> NAME/KEY: VARIANT
<222> LOCATION: 2,3,5,12,13,14,16,17,18,21,25,26,33
<223> OTHER INFORMATION: x" denotes any amino acid

<400> SEQUENCE: 50

Asp Xaa Xaa Gly Xaa Thr Pro Leu His Leu Ala Xaa Xaa Xaa Gly Xaa
1               5                   10                  15

Xaa Xaa Leu Val Xaa Val Leu Leu Xaa Xaa Gly Ala Asp Val Asn Ala
            20                  25                  30

Xaa


<210> SEQ ID NO 51
<211> LENGTH: 33
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2,3,5,13,14,26,33
<223> OTHER INFORMATION: x" denotes any amino acid
      x" in position 26 is selected from the group consisting of
      asparagine, histidine, or tyrosine

<400> SEQUENCE: 51

Asp Xaa Xaa Gly Xaa Thr Pro Leu His Leu Ala Ala Xaa Xaa Gly His
1               5                   10                  15

Leu Glu Ile Val Glu Val Leu Leu Lys Xaa Gly Ala Asp Val Asn Ala
            20                  25                  30

Xaa


<210> SEQ ID NO 52
<211> LENGTH: 24
<212> TYPE: PRT
<213> ORGANISM: Artificial Sequence
<220> FEATURE:
<223> OTHER INFORMATION: PT-rich linker

<400> SEQUENCE: 52

Gly Ser Pro Thr Pro Thr Pro Thr Thr Pro Thr Pro Thr Pro Thr Thr
1               5                   10                  15

Pro Thr Pro Thr Pro Thr Gly Ser
            20


<210> SEQ ID NO 53
<211> LENGTH: 22
<212> TYPE: PRT
<213> ORGANISM: Artificial Sequence
<220> FEATURE:
<223> OTHER INFORMATION: PT-rich linker

<400> SEQUENCE: 53

Gly Ser Pro Thr Pro Thr Pro Thr Thr Pro Thr Pro Thr Pro Thr Thr
1               5                   10                  15

Pro Thr Pro Thr Pro Thr
            20


<210> SEQ ID NO 54
<211> LENGTH: 5
<212> TYPE: PRT
<213> ORGANISM: Artificial Sequence
<220> FEATURE:
<223> OTHER INFORMATION: Consensus GS linker
```

<220> FEATURE:
<221> NAME/KEY: VARIANT
<222> LOCATION: 1..5
<223> OTHER INFORMATION: [Gly-Gly-Gly-Gly-Ser]n, wherein n is 1, 2, 3,
4, 5, or 6

<400> SEQUENCE: 54

Gly Gly Gly Gly Ser
1 5

<210> SEQ ID NO 55
<211> LENGTH: 32
<212> TYPE: PRT
<213> ORGANISM: Artificial Sequence
<220> FEATURE:
<223> OTHER INFORMATION: N-cap

<400> SEQUENCE: 55

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

<210> SEQ ID NO 56
<211> LENGTH: 32
<212> TYPE: PRT
<213> ORGANISM: Artificial Sequence
<220> FEATURE:
<223> OTHER INFORMATION: N-cap

<400> SEQUENCE: 56

Gly Ser Asp Leu Gly Lys Lys Leu Leu Gln Ala Ala Arg Ala Gly Gln
1 5 10 15

Leu Asp Glu Val Arg Ile Leu Leu Lys Ala Gly Ala Asp Val Asn Ala
20 25 30

<210> SEQ ID NO 57
<211> LENGTH: 32
<212> TYPE: PRT
<213> ORGANISM: Artificial Sequence
<220> FEATURE:
<223> OTHER INFORMATION: N-cap

<400> SEQUENCE: 57

Gly Ser Asp Leu Gly Lys Lys Leu Leu Gln Ala Ala Arg Ala Gly Gln
1 5 10 15

Leu Asp Glu Val Arg Ile Leu Leu Ala Ala Gly Ala Asp Val Asn Ala
20 25 30

<210> SEQ ID NO 58
<211> LENGTH: 28
<212> TYPE: PRT
<213> ORGANISM: Artificial Sequence
<220> FEATURE:
<223> OTHER INFORMATION: C-cap

<400> SEQUENCE: 58

Gln Asp Lys Ser Gly Lys Thr Pro Ala Asp Leu Ala Ala Arg Ala Gly
1 5 10 15

His Gln Asp Ile Ala Glu Val Leu Gln Lys Ala Ala
20 25

<210> SEQ ID NO 59
<211> LENGTH: 977
<212> TYPE: PRT

```
<213> ORGANISM: Artificial Sequence
<220> FEATURE:
<223> OTHER INFORMATION: Target domain of spike protein

<400> SEQUENCE: 59

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
    370                 375                 380

Glu Ala Val Gly Glu Ile Met Ser Leu Ser Ala Ala Thr Pro Lys His
```

-continued

```
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
        435                 440                 445

Gly Glu Ile Pro Lys Asp Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
        515                 520                 525

Asn Ser Thr Glu Ala Gly Gln Lys Leu Phe Asn Met Leu Arg Leu Gly
    530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
        595                 600                 605

Ser Ala Leu Gly Asp Lys Ala Tyr Glu Trp Asn Asp Asn Glu Met Tyr
    610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser Gly Gly Gly Ser Gly Gly Gly Ser Pro Lys Ser Ser Asp
                725                 730                 735

Lys Thr His Thr Cys Pro Pro Cys Pro Ala Pro Glu Leu Leu Gly Gly
            740                 745                 750

Pro Ser Val Phe Leu Phe Pro Pro Lys Pro Lys Asp Thr Leu Met Ile
        755                 760                 765

Ser Arg Thr Pro Glu Val Thr Cys Val Val Val Asp Val Ser His Glu
    770                 775                 780

Asp Pro Glu Val Lys Phe Asn Trp Tyr Val Asp Gly Val Glu Val His
785                 790                 795                 800

Asn Ala Lys Thr Lys Pro Arg Glu Glu Gln Tyr Asn Ser Thr Tyr Arg
                805                 810                 815
```

```
Val Val Ser Val Leu Thr Val Leu His Gln Asp Trp Leu Asn Gly Lys
            820                 825                 830

Glu Tyr Lys Cys Lys Val Ser Asn Lys Ala Leu Pro Ala Pro Ile Glu
        835                 840                 845

Lys Thr Ile Ser Lys Ala Lys Gly Gln Pro Arg Glu Pro Gln Val Tyr
    850                 855                 860

Thr Leu Pro Pro Ser Arg Asp Glu Leu Thr Lys Asn Gln Val Ser Leu
865                 870                 875                 880

Thr Cys Leu Val Lys Gly Phe Tyr Pro Ser Asp Ile Ala Val Glu Trp
                885                 890                 895

Glu Ser Asn Gly Gln Pro Glu Asn Asn Tyr Lys Thr Thr Pro Pro Val
            900                 905                 910

Leu Asp Ser Asp Gly Ser Phe Phe Leu Tyr Ser Lys Leu Thr Val Asp
        915                 920                 925

Lys Ser Arg Trp Gln Gln Gly Asn Val Phe Ser Cys Ser Val Met His
    930                 935                 940

Glu Ala Leu His Asn His Tyr Thr Gln Lys Ser Leu Ser Leu Ser Pro
945                 950                 955                 960

Gly Lys Gly Leu Asn Asp Ile Phe Glu Ala Gln Lys Ile Glu Trp His
                965                 970                 975

Glu


<210> SEQ ID NO 60
<211> LENGTH: 756
<212> TYPE: PRT
<213> ORGANISM: Artificial Sequence
<220> FEATURE:
<223> OTHER INFORMATION: Target domain of spike protein

<400> SEQUENCE: 60

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190
```

-continued

```
Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
    370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
        435                 440                 445

Gly Glu Ile Pro Lys Asp Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
        515                 520                 525

Asn Ser Thr Glu Ala Gly Gln Lys Leu Phe Asn Met Leu Arg Leu Gly
    530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590

Trp Ser Pro Tyr Ala Asp Gln Ser Ile Lys Val Arg Ile Ser Leu Lys
        595                 600                 605

Ser Ala Leu Gly Asp Lys Ala Tyr Glu Trp Asn Asp Asn Glu Met Tyr
```

```
    610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser Gly Gly Gly Ser Gly Gly Gly Ser His His His His His
                725                 730                 735

His His His His His Gly Leu Asn Asp Ile Phe Glu Ala Gln Lys Ile
            740                 745                 750

Glu Trp His Glu
        755


<210> SEQ ID NO 61
<211> LENGTH: 1209
<212> TYPE: PRT
<213> ORGANISM: Artificial Sequence
<220> FEATURE:
<223> OTHER INFORMATION: Target domain of spike protein

<400> SEQUENCE: 61

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
```

-continued

```
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640
```

-continued

```
Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Ser Val
            660                 665                 670

Ala Ser Gln Ser Ile Ile Ala Tyr Thr Met Ser Leu Gly Ala Glu Asn
        675                 680                 685

Ser Val Ala Tyr Ser Asn Asn Ser Ile Ala Ile Pro Thr Asn Phe Thr
    690                 695                 700

Ile Ser Val Thr Thr Glu Ile Leu Pro Val Ser Met Thr Lys Thr Ser
705                 710                 715                 720

Val Asp Cys Thr Met Tyr Ile Cys Gly Asp Ser Thr Glu Cys Ser Asn
                725                 730                 735

Leu Leu Leu Gln Tyr Gly Ser Phe Cys Thr Gln Leu Asn Arg Ala Leu
            740                 745                 750

Thr Gly Ile Ala Val Glu Gln Asp Lys Asn Thr Gln Glu Val Phe Ala
        755                 760                 765

Gln Val Lys Gln Ile Tyr Lys Thr Pro Pro Ile Lys Asp Phe Gly Gly
    770                 775                 780

Phe Asn Phe Ser Gln Ile Leu Pro Asp Pro Ser Lys Pro Ser Lys Arg
785                 790                 795                 800

Ser Phe Ile Glu Asp Leu Leu Phe Asn Lys Val Thr Leu Ala Asp Ala
                805                 810                 815

Gly Phe Ile Lys Gln Tyr Gly Asp Cys Leu Gly Asp Ile Ala Ala Arg
            820                 825                 830

Asp Leu Ile Cys Ala Gln Lys Phe Asn Gly Leu Thr Val Leu Pro Pro
        835                 840                 845

Leu Leu Thr Asp Glu Met Ile Ala Gln Tyr Thr Ser Ala Leu Leu Ala
    850                 855                 860

Gly Thr Ile Thr Ser Gly Trp Thr Phe Gly Ala Gly Ala Ala Leu Gln
865                 870                 875                 880

Ile Pro Phe Ala Met Gln Met Ala Tyr Arg Phe Asn Gly Ile Gly Val
                885                 890                 895

Thr Gln Asn Val Leu Tyr Glu Asn Gln Lys Leu Ile Ala Asn Gln Phe
            900                 905                 910

Asn Ser Ala Ile Gly Lys Ile Gln Asp Ser Leu Ser Ser Thr Ala Ser
        915                 920                 925

Ala Leu Gly Lys Leu Gln Asp Val Val Asn Gln Asn Ala Gln Ala Leu
    930                 935                 940

Asn Thr Leu Val Lys Gln Leu Ser Ser Asn Phe Gly Ala Ile Ser Ser
945                 950                 955                 960

Val Leu Asn Asp Ile Leu Ser Arg Leu Asp Lys Val Glu Ala Glu Val
                965                 970                 975

Gln Ile Asp Arg Leu Ile Thr Gly Arg Leu Gln Ser Leu Gln Thr Tyr
            980                 985                 990

Val Thr Gln Gln Leu Ile Arg Ala Ala Glu Ile Arg Ala Ser Ala Asn
        995                 1000                1005

Leu Ala Ala Thr Lys Met Ser Glu Cys Val Leu Gly Gln Ser Lys Arg
    1010                1015                1020

Val Asp Phe Cys Gly Lys Gly Tyr His Leu Met Ser Phe Pro Gln Ser
1025                1030                1035                1040

Ala Pro His Gly Val Val Phe Leu His Val Thr Tyr Val Pro Ala Gln
                1045                1050                1055
```

-continued

```
Glu Lys Asn Phe Thr Thr Ala Pro Ala Ile Cys His Asp Gly Lys Ala
            1060                1065                1070

His Phe Pro Arg Glu Gly Val Phe Val Ser Asn Gly Thr His Trp Phe
        1075                1080                1085

Val Thr Gln Arg Asn Phe Tyr Glu Pro Gln Ile Ile Thr Thr Asp Asn
    1090                1095                1100

Thr Phe Val Ser Gly Asn Cys Asp Val Val Ile Gly Ile Val Asn Asn
1105                1110                1115                1120

Thr Val Tyr Asp Pro Leu Gln Pro Glu Leu Asp Ser Phe Lys Glu Glu
                1125                1130                1135

Leu Asp Lys Tyr Phe Lys Asn His Thr Ser Pro Asp Val Asp Leu Gly
            1140                1145                1150

Asp Ile Ser Gly Ile Asn Ala Ser Val Val Asn Ile Gln Lys Glu Ile
        1155                1160                1165

Asp Arg Leu Asn Glu Val Ala Lys Asn Leu Asn Glu Ser Leu Ile Asp
    1170                1175                1180

Leu Gln Glu Leu Gly Lys Tyr Glu Gln Tyr Ile Lys Trp Pro Ala His
1185                1190                1195                1200

His His His His His His His His His
                1205


<210> SEQ ID NO 62
<211> LENGTH: 256
<212> TYPE: PRT
<213> ORGANISM: Artificial Sequence
<220> FEATURE:
<223> OTHER INFORMATION: Target domain of spike protein

<400> SEQUENCE: 62

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205
```

```
Pro Lys Lys Ser Thr Asn Leu Val Lys Asn Lys Cys Val Asn Phe Gly
    210                 215                 220

Gly Gly Ser Gly Gly Gly Ser His His His His His His His His His
225                 230                 235                 240

His Gly Leu Asn Asp Ile Phe Glu Ala Gln Lys Ile Glu Trp His Glu
                245                 250                 255


<210> SEQ ID NO 63
<211> LENGTH: 908
<212> TYPE: PRT
<213> ORGANISM: Artificial Sequence
<220> FEATURE:
<223> OTHER INFORMATION: Target domain of spike protein

<400> SEQUENCE: 63

Val Asn Leu Thr Thr Arg Thr Gln Leu Pro Pro Ala Tyr Thr Asn Ser
1               5                   10                  15

Phe Thr Arg Gly Val Tyr Tyr Pro Asp Lys Val Phe Arg Ser Ser Val
            20                  25                  30

Leu His Ser Thr Gln Asp Leu Phe Leu Pro Phe Phe Ser Asn Val Thr
        35                  40                  45

Trp Phe His Ala Ile His Val Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr Tyr His Lys Asn Asn Lys Ser Trp Met Glu Ser Glu Phe Arg Val
    130                 135                 140

Tyr Ser Ser Ala Asn Asn Cys Thr Phe Glu Tyr Val Ser Gln Pro Phe
145                 150                 155                 160

Leu Met Asp Leu Glu Gly Lys Gln Gly Asn Phe Lys Asn Leu Arg Glu
                165                 170                 175

Phe Val Phe Lys Asn Ile Asp Gly Tyr Phe Lys Ile Tyr Ser Lys His
            180                 185                 190

Thr Pro Ile Asn Leu Val Arg Asp Leu Pro Gln Gly Phe Ser Ala Leu
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320
```

-continued

```
Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Ala Asp
            660                 665                 670

Asp Asp Asp Lys Glu Pro Lys Ser Ser Asp Lys Thr His Thr Cys Pro
        675                 680                 685

Pro Cys Pro Ala Pro Glu Leu Leu Gly Gly Pro Ser Val Phe Leu Phe
    690                 695                 700

Pro Pro Lys Pro Lys Asp Thr Leu Met Ile Ser Arg Thr Pro Glu Val
705                 710                 715                 720

Thr Cys Val Val Val Asp Val Ser His Glu Asp Pro Glu Val Lys Phe
                725                 730                 735

Asn Trp Tyr Val Asp Gly Val Glu Val His Asn Ala Lys Thr Lys Pro
```

740 745 750

Arg Glu Glu Gln Tyr Asn Ser Thr Tyr Arg Val Val Ser Val Leu Thr
755 760 765

Val Leu His Gln Asp Trp Leu Asn Gly Lys Glu Tyr Lys Cys Lys Val
770 775 780

Ser Asn Lys Ala Leu Pro Ala Pro Ile Glu Lys Thr Ile Ser Lys Ala
785 790 795 800

Lys Gly Gln Pro Arg Glu Pro Gln Val Tyr Thr Leu Pro Pro Ser Arg
805 810 815

Asp Glu Leu Thr Lys Asn Gln Val Ser Leu Thr Cys Leu Val Lys Gly
820 825 830

Phe Tyr Pro Ser Asp Ile Ala Val Glu Trp Glu Ser Asn Gly Gln Pro
835 840 845

Glu Asn Asn Tyr Lys Thr Thr Pro Pro Val Leu Asp Ser Asp Gly Ser
850 855 860

Phe Phe Leu Tyr Ser Lys Leu Thr Val Asp Lys Ser Arg Trp Gln Gln
865 870 875 880

Gly Asn Val Phe Ser Cys Ser Val Met His Glu Ala Leu His Asn His
885 890 895

Tyr Thr Gln Lys Ser Leu Ser Leu Ser Pro Gly Lys
900 905

<210> SEQ ID NO 64
<211> LENGTH: 681
<212> TYPE: PRT
<213> ORGANISM: Artificial Sequence
<220> FEATURE:
<223> OTHER INFORMATION: Target domain of spike protein

<400> SEQUENCE: 64

Val Asn Leu Thr Thr Arg Thr Gln Leu Pro Pro Ala Tyr Thr Asn Ser
1 5 10 15

Phe Thr Arg Gly Val Tyr Tyr Pro Asp Lys Val Phe Arg Ser Ser Val
20 25 30

Leu His Ser Thr Gln Asp Leu Phe Leu Pro Phe Phe Ser Asn Val Thr
35 40 45

Trp Phe His Ala Ile His Val Ser Gly Thr Asn Gly Thr Lys Arg Phe
50 55 60

Asp Asn Pro Val Leu Pro Phe Asn Asp Gly Val Tyr Phe Ala Ser Thr
65 70 75 80

Glu Lys Ser Asn Ile Ile Arg Gly Trp Ile Phe Gly Thr Thr Leu Asp
85 90 95

Ser Lys Thr Gln Ser Leu Leu Ile Val Asn Asn Ala Thr Asn Val Val
100 105 110

Ile Lys Val Cys Glu Phe Gln Phe Cys Asn Asp Pro Phe Leu Gly Val
115 120 125

Tyr Tyr His Lys Asn Asn Lys Ser Trp Met Glu Ser Glu Phe Arg Val
130 135 140

Tyr Ser Ser Ala Asn Asn Cys Thr Phe Glu Tyr Val Ser Gln Pro Phe
145 150 155 160

Leu Met Asp Leu Glu Gly Lys Gln Gly Asn Phe Lys Asn Leu Arg Glu
165 170 175

Phe Val Phe Lys Asn Ile Asp Gly Tyr Phe Lys Ile Tyr Ser Lys His
180 185 190

Thr Pro Ile Asn Leu Val Arg Asp Leu Pro Gln Gly Phe Ser Ala Leu

-continued

```
        195                 200                 205

Glu Pro Leu Val Asp Leu Pro Ile Gly Ile Asn Ile Thr Arg Phe Gln
    210                 215                 220

Thr Leu Leu Ala Leu His Arg Ser Tyr Leu Thr Pro Gly Asp Ser Ser
225                 230                 235                 240

Ser Gly Trp Thr Ala Gly Ala Ala Ala Tyr Tyr Val Gly Tyr Leu Gln
                245                 250                 255

Pro Arg Thr Phe Leu Leu Lys Tyr Asn Glu Asn Gly Thr Ile Thr Asp
            260                 265                 270

Ala Val Asp Cys Ala Leu Asp Pro Leu Ser Glu Thr Lys Cys Thr Leu
        275                 280                 285

Lys Ser Phe Thr Val Glu Lys Gly Ile Tyr Gln Thr Ser Asn Phe Arg
    290                 295                 300

Val Gln Pro Thr Glu Ser Ile Val Arg Phe Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620
```

```
Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg Ala His
            660                 665                 670

His His His His His His His His His
        675                 680
```

```
<210> SEQ ID NO 65
<211> LENGTH: 730
<212> TYPE: PRT
<213> ORGANISM: Artificial Sequence
<220> FEATURE:
<223> OTHER INFORMATION: Target domain of spike protein

<400> SEQUENCE: 65

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300
```

-continued

```
Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Asp Pro Asp Tyr
            660                 665                 670

Lys Asp Asp Asp Asp Lys Ala Gly Pro Gly Trp Ser His Pro Gln Phe
        675                 680                 685

Glu Lys Gly Gly Gly Ser Gly Gly Gly Ser Gly Gly Gly Ser Trp Ser
    690                 695                 700

His Pro Gln Phe Glu Lys Gly Gly Gly Ser Gly Gly Gly Ser Gly Gly
705                 710                 715                 720
```

```
Gly Ser Trp Ser His Pro Gln Phe Glu Lys
                725                 730


<210> SEQ ID NO 66
<211> LENGTH: 227
<212> TYPE: PRT
<213> ORGANISM: Artificial Sequence
<220> FEATURE:
<223> OTHER INFORMATION: Target domain of spike protein

<400> SEQUENCE: 66

Thr Asn Leu Cys Pro Phe Gly Glu Val Phe Asn Ala Thr Arg Phe Ala
1               5                   10                  15

Ser Val Tyr Ala Trp Asn Arg Lys Arg Ile Ser Asn Cys Val Ala Asp
            20                  25                  30

Tyr Ser Val Leu Tyr Asn Ser Ala Ser Phe Ser Thr Phe Lys Cys Tyr
        35                  40                  45

Gly Val Ser Pro Thr Lys Leu Asn Asp Leu Cys Phe Thr Asn Val Tyr
    50                  55                  60

Ala Asp Ser Phe Val Ile Arg Gly Asp Glu Val Arg Gln Ile Ala Pro
65                  70                  75                  80

Gly Gln Thr Gly Lys Ile Ala Asp Tyr Asn Tyr Lys Leu Pro Asp Asp
                85                  90                  95

Phe Thr Gly Cys Val Ile Ala Trp Asn Ser Asn Asn Leu Asp Ser Lys
            100                 105                 110

Val Gly Gly Asn Tyr Asn Tyr Leu Tyr Arg Leu Phe Arg Lys Ser Asn
        115                 120                 125

Leu Lys Pro Phe Glu Arg Asp Ile Ser Thr Glu Ile Tyr Gln Ala Gly
    130                 135                 140

Ser Thr Pro Cys Asn Gly Val Glu Gly Phe Asn Cys Tyr Phe Pro Leu
145                 150                 155                 160

Gln Ser Tyr Gly Phe Gln Pro Thr Asn Gly Val Gly Tyr Gln Pro Tyr
                165                 170                 175

Arg Val Val Val Leu Ser Phe Glu Leu Leu His Ala Pro Ala Thr Val
            180                 185                 190

Cys Gly Pro Gly Gly Gly Ser Trp Ser His Pro Gln Phe Glu Lys Gly
        195                 200                 205

Gly Gly Ser Gly Gly Gly Ser Gly Gly Gly Ser Trp Ser His Pro Gln
    210                 215                 220

Phe Glu Lys
225


<210> SEQ ID NO 67
<211> LENGTH: 539
<212> TYPE: PRT
<213> ORGANISM: Artificial Sequence
<220> FEATURE:
<223> OTHER INFORMATION: Target domain of spike protein

<400> SEQUENCE: 67

Ser Val Ala Ser Gln Ser Ile Ile Ala Tyr Thr Met Ser Leu Gly Ala
1               5                   10                  15

Glu Asn Ser Val Ala Tyr Ser Asn Asn Ser Ile Ala Ile Pro Thr Asn
            20                  25                  30

Phe Thr Ile Ser Val Thr Thr Glu Ile Leu Pro Val Ser Met Thr Lys
        35                  40                  45

Thr Ser Val Asp Cys Thr Met Tyr Ile Cys Gly Asp Ser Thr Glu Cys
    50                  55                  60
```

-continued

```
Ser Asn Leu Leu Leu Gln Tyr Gly Ser Phe Cys Thr Gln Leu Asn Arg
65                  70                  75                  80

Ala Leu Thr Gly Ile Ala Val Glu Gln Asp Lys Asn Thr Gln Glu Val
                85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
    130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
        195                 200                 205

Leu Gln Ile Pro Phe Ala Met Gln Met Ala Tyr Arg Phe Asn Gly Ile
    210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
        275                 280                 285

Ser Ser Val Leu Asn Asp Ile Leu Ser Arg Leu Asp Lys Val Glu Ala
    290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
        355                 360                 365

Gln Ser Ala Pro His Gly Val Val Phe Leu His Val Thr Tyr Val Pro
    370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
        435                 440                 445

Asn Asn Thr Val Tyr Asp Pro Leu Gln Pro Glu Leu Asp Ser Phe Lys
    450                 455                 460

Glu Glu Leu Asp Lys Tyr Phe Lys Asn His Thr Ser Pro Asp Val Asp
465                 470                 475                 480
```

```
Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
            500                 505                 510

Ile Asp Leu Gln Glu Leu Gly Lys Tyr Glu Gln Tyr Ile Lys Trp Pro
        515                 520                 525

Ala His His His His His His His His His His
    530                 535


<210> SEQ ID NO 68
<211> LENGTH: 521
<212> TYPE: PRT
<213> ORGANISM: Artificial Sequence
<220> FEATURE:
<223> OTHER INFORMATION: Multi-specific binding protein

<400> SEQUENCE: 68

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Arg Glu Gly Ile Thr Pro Leu His Leu Ala Ala Gln His Gly
        35                  40                  45

His Leu Glu Ile Val Glu Val Leu Leu Lys Ala Gly Ala Asp Val Asn
    50                  55                  60

Ala Lys Asp Val Trp Gly Arg Thr Pro Leu His Leu Ala Ala Trp Gln
65                  70                  75                  80

Gly His Leu Glu Ile Val Glu Val Leu Leu Lys Ala Gly Ala Asp Val
                85                  90                  95

Asn Ala Lys Asp Leu Ala Gly Ala Thr Pro Leu His Val Ala Ala Leu
            100                 105                 110

Tyr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala Gly
145                 150                 155                 160

Ser Pro Thr Pro Thr Pro Thr Thr Pro Thr Pro Thr Pro Thr Thr Pro
                165                 170                 175

Thr Pro Thr Pro Thr Gly Ser Asp Leu Gly Lys Lys Leu Leu Gln Ala
            180                 185                 190

Ala Arg Ala Gly Gln Leu Asp Glu Val Arg Glu Leu Leu Lys Ala Gly
        195                 200                 205

Ala Asp Val Asn Ala Lys Asp Arg Glu Gly Lys Thr Pro Leu His Val
    210                 215                 220

Ala Ala Gln Glu Gly His Leu Glu Ile Val Glu Val Leu Leu Lys Ala
225                 230                 235                 240

Gly Ala Asp Val Asn Ala Lys Asp Val Trp Gly Arg Thr Pro Leu His
                245                 250                 255

Leu Ala Ala Trp Ile Gly His Leu Glu Ile Val Glu Val Leu Leu Lys
            260                 265                 270

Ala Gly Ala Asp Val Asn Ala Lys Asp Val Ser Gly Ala Thr Pro Leu
        275                 280                 285

His Ala Ala Ala Leu His Gly His Leu Glu Ile Val Glu Val Leu Leu
    290                 295                 300
```

```
Asn Ala Gly Ala Asp Val Asn Ala Gln Asp Lys Ser Gly Lys Thr Pro
305                 310                 315                 320

Ala Asp Leu Ala Ala Arg Ala Gly His Gln Asp Ile Ala Glu Val Leu
                325                 330                 335

Gln Lys Ala Ala Gly Ser Pro Thr Pro Thr Pro Thr Thr Pro Thr Pro
            340                 345                 350

Thr Pro Thr Thr Pro Thr Pro Thr Pro Thr Gly Ser Asp Leu Gly Lys
        355                 360                 365

Lys Leu Leu Gln Ala Ala Arg Ala Gly Gln Leu Asp Glu Val Arg Glu
    370                 375                 380

Leu Leu Lys Ala Gly Ala Asp Val Asn Ala Lys Asp Gln Glu Gly Ile
385                 390                 395                 400

Thr Pro Leu His Val Ala Ala His Gln Gly His Leu Glu Ile Val Glu
                405                 410                 415

Val Leu Leu Lys Ala Gly Ala Asp Val Asn Ala Lys Asp Val Trp Gly
            420                 425                 430

Arg Thr Pro Leu His Leu Ala Ala Trp Arg Gly His Leu Glu Ile Val
        435                 440                 445

Glu Val Leu Leu Lys Ala Gly Ala Asp Val Asn Ala Lys Asp His Ala
    450                 455                 460

Gly Ala Thr Pro Leu His Ala Ala Ala Leu Ser Gly His Leu Glu Ile
465                 470                 475                 480

Val Glu Val Leu Leu Lys Ala Gly Ala Asp Val Asn Ala Gln Asp Lys
                485                 490                 495

Ser Gly Lys Thr Pro Ala Asp Leu Ala Ala Arg Ala Gly His Gln Asp
            500                 505                 510

Ile Ala Glu Val Leu Gln Lys Ala Ala
        515                 520
```

<210> SEQ ID NO 69
<211> LENGTH: 455
<212> TYPE: PRT
<213> ORGANISM: Artificial Sequence
<220> FEATURE:
<223> OTHER INFORMATION: Multi-specific binding protein

<400> SEQUENCE: 69

```
Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Gln Glu Gly Ile Thr Pro Leu His Val Ala Ala His Gln Gly
        35                  40                  45

His Leu Glu Ile Val Glu Val Leu Leu Lys Ala Gly Ala Asp Val Asn
    50                  55                  60

Ala Lys Asp Val Trp Gly Arg Thr Pro Leu His Leu Ala Ala Trp Arg
65                  70                  75                  80

Gly His Leu Glu Ile Val Glu Val Leu Leu Lys Ala Gly Ala Asp Val
                85                  90                  95

Asn Ala Lys Asp His Ala Gly Ala Thr Pro Leu His Ala Ala Ala Leu
            100                 105                 110

Ser Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140
```

-continued

```
Arg Ala Gly His Gln Asp Ile Ala Glu Val Leu Gln Lys Ala Ala Gly
145                 150                 155                 160

Ser Pro Thr Pro Thr Pro Thr Thr Pro Thr Pro Thr Pro Thr Thr Pro
                165                 170                 175

Thr Pro Thr Pro Thr Gly Ser Asp Leu Gly His Lys Leu Leu Leu Ala
            180                 185                 190

Ala Gln Ala Gly Gln Asp Asp Glu Val Arg Ile Leu Leu Ala Ala Gly
        195                 200                 205

Ala Asp Val Asn Ala Lys Asp Val Phe Gly Gln Thr Pro Leu His Val
    210                 215                 220

Ala Ala Val Ala Gly His Leu Glu Ile Val Glu Val Leu Leu Lys Ala
225                 230                 235                 240

Gly Ala Asp Val Asn Ala Lys Asp Ser Ile Gly Tyr Thr Pro Leu His
                245                 250                 255

His Ala Ala Arg Val Gly His Leu Glu Ile Val Glu Val Leu Leu Lys
            260                 265                 270

Ala Gly Ala Asp Val Asn Ala Gln Asp Trp Ile Gly Ile Thr Pro Ala
        275                 280                 285

Asp Leu Ala Ala Phe Glu Gly His Glu Asp Ile Ala Glu Val Leu Gln
    290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Asp Leu Gly Gln Lys
                325                 330                 335

Leu Leu His Ala Ala Gln Tyr Gly Gln Asp Asp Glu Val Arg Ile Leu
            340                 345                 350

Leu Ala Ala Gly Ala Asp Val Asn Ala Lys Asp Lys Gln Gly Asn Thr
        355                 360                 365

Pro Leu His Ile Ala Ala Phe His Gly His Leu Glu Ile Val Glu Val
    370                 375                 380

Leu Leu Lys Ala Gly Ala Asp Val Asn Ala Lys Asp Gln Trp Gly Leu
385                 390                 395                 400

Thr Pro Leu His Leu Ala Ala Ala Trp Gly His Leu Glu Ile Val Glu
                405                 410                 415

Val Leu Leu Lys Ala Gly Ala Asp Val Asn Ala Gln Asp Asn Tyr Gly
            420                 425                 430

Gln Thr Pro Ala Asp Leu Ala Ala Glu Ser Gly His Glu Asp Ile Ala
        435                 440                 445

Glu Val Leu Gln Lys Ala Ala
    450                 455
```

<210> SEQ ID NO 70
<211> LENGTH: 477
<212> TYPE: DNA
<213> ORGANISM: Artificial Sequence
<220> FEATURE:
<223> OTHER INFORMATION: Nucleic acid encoding spike protein binding domain

<400> SEQUENCE: 70

```
ggcagcgatt tgggtaaaaa gctgctgcag gccgcgagag cgggccagtt ggacgaggtg      60

cgtgagctgt tgaaagcggg tgcagacgtt aatgctaaag accgcgaggg tatcactccg     120

ttgcatctgg cggcacagca cggtcatctt gagatcgtag aagtcttgtt gaaagctggt     180

gctgacgtca atgccaagga tgtttggggt cgtactccac tgcatctcgc ggcgtggcag     240
```

ggtcaccttg agattgtcga ggttttgctg aaagcgggcg ccgacgtcaa tgcgaaagat 300
ctggcaggcg cgacccctct gcatgttgcg gcgctgtacg gtcacctgga aatcgttgaa 360
gtcctcttga aggcgggtgc ggatgtaaac gcgcaggaca agagcggtaa aacgccggcc 420
gatctggcag cacgcgccgg tcaccaagat atcgcagaag tgctgcaaaa ggctgcg 477

<210> SEQ ID NO 71
<211> LENGTH: 477
<212> TYPE: DNA
<213> ORGANISM: Artificial Sequence
<220> FEATURE:
<223> OTHER INFORMATION: Nucleic acid encoding spike protein binding domain

<400> SEQUENCE: 71
ggtagcgacc tgggcaagaa actgctgcaa gccgcacgtg ccggtcagct ggacgaagtg 60
cgtgagttgt tgaaggctgg cgctgacgtg aacgcaaaag accgtgaggg taagacgccg 120
ttacacgtgg cagcgcaaga aggccacctg gagattgttg aagtgctgct caaagctggc 180
gcagacgtca acgctaaaga tgtgtggggt cgcactccgc tgcatctggc cgcgtggatt 240
ggtcatttgg aaattgtgga agttctgctc aaggccggcg ctgatgtcaa cgccaaagat 300
gtgagcggtg cgaccccgct gcacgcagcg gcgctgcacg gtcacttgga aatcgtggag 360
gttctgttga acgccggtgc tgatgttaac gcgcaagata aatcgggtaa gactccggcg 420
gatctggcgg ctcgtgcggg tcaccaggat attgccgaag ttttgcagaa agccgct 477

<210> SEQ ID NO 72
<211> LENGTH: 477
<212> TYPE: DNA
<213> ORGANISM: Artificial Sequence
<220> FEATURE:
<223> OTHER INFORMATION: Nucleic acid encoding spike protein binding domain

<400> SEQUENCE: 72
ggtagcgact tgggtaagaa actgttgcag gcagcgcgcg cgggtcaact ggacgaggtt 60
cgtgagcttt tgaaagccgg tgcggacgtt aacgcgaagg atcaagaagg cattacccca 120
ctgcacgtgg cggcacatca gggtcatctg gagatcgttg aggttctgct gaaggccgga 180
gcggatgtca acgcgaaaga cgtttggggc cgtaccccat tgcacctggc ggcgtggcgc 240
ggtcacctcg aaatcgtcga agtgttactg aaagctgggg cagatgtgaa cgccaaggac 300
cacgcgggtg cgacgccgct gcatgcggca gcgctgagcg gccatctgga aattgtcgaa 360
gtcctgctga aagccggcgc agatgttaat gcccaggata aatccggtaa gaccccggca 420
gacctggcag cgcgtgcggg ccaccaagac attgccgagg ttctgcaaaa agccgcg 477

<210> SEQ ID NO 73
<211> LENGTH: 1563
<212> TYPE: DNA
<213> ORGANISM: Artificial Sequence
<220> FEATURE:
<223> OTHER INFORMATION: Nucleic acid encoding multi-specific binding protein

<400> SEQUENCE: 73
ggcagcgatt tgggtaaaaa gctgctgcag gccgcgagag cgggccagtt ggacgaggtg 60
cgtgagctgt tgaaagcggg tgcagacgtt aatgctaaag accgcgaggg tatcactccg 120
ttgcatctgg cggcacagca cggtcatctt gagatcgtag aagtcttgtt gaaagctggt 180

-continued

```
gctgacgtca atgccaagga tgtttggggt cgtactccac tgcatctcgc ggcgtggcag    240
ggtcaccttg agattgtcga ggttttgctg aaagcgggcg ccgacgtcaa tgcgaaagat    300
ctggcaggcg cgacccctct gcatgttgcg gcgctgtacg gtcacctgga aatcgttgaa    360
gtcctcttga aggcgggtgc ggatgtaaac gcgcaggaca agagcggtaa aacgccggcc    420
gatctggcag cacgcgccgg tcaccaagat atcgcagaag tgctgcaaaa ggctgcgggt    480
agcccaaccc caacgccgac cactcctacc cctaccccaa ccaccccaac tccaactccg    540
actggtagcg acctgggcaa gaaactgctg caagccgcac gtgccggtca gctggacgaa    600
gtgcgtgagt tgttgaaggc tggcgctgac gtgaacgcaa aagaccgtga gggtaagacg    660
ccgttacacg tggcagcgca agaaggccac ctggagattg ttgaagtgct gctcaaagct    720
ggcgcagacg tcaacgctaa agatgtgtgg ggtcgcactc cgctgcatct ggccgcgtgg    780
attggtcatt tggaaattgt ggaagttctg ctcaaggccg gcgctgatgt caacgccaaa    840
gatgtgagcg gtgcgacccc gctgcacgca gcggcgctgc acggtcactt ggaaatcgtg    900
gaggttctgt tgaacgccgg tgctgatgtt aacgcgcaag ataaatcggg taagactccg    960
gcggatctgg cggctcgtgc gggtcaccag gatattgccg aagttttgca gaaagccgct   1020
ggttctccta cgccgacccc gacgacgccg actccaaccc cgaccacgcc gacgcctacc   1080
ccgaccggta gcgacttggg taagaaactg ttgcaggcag cgcgcgcggg tcaactggac   1140
gaggttcgtg agcttttgaa agccggtgcg gacgttaacg cgaaggatca agaaggcatt   1200
accccactgc acgtggcggc acatcagggt catctggaga tcgttgaggt tctgctgaag   1260
gccggagcgg atgtcaacgc gaaagacgtt tggggccgta ccccattgca cctggcggcg   1320
tggcgcggtc acctcgaaat cgtcgaagtg ttactgaaag ctggggcaga tgtgaacgcc   1380
aaggaccacg cgggtgcgac gccgctgcat gcggcagcgc tgagcggcca tctggaaatt   1440
gtcgaagtcc tgctgaaagc cggcgcagat gttaatgccc aggataaatc cggtaagacc   1500
ccggcagacc tggcagcgcg tgcgggccac caagacattg ccgaggttct gcaaaaagcc   1560
gcg                                                                 1563
```

<210> SEQ ID NO 74
<211> LENGTH: 2451
<212> TYPE: DNA
<213> ORGANISM: Artificial Sequence
<220> FEATURE:
<223> OTHER INFORMATION: Nucleic acid encoding multi-specific binding protein

<400> SEQUENCE: 74

```
ggatccgatc tgggcaaaaa gttgctggaa gcggcacgtg caggccagga cgatgaagtt     60
cgcgagctgt taaaagcagg cgcagatgtt aatgcgaagg actatttcag ccacacgccg    120
ttgcatttgg cggcacgtaa cggccacctg aaaatcgtgg aagtgctgtt aaaggctggt    180
gccgatgtga atgccaaaga ttttgcgggt aaaaccccgt tacacttggc ggcgaacgag    240
ggtcatttag agatcgtcga ggtcctgctt aaggctggcg cggacgtaaa tgcgcaagac    300
atcttcggca aaaccccggc tgacattgcg gcggatgcgg gccacgaaga tatcgccgaa    360
gtgttgcaaa aggcagcggg cagcccgacc ccaaccccta cgaccccgac tcctacgcct    420
acgactccga ctccgacccc tacgggtagc gatctgggta agaagctgct ggaagccgca    480
cgcgcaggcc aagacgacga agtccgtgag ctcctgaagg caggcgccga tgtcaatgca    540
aaagactact tttctcatac gccactgcac ctggcagccc gtaacggtca tctgaagatt    600
```

gtagaagtgt tgctgaaggc gggcgcagat gttaatgcaa aggactttgc gggcaagacc 660
ccgttgcacc ttgcggcgaa tgagggtcac ttagagattg tggaggtcct gttgaaggcc 720
ggtgccgacg tgaatgcaca agacattttc ggcaagacgc cggcagacat cgcagcggac 780
gcgggtcacg aggacatcgc tgaagttctg cagaaagctg cgggttcccc gacgccaacg 840
cctaccacgc ctacgccaac tcctaccacc ccgaccccga cgccgaccgg cagcgatttg 900
ggtaaaaagc tgctgcaggc cgcgagagcg ggccagttgg acgaggtgcg tgagctgttg 960
aaagcgggtg cagacgttaa tgctaaagac cgcgagggta tcactccgtt gcatctggcg 1020
gcacagcacg gtcatcttga gatcgtagaa gtcttgttga aagctggtgc tgacgtcaat 1080
gccaaggatg tttggggtcg tactccactg catctcgcgg cgtggcaggg tcaccttgag 1140
attgtcgagg ttttgctgaa agcgggcgcc gacgtcaatg cgaaagatct ggcaggcgcg 1200
acccctctgc atgttgcggc gctgtacggt cacctggaaa tcgttgaagt cctcttgaag 1260
gcgggtgcgg atgtaaacgc gcaggacaag agcggtaaaa cgccggccga tctggcagca 1320
cgcgccggtc accaagatat cgcagaagtg ctgcaaaagg ctgcgggtag cccaacccca 1380
acgccgacca ctcctacccc taccccaacc accccaactc caactccgac tggtagcgac 1440
ctgggcaaga aactgctgca agccgcacgt gccggtcagc tggacgaagt gcgtgagttg 1500
ttgaaggctg gcgctgacgt gaacgcaaaa gaccgtgagg gtaagacgcc gttacacgtg 1560
gcagcgcaag aaggccacct ggagattgtt gaagtgctgc tcaaagctgg cgcagacgtc 1620
aacgctaaag atgtgtgggg tcgcactccg ctgcatctgg ccgcgtggat tggtcatttg 1680
gaaattgtgg aagttctgct caaggccggc gctgatgtca acgccaaaga tgtgagcggt 1740
gcgaccccgc tgcacgcagc ggcgctgcac ggtcacttgg aaatcgtgga ggttctgttg 1800
aacgccggtg ctgatgttaa cgcgcaagat aaatcgggta agactccggc ggatctggcg 1860
gctcgtgcgg gtcaccagga tattgccgaa gttttgcaga aagccgctgg ttctcctacg 1920
ccgaccccga cgacgccgac tccaaccccg accacgccga cgcctacccc gaccggtagc 1980
gacttgggta agaaactgtt gcaggcagcg cgcgcgggtc aactggacga ggttcgtgag 2040
cttttgaaag ccggtgcgga cgttaacgcg aaggatcaag aaggcattac cccactgcac 2100
gtggcggcac atcagggtca tctggagatc gttgaggttc tgctgaaggc cggagcggat 2160
gtcaacgcga aagacgtttg ggccgtaccc ccattgcacc tggcggcgtg gcgcggtcac 2220
ctcgaaatcg tcgaagtgtt actgaaagct ggggcagatg tgaacgccaa ggaccacgcg 2280
ggtgcgacgc cgctgcatgc ggcagcgctg agcggccatc tggaaattgt cgaagtcctg 2340
ctgaaagccg gcgcagatgt taatgcccag gataaatccg gtaagacccc ggcagacctg 2400
gcagcgcgtg cgggccacca agacattgcc gaggttctgc aaaaagccgc g 2451

<210> SEQ ID NO 75
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 75

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly

-continued

```
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460
```

Pro Thr Pro Thr Pro Thr Thr Pro Thr Pro Thr Pro Thr Gly Ser Asp
465 470 475 480

Leu Gly Lys Lys Leu Leu Leu Ala Ala Arg Ala Gly Gln Leu Asp Glu
485 490 495

Val Arg Ile Leu Leu Lys Ala Gly Ala Asp Val Asn Ala Lys Asp Val
500 505 510

Phe Gly Gln Thr Pro Leu His Val Ala Ala Val Ala Gly His Leu Glu
515 520 525

Ile Val Glu Val Leu Leu Lys Ala Gly Ala Asp Val Asn Ala Lys Asp
530 535 540

Ser Ile Gly Tyr Thr Pro Leu His His Ala Ala Arg Val Gly His Leu
545 550 555 560

Glu Ile Val Glu Val Leu Leu Lys Ala Gly Ala Asp Val Asn Ala Lys
565 570 575

Asp Trp Ile Gly Ile Thr Pro Ala Asp Leu Ala Ala Phe Glu Gly His
580 585 590

Gln Asp Ile Ala Glu Val Leu Gln Lys Ala Ala Gly Ser Pro Thr Pro
595 600 605

Thr Pro Thr Thr Pro Thr Pro Thr Pro Thr Thr Pro Thr Pro Thr Pro
610 615 620

Thr Gly Ser Asp Leu Gly Gln Lys Leu Leu His Ala Ala Gln Ala Gly
625 630 635 640

Gln Leu Asp Glu Val Arg Ile Leu Leu Lys Ala Gly Ala Asp Val Asn
645 650 655

Ala Lys Asp Lys Gln Gly Asn Thr Pro Leu His Ile Ala Ala Phe His
660 665 670

Gly His Leu Glu Ile Val Glu Val Leu Leu Lys Ala Gly Ala Asp Val
675 680 685

Asn Ala Lys Asp Gln Trp Gly Leu Thr Pro Leu His Leu Ala Ala Ala
690 695 700

Trp Gly His Leu Glu Ile Val Glu Val Leu Leu Lys Ala Gly Ala Asp
705 710 715 720

Val Asn Ala Gln Asp Asn Tyr Gly Gln Thr Pro Ala Asp Leu Ala Ala
725 730 735

Glu Ser Gly His Gln Asp Ile Ala Glu Val Leu Gln Lys Ala Ala
740 745 750

<210> SEQ ID NO 76
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 76

Gly Ser Asp Leu Gly Lys Lys Leu Leu Leu Ala Ala Arg Ala Gly Gln
1 5 10 15

Leu Asp Glu Val Arg Ile Leu Leu Lys Ala Gly Ala Asp Val Asn Ala
20 25 30

Lys Asp Val Phe Gly Gln Thr Pro Leu His Val Ala Ala Val Ala Gly
35 40 45

His Leu Glu Ile Val Glu Val Leu Leu Lys Ala Gly Ala Asp Val Asn
50 55 60

Ala Lys Asp Ser Ile Gly Tyr Thr Pro Leu His His Ala Ala Arg Val
65 70 75 80

Gly His Leu Glu Ile Val Glu Val Leu Leu Lys Ala Gly Ala Asp Val
85 90 95

Asn Ala Lys Asp Trp Ile Gly Ile Thr Pro Ala Asp Leu Ala Ala Phe
100 105 110

Glu Gly His Gln Asp Ile Ala Glu Val Leu Gln Lys Ala Ala
115 120 125

<210> SEQ ID NO 77
<211> LENGTH: 126
<212> TYPE: PRT
<213> ORGANISM: Artificial Sequence
<220> FEATURE:
<223> OTHER INFORMATION: Spike protein binding domain

<400> SEQUENCE: 77

Gly Ser Asp Leu Gly Gln Lys Leu Leu His Ala Ala Gln Ala Gly Gln
1 5 10 15

Leu Asp Glu Val Arg Ile Leu Leu Lys Ala Gly Ala Asp Val Asn Ala
20 25 30

Lys Asp Lys Gln Gly Asn Thr Pro Leu His Ile Ala Ala Phe His Gly
35 40 45

His Leu Glu Ile Val Glu Val Leu Leu Lys Ala Gly Ala Asp Val Asn
50 55 60

Ala Lys Asp Gln Trp Gly Leu Thr Pro Leu His Leu Ala Ala Ala Trp
65 70 75 80

Gly His Leu Glu Ile Val Glu Val Leu Leu Lys Ala Gly Ala Asp Val
85 90 95

Asn Ala Gln Asp Asn Tyr Gly Gln Thr Pro Ala Asp Leu Ala Ala Glu
100 105 110

Ser Gly His Gln Asp Ile Ala Glu Val Leu Gln Lys Ala Ala
115 120 125

<210> SEQ ID NO 78
<211> LENGTH: 2253
<212> TYPE: PRT
<213> ORGANISM: Artificial Sequence
<220> FEATURE:
<223> OTHER INFORMATION: Nucleic acid encoding multi-specific binding protein

<400> SEQUENCE: 78

Gly Gly Ala Thr Cys Cys Gly Ala Cys Cys Thr Gly Gly Gly Thr Ala
1 5 10 15

Ala Ala Ala Ala Gly Cys Thr Gly Cys Thr Gly Gly Ala Gly Gly Cys
20 25 30

Ala Gly Cys Gly Cys Gly Thr Gly Cys Cys Gly Gly Thr Cys Ala Ala
35 40 45

Gly Ala Cys Gly Ala Cys Gly Ala Gly Gly Thr Thr Cys Gly Cys Gly
50 55 60

Ala Ala Thr Thr Gly Cys Thr Thr Ala Ala Ala Gly Cys Gly Gly Gly
65 70 75 80

Thr Gly Cys Ala Gly Ala Cys Gly Thr Cys Ala Ala Cys Gly Cys Cys
85 90 95

Ala Ala Ala Gly Ala Thr Thr Ala Thr Thr Thr Cys Thr Cys Thr Cys
100 105 110

Ala Thr Ala Cys Cys Cys Cys Gly Thr Thr Gly Cys Ala Thr Thr Thr
115 120 125

```
Ala Gly Cys Cys Gly Cys Gly Cys Gly Thr Ala Ala Thr Gly Gly Cys
    130                 135                 140

Cys Ala Thr Cys Thr Gly Ala Ala Gly Ala Thr Cys Gly Thr Cys Gly
145                 150                 155                 160

Ala Gly Gly Thr Cys Cys Thr Cys Thr Thr Gly Ala Ala Gly Gly Cys
                165                 170                 175

Ala Gly Gly Cys Gly Cys Gly Gly Ala Thr Gly Thr Cys Ala Ala Thr
            180                 185                 190

Gly Cys Gly Ala Ala Gly Gly Ala Thr Thr Thr Thr Gly Cys Gly Gly
        195                 200                 205

Gly Cys Ala Ala Ala Ala Cys Gly Cys Cys Gly Cys Thr Gly Cys Ala
    210                 215                 220

Cys Thr Thr Ala Gly Cys Gly Gly Cys Gly Ala Ala Cys Gly Ala Gly
225                 230                 235                 240

Gly Gly Thr Cys Ala Thr Thr Thr Ala Gly Ala Ala Ala Thr Cys Gly
                245                 250                 255

Thr Thr Gly Ala Ala Gly Thr Cys Cys Thr Gly Thr Thr Ala Ala Ala
            260                 265                 270

Ala Gly Cys Gly Gly Gly Cys Gly Cys Cys Gly Ala Thr Gly Thr Gly
        275                 280                 285

Ala Ala Thr Gly Cys Gly Cys Ala Gly Gly Ala Thr Ala Thr Thr Thr
    290                 295                 300

Thr Cys Gly Gly Thr Ala Ala Ala Ala Cys Gly Cys Cys Gly Gly Cys
305                 310                 315                 320

Gly Gly Ala Cys Ala Thr Thr Gly Cys Gly Gly Cys Ala Gly Ala Thr
                325                 330                 335

Gly Cys Gly Gly Gly Thr Cys Ala Thr Gly Ala Ala Gly Ala Thr Ala
            340                 345                 350

Thr Cys Gly Cys Ala Gly Ala Ala Gly Thr Cys Cys Thr Gly Cys Ala
        355                 360                 365

Gly Ala Ala Gly Gly Cys Ala Gly Cys Ala Gly Gly Cys Ala Gly Cys
    370                 375                 380

Cys Cys Thr Ala Cys Ala Cys Cys Thr Ala Cys Gly Cys Cys Gly Ala
385                 390                 395                 400

Cys Thr Ala Cys Gly Cys Cys Thr Ala Cys Gly Cys Cys Gly Ala Cys
                405                 410                 415

Thr Cys Cys Gly Ala Cys Thr Ala Cys Cys Cys Cys Gly Ala Cys Thr
            420                 425                 430

Cys Cys Gly Ala Cys Cys Cys Cys Gly Ala Cys Cys Gly Gly Ala Thr
        435                 440                 445

Cys Ala Gly Ala Cys Cys Thr Gly Gly Gly Thr Ala Ala Ala Ala Ala
    450                 455                 460

Gly Cys Thr Gly Cys Thr Gly Gly Ala Gly Gly Cys Ala Gly Cys Gly
465                 470                 475                 480

Cys Gly Thr Gly Cys Cys Gly Gly Thr Cys Ala Ala Gly Ala Cys Gly
                485                 490                 495

Ala Cys Gly Ala Gly Gly Thr Thr Cys Gly Cys Gly Ala Ala Thr Thr
            500                 505                 510

Gly Cys Thr Thr Ala Ala Ala Gly Cys Gly Gly Gly Thr Gly Cys Ala
        515                 520                 525

Gly Ala Cys Gly Thr Cys Ala Ala Cys Gly Cys Cys Ala Ala Ala Gly
    530                 535                 540

Ala Thr Thr Ala Thr Thr Thr Cys Thr Cys Thr Cys Ala Thr Ala Cys
```

545 550 555 560

Cys Cys Cys Gly Thr Thr Gly Cys Ala Thr Thr Thr Ala Gly Cys Cys
565 570 575

Gly Cys Gly Cys Gly Thr Ala Ala Thr Gly Gly Cys Cys Ala Thr Cys
580 585 590

Thr Gly Ala Ala Gly Ala Thr Cys Gly Thr Cys Gly Ala Gly Gly Thr
595 600 605

Cys Cys Thr Cys Thr Thr Gly Ala Ala Gly Gly Cys Ala Gly Gly Cys
610 615 620

Gly Cys Gly Gly Ala Thr Gly Thr Cys Ala Ala Thr Gly Cys Gly Ala
625 630 635 640

Ala Gly Gly Ala Thr Thr Thr Thr Gly Cys Gly Gly Gly Cys Ala Ala
645 650 655

Ala Ala Cys Gly Cys Cys Gly Cys Thr Gly Cys Ala Cys Thr Thr Ala
660 665 670

Gly Cys Gly Gly Cys Gly Ala Ala Cys Gly Ala Gly Gly Gly Thr Cys
675 680 685

Ala Thr Thr Thr Ala Gly Ala Ala Ala Thr Cys Gly Thr Thr Gly Ala
690 695 700

Ala Gly Thr Cys Cys Thr Gly Thr Thr Ala Ala Ala Ala Gly Cys Gly
705 710 715 720

Gly Gly Cys Gly Cys Cys Gly Ala Thr Gly Thr Gly Ala Ala Thr Gly
725 730 735

Cys Gly Cys Ala Gly Gly Ala Thr Ala Thr Thr Thr Thr Cys Gly Gly
740 745 750

Thr Ala Ala Ala Ala Cys Gly Cys Cys Gly Gly Cys Gly Gly Ala Cys
755 760 765

Ala Thr Thr Gly Cys Gly Gly Cys Ala Gly Ala Thr Gly Cys Gly Gly
770 775 780

Gly Thr Cys Ala Thr Gly Ala Ala Gly Ala Thr Ala Thr Cys Gly Cys
785 790 795 800

Ala Gly Ala Ala Gly Thr Cys Cys Thr Gly Cys Ala Gly Ala Ala Gly
805 810 815

Gly Cys Ala Gly Cys Ala Gly Gly Thr Thr Cys Cys Cys Cys Gly Ala
820 825 830

Cys Cys Cys Cys Thr Ala Cys Gly Cys Cys Ala Ala Cys Gly Ala Cys
835 840 845

Thr Cys Cys Gly Ala Cys Cys Cys Cys Ala Ala Cys Thr Cys Cys Ala
850 855 860

Ala Cys Gly Ala Cys Cys Cys Cys Thr Ala Cys Cys Cys Cys Gly Ala
865 870 875 880

Cys Cys Cys Cys Gly Ala Cys Cys Gly Gly Ala Thr Cys Ala Gly Ala
885 890 895

Cys Cys Thr Gly Gly Gly Thr Ala Ala Ala Ala Ala Ala Cys Thr Gly
900 905 910

Cys Thr Gly Cys Ala Ala Gly Cys Ala Gly Cys Ala Cys Gly Thr Gly
915 920 925

Cys Ala Gly Gly Thr Cys Ala Gly Cys Thr Gly Gly Ala Thr Gly Ala
930 935 940

Ala Gly Thr Thr Cys Gly Thr Gly Ala Ala Cys Thr Gly Cys Thr Gly
945 950 955 960

Ala Ala Ala Gly Cys Ala Gly Gly Cys Gly Cys Cys Gly Ala Thr Gly
965 970 975

```
Thr Thr Ala Ala Thr Gly Cys Ala Ala Ala Ala Gly Ala Thr Ala Gly
            980                 985                 990

Ala Gly Ala Gly Gly Gly Cys Ala Ala Gly Ala Cys Cys Cys Cys Gly
        995                 1000                1005

Cys Thr Gly Cys Ala Thr Gly Thr Gly Gly Cys Thr Gly Cys Thr Cys
    1010                1015                1020

Ala Ala Gly Ala Gly Gly Gly Thr Cys Ala Cys Cys Thr Gly Gly Ala
1025                1030                1035                1040

Ala Ala Thr Thr Gly Thr Thr Gly Ala Ala Gly Thr Thr Cys Thr Gly
                1045                1050                1055

Cys Thr Gly Ala Ala Ala Gly Cys Cys Gly Gly Thr Gly Cys Ala Gly
            1060                1065                1070

Ala Thr Gly Thr Thr Ala Ala Thr Gly Cys Ala Ala Ala Ala Gly Ala
        1075                1080                1085

Thr Gly Thr Gly Thr Gly Gly Gly Gly Cys Ala Gly Ala Ala Cys Cys
    1090                1095                1100

Cys Cys Gly Cys Thr Gly Cys Ala Thr Cys Thr Gly Gly Cys Thr Gly
1105                1110                1115                1120

Cys Thr Thr Gly Gly Ala Thr Cys Gly Gly Thr Cys Ala Cys Cys Thr
                1125                1130                1135

Gly Gly Ala Ala Ala Thr Thr Gly Thr Thr Gly Ala Ala Gly Thr Thr
            1140                1145                1150

Cys Thr Gly Cys Thr Gly Ala Ala Ala Gly Cys Cys Gly Gly Thr Gly
        1155                1160                1165

Cys Ala Gly Ala Thr Gly Thr Thr Ala Ala Thr Gly Cys Ala Ala Ala
    1170                1175                1180

Ala Gly Ala Thr Gly Thr Gly Thr Cys Thr Gly Gly Cys Gly Cys Thr
1185                1190                1195                1200

Ala Cys Cys Cys Cys Gly Cys Thr Gly Cys Ala Thr Gly Cys Gly Gly
                1205                1210                1215

Cys Thr Gly Cys Thr Cys Thr Gly Cys Ala Cys Gly Gly Thr Cys Ala
            1220                1225                1230

Cys Cys Thr Gly Gly Ala Ala Ala Thr Thr Gly Thr Thr Gly Ala Ala
        1235                1240                1245

Gly Thr Thr Cys Thr Gly Cys Thr Gly Ala Ala Cys Gly Cys Cys Gly
    1250                1255                1260

Gly Thr Gly Cys Ala Gly Ala Thr Gly Thr Thr Ala Ala Cys Gly Cys
1265                1270                1275                1280

Ala Cys Ala Gly Gly Ala Thr Ala Ala Ala Ala Gly Cys Gly Gly Thr
                1285                1290                1295

Ala Ala Ala Ala Cys Cys Cys Cys Thr Gly Cys Cys Gly Ala Thr Cys
            1300                1305                1310

Thr Gly Gly Cys Ala Gly Cys Thr Cys Gly Cys Gly Cys Cys Gly Gly
        1315                1320                1325

Thr Cys Ala Thr Cys Ala Gly Gly Ala Thr Ala Thr Thr Gly Cys Thr
    1330                1335                1340

Gly Ala Ala Gly Thr Gly Cys Thr Gly Cys Ala Gly Ala Ala Gly Gly
1345                1350                1355                1360

Cys Ala Gly Cys Ala Gly Gly Cys Ala Gly Cys Cys Cys Cys Ala Cys
                1365                1370                1375

Gly Cys Cys Ala Ala Cys Thr Cys Cys Thr Ala Cys Ala Ala Cys Cys
            1380                1385                1390
```

-continued

```
Cys Cys Cys Ala Cys Ala Cys Cys Thr Ala Cys Ala Cys Cys Gly Ala
        1395                1400                1405

Cys Gly Ala Cys Gly Cys Cys Gly Ala Cys Ala Cys Cys Gly Ala Cys
    1410                1415                1420

Thr Cys Cys Ala Ala Cys Cys Gly Gly Ala Thr Cys Ala Gly Ala Cys
1425                1430                1435                1440

Cys Thr Gly Gly Gly Thr Ala Ala Ala Ala Ala Ala Thr Thr Gly Thr
                1445                1450                1455

Thr Ala Thr Thr Gly Gly Cys Cys Gly Cys Thr Cys Gly Cys Gly Cys
            1460                1465                1470

Gly Gly Gly Cys Cys Ala Gly Cys Thr Gly Gly Ala Cys Gly Ala Gly
        1475                1480                1485

Gly Thr Ala Cys Gly Thr Ala Thr Cys Thr Thr Ala Thr Thr Gly Ala
    1490                1495                1500

Ala Gly Gly Cys Thr Gly Gly Gly Gly Cys Ala Gly Ala Cys Gly Thr
1505                1510                1515                1520

Cys Ala Ala Thr Gly Cys Gly Ala Ala Gly Gly Ala Cys Gly Thr Thr
                1525                1530                1535

Thr Thr Thr Gly Gly Ala Cys Ala Gly Ala Cys Thr Cys Cys Thr Cys
            1540                1545                1550

Thr Thr Cys Ala Thr Gly Thr Gly Gly Cys Cys Gly Cys Cys Gly Thr
        1555                1560                1565

Gly Gly Cys Cys Gly Gly Thr Cys Ala Thr Cys Thr Gly Gly Ala Gly
    1570                1575                1580

Ala Thr Thr Gly Thr Cys Gly Ala Ala Gly Thr Ala Thr Thr Ala Thr
1585                1590                1595                1600

Thr Ala Ala Ala Gly Gly Cys Thr Gly Gly Thr Gly Cys Ala Gly Ala
                1605                1610                1615

Thr Gly Thr Ala Ala Ala Thr Gly Cys Thr Ala Ala Ala Gly Ala Thr
            1620                1625                1630

Thr Cys Thr Ala Thr Cys Gly Gly Ala Thr Ala Cys Ala Cys Ala Cys
        1635                1640                1645

Cys Gly Thr Thr Gly Cys Ala Thr Cys Ala Thr Gly Cys Ala Gly Cys
    1650                1655                1660

Thr Cys Gly Cys Gly Thr Thr Gly Gly Ala Cys Ala Thr Thr Thr Ala
1665                1670                1675                1680

Gly Ala Gly Ala Thr Cys Gly Thr Cys Gly Ala Gly Gly Thr Cys Thr
                1685                1690                1695

Thr Gly Cys Thr Gly Ala Ala Ala Gly Cys Ala Gly Gly Thr Gly Cys
            1700                1705                1710

Cys Gly Ala Cys Gly Thr Thr Ala Ala Thr Gly Cys Cys Ala Ala Gly
        1715                1720                1725

Gly Ala Thr Thr Gly Gly Ala Thr Cys Gly Gly Gly Ala Thr Cys Ala
    1730                1735                1740

Cys Cys Cys Cys Ala Gly Cys Gly Gly Ala Thr Cys Thr Thr Gly Cys
1745                1750                1755                1760

Ala Gly Cys Ala Thr Thr Thr Gly Ala Gly Gly Gly Thr Cys Ala Cys
                1765                1770                1775

Cys Ala Gly Gly Ala Thr Ala Thr Thr Gly Cys Thr Gly Ala Ala Gly
            1780                1785                1790

Thr Thr Cys Thr Gly Cys Ala Gly Ala Ala Gly Gly Cys Ala Gly Cys
        1795                1800                1805

Ala Gly Gly Thr Thr Cys Gly Cys Cys Gly Ala Cys Cys Cys Cys Ala
```

```
    1810                1815                1820

Ala Cys Cys Cys Cys Thr Ala Cys Cys Ala Cys Thr Cys Cys Ala Ala
1825                1830                1835                1840

Cys Gly Cys Cys Gly Ala Cys Gly Cys Cys Thr Ala Cys Cys Ala Cys
                1845                1850                1855

Thr Cys Cys Ala Ala Cys Ala Cys Cys Ala Ala Cys Ala Cys Cys Ala
            1860                1865                1870

Ala Cys Gly Gly Gly Ala Thr Cys Ala Gly Ala Cys Cys Thr Gly Gly
        1875                1880                1885

Gly Thr Cys Ala Ala Ala Ala Gly Thr Thr Gly Thr Thr Ala Cys Ala
    1890                1895                1900

Cys Gly Cys Gly Gly Cys Thr Cys Ala Ala Gly Cys Gly Gly Gly Ala
1905                1910                1915                1920

Cys Ala Ala Thr Thr Ala Gly Ala Cys Gly Ala Gly Gly Thr Cys Cys
                1925                1930                1935

Gly Thr Ala Thr Thr Cys Thr Gly Cys Thr Thr Ala Ala Ala Gly Cys
            1940                1945                1950

Cys Gly Gly Gly Gly Cys Thr Gly Ala Thr Gly Thr Ala Ala Ala Thr
        1955                1960                1965

Gly Cys Ala Ala Ala Ala Gly Ala Cys Ala Ala Ala Cys Ala Gly Gly
    1970                1975                1980

Gly Cys Ala Ala Cys Ala Cys Ala Cys Cys Cys Thr Thr Ala Cys Ala
1985                1990                1995                2000

Thr Ala Thr Cys Gly Cys Gly Gly Cys Ala Thr Thr Cys Cys Ala Thr
                2005                2010                2015

Gly Gly Ala Cys Ala Thr Cys Thr Gly Gly Ala Gly Ala Thr Thr Gly
            2020                2025                2030

Thr Gly Gly Ala Ala Gly Thr Ala Cys Thr Gly Cys Thr Gly Ala Ala
        2035                2040                2045

Ala Gly Cys Cys Gly Gly Gly Gly Cys Ala Gly Ala Thr Gly Thr Cys
    2050                2055                2060

Ala Ala Cys Gly Cys Thr Ala Ala Ala Gly Ala Cys Cys Ala Ala Thr
2065                2070                2075                2080

Gly Gly Gly Gly Ala Thr Thr Gly Ala Cys Cys Cys Cys Cys Cys Thr
                2085                2090                2095

Thr Cys Ala Thr Thr Thr Gly Gly Cys Cys Gly Cys Thr Gly Cys Cys
            2100                2105                2110

Thr Gly Gly Gly Gly Cys Cys Ala Thr Thr Thr Gly Gly Ala Gly Ala
        2115                2120                2125

Thr Thr Gly Thr Ala Gly Ala Gly Gly Thr Ala Cys Thr Thr Cys Thr
    2130                2135                2140

Gly Ala Ala Gly Gly Cys Gly Gly Gly Gly Gly Cys Thr Gly Ala Thr
2145                2150                2155                2160

Gly Thr Thr Ala Ala Thr Gly Cys Cys Cys Ala Gly Gly Ala Thr Ala
                2165                2170                2175

Ala Cys Thr Ala Thr Gly Gly Gly Cys Ala Ala Ala Cys Thr Cys Cys
            2180                2185                2190

Thr Gly Cys Gly Gly Ala Thr Cys Thr Gly Gly Cys Gly Gly Cys Thr
        2195                2200                2205

Gly Ala Ala Thr Cys Thr Gly Gly Gly Cys Ala Cys Cys Ala Ala Gly
    2210                2215                2220

Ala Thr Ala Thr Thr Gly Cys Thr Gly Ala Ala Gly Thr Thr Cys Thr
2225                2230                2235                2240
```

Gly Cys Ala Gly Ala Ala Gly Gly Cys Gly Gly Cys Ala
2245 2250

<210> SEQ ID NO 79
<211> LENGTH: 455
<212> TYPE: PRT
<213> ORGANISM: Artificial Sequence
<220> FEATURE:
<223> OTHER INFORMATION: Multi-specific binding protein

<400> SEQUENCE: 79

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Arg Glu Gly Lys Thr Pro Leu His Val Ala Ala Gln Glu Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ile
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Ala Ala Ala Leu
100 105 110

His Gly His Leu Glu Ile Val Glu Val Leu Leu Asn Ala Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala Gly
145 150 155 160

Ser Pro Thr Pro Thr Pro Thr Thr Pro Thr Pro Thr Pro Thr Thr Pro
165 170 175

Thr Pro Thr Pro Thr Gly Ser Asp Leu Gly Lys Lys Leu Leu Leu Ala
180 185 190

Ala Arg Ala Gly Gln Leu Asp Glu Val Arg Ile Leu Leu Lys Ala Gly
195 200 205

Ala Asp Val Asn Ala Lys Asp Val Phe Gly Gln Thr Pro Leu His Val
210 215 220

Ala Ala Val Ala Gly His Leu Glu Ile Val Glu Val Leu Leu Lys Ala
225 230 235 240

Gly Ala Asp Val Asn Ala Lys Asp Ser Ile Gly Tyr Thr Pro Leu His
245 250 255

His Ala Ala Arg Val Gly His Leu Glu Ile Val Glu Val Leu Leu Lys
260 265 270

Ala Gly Ala Asp Val Asn Ala Lys Asp Trp Ile Gly Ile Thr Pro Ala
275 280 285

Asp Leu Ala Ala Phe Glu Gly His Gln Asp Ile Ala Glu Val Leu Gln
290 295 300

Lys Ala Ala Gly Ser Pro Thr Pro Thr Pro Thr Thr Pro Thr Pro Thr
305 310 315 320

Pro Thr Thr Pro Thr Pro Thr Pro Thr Gly Ser Asp Leu Gly Gln Lys
325 330 335

Leu Leu His Ala Ala Gln Ala Gly Gln Leu Asp Glu Val Arg Ile Leu
340 345 350

```
Leu Lys Ala Gly Ala Asp Val Asn Ala Lys Asp Lys Gln Gly Asn Thr
        355                 360                 365

Pro Leu His Ile Ala Ala Phe His Gly His Leu Glu Ile Val Glu Val
    370                 375                 380

Leu Leu Lys Ala Gly Ala Asp Val Asn Ala Lys Asp Gln Trp Gly Leu
385                 390                 395                 400

Thr Pro Leu His Leu Ala Ala Ala Trp Gly His Leu Glu Ile Val Glu
                405                 410                 415

Val Leu Leu Lys Ala Gly Ala Asp Val Asn Ala Gln Asp Asn Tyr Gly
            420                 425                 430

Gln Thr Pro Ala Asp Leu Ala Ala Glu Ser Gly His Gln Asp Ile Ala
        435                 440                 445

Glu Val Leu Gln Lys Ala Ala
    450                 455


<210> SEQ ID NO 80
<211> LENGTH: 477
<212> TYPE: DNA
<213> ORGANISM: Artificial Sequence
<220> FEATURE:
<223> OTHER INFORMATION: Nucleic acid encoding spike protein binding
      domain

<400> SEQUENCE: 80

ggatcagacc tgggtaaaaa actgctgcaa gcagcacgtg caggtcagct ggatgaagtt     60

cgtgaactgc tgaaagcagg cgccgatgtt aatgcaaaag atagagaggg caagaccccg    120

ctgcatgtgg ctgctcaaga gggtcacctg gaaattgttg aagttctgct gaaagccggt    180

gcagatgtta atgcaaaaga tgtgtggggc agaaccccgc tgcatctggc tgcttggatc    240

ggtcacctgg aaattgttga agttctgctg aaagccggtg cagatgttaa tgcaaaagat    300

gtgtctggcg ctaccccgct gcatgcggct gctctgcacg gtcacctgga aattgttgaa    360

gttctgctga acgccggtgc agatgttaac gcacaggata aaagcggtaa aacccctgcc    420

gatctggcag ctcgcgccgg tcatcaggat attgctgaag tgctgcagaa ggcagca       477


<210> SEQ ID NO 81
<211> LENGTH: 378
<212> TYPE: DNA
<213> ORGANISM: Artificial Sequence
<220> FEATURE:
<223> OTHER INFORMATION: Nucleic acid encoding spike protein binding
      domain

<400> SEQUENCE: 81

ggatcagacc tgggtaaaaa attgttattg gccgctcgcg cgggccagct ggacgaggta     60

cgtatcttat tgaaggctgg ggcagacgtc aatgcgaagg acgtttttgg acagactcct    120

cttcatgtgg ccgccgtggc cggtcatctg gagattgtcg aagtattatt aaaggctggt    180

gcagatgtaa atgctaaaga ttctatcgga tacacaccgt tgcatcatgc agctcgcgtt    240

ggacatttag agatcgtcga ggtcttgctg aaagcaggtg ccgacgttaa tgccaaggat    300

tggatcggga tcaccccagc ggatcttgca gcatttgagg gtcaccagga tattgctgaa    360

gttctgcaga aggcagca                                                   378


<210> SEQ ID NO 82
<211> LENGTH: 378
<212> TYPE: DNA
<213> ORGANISM: Artificial Sequence
```

<220> FEATURE:
<223> OTHER INFORMATION: Nucleic acid encoding spike protein binding domain

<400> SEQUENCE: 82
ggatcagacc tgggtcaaaa gttgttacac gcggctcaag cgggacaatt agacgaggtc 60
cgtattctgc ttaaagccgg ggctgatgta aatgcaaaag acaaacaggg caacacaccc 120
ttacatatcg cggcattcca tggacatctg gagattgtgg aagtactgct gaaagccggg 180
gcagatgtca acgctaaaga ccaatgggga ttgacccccc ttcatttggc cgctgcctgg 240
ggccatttgg agattgtaga ggtacttctg aaggcggggg ctgatgttaa tgcccaggat 300
aactatgggc aaactcctgc ggatctggcg gctgaatctg ggcaccaaga tattgctgaa 360
gttctgcaga aggcggca 378

<210> SEQ ID NO 83
<211> LENGTH: 1365
<212> TYPE: DNA
<213> ORGANISM: Artificial Sequence
<220> FEATURE:
<223> OTHER INFORMATION: Nucleic acid encoding multi-specific binding protein

<400> SEQUENCE: 83
ggatcagacc tgggtaaaaa actgctgcaa gcagcacgtg caggtcagct ggatgaagtt 60
cgtgaactgc tgaaagcagg cgccgatgtt aatgcaaaag atagagaggg caagaccccg 120
ctgcatgtgg ctgctcaaga gggtcacctg gaaattgttg aagttctgct gaaagccggt 180
gcagatgtta atgcaaaaga tgtgtggggc agaaccccgc tgcatctggc tgcttggatc 240
ggtcacctgg aaattgttga agttctgctg aaagccggtg cagatgttaa tgcaaaagat 300
gtgtctggcg ctaccccgct gcatgcggct gctctgcacg gtcacctgga aattgttgaa 360
gttctgctga acgccggtgc agatgttaac gcacaggata aaagcggtaa aacccctgcc 420
gatctggcag ctcgcgccgg tcatcaggat attgctgaag tgctgcagaa ggcagcaggc 480
agccccacgc caactcctac aacccccaca cctacaccga cgacgccgac accgactcca 540
accggatcag acctgggtaa aaaattgtta ttggccgctc gcgcgggcca gctggacgag 600
gtacgtatct tattgaaggc tggggcagac gtcaatgcga aggacgtttt tggacagact 660
cctcttcatg tggccgccgt ggccggtcat ctggagattg tcgaagtatt attaaaggct 720
ggtgcagatg taaatgctaa agattctatc ggatacacac cgttgcatca tgcagctcgc 780
gttggacatt tagagatcgt cgaggtcttg ctgaaagcag gtgccgacgt taatgccaag 840
gattggatcg ggatcacccc agcggatctt gcagcatttg agggtcacca ggatattgct 900
gaagttctgc agaaggcagc aggttcgccg accccaaccc ctaccactcc aacgccgacg 960
cctaccactc caacaccaac accaacggga tcagacctgg gtcaaaagtt gttacacgcg 1020
gctcaagcgg gacaattaga cgaggtccgt attctgctta aagccggggc tgatgtaaat 1080
gcaaaagaca aacagggcaa cacaccctta catatcgcgg cattccatgg acatctggag 1140
attgtggaag tactgctgaa agccggggca gatgtcaacg ctaaagacca atggggattg 1200 acccccctto atttggccgc tgcctggggc catttggaga ttgtagaggt acttctgaag 1260
gcgggggctg atgttaatgc ccaggataac tatgggcaaa ctcctgcgga tctggcggct 1320
gaatctgggc accaagatat tgctgaagtt ctgcagaagg cggca 1365

<210> SEQ ID NO 84

<211> LENGTH: 766
<212> TYPE: PRT
<213> ORGANISM: Artificial Sequence
<220> FEATURE:
<223> OTHER INFORMATION: Multi-specific binding protein

<400> SEQUENCE: 84

Gly Ser Asp Leu Gly Lys Lys Leu Leu Glu Ala Ala Arg Ala Gly Gln
1 5 10 15

Asp Asp Glu Val Arg Glu Leu Leu Lys Ala Gly Ala Asp Val Asn Ala
20 25 30

Lys Asp Tyr Phe Ser His Thr Pro Leu His Leu Ala Ala Arg Asn Gly
35 40 45

His Leu Lys Ile Val Glu Val Leu Leu Lys Ala Gly Ala Asp Val Asn
50 55 60

Ala Lys Asp Phe Ala Gly Lys Thr Pro Leu His Leu Ala Ala Asn Glu
65 70 75 80

Gly His Leu Glu Ile Val Glu Val Leu Leu Lys Ala Gly Ala Asp Val
85 90 95

Asn Ala Gln Asp Ile Phe Gly Lys Thr Pro Ala Asp Ile Ala Ala Asp
100 105 110

Ala Gly His Glu Asp Ile Ala Glu Val Leu Gln Lys Ala Ala Gly Ser
115 120 125

Pro Thr Pro Thr Pro Thr Thr Pro Thr Pro Thr Pro Thr Thr Pro Thr
130 135 140

Pro Thr Pro Thr Gly Ser Asp Leu Gly Lys Lys Leu Leu Glu Ala Ala
145 150 155 160

Arg Ala Gly Gln Asp Asp Glu Val Arg Glu Leu Leu Lys Ala Gly Ala
165 170 175

Asp Val Asn Ala Lys Asp Tyr Phe Ser His Thr Pro Leu His Leu Ala
180 185 190

Ala Arg Asn Gly His Leu Lys Ile Val Glu Val Leu Leu Lys Ala Gly
195 200 205

Ala Asp Val Asn Ala Lys Asp Phe Ala Gly Lys Thr Pro Leu His Leu
210 215 220

Ala Ala Asn Glu Gly His Leu Glu Ile Val Glu Val Leu Leu Lys Ala
225 230 235 240

Gly Ala Asp Val Asn Ala Gln Asp Ile Phe Gly Lys Thr Pro Ala Asp
245 250 255

Ile Ala Ala Asp Ala Gly His Glu Asp Ile Ala Glu Val Leu Gln Lys
260 265 270

Ala Ala Gly Ser Pro Thr Pro Thr Pro Thr Thr Pro Thr Pro Thr Pro
275 280 285

Thr Thr Pro Thr Pro Thr Pro Thr Gly Ser Asp Leu Gly Lys Lys Leu
290 295 300

Leu Gln Ala Ala Arg Ala Gly Gln Leu Asp Glu Val Arg Glu Leu Leu
305 310 315 320

Lys Ala Gly Ala Asp Val Asn Ala Lys Asp Arg Glu Gly Lys Thr Pro
325 330 335

Leu His Val Ala Ala Gln Glu Gly His Leu Glu Ile Val Glu Val Leu
340 345 350

Leu Lys Ala Gly Ala Asp Val Asn Ala Lys Asp Val Trp Gly Arg Thr
355 360 365

Pro Leu His Leu Ala Ala Trp Ile Gly His Leu Glu Ile Val Glu Val
370 375 380

```
Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Leu Ala Ala Arg Ala Gly Gln Leu Asp Glu
                485                 490                 495

Val Arg Ile Leu Leu Lys Ala Gly Ala Asp Val Asn Ala Lys Asp Val
            500                 505                 510

Phe Gly Gln Thr Pro Leu His Thr Ala Ala Val Ala Gly His Leu Glu
        515                 520                 525

Ile Val Glu Val Leu Leu Lys Ala Gly Ala Asp Val Asn Ala Lys Asp
    530                 535                 540

Lys Val Gly Tyr Thr Pro Leu His Leu Ala Ala Gln Ser Gly His Leu
545                 550                 555                 560

Glu Ile Val Glu Val Leu Leu Lys Ala Gly Ala Asp Val Asn Ala Lys
                565                 570                 575

Asp Val Val Gly Val Thr Pro Ala Asp Leu Ala Ala Phe Glu Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Pro Thr Pro Thr Pro Thr Thr Pro Thr Pro Thr Pro Thr
625                 630                 635                 640

Gly Ser Asp Leu Gly Gln Lys Leu Leu His Ala Ala Gln Ala Gly Gln
                645                 650                 655

Leu Asp Glu Val Arg Ile Leu Leu Lys Ala Gly Ala Asp Val Asn Ala
            660                 665                 670

Lys Asp Lys Gln Gly Asn Thr Pro Leu His Ile Ala Ala Phe His Gly
        675                 680                 685

His Leu Glu Ile Val Glu Val Leu Leu Lys Ala Gly Ala Asp Val Asn
    690                 695                 700

Ala Lys Asp Gln Trp Gly Leu Thr Pro Leu His Leu Ala Ala Ala Trp
705                 710                 715                 720

Gly His Leu Glu Ile Val Glu Val Leu Leu Lys Ala Gly Ala Asp Val
                725                 730                 735

Asn Ala Gln Asp Asn Tyr Gly Gln Thr Pro Ala Asp Leu Ala Ala Glu
            740                 745                 750

Ser Gly His Gln Asp Ile Ala Glu Val Leu Gln Lys Ala Ala
        755                 760                 765
```

<210> SEQ ID NO 85
<211> LENGTH: 126
<212> TYPE: PRT
<213> ORGANISM: Artificial Sequence
<220> FEATURE:

<223> OTHER INFORMATION: Spike protein binding domain

<400> SEQUENCE: 85

Gly Ser Asp Leu Gly Lys Lys Leu Leu Leu Ala Ala Arg Ala Gly Gln
1               5                   10                  15

Leu Asp Glu Val Arg Ile Leu Leu Lys Ala Gly Ala Asp Val Asn Ala
            20                  25                  30

Lys Asp Val Phe Gly Gln Thr Pro Leu His Thr Ala Ala Val Ala Gly
        35                  40                  45

His Leu Glu Ile Val Glu Val Leu Leu Lys Ala Gly Ala Asp Val Asn
    50                  55                  60

Ala Lys Asp Lys Val Gly Tyr Thr Pro Leu His Leu Ala Ala Gln Ser
65                  70                  75                  80

Gly His Leu Glu Ile Val Glu Val Leu Leu Lys Ala Gly Ala Asp Val
                85                  90                  95

Asn Ala Lys Asp Val Val Gly Val Thr Pro Ala Asp Leu Ala Ala Phe
            100                 105                 110

Glu Gly His Gln Asp Ile Ala Glu Val Leu Gln Lys Ala Ala
        115                 120                 125

<210> SEQ ID NO 86
<211> LENGTH: 2298
<212> TYPE: DNA
<213> ORGANISM: Artificial Sequence
<220> FEATURE:
<223> OTHER INFORMATION: Nucleic acid encoding multi-specific binding protein

<400> SEQUENCE: 86
ggatccgacc tgggtaaaaa gctgctggag gcagcgcgtg ccggtcaaga cgacgaggtt 60
cgcgaattgc ttaaagcggg tgcagacgtc aacgccaaag attatttctc tcataccccg 120
ttgcatttag ccgcgcgtaa tggccatctg aagatcgtcg aggtcctctt gaaggcaggc 180
gcggatgtca atgcgaagga ttttgcgggc aaaacgccgc tgcacttagc ggcgaacgag 240
ggtcatttag aaatcgttga agtcctgtta aaagcgggcg ccgatgtgaa tgcgcaggat 300
attttcggta aaacgccggc ggacattgcg gcagatgcgg gtcatgaaga tatcgcagaa 360
gtcctgcaga aggcagcagg cagccctaca cctacgccga ctacgcctac gccgactccg 420
actaccccga ctccgacccc gaccggatca gacctgggta aaaagctgct ggaggcagcg 480
cgtgccggtc aagacgacga ggttcgcgaa ttgcttaaag cgggtgcaga cgtcaacgcc 540
aaagattatt tctctcatac cccgttgcat ttagccgcgc gtaatggcca tctgaagatc 600
gtcgaggtcc tcttgaaggc aggcgcggat gtcaatgcga aggattttgc gggcaaaacg 660
ccgctgcact tagcggcgaa cgagggtcat ttagaaatcg ttgaagtcct gttaaaagcg 720
ggcgccgatg tgaatgcgca ggatattttc ggtaaaacgc cggcggacat tgcggcagat 780
gcgggtcatg aagatatcgc agaagtcctg cagaaggcag caggttcccc gaccccctacg 840 ccaacgactc cgaccccaac tccaacgacc cctaccccga ccccgaccgg atcagacctg 900
ggtaaaaaac tgctgcaagc agcacgtgca ggtcagctgg atgaagttcg tgaactgctg 960
aaagcaggcg ccgatgttaa tgcaaaagat agagagggca agaccccgct gcatgtggct 1020
gctcaagagg gtcacctgga aattgttgaa gttctgctga aagccggtgc agatgttaat 1080
gcaaaagatg tgtggggcag aaccccgctg catctggctg cttggatcgg tcacctggaa 1140
attgttgaag ttctgctgaa agccggtgca gatgttaatg caaaagatgt gtctggcgct 1200

-continued

```
accccgctgc atgcggctgc tctgcacggt cacctggaaa ttgttgaagt tctgctgaac   1260

gccggtgcag atgttaacgc acaggataaa agcggtaaaa cccctgccga tctggcagct   1320

cgcgccggtc atcaggatat tgctgaagtg ctgcagaagg cagcaggcag ccccacgcca   1380

actcctacaa cccccacacc tacaccgacg acgccgacac cgactccaac cggatcagac   1440

ctgggtaaaa agttgttact tgcagctcgc gccggccaat tggacgaagt ccgcatttta   1500

ctgaaggccg gtgcggatgt gaacgcgaaa gacgtgtttg ggcagacccc tcttcacacc   1560

gcagcagttg caggtcatct ggagatcgtg gaagtgcttt taaaagcggg tgcggacgtc   1620

aacgctaagg acaaagttgg gtacacgcca ctgcacttag ctgcacagtc aggacatctt   1680

gagattgtgg aggtcttgct gaaggcaggc gcagatgtga acgctaagga tgtcgttggg   1740

gttacgccgg cggatttggc agctttcgag ggacaccagg acattgctga agttctgcag   1800

aaggcagcag gttcgccgac cccaacccct accactccaa cgccgacgcc taccactcca   1860

acaccaacac caacgggatc accaactcca acaccgacca ccccgacccc taccccaaca   1920

ggatcagacc tgggtcaaaa gttgttacac gcggctcaag cgggacaatt agacgaggtc   1980

cgtattctgc ttaaagccgg ggctgatgta aatgcaaaag acaaacaggg caacacaccc   2040

ttacatatcg cggcattcca tggacatctg gagattgtgg aagtactgct gaaagccggg   2100

gcagatgtca acgctaaaga ccaatgggga ttgacccccc ttcatttggc cgctgcctgg   2160

ggccatttgg agattgtaga ggtacttctg aaggcggggg ctgatgttaa tgcccaggat   2220

aactatgggc aaactcctgc ggatctggcg gctgaatctg ggcaccaaga tattgctgaa   2280

gttctgcaga aggcggca                                                 2298
```

<210> SEQ ID NO 87
<211> LENGTH: 751
<212> TYPE: PRT
<213> ORGANISM: Artificial Sequence
<220> FEATURE:
<223> OTHER INFORMATION: Multi-specific binding protein

<400> SEQUENCE: 87

```
Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
```

-continued

```
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205

Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Leu Ala Ala Arg Ala Gly Gln Leu Asp Glu
                485                 490                 495

Val Arg Ile Leu Leu Lys Ala Gly Ala Asp Val Asn Ala Lys Asp Val
            500                 505                 510

Phe Gly Gln Thr Pro Leu His Thr Ala Ala Val Ala Gly His Leu Glu
        515                 520                 525

Ile Val Glu Val Leu Leu Lys Ala Gly Ala Asp Val Asn Ala Lys Asp
    530                 535                 540

Lys Val Gly Tyr Thr Pro Leu His Leu Ala Ala Gln Ser Gly His Leu
545                 550                 555                 560

Glu Ile Val Glu Val Leu Leu Lys Ala Gly Ala Asp Val Asn Ala Lys
                565                 570                 575

Asp Val Val Gly Val Thr Pro Ala Asp Leu Ala Ala Phe Glu Gly His
            580                 585                 590
```

```
Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620

Thr Gly Ser Asp Leu Gly Gln Lys Leu Leu His Ala Ala Gln Ala Gly
625                 630                 635                 640

Gln Leu Asp Glu Val Arg Ile Leu Leu Lys Ala Gly Ala Asp Val Asn
                645                 650                 655

Ala Lys Asp Lys Gln Gly Asn Thr Pro Leu His Ile Ala Ala Phe His
            660                 665                 670

Gly His Leu Glu Ile Val Glu Val Leu Leu Lys Ala Gly Ala Asp Val
        675                 680                 685

Asn Ala Lys Asp Gln Trp Gly Leu Thr Pro Leu His Leu Ala Ala Ala
    690                 695                 700

Trp Gly His Leu Glu Ile Val Glu Val Leu Leu Lys Ala Gly Ala Asp
705                 710                 715                 720

Val Asn Ala Gln Asp Asn Tyr Gly Gln Thr Pro Ala Asp Leu Ala Ala
                725                 730                 735

Glu Ser Gly His Gln Asp Ile Ala Glu Val Leu Gln Lys Ala Ala
            740                 745                 750


<210> SEQ ID NO 88
<211> LENGTH: 759
<212> TYPE: PRT
<213> ORGANISM: Artificial Sequence
<220> FEATURE:
<223> OTHER INFORMATION: Multi-specific binding protein

<400> SEQUENCE: 88

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Glu
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
    130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Tyr Phe Ser His Thr Pro Leu His Leu Ala
            180                 185                 190

Ala Arg Asn Gly His Leu Lys Ile Val Glu Val Leu Leu Lys Ala Gly
        195                 200                 205
```

```
Ala Asp Val Asn Ala Lys Asp Phe Ala Gly Lys Thr Pro Leu His Leu
    210                 215                 220

Ala Ala Asn Glu Gly His Leu Glu Ile Val Glu Val Leu Leu Lys Ala
225                 230                 235                 240

Gly Ala Asp Val Asn Ala Gln Asp Ile Phe Gly Lys Thr Pro Ala Asp
                245                 250                 255

Ile Ala Ala Asp Ala Gly His Glu Asp Ile Ala Glu Val Leu Gln Lys
            260                 265                 270

Ala Ala Gly Ser Pro Thr Pro Thr Pro Thr Thr Pro Thr Pro Thr Pro
        275                 280                 285

Thr Thr Pro Thr Pro Thr Pro Thr Gly Ser Asp Leu Gly Lys Lys Leu
    290                 295                 300

Leu Gln Ala Ala Arg Ala Gly Gln Leu Asp Glu Val Arg Glu Leu Leu
305                 310                 315                 320

Lys Ala Gly Ala Asp Val Asn Ala Lys Asp Arg Glu Gly Lys Thr Pro
                325                 330                 335

Leu His Val Ala Ala Gln Glu Gly His Leu Glu Ile Val Glu Val Leu
            340                 345                 350

Leu Lys Ala Gly Ala Asp Val Asn Ala Lys Asp Val Trp Gly Arg Thr
        355                 360                 365

Pro Leu His Leu Ala Ala Trp Ile Gly His Leu Glu Ile Val Glu Val
    370                 375                 380

Leu Leu Lys Ala Gly Ala Asp Val Asn Ala Lys Asp Val Ser Gly Ala
385                 390                 395                 400

Thr Pro Leu His Ala Ala Ala Leu His Gly His Leu Glu Ile Val Glu
                405                 410                 415

Val Leu Leu Asn Ala Gly Ala Asp Val Asn Ala Gln Asp Lys Ser Gly
            420                 425                 430

Lys Thr Pro Ala Asp Leu Ala Ala Arg Ala Gly His Gln Asp Ile Ala
        435                 440                 445

Glu Val Leu Gln Lys Ala Ala Gly Ser Pro Thr Pro Thr Pro Thr Thr
    450                 455                 460

Pro Thr Pro Thr Pro Thr Thr Pro Thr Pro Thr Pro Thr Gly Ser Asp
465                 470                 475                 480

Leu Gly Lys Lys Leu Leu Leu Ala Ala Arg Ala Gly Gln Leu Asp Glu
                485                 490                 495

Val Arg Ile Leu Leu Lys Ala Gly Ala Asp Val Asn Ala Lys Asp Val
            500                 505                 510

Phe Gly Gln Thr Pro Leu His Thr Ala Ala Val Ala Gly His Leu Glu
        515                 520                 525

Ile Val Glu Val Leu Leu Lys Ala Gly Ala Asp Val Asn Ala Lys Asp
    530                 535                 540

Lys Val Gly Tyr Thr Pro Leu His Leu Ala Ala Gln Ser Gly His Leu
545                 550                 555                 560

Glu Ile Val Glu Val Leu Leu Lys Ala Gly Ala Asp Val Asn Ala Lys
                565                 570                 575

Asp Val Val Gly Val Thr Pro Ala Asp Leu Ala Ala Phe Glu Gly His
            580                 585                 590

Gln Asp Ile Ala Glu Val Leu Gln Lys Ala Ala Gly Ser Pro Thr Pro
        595                 600                 605

Thr Pro Thr Thr Pro Thr Pro Thr Pro Thr Thr Pro Thr Pro Thr Pro
    610                 615                 620
```

Thr Gly Ser Pro Thr Pro Thr Pro Thr Gly Ser Asp Leu Gly Gln Lys
625 630 635 640

Leu Leu His Ala Ala Gln Ala Gly Gln Leu Asp Glu Val Arg Ile Leu
645 650 655

Leu Lys Ala Gly Ala Asp Val Asn Ala Lys Asp Lys Gln Gly Asn Thr
660 665 670

Pro Leu His Ile Ala Ala Phe His Gly His Leu Glu Ile Val Glu Val
675 680 685

Leu Leu Lys Ala Gly Ala Asp Val Asn Ala Lys Asp Gln Trp Gly Leu
690 695 700

Thr Pro Leu His Leu Ala Ala Ala Trp Gly His Leu Glu Ile Val Glu
705 710 715 720

Val Leu Leu Lys Ala Gly Ala Asp Val Asn Ala Gln Asp Asn Tyr Gly
725 730 735

Gln Thr Pro Ala Asp Leu Ala Ala Glu Ser Gly His Gln Asp Ile Ala
740 745 750

Glu Val Leu Gln Lys Ala Ala
755

<210> SEQ ID NO 89
<211> LENGTH: 455
<212> TYPE: PRT
<213> ORGANISM: Artificial Sequence
<220> FEATURE:
<223> OTHER INFORMATION: Multi-specific binding protein

<400> SEQUENCE: 89

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Arg Glu Gly Lys Thr Pro Leu His Val Ala Ala Gln Glu Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ile
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Ala Ala Ala Leu
100 105 110

His Gly His Leu Glu Ile Val Glu Val Leu Leu Asn Ala Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala Gly
145 150 155 160

Ser Pro Thr Pro Thr Pro Thr Thr Pro Thr Pro Thr Pro Thr Thr Pro
165 170 175

Thr Pro Thr Pro Thr Gly Ser Asp Leu Gly Lys Lys Leu Leu Leu Ala
180 185 190

Ala Arg Ala Gly Gln Leu Asp Glu Val Arg Ile Leu Leu Lys Ala Gly
195 200 205

Ala Asp Val Asn Ala Lys Asp Val Phe Gly Gln Thr Pro Leu His Thr
210 215 220

Ala Ala Val Ala Gly His Leu Glu Ile Val Glu Val Leu Leu Lys Ala
225 230 235 240

Gly Ala Asp Val Asn Ala Lys Asp Lys Val Gly Tyr Thr Pro Leu His
245 250 255

Leu Ala Ala Gln Ser Gly His Leu Glu Ile Val Glu Val Leu Leu Lys
260 265 270

Ala Gly Ala Asp Val Asn Ala Lys Asp Val Val Gly Val Thr Pro Ala
275 280 285

Asp Leu Ala Ala Phe Glu Gly His Gln Asp Ile Ala Glu Val Leu Gln
290 295 300

Lys Ala Ala Gly Ser Pro Thr Pro Thr Pro Thr Thr Pro Thr Pro Thr
305 310 315 320

Pro Thr Thr Pro Thr Pro Thr Pro Thr Gly Ser Asp Leu Gly Gln Lys
325 330 335

Leu Leu His Ala Ala Gln Ala Gly Gln Leu Asp Glu Val Arg Ile Leu
340 345 350

Leu Lys Ala Gly Ala Asp Val Asn Ala Lys Asp Lys Gln Gly Asn Thr
355 360 365

Pro Leu His Ile Ala Ala Phe His Gly His Leu Glu Ile Val Glu Val
370 375 380

Leu Leu Lys Ala Gly Ala Asp Val Asn Ala Lys Asp Gln Trp Gly Leu
385 390 395 400

Thr Pro Leu His Leu Ala Ala Ala Trp Gly His Leu Glu Ile Val Glu
405 410 415

Val Leu Leu Lys Ala Gly Ala Asp Val Asn Ala Gln Asp Asn Tyr Gly
420 425 430

Gln Thr Pro Ala Asp Leu Ala Ala Glu Ser Gly His Gln Asp Ile Ala
435 440 445

Glu Val Leu Gln Lys Ala Ala
450 455

<210> SEQ ID NO 90
<211> LENGTH: 463
<212> TYPE: PRT
<213> ORGANISM: Artificial Sequence
<220> FEATURE:
<223> OTHER INFORMATION: Multi-specific binding protein

<400> SEQUENCE: 90

Gly Ser Asp Leu Gly Lys Lys Leu Leu Gln Ala Ala Arg Ala Gly Gln
1 5 10 15

Leu Asp Glu Val Arg Glu Leu Leu Lys Ala Gly Ala Asp Val Asn Ala
20 25 30

Lys Asp Arg Glu Gly Lys Thr Pro Leu His Val Ala Ala Gln Glu Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ile
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Ala Ala Ala Leu
100 105 110

His Gly His Leu Glu Ile Val Glu Val Leu Leu Asn Ala Gly Ala Asp
115 120 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala Gly
145                 150                 155                 160

Ser Pro Thr Pro Thr Pro Thr Thr Pro Thr Pro Thr Pro Thr Thr Pro
                165                 170                 175

Thr Pro Thr Pro Thr Gly Ser Asp Leu Gly Lys Lys Leu Leu Leu Ala
            180                 185                 190

Ala Arg Ala Gly Gln Leu Asp Glu Val Arg Ile Leu Leu Lys Ala Gly
        195                 200                 205

Ala Asp Val Asn Ala Lys Asp Val Phe Gly Gln Thr Pro Leu His Thr
    210                 215                 220

Ala Ala Val Ala Gly His Leu Glu Ile Val Glu Val Leu Leu Lys Ala
225                 230                 235                 240

Gly Ala Asp Val Asn Ala Lys Asp Lys Val Gly Tyr Thr Pro Leu His
                245                 250                 255

Leu Ala Ala Gln Ser Gly His Leu Glu Ile Val Glu Val Leu Leu Lys
            260                 265                 270

Ala Gly Ala Asp Val Asn Ala Lys Asp Val Val Gly Val Thr Pro Ala
        275                 280                 285

Asp Leu Ala Ala Phe Glu Gly His Gln Asp Ile Ala Glu Val Leu Gln
    290                 295                 300

Lys Ala Ala Gly Ser Pro Thr Pro Thr Pro Thr Thr Pro Thr Pro Thr
305                 310                 315                 320

Pro Thr Thr Pro Thr Pro Thr Pro Thr Gly Ser Pro Thr Pro Thr Pro
                325                 330                 335

Thr Gly Ser Asp Leu Gly Gln Lys Leu Leu His Ala Ala Gln Ala Gly
            340                 345                 350

Gln Leu Asp Glu Val Arg Ile Leu Leu Lys Ala Gly Ala Asp Val Asn
        355                 360                 365

Ala Lys Asp Lys Gln Gly Asn Thr Pro Leu His Ile Ala Ala Phe His
    370                 375                 380

Gly His Leu Glu Ile Val Glu Val Leu Leu Lys Ala Gly Ala Asp Val
385                 390                 395                 400

Asn Ala Lys Asp Gln Trp Gly Leu Thr Pro Leu His Leu Ala Ala Ala
                405                 410                 415

Trp Gly His Leu Glu Ile Val Glu Val Leu Leu Lys Ala Gly Ala Asp
            420                 425                 430

Val Asn Ala Gln Asp Asn Tyr Gly Gln Thr Pro Ala Asp Leu Ala Ala
        435                 440                 445

Glu Ser Gly His Gln Asp Ile Ala Glu Val Leu Gln Lys Ala Ala
    450                 455                 460

<210> SEQ ID NO 91
<211> LENGTH: 470
<212> TYPE: PRT
<213> ORGANISM: Artificial Sequence
<220> FEATURE:
<223> OTHER INFORMATION: Multi-specific binding protein

<400> SEQUENCE: 91

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Arg Glu Gly Lys Thr Pro Leu His Val Ala Ala Gln Glu Gly
35 40 45

His Leu Glu Ile Val Glu Val Leu Leu Lys Ala Gly Ala Asp Val Asn
50 55 60

Ala Lys Asp Val Trp Gly Arg Thr Pro Leu His Leu Ala Ala Trp Ile
65 70 75 80

Gly His Leu Glu Ile Val Glu Val Leu Leu Lys Ala Gly Ala Asp Val
85 90 95

Asn Ala Lys Asp Val Ser Gly Ala Thr Pro Leu His Ala Ala Ala Leu
100 105 110

His Gly His Leu Glu Ile Val Glu Val Leu Leu Asn Ala Gly Ala Asp
115 120 125

Val Asn Ala Gln Asp Lys Ser Gly Lys Thr Pro Ala Asp Leu Ala Ala
130 135 140

Arg Ala Gly His Gln Asp Ile Ala Glu Val Leu Gln Lys Ala Ala Gly
145 150 155 160

Ser Pro Thr Pro Thr Pro Thr Thr Pro Thr Pro Thr Pro Thr Thr Pro
165 170 175

Thr Pro Thr Pro Thr Gly Ser Asp Leu Gly Lys Lys Leu Leu Leu Ala
180 185 190

Ala Arg Ala Gly Gln Leu Asp Glu Val Arg Ile Leu Leu Lys Ala Gly
195 200 205

Ala Asp Val Asn Ala Lys Asp Val Phe Gly Gln Thr Pro Leu His Thr
210 215 220

Ala Ala Val Ala Gly His Leu Glu Ile Val Glu Val Leu Leu Lys Ala
225 230 235 240

Gly Ala Asp Val Asn Ala Lys Asp Lys Val Gly Tyr Thr Pro Leu His
245 250 255

Leu Ala Ala Gln Ser Gly His Leu Glu Ile Val Glu Val Leu Leu Lys
260 265 270

Ala Gly Ala Asp Val Asn Ala Lys Asp Val Val Gly Val Thr Pro Ala
275 280 285

Asp Leu Ala Ala Phe Glu Gly His Gln Asp Ile Ala Glu Val Leu Gln
290 295 300

Lys Ala Ala Gly Ser Pro Thr Pro Thr Pro Thr Thr Pro Thr Pro Thr
305 310 315 320

Pro Thr Thr Pro Thr Pro Thr Pro Thr Gly Ser Pro Thr Pro Thr Pro
325 330 335

Thr Thr Pro Thr Pro Thr Pro Thr Gly Ser Asp Leu Gly Gln Lys Leu
340 345 350

Leu His Ala Ala Gln Ala Gly Gln Leu Asp Glu Val Arg Ile Leu Leu
355 360 365

Lys Ala Gly Ala Asp Val Asn Ala Lys Asp Lys Gln Gly Asn Thr Pro
370 375 380

Leu His Ile Ala Ala Phe His Gly His Leu Glu Ile Val Glu Val Leu
385 390 395 400

Leu Lys Ala Gly Ala Asp Val Asn Ala Lys Asp Gln Trp Gly Leu Thr
405 410 415

Pro Leu His Leu Ala Ala Ala Trp Gly His Leu Glu Ile Val Glu Val
420 425 430

Leu Leu Lys Ala Gly Ala Asp Val Asn Ala Gln Asp Asn Tyr Gly Gln
435 440 445

Thr Pro Ala Asp Leu Ala Ala Glu Ser Gly His Gln Asp Ile Ala Glu 450 455 460

Val Leu Gln Lys Ala Ala
465 470

<210> SEQ ID NO 92
<211> LENGTH: 378
<212> TYPE: DNA
<213> ORGANISM: Artificial Sequence
<220> FEATURE:
<223> OTHER INFORMATION: Nucleic acid encoding spike protein binding domain

<400> SEQUENCE: 92
ggatcagacc tgggtaaaaa gttgttactt gcagctcgcg ccggccaatt ggacgaagtc 60
cgcattttac tgaaggccgg tgcggatgtg aacgcgaaag acgtgtttgg gcagacccct 120
cttcacaccg cagcagttgc aggtcatctg gagatcgtgg aagtgctttt aaaagcgggt 180
gcggacgtca acgctaagga caaagttggg tacacgccac tgcacttagc tgcacagtca 240
ggacatcttg agattgtgga ggtcttgctg aaggcaggcg cagatgtgaa cgctaaggat 300
gtcgttgggg ttacgccggc ggatttggca gctttcgagg gacaccagga cattgctgaa 360
gttctgcaga aggcagca 378

<210> SEQ ID NO 93
<211> LENGTH: 2253
<212> TYPE: DNA
<213> ORGANISM: Artificial Sequence
<220> FEATURE:
<223> OTHER INFORMATION: Nucleic acid encoding multi-specific binding protein

<400> SEQUENCE: 93
ggatccgacc tgggtaaaaa gctgctggag gcagcgcgtg ccggtcaaga cgacgaggtt 60
cgcgaattgc ttaaagcggg tgcagacgtc aacgccaaag attatttctc tcataccccg 120
ttgcatttag ccgcgcgtaa tggccatctg aagatcgtcg aggtcctctt gaaggcaggc 180
gcggatgtca atgcgaagga ttttgcgggc aaaacgccgc tgcacttagc ggcgaacgag 240
ggtcatttag aaatcgttga agtcctgtta aaagcgggcg ccgatgtgaa tgcgcaggat 300
attttcggta aaacgccggc ggacattgcg gcagatgcgg gtcatgaaga tatcgcagaa 360
gtcctgcaga aggcagcagg cagccctaca cctacgccga ctacgcctac gccgactccg 420
actaccccga ctccgacccc gaccggatca gacctgggta aaaagctgct ggaggcagcg 480
cgtgccggtc aagacgacga ggttcgcgaa ttgcttaaag cgggtgcaga cgtcaacgcc 540
aaagattatt tctctcatac cccgttgcat ttagccgcgc gtaatggcca tctgaagatc 600
gtcgaggtcc tcttgaaggc aggcgcggat gtcaatgcga aggattttgc gggcaaaacg 660
ccgctgcact tagcggcgaa cgagggtcat ttagaaatcg ttgaagtcct gttaaaagcg 720
ggcgccgatg tgaatgcgca ggatattttc ggtaaaacgc cggcggacat tgcggcagat 780
gcgggtcatg aagatatcgc agaagtcctg cagaaggcag caggttcccc gacccctacg 840
ccaacgactc cgaccccaac tccaacgacc cctaccccga ccccgaccgg atcagacctg 900
ggtaaaaaac tgctgcaagc agcacgtgca ggtcagctgg atgaagttcg tgaactgctg 960
aaagcaggcg ccgatgttaa tgcaaaagat agagagggca agaccccgct gcatgtggct 1020
gctcaagagg gtcacctgga aattgttgaa gttctgctga aagccggtgc agatgttaat 1080
gcaaaagatg tgtggggcag aaccccgctg catctggctg cttggatcgg tcacctggaa 1140

-continued

```
attgttgaag ttctgctgaa agccggtgca gatgttaatg caaaagatgt gtctggcgct   1200

accccgctgc atgcggctgc tctgcacggt cacctggaaa ttgttgaagt tctgctgaac   1260

gccggtgcag atgttaacgc acaggataaa agcggtaaaa cccctgccga tctggcagct   1320

cgcgccggtc atcaggatat tgctgaagtg ctgcagaagg cagcaggcag ccccacgcca   1380

actcctacaa cccccacacc tacaccgacg acgccgacac cgactccaac cggatcagac   1440

ctgggtaaaa agttgttact tgcagctcgc gccggccaat tggacgaagt ccgcatttta   1500

ctgaaggccg gtgcggatgt gaacgcgaaa gacgtgtttg ggcagacccc tcttcacacc   1560

gcagcagttg caggtcatct ggagatcgtg gaagtgcttt taaaagcggg tgcggacgtc   1620

aacgctaagg acaaagttgg gtacacgcca ctgcacttag ctgcacagtc aggacatctt   1680

gagattgtgg aggtcttgct gaaggcaggc gcagatgtga acgctaagga tgtcgttggg   1740

gttacgccgg cggatttggc agctttcgag ggacaccagg acattgctga agttctgcag   1800

aaggcagcag gttcgccgac cccaacccct accactccaa cgccgacgcc taccactcca   1860

acaccaacac caacgggatc agacctgggt caaaagttgt tacacgcggc tcaagcggga   1920

caattagacg aggtccgtat tctgcttaaa gccggggctg atgtaaatgc aaaagacaaa   1980

cagggcaaca cacccttaca tatcgcggca ttccatggac atctggagat tgtggaagta   2040

ctgctgaaag ccggggcaga tgtcaacgct aaagaccaat ggggattgac ccccccttcat   2100

ttggccgctg cctggggcca tttggagatt gtagaggtac ttctgaaggc gggggctgat   2160

gttaatgccc aggataacta tgggcaaact cctgcggatc tggcggctga atctgggcac   2220

caagatattg ctgaagttct gcagaaggcg gca                                  2253
```

<210> SEQ ID NO 94
<211> LENGTH: 2277
<212> TYPE: DNA
<213> ORGANISM: Artificial Sequence
<220> FEATURE:
<223> OTHER INFORMATION: Nucleic acid encoding multi-specific binding
      protein

<400> SEQUENCE: 94

```
ggatccgacc tgggtaaaaa gctgctggag gcagcgcgtg ccggtcaaga cgacgaggtt     60

cgcgaattgc ttaaagcggg tgcagacgtc aacgccaaag attatttctc tcataccccg    120

ttgcatttag ccgcgcgtaa tggccatctg aagatcgtcg aggtcctctt gaaggcaggc    180

gcggatgtca atgcgaagga ttttgcgggc aaaacgccgc tgcacttagc ggcgaacgag    240

ggtcatttag aaatcgttga agtcctgtta aaagcgggcg ccgatgtgaa tgcgcaggat    300

attttcggta aaacgccggc ggacattgcg gcagatgcgg gtcatgaaga tatcgcagaa    360

gtcctgcaga aggcagcagg cagccctaca cctacgccga ctacgcctac gccgactccg    420

actaccccga ctccgacccc gaccggatca gacctgggta aaaagctgct ggaggcagcg    480

cgtgccggtc aagacgacga ggttcgcgaa ttgcttaaag cgggtgcaga cgtcaacgcc    540

aaagattatt tctctcatac cccgttgcat ttagccgcgc gtaatggcca tctgaagatc    600

gtcgaggtcc tcttgaaggc aggcgcggat gtcaatgcga aggattttgc gggcaaaacg    660

ccgctgcact tagcggcgaa cgagggtcat ttagaaatcg ttgaagtcct gttaaaagcg    720

ggcgccgatg tgaatgcgca ggatattttc ggtaaaacgc cggcggacat tgcggcagat    780

gcgggtcatg aagatatcgc agaagtcctg cagaaggcag caggttcccc gacccctacg    840

ccaacgactc cgaccccaac tccaacgacc cctaccccga ccccgaccgg atcagacctg    900
```

-continued ggtaaaaaac tgctgcaagc agcacgtgca ggtcagctgg atgaagttcg tgaactgctg 960
aaagcaggcg ccgatgttaa tgcaaaagat agagagggca agaccccgct gcatgtggct 1020
gctcaagagg gtcacctgga aattgttgaa gttctgctga aagccggtgc agatgttaat 1080
gcaaaagatg tgtggggcag aaccccgctg catctggctg cttggatcgg tcacctggaa 1140
attgttgaag ttctgctgaa agccggtgca gatgttaatg caaaagatgt gtctggcgct 1200
accccgctgc atgcggctgc tctgcacggt cacctggaaa ttgttgaagt tctgctgaac 1260
gccggtgcag atgttaacgc acaggataaa agcggtaaaa cccctgccga tctggcagct 1320
cgcgccggtc atcaggatat tgctgaagtg ctgcagaagg cagcaggcag ccccacgcca 1380
actcctacaa cccccacacc tacaccgacg acgccgacac cgactccaac cggatcagac 1440
ctgggtaaaa agttgttact tgcagctcgc gccggccaat tggacgaagt ccgcatttta 1500
ctgaaggccg gtgcggatgt gaacgcgaaa gacgtgtttg ggcagacccc tcttcacacc 1560
gcagcagttg caggtcatct ggagatcgtg gaagtgcttt taaaagcggg tgcggacgtc 1620
aacgctaagg acaaagttgg gtacacgcca ctgcacttag ctgcacagtc aggacatctt 1680
gagattgtgg aggtcttgct gaaggcaggc gcagatgtga acgctaagga tgtcgttggg 1740
gttacgccgg cggatttggc agctttcgag ggacaccagg acattgctga agttctgcag 1800
aaggcagcag gttcgccgac cccaacccct accactccaa cgccgacgcc taccactcca 1860
acaccaacac caacgggatc accgacccct accccaacag gatcagacct gggtcaaaag 1920
ttgttacacg cggctcaagc gggacaatta gacgaggtcc gtattctgct taaagccggg 1980
gctgatgtaa atgcaaaaga caaacagggc aacacaccct tacatatcgc ggcattccat 2040
ggacatctgg agattgtgga agtactgctg aaagccgggg cagatgtcaa cgctaaagac 2100
caatggggat tgacccccct tcatttggcc gctgcctggg gccatttgga gattgtagag 2160
gtacttctga aggcgggggc tgatgttaat gcccaggata actatgggca aactcctgcg 2220
gatctggcgg ctgaatctgg gcaccaagat attgctgaag ttctgcagaa ggcggca 2277

<210> SEQ ID NO 95
<211> LENGTH: 1365
<212> TYPE: DNA
<213> ORGANISM: Artificial Sequence
<220> FEATURE:
<223> OTHER INFORMATION: Nucleic acid encoding multi-specific binding protein

<400> SEQUENCE: 95
ggatcagacc tgggtaaaaa actgctgcaa gcagcacgtg caggtcagct ggatgaagtt 60
cgtgaactgc tgaaagcagg cgccgatgtt aatgcaaaag atagagaggg caagaccccg 120
ctgcatgtgg ctgctcaaga gggtcacctg gaaattgttg aagttctgct gaaagccggt 180
gcagatgtta atgcaaaaga tgtgtggggc agaaccccgc tgcatctggc tgcttggatc 240
ggtcacctgg aaattgttga agttctgctg aaagccggtg cagatgttaa tgcaaaagat 300
gtgtctggcg ctaccccgct gcatgcggct gctctgcacg gtcacctgga aattgttgaa 360
gttctgctga acgccggtgc agatgttaac gcacaggata aaagcggtaa aacccctgcc 420
gatctggcag ctcgcgccgg tcatcaggat attgctgaag tgctgcagaa ggcagcaggc 480
agccccacgc caactcctac aacccccaca cctacaccga cgacgccgac accgactcca 540
accggatcag acctgggtaa aaagttgtta cttgcagctc gcgccggcca attggacgaa 600
gtccgcattt tactgaaggc cggtgcggat gtgaacgcga aagacgtgtt tgggcagacc 660

-continued

```
cctcttcaca ccgcagcagt tgcaggtcat ctggagatcg tggaagtgct tttaaaagcg    720
ggtgcggacg tcaacgctaa ggacaaagtt gggtacacgc cactgcactt agctgcacag    780
tcaggacatc ttgagattgt ggaggtcttg ctgaaggcag gcgcagatgt gaacgctaag    840
gatgtcgttg gggttacgcc ggcggatttg gcagctttcg agggacacca ggacattgct    900
gaagttctgc agaaggcagc aggttcgccg accccaaccc ctaccactcc aacgccgacg    960
cctaccactc caacaccaac accaacggga tcagacctgg gtcaaaagtt gttacacgcg   1020
gctcaagcgg gacaattaga cgaggtccgt attctgctta aagccggggc tgatgtaaat   1080
gcaaaagaca aacagggcaa cacaccctta catatcgcgg cattccatgg acatctggag   1140
attgtggaag tactgctgaa agccggggca gatgtcaacg ctaaagacca atggggattg   1200
acccccctte atttggccgc tgcctggggc catttggaga ttgtagaggt acttctgaag   1260
gcgggggctg atgttaatgc ccaggataac tatgggcaaa ctcctgcgga tctggcggct   1320
gaatctgggc accaagatat tgctgaagtt ctgcagaagg cggca                     1365
```

ANKYRIN REPEAT BINDING PROTEINS AND THEIR USES

FIELD OF THE INVENTION

The present invention relates to recombinant binding proteins comprising one or more designed ankyrin repeat domains with binding specificity for coronavirus spike proteins, nucleic acids encoding such proteins, pharmaceutical compositions comprising such proteins or nucleic acids, and the use of such proteins, nucleic acids or pharmaceutical compositions in the treatment of coronavirus diseases, particularly diseases caused by SARS-CoV-2.

BACKGROUND OF THE INVENTION

With a positive-stranded RNA genome of 28 to 32 kb, the Coronaviridae are the largest enveloped RNA viruses. Coronaviruses infect many different mammalian and avian species. They are responsible for a variety of acute and chronic diseases of the respiratory, hepatic, gastrointestinal, and neurological systems. The common cold is an example of a mild form of coronavirus infection. The 2003 SARS outbreak and the 2012 MERS outbreaks were both caused by coronaviruses. SARS-CoV-2 (also called 2019-nCoV) is the virus strain that causes COVID-19.

Coronaviruses have four structural proteins, known as the spike protein, envelope protein, membrane protein, and nucleocapsid protein. The spike protein is the viral membrane protein responsible for cell entry.

Coronaviruses make use of a densely glycosylated spike protein to gain entry into host cells. The spike protein consists of three subunits and is a trimeric class I fusion protein that exists in a metastable prefusion conformation that undergoes a substantial structural rearrangement to fuse the viral membrane with the host cell membrane. This process is triggered when the S1 subunit binds to a host cell receptor. Receptor binding destabilizes the prefusion trimer, resulting in shedding of the S1 subunit and transition of the S2 subunit to a stable post-fusion conformation. To engage a host cell receptor, the receptor-binding domain (RBD) of S1 undergoes hinge-like conformational movements that transiently hide or expose the determinants of receptor binding. These two states are referred to as the "down" conformation and the "up" conformation, where down corresponds to the receptor-inaccessible state and up corresponds to the receptor accessible state, which is thought to be less stable. Once the spike protein is in the "up" conformation, binding to the angiotensin-converting enzyme 2 (ACE2) receptor in the host cell can occur, allowing the virus into the cell. "Activation" of the spike protein to the "up" conformation can be carried out by enzymes such as furin or TMPRSS2 which act by opening the spike protein, allowing the nucleocapsid protein out of the viral capsid and into the cell, resulting in infection.

Once the cell is infected with the coronavirus, treatment options become more difficult as the immune system (or therapeutic agent) must only target virus-infected cells, without damaging non-infected cells.

Because of the indispensable function of the spike protein, it represents a target for antibody-mediated neutralization. Thus, one approach to coronavirus therapy is to inhibit binding of the virus to the cell by neutralizing the spike proteins, preventing infection of the cell.

DARPin® proteins are genetically engineered ankyrin repeat proteins, which can function like antibody mimetic proteins, typically exhibiting highly specific and high-affinity target binding. DARPin® proteins comprise one or more designed ankyrin repeat domains. Designed ankyrin repeat domains are derived from natural ankyrin repeat proteins and each designed ankyrin repeat domain typically binds a target protein with high specificity and affinity. Due to their high specificity, stability, potency and affinity and due to their flexibility in formatting to generate mono-, bi- or multi-specific proteins, DARPin® proteins are attractive therapeutic agents for a wide variety of clinical applications. For example, WO 2011/135067 describes DARPin® proteins for use in the treatment of cancer and other pathological conditions including eye diseases such as age-related macular degeneration. DARPin® is a registered trademark owned by Molecular Partners AG.

The technical problem underlying the present invention is identifying novel recombinant binding proteins comprising one or more designed ankyrin repeat domains with binding specificity for coronavirus, preferably SARS-CoV-2. Such recombinant binding proteins may be useful for inhibiting binding of the coronavirus to cells and for preventing viral infection of cells. Such recombinant binding proteins and pharmaceutical compositions comprising such proteins may further be useful for methods of preventing, treating or diagnosing coronavirus diseases, such as coronavirus diseases caused by SARS-CoV-2, and/or for methods of detecting coronavirus, preferably SARS-CoV-2.

SUMMARY OF THE INVENTION

Based on the disclosure provided herein, those skilled in the art will recognize, or be able to ascertain using no more than routine experimentation, many equivalents to the specific embodiments of the invention described herein. Such equivalents are intended to be encompassed by the following embodiments (E).

1. In a first embodiment, the present invention relates to a recombinant binding protein comprising a first ankyrin repeat domain, wherein said first ankyrin repeat domain comprises an amino acid sequence that has at least about 90% sequence identity with an ankyrin repeat domain selected from the group consisting of SEQ ID NOs 1 to 11, 76, 77 and 85.

1a. In embodiment 1a, the present invention relates to a recombinant binding protein comprising a first ankyrin repeat domain, wherein said first ankyrin repeat domain comprises an amino acid sequence that has at least about 90% sequence identity with an ankyrin repeat domain selected from the group consisting of SEQ ID NOs 1 to 11.

1b. In embodiment 1b, the present invention relates to a recombinant binding protein comprising a first ankyrin repeat domain, wherein said first ankyrin repeat domain comprises an amino acid sequence that has at least about 90% sequence identity with an ankyrin repeat domain selected from the group consisting of SEQ ID NOs 1 to 11, 76 and 77.

2. In a second embodiment, the present invention relates to the recombinant binding protein according to embodiment 1, wherein said first ankyrin repeat domain comprises an amino acid sequence that has at least about 95% sequence identity with an ankyrin repeat domain selected from the group consisting of SEQ ID NOs 1 to 11, 76, 77 and 85.

2a. In embodiment 2a, the present invention relates to the recombinant binding protein according to embodiment 1a, wherein said first ankyrin repeat domain comprises an amino acid sequence that has at least about 95% sequence identity with an ankyrin repeat domain selected from the group consisting of SEQ ID NOs 1 to 11.

2b. In embodiment 2b, the present invention relates to the recombinant binding protein according to embodiment 1b, wherein said first ankyrin repeat domain comprises an amino acid sequence that has at least about 95% sequence identity with an ankyrin repeat domain selected from the group consisting of SEQ ID NOs 1 to 11, 76 and 77.

3. In a third embodiment, the present invention relates to the recombinant binding protein according to embodiment 1, wherein said first ankyrin repeat domain is selected from the group consisting of SEQ ID NOs 1 to 11, 76, 77 and 85.

3a. In embodiment 3a, the present invention relates to the recombinant binding protein according to embodiment 1a, wherein said first ankyrin repeat domain is selected from the group consisting of SEQ ID NOs 1 to 11.

3b. In embodiment 3b, the present invention relates to the recombinant binding protein according to embodiment 1b, wherein said first ankyrin repeat domain is selected from the group consisting of SEQ ID NOs 1 to 11, 76 and 77.

4. In a fourth embodiment, the present invention relates to the recombinant binding protein according to any one of embodiments 1 to 3 further comprising a second ankyrin repeat domain, wherein said second ankyrin repeat domain comprises an amino acid sequence that has at least about 90% sequence identity with an ankyrin repeat domain selected from the group consisting of SEQ ID NOs 1 to 11, 76, 77 and 85.

4a. In embodiment 4a, the present invention relates to the recombinant binding protein according to any one of embodiments 1a, 2a or 3a further comprising a second ankyrin repeat domain, wherein said second ankyrin repeat domain comprises an amino acid sequence that has at least about 90% sequence identity with an ankyrin repeat domain selected from the group consisting of SEQ ID NOs 1 to 11.

4b. In embodiment 4b, the present invention relates to the recombinant binding protein according to any one of embodiments 1b, 2b or 3b further comprising a second ankyrin repeat domain, wherein said second ankyrin repeat domain comprises an amino acid sequence that has at least about 90% sequence identity with an ankyrin repeat domain selected from the group consisting of SEQ ID NOs 1 to 11, 76 and 77.

5. In a fifth embodiment, the present invention relates to the recombinant binding protein according to embodiment 4, wherein said second ankyrin repeat domain comprises an amino acid sequence that has at least about 95% sequence identity with an ankyrin repeat domain selected from the group consisting of SEQ ID NOs 1 to 11, 76, 77 and 85.

5a. In embodiment 5a, the present invention relates to the recombinant binding protein according to embodiment 4a, wherein said second ankyrin repeat domain comprises an amino acid sequence that has at least about 95% sequence identity with an ankyrin repeat domain selected from the group consisting of SEQ ID NOs 1 to 11.

5b. In embodiment 5b, the present invention relates to the recombinant binding protein according to embodiment 4b, wherein said second ankyrin repeat domain comprises an amino acid sequence that has at least about 95% sequence identity with an ankyrin repeat domain selected from the group consisting of SEQ ID NOs 1 to 11, 76 and 77.

6. In a sixth embodiment, the present invention relates to the recombinant binding protein according to embodiment 4, wherein said second ankyrin repeat domain is selected from the group consisting of SEQ ID NOs 1 to 11, 76, 77 and 85.

6a. In embodiment 6a, the present invention relates to the recombinant binding protein according to embodiment 4a, wherein said second ankyrin repeat domain is selected from the group consisting of SEQ ID NOs 1 to 11.

6b. In embodiment 6b, the present invention relates to the recombinant binding protein according to embodiment 4b, wherein said second ankyrin repeat domain is selected from the group consisting of SEQ ID NOs 1 to 11, 76 and 77.

7. In a seventh embodiment, the present invention relates to the recombinant binding protein according to any one of embodiments 4 to 6 further comprising a third ankyrin repeat domain, wherein said third ankyrin repeat domain comprises an amino acid sequence that has at least about 90% sequence identity with an ankyrin repeat domain selected from the group consisting of SEQ ID NOs 1 to 11, 76, 77 and 85.

7a. In embodiment 7a, the present invention relates to the recombinant binding protein according to any one of embodiments 4a, 5a or 6a further comprising a third ankyrin repeat domain, wherein said third ankyrin repeat domain comprises an amino acid sequence that has at least about 90% sequence identity with an ankyrin repeat domain selected from the group consisting of SEQ ID NOs 1 to 11.

7b. In embodiment 7b, the present invention relates to the recombinant binding protein according to any one of embodiments 4b, 5b or 6b further comprising a third ankyrin repeat domain, wherein said third ankyrin repeat domain comprises an amino acid sequence that has at least about 90% sequence identity with an ankyrin repeat domain selected from the group consisting of SEQ ID NOs 1 to 11, 76 and 77.

8. In an eighth embodiment, the present invention relates to the recombinant binding protein according to embodiment 7, wherein said third ankyrin repeat domain comprises an amino acid sequence that has at least about 95% sequence identity with an ankyrin repeat domain selected from the group consisting of SEQ ID NOs 1 to 11, 76, 77 and 85.

8a. In embodiment 8a, the present invention relates to the recombinant binding protein according to embodiment 7a, wherein said third ankyrin repeat domain comprises an amino acid sequence that has at least about 95% sequence identity with an ankyrin repeat domain selected from the group consisting of SEQ ID NOs 1 to 11.

8b. In embodiment 8b, the present invention relates to the recombinant binding protein according to embodiment 7b, wherein said third ankyrin repeat domain comprises an amino acid sequence that has at least about 95% sequence identity with an ankyrin repeat domain selected from the group consisting of SEQ ID NOs 1 to 11, 76 and 77.

9. In a ninth embodiment, the present invention relates to the recombinant binding protein according to embodiment 7, wherein said third ankyrin repeat domain is selected from the group consisting of SEQ ID NOs 1 to 11, 76, 77 and 85.

9a. In embodiment 9a, the present invention relates to the recombinant binding protein according to embodiment 7a, wherein said third ankyrin repeat domain is selected from the group consisting of SEQ ID NOs 1 to 11.

9b. In embodiment 9b, the present invention relates to the recombinant binding protein according to embodiment 7b, wherein said third ankyrin repeat domain is selected from the group consisting of SEQ ID NOs 1 to 11, 76 and 77.

10. In a tenth embodiment, the present invention relates to the recombinant binding protein according to embodiment 7, 7a or 7b, wherein said first, second and third ankyrin repeat domains comprise amino acid sequences and are arranged, from the N-terminus to C-terminus, as follows:

(i) amino acid sequences having at least about 90% sequence identity with SEQ ID NOs 6, 1 and 3;

(ii) amino acid sequences having at least about 90% sequence identity with SEQ ID NOs 4, 2 and 1;

(iii) amino acid sequences having at least about 90% sequence identity with SEQ ID NOs 4, 6 and 3;

(iv) amino acid sequences having at least about 90% sequence identity with SEQ ID NOs 6, 3 and 6;

(v) amino acid sequences having at least about 90% sequence identity with SEQ ID NOs 7, 3 and 6;

(vi) amino acid sequences having at least about 90% sequence identity with SEQ ID NOs 8, 4 and 1;

(vii) amino acid sequences having at least about 90% sequence identity with SEQ ID NOs 3, 6 and 7;

(viii) amino acid sequences having at least about 90% sequence identity with SEQ ID NOs 4, 1 and 8;

(ix) amino acid sequences having at least about 90% sequence identity with SEQ ID NOs 3, 6 and 9;

(x) amino acid sequences having at least about 90% sequence identity with SEQ ID NOs 9, 3 and 6;

(xi) amino acid sequences having at least about 90% sequence identity with SEQ ID NOs 1, 6 and 9;

(xii) amino acid sequences having at least about 90% sequence identity with SEQ ID NOs 9, 6 and 1;

(xiii) amino acid sequences having at least about 90% sequence identity with SEQ ID NOs 6, 9 and 10;

(xiv) amino acid sequences having at least about 90% sequence identity with SEQ ID NOs 3, 9 and 11;

(xv) amino acid sequences having at least about 90% sequence identity with SEQ ID NOs 10, 9 and 6;

(xvi) amino acid sequences having at least about 90% sequence identity with SEQ ID NOs 11, 9 and 3;

(xvii) amino acid sequences having at least about 90% sequence identity with SEQ ID NOs 5, 1 and 3;

(xviii) amino acid sequences having at least about 90% sequence identity with SEQ ID NOs 1, 2 and 5;

(xix) amino acid sequences having at least about 90% sequence identity with SEQ ID NOs 3, 5 and 6;

(xx) amino acid sequences having at least about 90% sequence identity with SEQ ID NOs 6, 3 and 5;

(xxi) amino acid sequences having at least about 90% sequence identity with SEQ ID NOs 7, 3 and 5;

(xxii) amino acid sequences having at least about 90% sequence identity with SEQ ID NOs 8, 5 and 6;

(xxiii) amino acid sequences having at least about 90% sequence identity with SEQ ID NOs 6, 10 and 11;

(xxiv) amino acid sequences having at least about 90% sequence identity with SEQ ID NOs 3, 10 and 10;

(xxv) amino acid sequences having at least about 90% sequence identity with SEQ ID NOs 5, 6 and 9;

(xxvi) amino acid sequences having at least about 90% sequence identity with SEQ ID NOs 9, 3 and 5;

(xxvii) amino acid sequences having at least about 90% sequence identity with SEQ ID NOs 9, 6 and 5;

(xxviii) amino acid sequences having at least about 90% sequence identity with SEQ ID NOs 5, 9 and 10;

(xxix) amino acid sequences having at least about 90% sequence identity with SEQ ID NOs 6, 9 and 11;

(xxx) amino acid sequences having at least about 90% sequence identity with SEQ ID NOs 10, 9 and 5;

(xxxi) amino acid sequences having at least about 90% sequence identity with SEQ ID NOs 11, 9 and 6;

(xxxii) amino acid sequences having at least about 90% sequence identity with SEQ ID NOs 3, 76 and 77;

or (xxxiii) amino acid sequences having at least about 90% sequence identity with SEQ ID NOs 3, 85 and 77.

10a. In embodiment 10a, the present invention relates to the recombinant binding protein according to embodiment 10 (xx).

10b. In embodiment 10b, the present invention relates to a recombinant binding protein comprising a polypeptide, wherein said polypeptide has an amino acid sequence that has at least about 90% sequence identity with SEQ ID NO: 68.

10c. In embodiment 10c, the present invention relates to a recombinant binding protein comprising a polypeptide, wherein said polypeptide has an amino acid sequence that has at least about 95% sequence identity with SEQ ID NO: 68.

10d. In embodiment 10d, the present invention relates to a recombinant binding protein comprising a polypeptide, wherein said polypeptide has the amino acid sequence of SEQ ID NO: 68.

10e. In embodiment 10e, the present invention relates to the recombinant binding protein according to embodiment 10 (xxviii).

10f. In embodiment 10f, the present invention relates to a recombinant binding protein comprising a polypeptide, wherein said polypeptide has an amino acid sequence that has at least about 90% sequence identity with SEQ ID NO: 69.

10g. In embodiment 10g, the present invention relates to a recombinant binding protein comprising a polypeptide, wherein said polypeptide has an amino acid sequence that has at least about 95% sequence identity with SEQ ID NO: 69.

10h. In embodiment 10h, the present invention relates to a recombinant binding protein comprising a polypeptide, wherein said polypeptide has the amino acid sequence of SEQ ID NO: 69.

10i. In embodiment 10i, the present invention relates to the recombinant binding protein according to embodiment 10 (xxxii).

10j. In embodiment 10j, the present invention relates to a recombinant binding protein comprising a polypeptide, wherein said polypeptide has an amino acid sequence that has at least about 90% sequence identity with SEQ ID NO: 79.

10k. In embodiment 10k, the present invention relates to a recombinant binding protein comprising a polypeptide, wherein said polypeptide has an amino acid sequence that has at least about 95% sequence identity with SEQ ID NO: 79.

10l. In embodiment 10l, the present invention relates to a recombinant binding protein comprising a polypeptide, wherein said polypeptide has the amino acid sequence of SEQ ID NO: 79.

10m. In embodiment 10m, the present invention relates to the recombinant binding protein according to embodiment 10 (xxxiii).

10n. In embodiment 10n, the present invention relates to a recombinant binding protein comprising a polypeptide, wherein said polypeptide has an amino acid sequence that has at least about 90% sequence identity with a sequence selected from the group consisting of SEQ ID NOs: 89 to 91.

10o. In embodiment 10o, the present invention relates to a recombinant binding protein comprising a polypeptide, wherein said polypeptide has an amino acid sequence that has at least about 95% sequence identity with a sequence selected from the group consisting of SEQ ID NOs: 89 to 91.

10p. In embodiment 10p, the present invention relates to a recombinant binding protein comprising a polypeptide, wherein said polypeptide has an amino acid sequence selected from the group consisting of SEQ ID NOs: 89 to 91.

11. In an eleventh embodiment, the present invention relates to the recombinant binding protein according to any one of embodiments 1 to 10p, wherein said binding protein binds to a coronavirus spike protein.

12. In a twelfth embodiment, the present invention relates to the recombinant binding protein according to embodiment 11, wherein said spike protein is SARS-CoV-2 spike protein.

13. In a thirteenth embodiment, the present invention relates to the recombinant binding protein according to any one of embodiments 11 and 12, wherein said first, second and/or third ankyrin repeat domain binds said coronavirus spike protein with a dissociation constant ($K_D$) of or below about 100 nM.

14. In a fourteenth embodiment, the present invention relates to a recombinant binding protein comprising at least one ankyrin repeat domain, wherein said ankyrin repeat domain binds a coronavirus spike protein with a dissociation constant ($K_D$) of or below about 100 nM.

15. In a fifteenth embodiment, the present invention relates to the recombinant binding protein according to any preceding embodiment further comprising at least one serum albumin binding domain.

16. In a sixteenth embodiment, the present invention relates to the recombinant binding protein according to embodiment 15, wherein said serum abumin binding domain comprises an amino acid sequence that has at least about 90% sequence identity with a sequence selected from the group consisting of SEQ ID NOs: 47-49.

16a. In embodiment 16a, the present invention relates to a recombinant binding protein according to any one of embodiments 15 and 16, wherein said recombinant binding protein has a terminal half-life in mice of at least about 30 hours, preferably at least about 35 hours, at least about 40 hours, or at least about 45 hours.

17. In a seventeenth embodiment, the present invention relates to a recombinant binding protein comprising a polypeptide, wherein said polypeptide has an amino acid sequence that has at least about 90% sequence identity with a sequence selected from the group consisting of SEQ ID NOs: 12-42, 75, 84, 87 and 88.

17a. In embodiment 17a, the present invention relates to a recombinant binding protein comprising a polypeptide, wherein said polypeptide has an amino acid sequence that has at least about 90% sequence identity with SEQ ID NO: 31.

17b. In embodiment 17b, the present invention relates to a recombinant binding protein comprising a polypeptide, wherein said polypeptide has an amino acid sequence that has at least about 90% sequence identity with SEQ ID NO: 39.

17c. In embodiment 17c, the present invention relates to a recombinant binding protein comprising a polypeptide, wherein said polypeptide has an amino acid sequence that has at least about 90% sequence identity with SEQ ID NO: 75.

17d. In embodiment 17d, the present invention relates to a recombinant binding protein comprising a polypeptide, wherein said polypeptide has an amino acid sequence that has at least about 90% sequence identity with SEQ ID NO: 84.

17e. In embodiment 17e, the present invention relates to a recombinant binding protein comprising a polypeptide, wherein said polypeptide has an amino acid sequence that has at least about 90% sequence identity with SEQ ID NO: 87.

17f. In embodiment 17f, the present invention relates to a recombinant binding protein comprising a polypeptide, wherein said polypeptide has an amino acid sequence that has at least about 90% sequence identity with SEQ ID NO: 88.

17g. In embodiment 17g, the present invention relates to a recombinant binding protein comprising a polypeptide, wherein said polypeptide has an amino acid sequence that has at least about 90% sequence identity with a sequence selected from the group consisting of SEQ ID NOs: 12-42.

17h. In embodiment 17h, the present invention relates to a recombinant binding protein comprising a polypeptide, wherein said polypeptide has an amino acid sequence that has at least about 90% sequence identity with a sequence selected from the group consisting of SEQ ID NOs: 12-42 and 75.

18. In an eighteenth embodiment, the present invention relates to the recombinant binding protein according to embodiment 17, wherein said polypeptide has an amino acid sequence that has at least about 95% sequence identity with a sequence selected from the group consisting of SEQ ID NOs: 12-42, 75, 84, 87 and 88.

18a. In embodiment 18a, the present invention relates to a recombinant binding protein comprising a polypeptide, wherein said polypeptide has an amino acid sequence that has at least about 95% sequence identity with SEQ ID NO: 31.

18b. In embodiment 18b, the present invention relates to a recombinant binding protein comprising a polypeptide, wherein said polypeptide has an amino acid sequence that has at least about 95% sequence identity with SEQ ID NO: 39.

18c. In embodiment 18c, the present invention relates to a recombinant binding protein comprising a polypeptide, wherein said polypeptide has an amino acid sequence that has at least about 95% sequence identity with SEQ ID NO: 75.

18d. In embodiment 18d, the present invention relates to a recombinant binding protein comprising a polypeptide, wherein said polypeptide has an amino acid sequence that has at least about 95% sequence identity with SEQ ID NO: 84.

18e. In embodiment 18e, the present invention relates to a recombinant binding protein comprising a polypeptide, wherein said polypeptide has an amino acid sequence that has at least about 95% sequence identity with SEQ ID NO: 87.

18f. In embodiment 18f, the present invention relates to a recombinant binding protein comprising a polypeptide, wherein said polypeptide has an amino acid sequence that has at least about 95% sequence identity with SEQ ID NO: 88.

18g. In embodiment 18g, the present invention relates to the recombinant binding protein according to embodiment 17g, wherein said polypeptide has an amino acid sequence that has at least about 95% sequence identity with a sequence selected from the group consisting of SEQ ID NOs: 12-42.

18h. In embodiment 18h, the present invention relates to the recombinant binding protein according to embodiment 17h, wherein said polypeptide has an amino acid sequence that has at least about 95% sequence identity with a sequence selected from the group consisting of SEQ ID NOs: 12-42 and 75.

19. In a nineteenth embodiment, the present invention relates to the recombinant binding protein according to embodiment 17, wherein said polypeptide has an amino acid sequence that is selected from the group consisting of SEQ ID NOs: 12-42, 75, 84, 87 and 88.

19a. In embodiment 19a, the present invention relates to a recombinant binding protein comprising a polypeptide, wherein said polypeptide has the amino acid sequence of SEQ ID NO: 31.

19b. In embodiment 19b, the present invention relates to a recombinant binding protein comprising a polypeptide, wherein said polypeptide has the amino acid sequence of SEQ ID NO: 39.

19c. In embodiment 19c, the present invention relates to a recombinant binding protein comprising a polypeptide, wherein said polypeptide has the amino acid sequence of SEQ ID NO: 75.

19d. In embodiment 19d, the present invention relates to a recombinant binding protein comprising a polypeptide, wherein said polypeptide has the amino acid sequence of SEQ ID NO: 84.

19e. In embodiment 19e, the present invention relates to a recombinant binding protein comprising a polypeptide, wherein said polypeptide has the amino acid sequence of SEQ ID NO: 87.

19f. In embodiment 19f, the present invention relates to a recombinant binding protein comprising a polypeptide, wherein said polypeptide has the amino acid sequence of SEQ ID NO: 88.

19g. In embodiment 19g, the present invention relates to the recombinant binding protein according to embodiment 17g, wherein said polypeptide has an amino acid sequence that is selected from the group consisting of SEQ ID NOs: 12-42.

19h. In embodiment 19h, the present invention relates to the recombinant binding protein according to embodiment 17h, wherein said polypeptide has an amino acid sequence that is selected from the group consisting of SEQ ID NOs: 12-42 and 75.

20. In a twentieth embodiment, the present invention relates to the recombinant binding protein according to any one of embodiments 17 to 19h, wherein said binding protein binds to a coronavirus spike protein.

21. In a twenty-first embodiment, the present invention relates to the recombinant binding protein according to embodiment 20, wherein said spike protein is SARS-CoV-2 spike protein.

22. In a twenty-second embodiment, the present invention relates to the recombinant binding protein according to any one of embodiments 20 and 21, wherein said binding protein binds said coronavirus spike protein with a dissociation constant ($K_D$) of or below about 100 nM.

23. In a twenty-third embodiment, the present invention relates to the recombinant binding protein according to any one of embodiments 1 to 22, wherein said binding protein is capable of inhibiting infection of cells by a coronavirus.

24. In a twenty-fourth embodiment, the present invention relates to the recombinant binding protein according to any one of embodiments 1 to 22, wherein said binding protein is capable of inhibiting infection of cells by SARS-CoV-2.

25. In a twenty-fifth embodiment, the present invention relates to a nucleic acid encoding a recombinant binding protein according to any one of embodiments 1 to 24.

25a. In embodiment 25a, the present invention relates to a nucleic acid encoding a recombinant binding protein according to one of the preceding embodiments, wherein said nucleic acid comprises or consists of SEQ ID NO 70 or a variant thereof encoding the same amino acid sequence as SEQ ID NO 70.

25b. In embodiment 25b, the present invention relates to a nucleic acid encoding a recombinant binding protein according to one of the preceding embodiments, wherein said nucleic acid comprises or consists of SEQ ID NO 71 or a variant thereof encoding the same amino acid sequence as SEQ ID NO 71.

25c. In embodiment 25c, the present invention relates to a nucleic acid encoding a recombinant binding protein according to one of the preceding embodiments, wherein said nucleic acid comprises or consists of SEQ ID NO 72 or a variant thereof encoding the same amino acid sequence as SEQ ID NO 72.

25d. In embodiment 25d, the present invention relates to a nucleic acid encoding a recombinant binding protein according to one of the preceding embodiments, wherein said nucleic acid comprises or consists of SEQ ID NO 73 or a variant thereof encoding the same amino acid sequence as SEQ ID NO 73.

25e. In embodiment 25e, the present invention relates to a nucleic acid encoding a recombinant binding protein according to one of the preceding embodiments, wherein said nucleic acid comprises or consists of SEQ ID NO 74 or a variant thereof encoding the same amino acid sequence as SEQ ID NO 74.

25f. In embodiment 25f, the present invention relates to a nucleic acid encoding a recombinant binding protein according to one of the preceding embodiments, wherein said nucleic acid comprises or consists of SEQ ID NO 80 or a variant thereof encoding the same amino acid sequence as SEQ ID NO 80.

25g. In embodiment 25g, the present invention relates to a nucleic acid encoding a recombinant binding protein according to one of the preceding embodiments, wherein said nucleic acid comprises or consists of SEQ ID NO 81 or a variant thereof encoding the same amino acid sequence as SEQ ID NO 81.

25h. In embodiment 25h, the present invention relates to a nucleic acid encoding a recombinant binding protein according to one of the preceding embodiments, wherein said nucleic acid comprises or consists of SEQ ID NO 82 or a variant thereof encoding the same amino acid sequence as SEQ ID NO 82.

25i. In embodiment 25i, the present invention relates to a nucleic acid encoding a recombinant binding protein according to one of the preceding embodiments, wherein said nucleic acid comprises or consists of SEQ ID NO 83 or a variant thereof encoding the same amino acid sequence as SEQ ID NO 83.

25j. In embodiment 25j, the present invention relates to a nucleic acid encoding a recombinant binding protein according to one of the preceding embodiments, wherein said nucleic acid comprises or consists of SEQ ID NO 78 or a variant thereof encoding the same amino acid sequence as SEQ ID NO 78.

25k. In embodiment 25k, the present invention relates to a nucleic acid encoding a recombinant binding protein according to one of the preceding embodiments, wherein said nucleic acid comprises or consists of SEQ ID NO 86 or a variant thereof encoding the same amino acid sequence as SEQ ID NO 86.

25l. In embodiment 25l, the present invention relates to a nucleic acid encoding a recombinant binding protein according to one of the preceding embodiments, wherein said nucleic acid comprises or consists of SEQ ID NO 92 or a variant thereof encoding the same amino acid sequence as SEQ ID NO 92.

25m. In embodiment 25m, the present invention relates to a nucleic acid encoding a recombinant binding protein according to one of the preceding embodiments, wherein said nucleic acid comprises or consists of SEQ ID NO 93 or a variant thereof encoding the same amino acid sequence as SEQ ID NO 93.

25n. In embodiment 25n, the present invention relates to a nucleic acid encoding a recombinant binding protein according to one of the preceding embodiments, wherein said nucleic acid comprises or consists of SEQ ID NO 94 or a variant thereof encoding the same amino acid sequence as SEQ ID NO 94.

250. In embodiment 250, the present invention relates to a nucleic acid encoding a recombinant binding protein according to one of the preceding embodiments, wherein said nucleic acid comprises or consists of SEQ ID NO 95 or a variant thereof encoding the same amino acid sequence as SEQ ID NO 95.

26. In a twenty-sixth embodiment, the present invention relates to a host cell comprising the nucleic acid molecule of any one of embodiments 25 to 250.

27. In a twenty-seventh embodiment, the present invention relates to a method of making the recombinant binding protein according to any one of embodiments 1 to 24, comprising culturing the host cell of embodiment 26 under conditions wherein said recombinant binding protein is expressed.

28. In a twenty-eighth embodiment, the present invention relates to a pharmaceutical composition comprising the binding protein of any one of embodiments 1 to 24 or the nucleic acid of any one of embodiments 25 to 250, and a pharmaceutically acceptable carrier or excipient.

29. In a twenty-ninth embodiment, the present invention relates to a method of treating a coronavirus infection in a subject, the method comprising the step of administering an effective amount of at least one binding protein according to any one of embodiments 1 to 24, or of the nucleic acid of any one of embodiments 25 to 250, or of the pharmaceutical composition according to embodiment 28, to a subject in need thereof.

29a. In embodiment 29a, the present invention relates to a method of treating according to embodiment 29, wherein said method is a therapeutic treatment method.

29b. In embodiment 29b, the present invention relates to a method of treating according to embodiment 29, wherein said method is a prophylactic treatment method.

29c. In embodiment 29c, the present invention relates to a method of preventing a coronavirus infection in a subject, the method comprising the step of administering an effective amount of at least one binding protein according to any one of embodiments 1 to 24, or of the nucleic acid of any one of embodiments 25 to 25o, or of the pharmaceutical composition according to embodiment 28, to a subject in need thereof.

29d. In embodiment 29d, the present invention relates to at least one binding protein according to any one of embodiments 1 to 24, or the nucleic acid of any one of embodiments 25 to 25o, or the pharmaceutical composition according to embodiment 28 for use in a method of diagnosing a coronavirus infection in a subject.

29e. In embodiment 29e, the present invention relates to a method of diagnosing a coronavirus infection in a subject comprising the steps of contacting a sample from the subject in vitro or ex vivo with at least one binding protein according to any one of embodiments 1 to 24.

29f. In embodiment 29f, the present invention relates to a method of detecting a coronavirus infection in a subject, said method comprising:

a) obtaining a sample from a subject;

b) contacting said sample with at least one binding protein according to any one of embodiments 1 to 24; and c) detecting the presence of a coronavirus infection.

29g. In embodiment 29g, the present invention relates to at least one binding protein according to any one of embodiments 1 to 24, or of the nucleic acid of any one of embodiments 25 to 250, or of the pharmaceutical composition according to embodiment 28 for use in treating or preventing a coronavirus infection in a subject.

30. In a thirtieth embodiment, the present invention relates to the method according to any one of embodiments 29 to 29g, wherein the coronavirus infection is caused by SARS-CoV-2.

31. In a thirty-first embodiment, the present invention relates to the method according to any one of embodiments 29, 29a, 29b, 29c, 29e, 29f, 29g and 30, or the use according to embodiment 29d wherein said subject is a human.

BRIEF DESCRIPTION OF THE FIGURES

In FIG. 9*c*, the upper panel represents SEQ ID NO: 9 and the lower panel represents SEQ ID NO: 10.

FIG. 15*a* is an SPR (surface plasmon resonance) trace showing high affinity binding to the coronavirus spike protein. No loss of target binding was observed over time. FIG. 15*b* shows a size exclusion chromatography (SEC) profile (molar mass vs time). No aggregates or oligomers were observed. No unfolding was detectable up to 85° C. on CD (circular dichroism) spectra (not provided).

FIG. 29: (A) A visual representation of the ALE109 constructs generated for knock out experiments. For each knock out (k.o.) construct, the indicated SARS-CoV-2-binding DARPin® domain was replaced with a non-binding DARPin® domain. HSA: HSA-binding DARPin® domain, RBD: RBD-binding DARPin® domain, NTD: NTD-binding DARPin® domain, S2: S2-binding DARPin® domain, see Example 11. (B) Neutralization profiles of ALE109 and k.o. constructs against VSV-SARS-CoV-2 pseudoviruses expressing the wild-type spike protein. (C) Upper panel: protective effect of DARPin® molecules against SARS-CoV-2 (100 pfu)-mediated cytopathic effect. Depicted are the percentage of cell protection conferred by ALE109 or the k.o. constructs. Cell protection was determined after 3 days of incubation by measuring intracellular ATP levels in a cell viability assay using Cell Titer-Glo. Lower panel: inhibition of SARS-CoV-2 viral replication quantified by real-time RT-PCR and expressed as percentage of viral genome equivalents present in the supernatant of Vero E6 cells exposed to 100 pfu SARS-CoV-2 with increasing amounts of ALE109 or k.o. constructs. (D) $IC_{50}/EC_{50}$ values and potency ranking of the constructs analyzed.

FIG. 31: Tables showing the cytopathic effects observed in Example 12. The DARPin® binding protein R1b is called RBD-2 in this Figure.

FIG. 36. Average and SEM of body weight measurements of all five study groups over the time course from day 0 to day 5.

FIG. 37*a* to 37*d*: Virus quantification by live virus titration of lung homogenate at day 3 (A) and at day 5 (B) and by qPCR measurement of genome copies in the lung at day 3 (C) and at day 5 (D), of three animals for each of the time points.

FIG. 38*a* to 38*d*: Sum of the averaged histopathological scores grouped into four categories for signs of inflammation (A), affected blood vessels (B), alveoli (C) or bronchi (D).

DETAILED DESCRIPTION OF THE INVENTION

Overview

Disclosed herein are recombinant binding proteins comprising one or more designed ankyrin repeat domains with binding specificity for coronavirus spike proteins, particularly SARS-CoV-2 spike proteins. Also disclosed are nucleic acids encoding the binding proteins, pharmaceutical compositions comprising the binding proteins or nucleic acids, and methods of using the binding proteins, nucleic acids, or pharmaceutical compositions.

Figure 1:
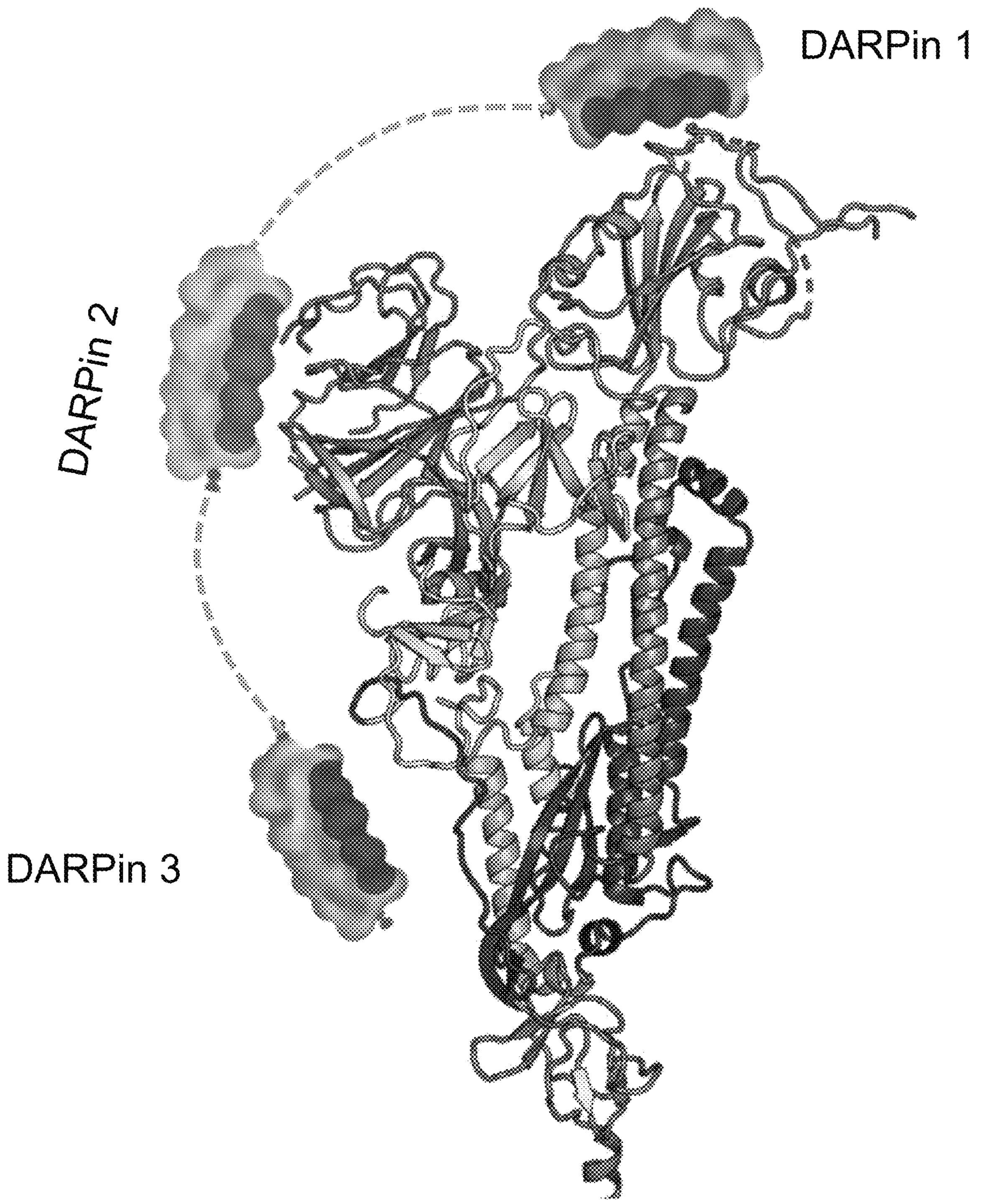
FIG. 1: 2019-nCoV spike protein protomer showing the proposed binding sites for different ankyrin repeat proteins (DARPin® proteins).
Figure 2:
FIG. 2: 2019-nCoV spike protein protomer in down conformation.
Figure 3:
FIG. 3: 2019-nCoV spike protein protomer in up conformation, showing the hACE2 binding site elevated. hACE2 is thought to bind to the up conformation of the spike protein, but not to the down conformation.
Figure 4:
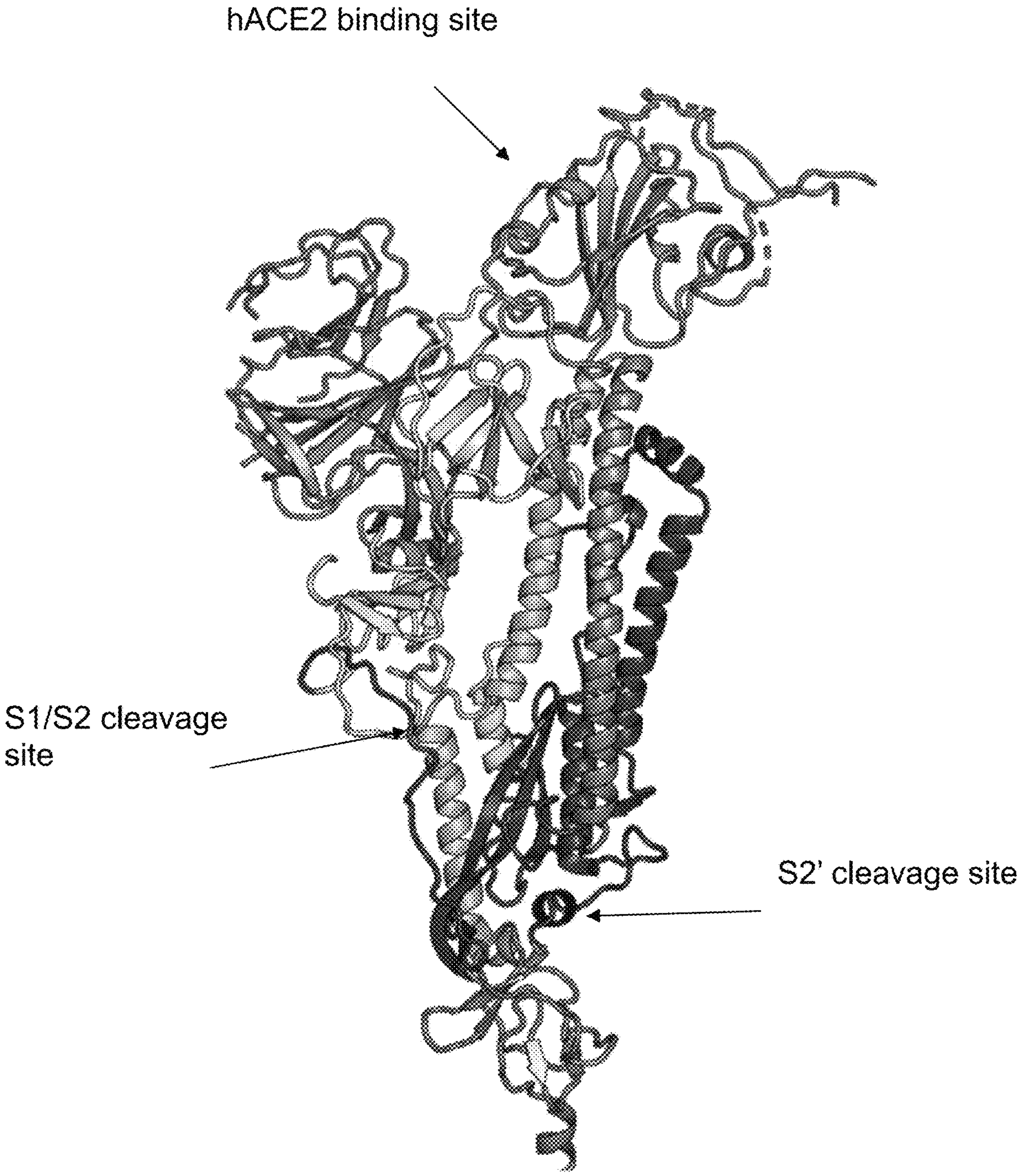
FIG. 4: 2019-nCoV spike protein protomer, indicating the location of the hACE2 binding site, S1/S2 cleavage site and S2' cleavage site. During molecular maturation, the spike protein trimerizes and is cleaved at the S1/S2 site. It is displayed at the membrane as a non-covalent complex. A concerted action of receptor-binding and proteolytic processing of the spike protein is required for membrane fusion. An initial energy barrier for conformational transition is necessary. Without wishing to be bound by theory, this energy barrier is overcome by (i) binding to the hACE2 receptor; and (ii) proteolytic priming at the S2' site. The interaction with ACE2 at the host cell surface is believed to trigger the cleavage of the S2' site. This cleavage has been proposed to activate the protein for membrane fusion via extensive irreversible conformational changes.

The recombinant binding proteins according to the present invention bind to the coronavirus spike protein at one or more binding sites, thereby neutralizing the virus. These binding sites are illustrated in FIG. 1. In one embodiment, the recombinant binding proteins bind to three sites on the spike protein.

Without wishing to be bound by theory, the designed ankyrin repeat proteins of the present invention are believed to act by (i) inhibiting receptor binding; (ii) providing allosteric inhibition of spike protein conformational change; and/or (iii) blocking protease sites needed for spike protein activation. As shown in FIG. 1, designed ankyrin repeat domain 1 (DARPin® 1) is understood to act by blocking angiotensin-converting enzyme 2 (ACE2) receptor binding. Designed ankyrin repeat domains 1 and 2 (DARPin® 1 and 2) are further understood to act by preventing conformational change in the spike protein, effectively locking the spike protein in the closed configuration. Designed ankyrin repeat domain 3 (DARPin® 3) is understood to further inhibit conformational change and to block protease binding. These designed ankyrin repeat domains can bind and/or inhibit the spike protein as individual proteins. Multi-epitope targeting by multi-domain, multi-specific proteins is believed to provide even more potent neutralization of the spike proteins, and to minimise the likelihood of escape mutations.

Further advantages to the described designed ankyrin repeat proteins are that they may reduce the incidence of Acute Lung Inflammation (ALI) due to lack of Fc-mediated macrophage or complement activation (as described by Liu et al., JCI Insight, 2019 4(4):e123158). Designed ankyrin repeat proteins may also address epitopes which are not accessible with monoclonal antibodies.

Further advantages to the described designed ankyrin repeat proteins are that they have low immunogenic potential and no off-target effects. DARPin® candidates also display favorable development properties including rapid, low-cost and high-yield manufacturing and up to several years of shelf-life at 4° C.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The terms "comprising", "having", "including" and "containing" are to be construed as open-ended terms unless otherwise noted. If aspects of the invention are described as "comprising" a feature, embodiments also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art. The term "about" as used herein is equivalent to ±10% of a given numerical value, unless otherwise stated.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

The term "nucleic acid" or "nucleic acid molecule" refers to a polynucleotide molecule, which may be a ribonucleic acid (RNA) or deoxyribonucleic acid (DNA) molecule, either single stranded or double stranded, and includes modified and artificial forms of DNA or RNA. A nucleic acid molecule may either be present in isolated form or be comprised in recombinant nucleic acid molecules or vectors.

In the context of the present invention the term "protein" refers to a molecule comprising a polypeptide, wherein at least part of the polypeptide has, or is able to acquire, a defined three-dimensional arrangement by forming secondary, tertiary, and/or quaternary structures within a single polypeptide chain and/or between multiple polypeptide chains. If a protein comprises two or more polypeptide chains, the individual polypeptide chains may be linked non-covalently or covalently, e.g. by a disulfide bond between two polypeptides. A part of a protein, which individually has, or is able to acquire, a defined three-dimensional arrangement by forming secondary and/or tertiary structure, is termed "protein domain". Such protein domains are well known to the practitioner skilled in the art.

The term "recombinant" as used in recombinant protein, recombinant polypeptide and the like, means that said protein or polypeptide is produced by the use of recombinant DNA technologies well known to the practitioner skilled in the art. For example, a recombinant DNA molecule (e.g.

produced by gene synthesis) encoding a polypeptide can be cloned into a bacterial expression plasmid (e.g. pQE30, QIAgen), yeast expression plasmid, mammalian expression plasmid, or plant expression plasmid, or a DNA enabling in vitro expression. If, for example, such a recombinant bacterial expression plasmid is inserted into appropriate bacteria (e.g. *Escherichia coli*), these bacteria can produce the polypeptide(s) encoded by this recombinant DNA. The correspondingly produced polypeptide or protein is called a recombinant polypeptide or recombinant protein.

In the context of the present invention, the term "binding protein" refers to a protein comprising a binding domain. A binding protein may also comprise two, three, four, five or more binding domains. Preferably, said binding protein is a recombinant binding protein. More preferably, the binding proteins of the instant invention comprise an ankyrin repeat domain with binding specificity for a coronavirus spike protein.

The term "target" refers to an individual molecule such as a nucleic acid molecule, a peptide, polypeptide or protein, a carbohydrate, or any other naturally occurring molecule, including any part of such individual molecule, or to complexes of two or more of such molecules, or to a whole cell or a tissue sample, or to any non-natural compound. Preferably, a target is a naturally occurring or non-natural polypeptide or protein, or a polypeptide or protein containing chemical modifications, for example, naturally occurring or non-natural phosphorylation, acetylation, or methylation.

In the context of the present invention, the term "polypeptide" relates to a molecule consisting of a chain of multiple, i.e. two or more, amino acids linked via peptide bonds. Preferably, a polypeptide consists of more than eight amino acids linked via peptide bonds. The term "polypeptide" also includes multiple chains of amino acids, linked together by S—S bridges of cysteines. Polypeptides are well-known to the person skilled in the art.

Patent application WO2002/020565 and Forrer et al., 2003 (Forrer, P., Stumpp, M. T., Binz, H. K., Plückthun, A., 2003. FEBS Letters 539, 2-6), contain a general description of repeat protein features and repeat domain features, techniques and applications. The term "repeat protein" refers to a protein comprising one or more repeat domains. Preferably, a repeat protein comprises one, two, three, four, five or six repeat domains. Furthermore, said repeat protein may comprise additional non-repeat protein domains, polypeptide tags and/or peptide linkers. The repeat domains can be binding domains.

The term "repeat domain" refers to a protein domain comprising two or more consecutive repeat modules as structural units, wherein said repeat modules have structural and sequence homology. Preferably, a repeat domain also comprises an N-terminal and/or a C-terminal capping module. For clarity, a capping module can be a repeat module. Such repeat domains, repeat modules, and capping modules, sequence motives, as well as structural homology and sequence homology are well known to the practitioner in the art from examples of ankyrin repeat domains (Binz et al., J. Mol. Biol. 332, 489-503, 2003; Binz et al., Nature Biotech. 22(5): 575-582 (2004); WO2002/020565; WO2012/069655), leucine-rich repeat domains (WO2002/020565), tetratricopeptide repeat domains (Main, E. R., Xiong, Y., Cocco, M. J., D'Andrea, L., Regan, L., Structure 11(5), 497-508, 2003), and armadillo repeat domains (WO2009/040338). It is further well known to the practitioner in the art, that such repeat domains are different from proteins comprising repeated amino acid sequences, where every repeated amino acid sequence is able to form an individual domain (for example FN3 domains of Fibronectin).

The term "ankyrin repeat domain" refers to a repeat domain comprising two or more consecutive ankyrin repeat modules as structural units, wherein said ankyrin repeat modules have structural and sequence homology.

The term "designed" as used in designed repeat protein, designed repeat domain and the like refers to the property that such repeat proteins and repeat domains, respectively, are man-made and do not occur in nature. The binding proteins of the instant invention are designed repeat proteins and they comprise at least one designed repeat domain. Preferably, the designed repeat domain is a designed ankyrin repeat domain.

The term "target interaction residues" refers to amino acid residues of a repeat module, which contribute to the direct interaction with a target.

The terms "framework residues" or "framework positions" refer to amino acid residues of a repeat module, which contribute to the folding topology, i.e. which contribute to the fold of said repeat module or which contribute to the interaction with a neighboring module. Such contribution may be the interaction with other residues in the repeat module, or the influence on the polypeptide backbone conformation as found in α-helices or β-sheets, or the participation in amino acid stretches forming linear polypeptides or loops. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

The term "repeat modules" refers to the repeated amino acid sequence and structural units of the designed repeat domains, which are originally derived from the repeat units of naturally occurring repeat proteins. Each repeat module comprised in a repeat domain is derived from one or more repeat units of a family or subfamily of naturally occurring repeat proteins, preferably the family of ankyrin repeat proteins. Furthermore, each repeat module comprised in a repeat domain may comprise a "repeat sequence motif" deduced from homologous repeat modules obtained from repeat domains selected on a target, e.g. as described in Example 1, and having the same target specificity.

Accordingly, the term "ankyrin repeat module" refers to a repeat module, which is originally derived from the repeat units of naturally occurring ankyrin repeat proteins. Ankyrin repeat proteins are well known to the person skilled in the art.

Repeat modules may comprise positions with amino acid residues which have not been randomized in a library for the purpose of selecting target-specific repeat domains ("non-randomized positions" or "fixed positions" used interchangeably herein) and positions with amino acid residues which have been randomized in the library for the purpose of selecting target-specific repeat domains ("randomized positions"). The non-randomized positions comprise framework residues. The randomized positions comprise target interaction residues. "Have been randomized" means that two or more amino acids were allowed at an amino acid position of a repeat module, for example, wherein any of the usual twenty naturally occurring amino acids were allowed, or wherein most of the twenty naturally occurring amino acids were allowed, such as amino acids other than cysteine, or amino acids other than glycine, cysteine and proline.

The term "repeat sequence motif" refers to an amino acid sequence, which is deduced from one or more repeat modules. Preferably, said repeat modules are from repeat domains having binding specificity for the same target. Such repeat sequence motifs comprise framework residue positions and target interaction residue positions. Said framework residue positions correspond to the positions of framework residues of the repeat modules. Likewise, said target interaction residue positions correspond to the positions of target interaction residues of the repeat modules. Repeat sequence motifs comprise non-randomized positions and randomized positions.

The term "repeat unit" refers to amino acid sequences comprising sequence motifs of one or more naturally occurring proteins, wherein said "repeat units" are found in multiple copies, and exhibit a defined folding topology common to all said motifs determining the fold of the protein. Examples of such repeat units include leucine-rich repeat units, ankyrin repeat units, armadillo repeat units, tetratricopeptide repeat units, HEAT repeat units, and leucine-rich variant repeat units.

The term "ankyrin repeat domain" refers to a domain that comprises at least one ankyrin repeat motif, which is originally derived from the repeat units of naturally occurring ankyrin repeat proteins. In general, the ankyrin repeat motif comprises about 33 residues that form two alpha helices, separated by loops. Ankyrin repeat proteins are known in the art. See, for example, International Patent Publication Nos. WO 2002/020565, WO 2010/060748, WO 2011/135067, WO 2012/069654, WO 2012/069655, WO 2014/001442, WO 2014/191574, WO 2014/083208, WO 2016/156596, and WO 2018/054971, all of which are incorporated by reference in their entireties. Ankyrin repeat domains optionally further comprise appropriate capping modules.

Ankyrin repeat domains may be modularly assembled into larger ankyrin repeat proteins according to the present disclosure, optionally with half-life extension domains, using standard recombinant DNA technologies (see, e.g., Forrer, P., et al., FEBS letters 539, 2-6, 2003, WO 2012/069655, WO 2002/020565).

An ankyrin repeat domain "specifically binds" or "preferentially binds" (used interchangeably herein) to a target if it reacts or associates more frequently, more rapidly, with greater duration and/or with greater affinity with a particular target (e.g., cell or substance) than it does with alternative targets (e.g., cells or substances). For example, an ankyrin repeat domain that specifically binds to coronavirus spike protein is an ankyrin repeat domain that binds coronavirus spike protein with greater affinity, avidity, more readily, and/or with greater duration than it binds to other non-coronavirus spike proteins. It is also understood by reading this definition that, for example, an ankyrin repeat domain which specifically or preferentially binds to a first target may or may not specifically or preferentially bind to a second target. As such, "specific binding" does not necessarily require (although it can include) exclusive binding. In general, under designated assay conditions, an ankyrin repeat domain binds preferentially to a particular target molecule and does not bind in a significant amount to other components present in a test sample.

A variety of assay formats may be used to select or characterize an ankyrin repeat domain that specifically binds a molecule of interest. For example, solid-phase ELISA immunoassay, immunoprecipitation, BIAcore™ (GE Healthcare, Piscataway, N.J.), fluorescence-activated cell sorting (FACS), Octet™ (ForteBio, Inc., Menlo Park, Calif.) and Western blot analysis are among many assays that may be used to identify an ankyrin repeat domain that specifically reacts with a target. Typically, a specific or selective reaction will be at least twice background signal or noise and more typically more than 10 times background. Even more specifically, an ankyrin repeat domain is said to "specifically bind" a target when the equilibrium dissociation constant ($K_D$) value is <1 μM, such as <100 nM, <10 nM, <1 nM, <100 pM, <10 pM, or <1 pM.

The $K_D$ value is often referred to as binding affinity. Binding affinity measures the strength of the sum total of non-covalent interactions between contact residue(s) of one binding partner and contact residue(s) of its binding partner. Unless indicated otherwise, as used herein, binding affinity refers to binding affinity that reflects a 1:1 interaction between members of a binding pair or binding partners. In case of a binding protein comprising two binding domains for one binding partner, binding affinity may refer to binding affinity that reflects a 1:2 interaction between the binding protein and the binding partner.

A variety of methods of measuring binding affinity are known in the art, any of which can be used for purposes of the present invention. For example, as exemplified herein, the binding affinity can be expressed as $K_D$ value, which refers to the dissociation rate of a particular ankyrin repeat domain and its binding target. $K_D$ is the ratio of the rate of dissociation, also called the "off-rate (Kw)", to the association rate, or "on-rate ($K_{on}$)". Thus, $K_D$ equals $K_{off}/K_{on}$ and is expressed as a molar concentration (M), and the smaller the $K_D$, the stronger the affinity of binding.

$K_D$ values can be determined using any suitable method. One exemplary method for measuring $K_D$ is surface plasmon resonance (SPR) (see, e.g., Nguyen et al. Sensors (Basel). 2015 May 5; 15(5):10481-510). $K_D$ value may be measured by SPR using a biosensor system such as a BIACORE® system. BIAcore kinetic analysis comprises analyzing the binding and dissociation of an antigen from chips with immobilized molecules (e.g., molecules comprising epitope binding domains), on their surface. Another method for determining the $K_D$ of a protein is by using Bio-Layer Interferometry (see, e.g., Shah et al. J Vis Exp. 2014; (84): 51383). $K_D$ value may be measured using OCTET® technology (Octet QKe system, ForteBio). Alternatively, or in addition, a KinExA® (Kinetic Exclusion Assay) assay, available from Sapidyne Instruments (Boise, Id.) can also be used. Any method suitable for assessing the binding affinity between two binding partners is encompassed herein. Surface plasmon resonance (SPR) is particularly preferred. Most preferably, the $K_D$ values are determined in PBS and by SPR.

The term "PBS" means a phosphate buffered water solution containing 137 mM NaCl, 10 mM phosphate and 2.7 mM KCl and having a pH of 7.4.

The term "treat," as well as words related thereto, does not necessarily imply 100% or complete cure. Rather, there are varying degrees of treatment of which one of ordinary skill in the art recognizes as having a potential benefit or therapeutic effect. In this respect, the methods of treating coronavirus infections described herein can provide any amount or any level of treatment. Furthermore, the treatment provided by the method of the present disclosure can include treatment of (i.e., relief from) one or more conditions or symptoms. In exemplary aspects, the methods treat by way increasing the survival of the subject. The term "treatment" also includes prophylactic (preventive) treatment.

Therapeutic responses in any given disease or condition can be determined by standardized response criteria specific to that disease or condition. The subject undergoing therapy may experience the beneficial effect of an improvement in the symptoms associated with the disease.

Recombinant Binding Proteins that Target Coronavirus Spike Proteins

Described herein are recombinant binding proteins comprising one, two, three or more designed ankyrin repeat domains with binding specificity for coronavirus spike proteins. In a preferred embodiment, such recombinant binding proteins comprising two, three or more designed ankyrin repeat domains with binding specificity for coronavirus spike proteins target two, three or more different epitopes on coronavirus spike proteins.

The described recombinant binding proteins, or binding domains thereof, comprising designed ankyrin repeat motifs or modules are also referred herein as DARPin® proteins. See Stumpp et al., Curr Opin Drug Discov Devel. 10(2): 153-9 (2007); and Binz et al., Nature Biotech. 22(5): 575-582 (2004). DARPin® proteins can be considered as antibody mimetics with high specificity and high binding affinity to a target protein. In general, a DARPin® protein comprises at least one ankyrin repeat domain, for example, at least 1, 2, 3, 4, 5, or more ankyrin repeat domains.

The ankyrin repeat domains described herein generally comprise a core scaffold that provides structure, and target binding residues that bind to a target. The structural core includes conserved amino acid residues, and the target binding surface includes amino acid residues that differ depending on the target.

International Patent Publication No. WO 2002/020565 and Binz et al., Nature Biotech. 22(5): 575-582 (2004) describe libraries of ankyrin repeat proteins that can be used for the selection/screening of a protein that binds specifically to a target. Methods of making such libraries are also provided.

Multiple ankyrin repeat domains can be linked (either through a covalent bond or non-covalent association) to form bispecific or multi-specific molecules. One such molecule is shown in FIG. 1, where three separate coronavirus spike protein binding domains are linked to form a multi-specific molecule. The linkers are illustrated by dashed lines joining the three binding domains.

Coronavirus Spike Protein

As set out above, the coronavirus spike protein is an attractive therapeutic target. Neutralizing the coronavirus spike protein can prevent infection of mammalian cells, stopping the coronavirus disease from taking hold in a subject. The recombinant binding proteins according to the present invention are specific for a mammalian coronavirus. Preferably, the designed ankyrin repeat proteins are specific for a coronavirus of mice, rat, dog, rabbit, monkey or human origin. More preferably, the designed ankyrin repeat proteins are specific for a coronavirus of human origin. The coronavirus SARS-CoV-2 is most preferred. As used herein, the term "SARS-CoV-2" includes both wild-type virus (such as SARS-CoV-2 found in infected humans at the beginning of the COVID-19 pandemic) and mutated forms or variants thereof. In one embodiment, the term "SARS-CoV-2" includes wild type and the specific variants B.1.1.7 (the so-called "UK variant") and B.1.351 (the so-called "South African variant").

The recombinant binding protein described herein comprises an ankyrin repeat domain that specifically binds to coronavirus spike protein. In one embodiment, the recombinant binding protein described herein comprises two, three or more ankyrin repeat domains that specifically bind to coronavirus spike protein. In one embodiment, the recombinant binding protein described herein comprises one, two, three or more ankyrin repeat domains that specifically bind to SARS-CoV-2 spike protein.

The target domains of interest in this disclosure on the coronavirus spike protein include, but are not limited to, the receptor binding domain (RBD domain); the S1 NTD domain; and the S2 domain. These domains are known in the art (see, e.g. Wrapp et al., Science 367, 1260-1263 (2020).

Ankyrin repeat domains according to the present invention that bind coronavirus spike protein are provided in Table 1:

TABLE 1

| SEQ ID NO | DARPin ® protein name | Abbreviation | Spike Protein Target Domain |
|---|---|---|---|
| SEQ ID NO 1 | vS07_19G10 | R2a | RBD |
| SEQ ID NO 2 | vS07_06F12 | R1a | RBD |
| SEQ ID NO 3 | vS07_12C06 | R1b | RBD |
| SEQ ID NO 4 | vS07_22E12 | R3a | RBD |
| SEQ ID NO 5 | vS07_23E04 | R3c | RBD |
| SEQ ID NO 6 | vS07_29B10 | R3b | RBD |
| SEQ ID NO 7 | vS07_07F02 | RN1 | RBD |
| SEQ ID NO 8 | vS07_26C03 | RN2 | RBD |
| SEQ ID NO 9 | vS07_08F10 | S1a | S1-NTD |
| SEQ ID NO 10 | vS07_14G03 | S2a | S2 |
| SEQ ID NO 11 | vS07_18A05 | S2b | S2 |
| SEQ ID NO 76 | vS07_08F10v27 | | S1-NTD |
| SEQ ID NO 77 | vS07_14G03v19 | | S2 |
| SEQ ID NO 85 | vS07_08F10v47 | | S1-NTD |

Thus, in one embodiment, the present invention relates to a recombinant binding protein comprising a first ankyrin repeat domain, wherein said first ankyrin repeat domain comprises an amino acid sequence that has at least about 90% sequence identity with an ankyrin repeat domain selected from the group consisting of SEQ ID NOs 1 to 11, 76, 77 and 85, as illustrated in Table 1 above.

In one embodiment, the present invention relates to a recombinant binding protein comprising a first ankyrin repeat domain, wherein said first ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76, 77 and 85, as illustrated in Table 1 above. In one embodiment, the present invention relates to a recombinant binding protein comprising a first ankyrin repeat domain, wherein said first ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76 and 77, as illustrated in Table 1 above. In one embodiment, the present invention relates to a recombinant binding protein comprising a first ankyrin repeat domain, wherein said first ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, as illustrated in Table 1 above.

In one embodiment, the present invention relates to a recombinant binding protein comprising a first ankyrin repeat domain, wherein said first ankyrin repeat domain is selected from the group consisting of SEQ ID NOs 1 to 11, 76, 77 and 85, as illustrated in Table 1 above.

The ankyrin repeat domains listed in Table 1 may be combined in any manner to provide a bi-specific or multi-specific molecule. The first, second and third ankyrin repeat domains may have identical sequences. The first, second and third ankyrin repeat domains may have different sequences.

Thus, in one embodiment, the present invention relates to a recombinant binding protein further comprising a second ankyrin repeat domain, wherein said second ankyrin repeat domain comprises an amino acid sequence that has at least about 90% sequence identity with an ankyrin repeat domain selected from the group consisting of SEQ ID NOs 1 to 11, 76, 77 and 85, as illustrated in Table 1 above.

In one embodiment, the present invention relates to a recombinant binding protein comprising a second ankyrin repeat domain, wherein said second ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76, 77 and 85, as illustrated in Table 1 above. In one embodiment, the present invention relates to a recombinant binding protein comprising a second ankyrin repeat domain, wherein said second ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76 and 77, as illustrated in Table 1 above. In one embodiment, the present invention relates to a recombinant binding protein comprising a second ankyrin repeat domain, wherein said second ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, as illustrated in Table 1 above.

In one embodiment, the present invention relates to a recombinant binding protein comprising a second ankyrin repeat domain, wherein said second ankyrin repeat domain is selected from the group consisting of SEQ ID NOs 1 to 11, 76, 77 and 85, as illustrated in Table 1 above.

In one embodiment, the present invention relates to a recombinant binding protein as defined above further comprising a third ankyrin repeat domain, wherein said third ankyrin repeat domain comprises an amino acid sequence that has at least about 90% sequence identity with an ankyrin repeat domain selected from the group consisting of SEQ ID NOs 1 to 11, 76, 77 and 85, as illustrated in Table 1 above.

In one embodiment, the present invention relates a recombinant binding protein as defined above further comprising a third ankyrin repeat domain, wherein said third ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76, 77 and 85, as illustrated in Table 1 above. In one embodiment, the present invention relates a recombinant binding protein as defined above further comprising a third ankyrin repeat domain, wherein said third ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, 76 and 77, as illustrated in Table 1 above. In one embodiment, the present invention relates a recombinant binding protein as defined above further comprising a third ankyrin repeat domain, wherein said third ankyrin repeat domain comprises an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, about 92%, about 93%, about 94%, about 95%, about 96%, about 97%, about 98% or about 99% sequence identity with an ankyrin repeat domain selected from the group consisting of SEQ ID NOs 1 to 11, as illustrated in Table 1 above.

In one embodiment, the present invention relates to a recombinant binding protein as defined above further comprising a third ankyrin repeat domain, wherein said third ankyrin repeat domain is selected from the group consisting of SEQ ID NOs 1 to 11, 76, 77 and 85, as illustrated in Table 1 above.

The present invention further relates to specific combinations of first, second and third ankyrin repeat domains having amino acid sequences and being arranged from the N-terminus to the C-terminus as follows:

(i) amino acid sequences having at least about 90% sequence identity with SEQ ID NOs 6, 1 and 3;

(ii) amino acid sequences having at least about 90% sequence identity with SEQ ID NOs 4, 2 and 1;

(iii) amino acid sequences having at least about 90% sequence identity with SEQ ID NOs 4, 6 and 3;

(iv) amino acid sequences having at least about 90% sequence identity with SEQ ID NOs 6, 3 and 6;

(v) amino acid sequences having at least about 90% sequence identity with SEQ ID NOs 7, 3 and 6;

(vi) amino acid sequences having at least about 90% sequence identity with SEQ ID NOs 8, 4 and 1;

(vii) amino acid sequences having at least about 90% sequence identity with SEQ ID NOs 3, 6 and 7;

(viii) amino acid sequences having at least about 90% sequence identity with SEQ ID NOs 4, 1 and 8;

(ix) amino acid sequences having at least about 90% sequence identity with SEQ ID NOs 3, 6 and 9;

(x) amino acid sequences having at least about 90% sequence identity with SEQ ID NOs 9, 3 and 6;

(xi) amino acid sequences having at least about 90% sequence identity with SEQ ID NOs 1, 6 and 9;

(xii) amino acid sequences having at least about 90% sequence identity with SEQ ID NOs 9, 6 and 1;

(xiii) amino acid sequences having at least about 90% sequence identity with SEQ ID NOs 6, 9 and 10;

(xiv) amino acid sequences having at least about 90% sequence identity with SEQ ID NOs 3, 9 and 11;

(xv) amino acid sequences having at least about 90% sequence identity with SEQ ID NOs 10, 9 and 6;

(xvi) amino acid sequences having at least about 90% sequence identity with SEQ ID NOs 11, 9 and 3;

(xvii) amino acid sequences having at least about 90% sequence identity with SEQ ID NOs 5, 1 and 3;

(xviii) amino acid sequences having at least about 90% sequence identity with SEQ ID NOs 1, 2 and 5;

(xix) amino acid sequences having at least about 90% sequence identity with SEQ ID NOs 3, 5 and 6;

(xx) amino acid sequences having at least about 90% sequence identity with SEQ ID NOs 6, 3 and 5;

(xxi) amino acid sequences having at least about 90% sequence identity with SEQ ID NOs 7, 3 and 5;

(xxii) amino acid sequences having at least about 90% sequence identity with SEQ ID NOs 8, 5 and 6;

(xxiii) amino acid sequences having at least about 90% sequence identity with SEQ ID NOs 6, 10 and 11;

(xxiv) amino acid sequences having at least about 90% sequence identity with SEQ ID NOs 3, 10 and 10;

(xxv) amino acid sequences having at least about 90% sequence identity with SEQ ID NOs 5, 6 and 9;

(xxvi) amino acid sequences having at least about 90% sequence identity with SEQ ID NOs 9, 3 and 5;

(xxvii) amino acid sequences having at least about 90% sequence identity with SEQ ID NOs 9, 6 and 5;

(xxviii) amino acid sequences having at least about 90% sequence identity with SEQ ID NOs 5, 9 and 10;

(xxix) amino acid sequences having at least about 90% sequence identity with SEQ ID NOs 6, 9 and 11;

(xxx) amino acid sequences having at least about 90% sequence identity with SEQ ID NOs 10, 9 and 5;

(xxxi) amino acid sequences having at least about 90% sequence identity with SEQ ID NOs 11, 9 and 6;

(xxxii) amino acid sequences having at least about 90% sequence identity with SEQ ID NOs 3, 76 and 77;

or (xxxiii) amino acid sequences having at least about 90% sequence identity with SEQ ID NOs 3, 85 and 77.

In one embodiment, the present invention relates to the recombinant binding protein according to embodiment (xx) as listed above. In a further embodiment, the present invention relates to a recombinant binding protein comprising a polypeptide, wherein said polypeptide has an amino acid sequence that has at least about 90%, about 91%, about 92%, about 93%, about 94%, about 95%, about 96%, about 97%, about 98% or about 99% sequence identity with SEQ ID NO: 68. In another embodiment, the recombinant binding protein comprises a polypeptide, wherein said polypeptide has the amino acid sequence of SEQ ID NO: 68.

In one embodiment, the present invention relates to the recombinant binding protein according to embodiment (xxviii), as listed above. In a further embodiment, the present invention relates to a recombinant binding protein comprising a polypeptide, wherein said polypeptide has an amino acid sequence that has at least about 90%, about 91%, about 92%, about 93%, about 94%, about 95%, about 96%, about 97%, about 98% or about 99% sequence identity with SEQ ID NO: 69. In another embodiment, the recombinant binding protein comprises a polypeptide, wherein said polypeptide has the amino acid sequence of SEQ ID NO: 69.

In one embodiment, the present invention relates to the recombinant binding protein according to (xxxii), as listed above. In a further embodiment, the present invention relates to a recombinant binding protein comprising a polypeptide, wherein said polypeptide has an amino acid sequence that has at least about 90%, about 91%, about 92%, about 93%, about 94%, about 95%, about 96%, about 97%, about 98% or about 99% sequence identity with SEQ ID NO: 79. In another embodiment, the recombinant binding protein comprises a polypeptide, wherein said polypeptide has the amino acid sequence of SEQ ID NO: 79.

In one embodiment, the present invention relates to the recombinant binding protein according to (xxxiii), as listed above. In a further embodiment, the present invention relates to a recombinant binding protein comprising a polypeptide, wherein said polypeptide has an amino acid sequence that has at least about 90%, about 91%, about 92%, about 93%, about 94%, about 95%, about 96%, about 97%, about 98% or about 99% sequence identity with a sequence selected from the group consisting of SEQ ID NOs: 89 to 91.

In another embodiment, the recombinant binding protein comprises a polypeptide, wherein said polypeptide has an amino acid sequence selected from the group consisting of SEQ ID NOs: 89 to 91.

In another embodiment, the recombinant binding protein of the present invention binds to a coronavirus spike protein. In another embodiment, the spike protein is SARS-CoV-2 spike protein.

In another embodiment, the recombinant binding protein of the invention comprising at least one ankyrin repeat domain binds to a coronavirus spike protein with a binding affinity ($K_D$) of or below about 100 nM. In another embodiment, the spike protein is SARS-CoV-2 spike protein.

In another embodiment, the recombinant binding protein of the invention comprises first, second and/or third ankyrin repeat domains and said first, second and/or third ankyrin repeat domains bind to a coronavirus spike protein with a binding affinity ($K_D$) of or below about 100 nM. In another embodiment, the spike protein is SARS-CoV-2 spike protein.

In exemplary embodiments, the recombinant binding protein of the invention binds coronavirus spike protein, preferably SARS-CoV-2 spike protein, with an $K_D$ value of, or less than: about 100 nM; about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 250 pM, about 200 pM, about 150 pM, about 100 pM, about 50 pM, about 40 pM, about 30 pM, about 25 pM, about 20 pM, about 15 pM, about 10 pM, about 5 pM, or about 1 pM. In one exemplary embodiment, the recombinant binding protein binds coronavirus spike protein, preferably SARS-CoV-2 spike protein, with a $K_D$ value of less than or equal to about 10 nM. In another exemplary embodiment, the recombinant binding protein binds coronavirus spike protein, preferably SARS-CoV-2 spike protein, with a K) value of less than or equal to about 1 nM.

In certain embodiments, the coronavirus spike protein is human coronavirus spike protein. In certain embodiments, the coronavirus spike protein is human SARS-CoV-2 spike protein.

In certain embodiments, the recombinant binding protein may further comprise at least one human serum albumin binding domain. In embodiments, the at least one human serum albumin domain may be located at the N-terminus, the C-terminus, or both.

In certain embodiments, the serum albumin binding domain comprises an amino acid sequence that has at least 90% sequence identity with a sequence selected from the group consisting of SEQ ID NOs: 47-49. In one embodiment, the serum albumin binding domain comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with SEQ ID NO: 47.

In further embodiments, the recombinant binding protein of the invention has a terminal half-life in mice of at least about 30 hours, preferably at least about 35 hours, more preferably at least about 40 hours, and more preferably at least about 45 hours. Said terminal half-life is preferably determined in Balb/c mice, as described in Example 9.

Particularly preferred combinations of ankyrin repeat domains are listed in Table 2, wherein H denotes human serum albumin and R3b, R2a etc are as defined in Table 1 above:

TABLE 2

| | | 5 Domain DARPin ® Designs | | | | |
|---|---|---|---|---|---|---|
| # | | 1 | 2 | 3 | 4 | 5 |
| 1 | SEQ ID NO: 12 | H | H | R3b | R2a | Rib |
| 2 | SEQ ID NO: 13 | H | H | R3a | R1a | R2a |
| 3 | SEQ ID NO: 14 | H | H | R3a | R3b | R1b |
| 4 | SEQ ID NO: 15 | H | H | R3b | R1b | R3b |
| 5 | SEQ ID NO: 16 | H | H | RN1 | R1b | R3b |
| 6 | SEQ ID NO: 17 | H | H | RN2 | R3a | R2a |
| 7 | SEQ ID NO: 18 | H | H | R1b | R3b | RN1 |
| 8 | SEQ ID NO: 19 | H | H | R3a | R2a | RN2 |
| 9 | SEQ ID NO: 20 | H | H | R1b | R3b | S1a |
| 10 | SEQ ID NO: 21 | H | H | S1a | R1b | R3b |
| 11 | SEQ ID NO: 22 | H | H | R2a | R3b | Sia |
| 12 | SEQ ID NO: 23 | H | H | S1a | R3b | R2a |
| 13 | SEQ ID NO: 24 | H | H | R3b | S1a | S2a |
| 14 | SEQ ID NO: 25 | H | H | R1b | S1a | S2b |
| 15 | SEQ ID NO: 26 | H | H | S2a | S1a | R3b |
| 16 | SEQ ID NO: 27 | H | H | S2b | S1a | R1b |
| 17 | SEQ ID NO: 28 | H | H | R3c | R2a | R1b |
| 18 | SEQ ID NO: 29 | H | H | R2a | R1a | R3c |
| 19 | SEQ ID NO: 30 | H | H | R1b | R3c | R3b |
| 20 | SEQ ID NO: 31 | H | H | R3b | R1b | R3c |
| 21 | SEQ ID NO: 32 | H | H | RN1 | R1b | R3c |
| 22 | SEQ ID NO: 33 | H | H | RN2 | R3c | R3b |
| 23 | SEQ ID NO: 34 | H | H | R3b | S2a | S2b |
| 24 | SEQ ID NO: 35 | H | H | R1b | S2a | S2a |
| 25 | SEQ ID NO: 36 | H | H | R3c | R3b | S1a |
| 26 | SEQ ID NO: 37 | H | H | S1a | R1b | R3c |
| 27 | SEQ ID NO: 38 | H | H | S1a | R3b | R3c |
| 28 | SEQ ID NO: 39 | H | H | R3c | S1a | S2a |
| 29 | SEQ ID NO: 40 | H | H | R3b | S1a | S2b |
| 30 | SEQ ID NO: 41 | H | H | S2a | S1a | R3c |
| 31 | SEQ ID NO: 42 | H | H | S2b | S1a | R3b |
| 32 | SEQ ID NO: 75 | H | H | R1b | SEQ ID NO 76 | SEQ ID NO 77 |
| 33 | SEQ ID NOs: 84, 87 and 88 | H | H | R1b | SEQ ID NO 85 | SEQ ID NO 77 |

In another embodiment, the present invention relates to a recombinant binding protein comprising a polypeptide, wherein said polypeptide has an amino acid sequence that has at least about 90% sequence identity with a sequence selected from the group consisting of SEQ ID NOs: 12-42, 75, 84, 87 and 88. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with a sequence selected from the group consisting of SEQ ID NOs: 12-42, 75, 84, 87 and 88. In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with a sequence selected from the group consisting of SEQ ID NOs: 12-42 and 75. In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with a sequence selected from the group consisting of SEQ ID NOs: 12-42. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM.

In another embodiment, the present invention relates to a recombinant binding protein comprising a polypeptide, wherein said polypeptide has an amino acid sequence that is selected from the group consisting of SEQ ID NOs: 12-42, 75, 84, 87 and 88. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM.

In another embodiment, the present invention relates to the recombinant binding protein as described herein, wherein said binding protein is capable of inhibiting infection of cells by a coronavirus. In another embodiment, the present invention relates to the recombinant binding protein as described herein, wherein said binding protein is capable of inhibiting infection of cells by SARS-CoV-2.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 31. In another embodiment, the recombinant binding protein comprises a polypeptide, wherein said polypeptide has the amino acid sequence of SEQ ID NO: 31. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein binds said coronavirus spike protein with a binding affinity ($K_D$) of or below about 1 nM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 40 hours. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.1 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 31, and wherein said binding protein binds to SARS-CoV-2 spike protein with a binding affinity ($K_D$) of or below about 1 nM, wherein said binding protein has a terminal half-life in mice of at least about 40 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 39. In another embodiment, the recombinant binding protein comprises a polypeptide, wherein said polypeptide has the amino acid sequence of SEQ ID NO: 39. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein binds said coronavirus spike protein with a binding affinity ($K_D$) of or below about 1 nM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 20 hours. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.4 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 39, and wherein said binding protein binds to SARS-CoV-2 spike protein with a binding affinity ($K_D$) of or below about 1 nM, wherein said binding protein has a terminal half-life in mice of at least about 20 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 75. In another embodiment, the recombinant binding protein comprises a polypeptide, wherein said polypeptide has the amino acid sequence of SEQ ID NO: 75. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 30 hours. In one embodiment, said binding protein binds said coronavirus spike protein with a binding affinity ($K_D$) of or below about 1 nM. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.4 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 75, and wherein said binding protein binds to SARS-CoV-2 spike protein with a binding affinity ($K_D$) of or below about 1 nM, wherein said binding protein has a terminal half-life in mice of at least about 30 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 84. In another embodiment, the recombinant binding protein comprises a polypeptide, wherein said polypeptide has the amino acid sequence of SEQ ID NO: 84. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 40 hours. In one embodiment, said binding protein binds said coronavirus spike protein with a binding affinity ($K_D$) of or below about 1 nM. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.4 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 84, and wherein said binding protein binds to SARS-CoV-2 spike protein with a binding affinity ($K_D$) of or below about 1 nM, wherein said binding protein has a terminal half-life in mice of at least about 40 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 87. In another embodiment, the recombinant binding protein comprises a polypeptide, wherein said polypeptide has the amino acid sequence of SEQ ID NO: 87. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 35 hours. In one embodiment, said binding protein binds said coronavirus spike protein with a binding affinity ($K_D$) of or below about 1 nM. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.4 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 87, and wherein said binding protein binds to SARS-CoV-2 spike protein with a binding affinity ($K_D$) of or below about 1 nM, wherein said binding protein has a terminal half-life in mice of at least about 35 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

In another embodiment, the present invention relates to a recombinant binding protein comprising a polypeptide, wherein said polypeptide has an amino acid sequence that has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 88. In another embodiment, the recombinant binding protein comprises a polypeptide, wherein said polypeptide has the amino acid sequence of SEQ ID NO: 88. In one embodiment, said binding protein binds to a coronavirus spike protein. In one embodiment, said spike protein is SARS-CoV-2 spike protein. In one embodiment, said binding protein binds said coronavirus spike protein with a binding affinity ($K_D$) of or below about 100 nM, of or below about 10 nM, of or below about 1 nM, of or below about 100 pM, of or below about 10 pM, or of or below about 1 pM. In one embodiment, said binding protein has a terminal half-life in mice of at least about 20 hours, at least about 25 hours, at least about 30 hours, at least about 35 hours, at least about 40 hours, or at least about 45 hours. In one embodiment, said binding protein has a terminal half-life in mice of at least about 40 hours. In one embodiment, said binding protein binds said coronavirus spike protein with a binding affinity ($K_D$) of or below about 1 nM. In one embodiment, said binding protein exhibits a high thermal stability with a Tm above 50° C., above 60° C., above 70° C., or above 80° C. In one embodiment, said binding protein exhibits a high thermal stability with a Tm above 60° C. In one embodiment, said binding protein inhibits viral entry of SARS-CoV-2 VSV pseudovirus in VeroE6 cells with an $IC_{50}$ value of or below 100 nM, of or below 10 nM, of or below 1 nM, or of or below 0.5 nM. In one embodiment, said binding protein inhibits viral entry of SARS-CoV-2 VSV pseudovirus in VeroE6 cells with an $IC_{50}$ value of or below 1 nM. In one embodiment, said binding protein inhibits viral entry of SARS-CoV-2 in VeroE6 cells with an $IC_{50}$ value of or below 100 nM, of or below 10 nM, of or below 1 nM, or of or below 0.4 nM. In one embodiment, said binding protein inhibits viral entry of SARS-CoV-2 in VeroE6 cells with an $IC_{50}$ value of or below 1 nM. In one embodiment, said binding protein has a combination of two, three, four, five or six properties selected from the properties listed in this paragraph relating to amino acid sequence, binding affinity, terminal half-life, thermal stability, $IC_{50}$ of SARS-CoV-2 VSV pseudovirus inhibition and $IC_{50}$ of SARS-CoV-2 inhibition. In one exemplary embodiment, the present invention relates to a recombinant binding protein comprising a polypeptide, wherein said polypeptide has an amino acid sequence that has at least about 90% sequence identity with SEQ ID NO: 88, and wherein said binding protein binds to SARS-CoV-2 spike protein with a binding affinity ($K_D$) of or below about 1 nM, wherein said binding protein has a terminal half-life in mice of at least about 40 hours, wherein said binding protein exhibits a high thermal stability with a Tm above 60° C., wherein said binding protein inhibits viral entry of SARS-CoV-2 VSV pseudovirus in VeroE6 cells with an $IC_{50}$ value of or below 1 nM, and/or wherein said binding protein inhibits viral entry of SARS-CoV-2 in VeroE6 cells with an $IC_{50}$ value of or below 1 nM.

Half-Life Extending Moieties

The "half-life extending moiety" extends the serum half-life in vivo of the recombinant binding proteins described herein, compared to the same protein without the half-life extending moiety. Examples of half-life extending moieties include, but are not limited to, polyhistidine, Glu-Glu, glutathione S transferase (GST), thioredoxin, protein A, protein G, an immunoglobulin domain, maltose binding protein (MBP), human serum albumin (HSA) binding domain, or polyethylene glycol (PEG). In some embodiments, the half-life extending moieties are glutathione S transferase (GST), protein A, protein G, an immunoglobulin domain, human serum albumin (HSA) binding domain, or polyethylene glycol (PEG).

In some embodiments, the recombinant binding protein described herein comprises an ankyrin repeat domain that specifically binds serum albumin (such as preferably human serum albumin), also referred herein as "serum albumin binding domain". The recombinant binding protein described herein may also comprise more than one serum albumin binding domain, for example, two or three or more serum albumin binding domains. Thus, the recombinant binding protein described herein may comprise a first and a second serum albumin binding domain, or a first, a second and a third serum albumin binding domain. The embodiments provided below describe such a first serum albumin binding domain, second serum albumin binding domain, and/or third serum albumin binding domain.

In some embodiments, the half-life extending moiety described herein comprises a serum albumin binding domain comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 47 to 49. In an exemplary embodiment, the half-life extending moiety described herein comprises an amino acid sequence that is at least 90% identical to any one of SEQ ID NOs: 47 to 49. In some embodiments, the half-life extending moiety described herein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 47. In an exemplary embodiment, the half-life extending moiety described herein comprises an amino acid sequence that is at least 90% identical to SEQ ID NO: 47.

In some embodiments, two or more serum albumin binding domains are preferred. In some embodiments, two serum albumin binding domains are located at the N-terminus. In exemplary embodiments, the recombinant binding protein comprises, from the N-terminus to C-terminus: (i) an ankyrin repeat domain that specifically binds serum albumin; (ii) an ankyrin repeat domain that specifically binds serum albumin; and (iii) one or more ankyrin repeat domains that specifically bind coronavirus spike protein. In certain embodiments, the N-terminal serum albumin binding domain (also referred to herein as serum albumin binding domain 1) comprises an amino acid sequence that is at least 90%, at least 91%, at least 92%, at least 93%, at least 94%, at least 95%, at least 96%, at least 97%, at least 98%, at least 99%, or 100% identical to SEQ ID NO: 47. In certain embodiments, the second serum albumin binding domain (also referred to herein as serum albumin binding domain 2) comprises an amino acid sequence that is at least 90%, at least 91%, at least 92%, at least 93%, at least 94%, at least 95%, at least 96%, at least 97%, at least 98%, at least 99%, or 100% identical to SEQ ID NO: 47.

In some embodiments, the half-life extending moiety comprises an immunoglobulin domain. In some embodiments, the immunoglobulin domain comprises an Fc domain. In some embodiments, the Fc domain is derived from any one of the known heavy chain isotypes: IgG (γ), IgM (μ), IgD (δ), IgE (ε), or IgA (α). In some embodiments, the Fc domain is derived from any one of the known heavy chain isotypes or subtypes: $IgG_1$ (γ1), $IgG_2$ (γ2), $IgG_3$(γ3), $IgG_4$ (γ4), $IgA_1$ (α1), $IgA_2$ (α2). In some embodiments, the Fc domain is the Fc domain of human $IgG_1$.

In some embodiments, the Fc domain comprises an uninterrupted native sequence (i.e., wild type sequence) of an Fc domain. In some embodiments, the immunoglobulin Fc domain comprises a variant Fc domain resulting in altered biological activity. For example, at least one point mutation or deletion may be introduced into the Fc domain so as to reduce or eliminate the effector activity (e.g., International Patent Publication No. WO 2005/063815), and/or to increase the homogeneity during the production of the recombinant binding protein. In some embodiments, the Fc domain is the Fc domain of human $IgG_1$ and comprises one or more of the following effector-null substitutions: L234A, L235A, and G237A (Eu numbering). In some embodiments, the Fc domain does not comprise the lysine located at the C-terminal position of human $IgG_1$ (i.e., K447 by Eu numbering). The absence of the lysine may increase homogeneity during the production of the recombinant binding protein. In some embodiments, the Fc domain comprises the lysine located at the C-terminal position (K447, Eu numbering).

Ankyrin Repeat Domains

In some embodiments, no more than 10, no more than 9, no more than 8, no more than 7, no more than 6, no more than 5, no more than 4, no more than 3, no more than 2, or no more than 1 substitution is made in any ankyrin repeat domain of a recombinant binding protein of the invention relative to the sequences of SEQ ID NOs: 1 to 11, 47, 76, 77 and 85. In some embodiments, no more than 5 substitutions are made relative to the sequences of SEQ ID NOs: 1 to 11, 47, 76, 77 and 85. In some embodiments, no more than 4 substitutions are made relative to the sequences of SEQ ID NOs: 1 to 11, 47, 76, 77 and 85. In some embodiments, no more than 3 substitutions are made relative to the sequences of SEQ ID NOs: 1 to 11, 47, 76, 77 and 85. In some embodiments, no more than 2 substitutions are made relative to the sequences of SEQ ID NOs: 1 to 11, 47, 76, 77 and 85. In some embodiments, no more than 1 substitution is made relative to the sequences of SEQ ID NOs: 1 to 11, 47, 76, 77 and 85. In some embodiments, the substitution(s) do not change the $K_D$ value by more than 1000-fold, more than 100-fold, or more than 10-fold, compared to the $K_D$ value of the protein comprising the sequences of SEQ ID NOs: 1 to 11, 47, 76, 77 and 85. In certain embodiments, the substitution is a conservative substitution according to Table 3. In certain embodiments, the substitution is made outside the structural core residues of the ankyrin repeat domain, e.g. in the beta loops that connect the alpha-helices.

TABLE 3

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

In certain embodiments, the substitution is made within the structural core residues of the ankyrin repeat domain. For example, the ankyrin domain may comprise the consensus sequence: DxxGxTPLHLAxxxGxxxIVxVLLxxGADVNAx (SEQ ID NO: 50), wherein "x" denotes any amino acid (preferably not cysteine, glycine, or proline); or DxxGxTPLHLAAxxGHLEIVEVLLKzGADVNAx (SEQ ID NO: 51), wherein "x" denotes any amino acid (preferably not cysteine, glycine, or proline), and "z" is selected from the group consisting of asparagine, histidine, or tyrosine. In one embodiment, the substitution is made to residues designated as "x". In another embodiment, the substitution is made outside the residues designated as "x".

In addition, the second last position of any ankyrin repeat domain of a recombinant binding protein of the invention can be "A" or "L", and/or the last position can be "A" or "N". Accordingly, in some embodiments, each ankyrin repeat domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 1 to 11, 47, 76, 77 and 85, and wherein optionally A at the second last position is substituted with L and/or A at the last position is substituted with N. In an exemplary embodiment, each spike protein binding domain comprises an amino acid sequence that is at least 90% identical to any one of SEQ ID NOs: 1 to 11, 47, 76, 77 and 85, and wherein optionally A at the second last position is substituted with L and/or A at the last position is substituted with N. Furthermore, the sequence of any ankyrin repeat domain comprised in a binding protein of the invention may optionally comprise at its N-terminus, a G, an S, or a GS (see below).

In addition, each ankyrin repeat domain comprised in a recombinant binding protein of the invention may optionally comprise a "G," an "S," or a "GS" sequence at its N-terminus. Accordingly, in some embodiments, each ankyrin repeat domain comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 1 to 11, 47, 76, 77 and 85, and further comprises at its N-terminus a GS (as e.g. in SEQ ID NOs: 1 to 11, 47, 76, 77 and 85) or only a G or an S instead of the GS.

In certain embodiments, the affinity between the recombinant binding protein and its target (spike protein or serum albumin) is described in terms of $K_D$. In exemplary embodiments, the $K_D$ is about $10^{-1}$ M or less, about $10^{-2}$ M or less, about $10^{-3}$ M or less, about $10^{-4}$ M or less, about $10^{-5}$ M or less, about $10^{-6}$ M or less, about $10^{-7}$ M or less, about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-11}$ M or less, from about $10^{-5}$ M to about $10^{-15}$ M, from about $10^{-6}$ M to about $10^{-15}$ M, from about $10^{-7}$ M to about $10^{-5}$ M, from about $10^{-8}$ M to about $10^{-15}$ M, from about $10^{-9}$ M to about $10^{-15}$ M, from about $10^{-10}$ M to about $10^{-15}$ M, from about $10^{-5}$ M to about $10^{-11}$ M, from about $10^{-6}$ M to about $10^{-14}$ M, from about $10^{-7}$ M to about $10^{-14}$ M, from about $10^{-8}$ M to about $10^{-14}$ M, from about $10^{-9}$ M to about $10^{-14}$ M, from about $10^{-10}$ M to about $10^{-14}$ M, from about $10^{-5}$ M to about $10^{-13}$ M, from about $10^{-6}$ M to about $10^{-13}$ M, from about $10^{-7}$ M to about $10^{-13}$ M, from about $10^{-8}$ M to about $10^{-13}$ M, from about $10^{-9}$ M to about $10^{-13}$ M, or from about $10^{-10}$ M to about $10^{-13}$ M.

In exemplary embodiments, the recombinant binding protein binds spike protein or serum albumin with an $K_D$ value of, or less than: about 900 nM, about 800 nM, about 700 nM, about 600 nM, about 500 nM, about 400 nM, about 300 nM, about 250 nM, about 200 nM, about 150 nM, about 100 nM, about 50 nM, about 40 nM, about 30 nM, about 20 nM, about 10 nM, about 5 nM, about 2 nM, about 1 nM, about 900 pM, about 800 pM, about 700 pM, about 600 pM, about 500 pM, about 400 pM, about 300 pM, about 200 pM, about 100 pM, about 10 pM, or about 1 pM. In one exemplary embodiment, the recombinant binding protein binds spike protein or serum albumin with a $K_D$ value of less than or equal to 100 nM. In another exemplary embodiment, the recombinant binding protein binds spike protein or serum albumin with a $K_D$ value of less than or equal to 10 nM.

Linkers

The recombinant binding proteins described herein may comprise a linker. A "linker" is a molecule or group of molecules that binds two separate entities (for example DARPin® 1 and DARPin 2® as shown in FIG. 1) to one another and can provide spacing and flexibility between the two entities such that they are able to achieve a conformation in which they can bind their respective targets. Protein linkers are particularly preferred, and they may be expressed as a component of the recombinant binding protein using standard recombinant DNA techniques well-known in the art.

The ankyrin repeat domains can be linked either covalently, for example, by a disulfide bond, a polypeptide bond or a crosslinking agent; or non-covalently, to produce a heterodimeric protein. The recombinant binding protein can comprise linkers between the coronavirus spike binding domains, and the optional half-life extending moiety.

In some embodiments, the linker is a peptidyl linker. In some embodiments, the peptidyl linker comprises about 1 to 50 amino acid residues. Exemplary linkers includes, e.g., a glycine rich peptide; a peptide comprising glycine and serine; a peptide having a sequence $[Gly-Gly-Ser]_n$, wherein n is 1, 2, 3, 4, 5, or 6; or a peptide having a sequence $[Gly-Gly-Gly-Gly-Ser]_n$ (SEQ ID NO: 54), wherein n is 1, 2, 3, 4, 5, or 6. A glycine rich peptide linker comprises a peptide linker, wherein at least 25% of the residues are glycine. Glycine rich peptide linkers are well known in the art (e.g., Chichili et al. Protein Sci. 2013 February; 22(2): 153-167).

In some embodiments, the peptidyl linker is a proline-threonine rich peptide linker. In an exemplary embodiment, the linker is the proline-threonine rich peptide linker of SEQ ID NO: 52. In another exemplary embodiment, the linker is the proline-threonine rich peptide linker of SEQ ID NO: 53.

In some embodiments, the linker comprises the amino acid sequence of SEQ ID NO: 53. Examples of longer proline-threonine rich peptide linkers are found in SEQ ID NOs: 84 and 88.

N-Terminal and C-Terminal Capping Sequences

The ankyrin repeat domains of the recombinant binding protein disclosed herein may comprise N-terminal or C-terminal capping sequences. Capping sequences refers to additional polypeptide sequences fused to the N- or C-terminal end of the ankyrin repeat sequence motif(s), wherein said capping sequences form tight tertiary interactions (i.e. tertiary structure interactions) with the ankyrin repeat sequence motif(s), thereby providing a cap that shields the hydrophobic core of the ankyrin repeat domain at the side from exposing to the solvent.

The N- and/or C-terminal capping sequences may be derived from, a capping unit or other structural unit found in a naturally occurring repeat protein adjacent to a repeat unit. Examples of capping sequences are described in International Patent Publication Nos. WO 2002/020565 and WO 2012/069655, in U.S. Patent Publication No. US 2013/

0296221, and by Interlandi et al., J Mol Biol. 2008 Jan. 18; 375(3):837-54. Examples of N-terminal ankyrin capping modules (i.e. N-terminal capping repeats) are SEQ ID NOs: 55 to 57 and examples of ankyrin C-terminal capping modules (i.e. C-terminal capping repeats) includes SEQ ID NO: 58.

Nucleic Acids & Methods

In one embodiment, the present invention relates to a nucleic acid encoding a recombinant binding protein as defined herein.

In one embodiment, the present invention relates to a nucleic acid encoding a recombinant binding protein according to one of the preceding embodiments, wherein said nucleic acid comprises or consists of SEQ ID NO 70 or a variant thereof encoding the same amino acid sequence as SEQ ID NO 70.

In one embodiment, the present invention relates to a nucleic acid encoding a recombinant binding protein according to one of the preceding embodiments, wherein said nucleic acid comprises or consists of SEQ ID NO 71 or a variant thereof encoding the same amino acid sequence as SEQ ID NO 71.

In one embodiment, the present invention relates to a nucleic acid encoding a recombinant binding protein according to one of the preceding embodiments, wherein said nucleic acid comprises or consists of SEQ ID NO 72 or a variant thereof encoding the same amino acid sequence as SEQ ID NO 72.

In one embodiment, the present invention relates to a nucleic acid encoding a recombinant binding protein according to one of the preceding embodiments, wherein said nucleic acid comprises or consists of SEQ ID NO 73 or a variant thereof encoding the same amino acid sequence as SEQ ID NO 73.

In one embodiment, the present invention relates to a nucleic acid encoding a recombinant binding protein according to one of the preceding embodiments, wherein said nucleic acid comprises or consists of SEQ ID NO 74 or a variant thereof encoding the same amino acid sequence as SEQ ID NO 74.

In one embodiment, the present invention relates to a nucleic acid encoding a recombinant binding protein according to one of the preceding embodiments, wherein said nucleic acid comprises or consists of SEQ ID NO 80 or a variant thereof encoding the same amino acid sequence as SEQ ID NO 80.

In one embodiment, the present invention relates to a nucleic acid encoding a recombinant binding protein according to one of the preceding embodiments, wherein said nucleic acid comprises or consists of SEQ ID NO 81 or a variant thereof encoding the same amino acid sequence as SEQ ID NO 81.

In one embodiment, the present invention relates to a nucleic acid encoding a recombinant binding protein according to one of the preceding embodiments, wherein said nucleic acid comprises or consists of SEQ ID NO 82 or a variant thereof encoding the same amino acid sequence as SEQ ID NO 82.

In one embodiment, the present invention relates to a nucleic acid encoding a recombinant binding protein according to one of the preceding embodiments, wherein said nucleic acid comprises or consists of SEQ ID NO 83 or a variant thereof encoding the same amino acid sequence as SEQ ID NO 83.

In one embodiment, the present invention relates to a nucleic acid encoding a recombinant binding protein according to one of the preceding embodiments, wherein said nucleic acid comprises or consists of SEQ ID NO 78 or a variant thereof encoding the same amino acid sequence as SEQ ID NO 78.

In one embodiment, the present invention relates to a nucleic acid encoding a recombinant binding protein according to one of the preceding embodiments, wherein said nucleic acid comprises or consists of SEQ ID NO 86 or a variant thereof encoding the same amino acid sequence as SEQ ID NO 86.

In one embodiment, the present invention relates to a nucleic acid encoding a recombinant binding protein according to one of the preceding embodiments, wherein said nucleic acid comprises or consists of SEQ ID NO 92 or a variant thereof encoding the same amino acid sequence as SEQ ID NO 92.

In one embodiment, the present invention relates to a nucleic acid encoding a recombinant binding protein according to one of the preceding embodiments, wherein said nucleic acid comprises or consists of SEQ ID NO 93 or a variant thereof encoding the same amino acid sequence as SEQ ID NO 93.

In one embodiment, the present invention relates to a nucleic acid encoding a recombinant binding protein according to one of the preceding embodiments, wherein said nucleic acid comprises or consists of SEQ ID NO 94 or a variant thereof encoding the same amino acid sequence as SEQ ID NO 94.

In one embodiment, the present invention relates to a nucleic acid encoding a recombinant binding protein according to one of the preceding embodiments, wherein said nucleic acid comprises or consists of SEQ ID NO 95 or a variant thereof encoding the same amino acid sequence as SEQ ID NO 95.

The present invention further relates to a vector comprising said nucleic acid molecule. In one embodiment, said vector is an expression vector.

The present invention further relates to a host cell comprising said nucleic acid molecule or said vector.

In one embodiment, the present invention relates to a method of making the recombinant binding protein as defined herein, comprising culturing the host cell defined herein under conditions wherein said recombinant binding protein is expressed.

Compositions, Uses and Methods of Treatment

The recombinant binding proteins described herein can be used to treat a subject infected with the coronavirus. In one embodiment, the subject is infected with coronavirus SARS-CoV-2.

Thus, in one embodiment, the present invention relates to a pharmaceutical composition comprising the binding protein or nucleic acid as defined herein and a pharmaceutically acceptable carrier or excipient.

The pharmaceutical compositions may comprise a pharmaceutically acceptable carrier, diluent, or excipient. Standard pharmaceutical carriers include a phosphate buffered saline solution, water, emulsions such as an oil/water or water/oil emulsion, and various types of wetting agents.

The pharmaceutical compositions can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, colouring agents, desiccants, detergents, diluents, disinfectants, disintegrants, dispersing agents, dissolution enhancing agents, dyes, emollients, emulsifying agents, emulsion stabilizers, fillers, film forming agents, flavour enhancers, flavouring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the Handbook of Pharmaceutical Excipients, Third Edition, A. H. Kibbe (Pharmaceutical Press, London, UK, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety.

The pharmaceutical compositions can be formulated to achieve a physiologically compatible pH. In some embodiments, the pH of the pharmaceutical composition can be, for example, between about 4 or about 5 and about 8.0, or between about 4.5 and about 7.5, or between about 5.0 and about 7.5. In exemplary embodiments, the pH of the pharmaceutical composition is between 5.5 and 7.5.

In another embodiment, the present invention relates to a method of treating a coronavirus infection in a subject, the method comprising the step of administering an effective amount of at least one binding protein as defined herein, or the nucleic acid as defined herein, or of the pharmaceutical composition as defined herein, to a subject in need thereof. The subject may be exhibiting any of the symptoms associated with a coronavirus infection, with differing degrees of severity, when the method of treating is administered.

In some embodiments, a single administration of the method of treating may be sufficient. In other embodiments, repeated administration may be necessary. Various factors will impact on the number and frequency of administrations, such as the age and general health of the subject, as well as the state of the subject's coronavirus infection and the severity of the symptoms associated with coronavirus infection.

In some embodiments, the method is a prophylactic method, i.e. a method of preventing a coronavirus infection in a subject. In such methods, an effective amount of at least one binding protein as defined herein, or the nucleic acid as defined herein, or of the pharmaceutical composition as defined herein is administered to a subject. Typically, the subject will not be exhibiting any of the symptoms associated with a coronavirus infection when the prophylactic method is administered.

In some embodiments, a single administration of the prophylactic method may be sufficient. In other embodiments, repeated administration may be necessary. Various factors will impact on the number and frequency of administrations, such as the age and general health of the subject, as well as the subject's risk of exposure to a coronavirus.

In certain embodiments, the coronavirus infection is caused by SARS-CoV-2. In certain embodiments, the subject is a human.

The binding proteins described herein can be administered to the subject via any suitable route of administration, such as parenteral, nasal, oral, pulmonary, topical, vaginal, or rectal administration.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. For additional details, see Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)).

The binding proteins described herein may be used in combination with another therapeutic agent, such as an analgesic. Each therapeutic agent may be administered simultaneously (e.g., in the same medicament or at the same time), concurrently (i.e., in separate medicaments administered one right after the other in any order) or sequentially in any order. Sequential administration may be useful when the therapeutic agents in the combination therapy are in different dosage forms (e.g., one agent is a tablet or capsule and another agent is a sterile liquid) and/or are administered on different dosing schedules, e.g., an analgesic that is administered at least daily and a biotherapeutic that is administered less frequently, such as once weekly or once every two weeks.

Methods of Detection or Diagnosis

In one embodiment, the present invention relates to at least one binding protein described herein for use in a method of diagnosing a coronavirus infection in a subject.

In one embodiment, the present invention relates to a method of diagnosing a coronavirus infection in a subject comprising the steps of contacting a sample from the subject in vitro or ex vivo with at least one binding protein as described herein.

In one embodiment, the present invention relates to a method of detecting a coronavirus in a subject, said method comprising:

a) obtaining a sample from a subject;

b) contacting said sample with at least one binding protein as described herein; and c) detecting the presence of a coronavirus.

In said methods and uses, the sample may be obtained from a bodily fluid such as blood, cerebrospinal fluid, plasma or urine. Samples may also be obtained from mucus (such as via nasal, oropharyngeal or vaginal swabs) or may be solid tissue samples (e.g. from biopsy).

Samples may be stored before use in any of these methods. For example, samples may be subject to cryogenic freezing for a suitable period of time before use in said methods.

In said methods and uses, the subject may be exhibiting symptoms associated with a coronavirus infection, with differing degrees of severity. Alternatively, the subject may be asymptomatic. The methods and uses may also be carried out on samples obtained from non-living subjects to investigate cause of death.

EXAMPLES

Starting materials and reagents disclosed below are known to those skilled in the art, are commercially available and/or can be prepared using well-known techniques.

Materials

Chemicals were purchased from Sigma-Aldrich (USA). Oligonucleotides were from Microsynth (Switzerland). Unless stated otherwise, DNA polymerases, restriction enzymes and buffers were from New England Biolabs (USA) or Fermentas/Thermo Fisher Scientific (USA). Inducible *E. coli* expression strains were used for cloning and protein production, e.g. *E. coli* XL1-blue (Stratagene, USA) or BL21 (Novagen, USA).

Molecular Biology

Unless stated otherwise, methods are performed according to known protocols (see, e.g., Sambrook J., Fritsch E. F. and Maniatis T., Molecular Cloning: A Laboratory Manual, Cold Spring Harbor Laboratory 1989, New York).

Cells and Viruses

Vero E6 cells (African green monkey kidney cells, ATCC® CRL1586™) purchased from ATCC (Manassas, Va. 20110 USA) were passaged in cell culture medium DMEM (FG0445) containing 10% FBS and supplements (2 mM L-Glutamine, Non-essential amino acids and 100 U/ml Penicillin 100 μg/ml Streptomycin and HEPES, all from Biochrom, Berlin, Germany) at 37° C. without $CO_2$. SARS-CoV-2 (2019-nCoV/IDF0372/2020) was propagated in Vero E6 cells in MEM containing 2% FBS and supplements (2%-FBS-MEM) at 37° C. Viruses were cultured without $CO_2$ in non-vented flasks, 24 well-, or 96 well-plates covered with sealing foil (Biorad, microseal B-film, MSB 1001) for the duration of experiments.

Designed Ankyrin Repeat Protein Libraries

Methods to generate designed ankyrin repeat protein libraries have been described, e.g. in U.S. Pat. No. 7,417,130; Binz et al. 2003, loc. cit.; Binz et al. 2004, loc. cit. By such methods designed ankyrin repeat protein libraries having randomized ankyrin repeat modules and/or randomized capping modules can be constructed. For example, such libraries could accordingly be assembled based on a fixed N-terminal capping module or a randomized N-terminal capping module, one or more randomized repeat modules, and a fixed C-terminal capping module or a randomized C-terminal capping module. Preferably, such libraries are assembled to not have any of the amino acids C, G, M, N (in front of a G residue) and P at randomized positions of repeat or capping modules.

Furthermore, such randomized modules in such libraries may comprise additional polypeptide loop insertions with randomized amino acid positions. Examples of such polypeptide loop insertions are complement determining region (CDR) loop libraries of antibodies or de novo generated peptide libraries. For example, such a loop insertion could be designed using the structure of the N-terminal ankyrin repeat domain of human ribonuclease L (Tanaka, N., Nakanishi, M, Kusakabe, Y, Goto, Y., Kitade, Y, Nakamura, K. T., EMBO J. 23(30), 3929-3938, 2004) as guidance. In analogy to this ankyrin repeat domain where ten amino acids are inserted in the beta-turn present close to the border of two ankyrin repeats, ankyrin repeat protein libraries may contain randomized loops (with fixed and randomized positions) of variable length (e.g. 1 to 20 amino acids) inserted in one or more beta-turns of an ankyrin repeat domain.

Any such N-terminal capping module of an ankyrin repeat protein library preferably possesses the RILLAA, RILLKA or RELLKA motif (e.g. present from position 21 to 26 in SEQ ID NO: 55) and any such C-terminal capping module of an ankyrin repeat protein library preferably possesses the KLN, KLA or KAA motif (e.g. present at the last three amino acids in SEQ ID NO: 58).

The design of such an ankyrin repeat protein library may be guided by known structures of an ankyrin repeat domain interacting with a target. Examples of such structures, identified by their Protein Data Bank (PDB) unique accession or identification codes (PDB-IDs), are 1WDY, 3V31, 3V30, 3V2X, 3V2O, 3UXG, 3TWQ-3TWX, 1N11, 1S70 and 2ZGD.

Examples of designed ankyrin repeat protein libraries, such as N2C and N3C designed ankyrin repeat protein libraries, have been described (U.S. Pat. No. 7,417,130; Binz et al. 2003, loc. cit.; Binz et al. 2004, loc. cit.). The digit in N2C and N3C describes the number of randomized repeat modules present between the N-terminal and C-terminal capping modules.

The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of an ankyrin repeat module of the current disclosure and consequently position 33 of an ankyrin repeat module of Binz et al. 2004, loc. cit. corresponds to position 1 of a following ankyrin repeat module of the current disclosure.

Example 1: Selection of Binding Proteins Comprising an Ankyrin Repeat Domain with Binding Specificity for SARS-CoV-2 Spike Protein Summary Using ribosome display (Hanes, J. and Plückthun, A., PNAS 94, 4937-42, 1997), multiple ankyrin repeat domains with binding specificity for different domains of the SARS-CoV-2 spike protein (RBD domain; S1 NTD domain; S2 domain) were selected from DARPin® libraries in a way similar to the one described by Binz et al. 2004 (loc. cit.), with specific conditions and additional de-selection steps. The binding and specificity of the selected clones towards recombinant SARS-CoV-2 spike protein target domains were assessed by *E. coli* crude extract Homogeneous Time Resolved Fluorescence (HTRF), indicating that multiple SARS-CoV-2 spike protein specific binding proteins were successfully selected. For example, the ankyrin repeat domains of SEQ ID NOs: 1 to 11 constitute amino acid sequences of selected binding proteins comprising an ankyrin repeat domain with binding specificity for SARS-CoV-2 spike protein.

Spike Protein Domains as Target and Selection Material

Spike protein domains were used as target and selection material. Proteins used for selections comprised SARS-CoV-2 S protein ectodomain (SARS2-Secto-d72-GCN4-Streptag), SARS-Cov-2 S protein (S1+S2 ECT, His-tag; Sinobiological 40589-V08B1), Bio-COVID-19_S1 protein-_His_Avitag (Acro Biosystems), SARS2-S1-Flag-3Streptag, COVID-19_Sprotein_RBD_Fc (Acro Biosystems), and SARS2-S1B-2Streptag. Such target proteins were selected from the polypeptides of SEQ ID NOs: 43 to 45 and 59 to 67. Proteins were biotinylated using standard methods.

Selection of SARS-CoV-2 Spike Protein-Specific Ankyrin Repeat Proteins by Ribosome Display Designed ankyrin repeat protein libraries (N2C and N3C) were used in ribosome display selections against the SARS-CoV-2 spike protein fragments (see Binz et al., *Nat Biotechnol* 22, 575-582 (2004); Zahnd et al., *Nat Methods* 4, 269-279 (2007); Hanes et al., *Proc Natl Acad Sci USA* 95, 14130-14135 (1998)).

Four selection rounds were performed per target and library. The four rounds of selection employed standard ribosome display selection, using decreasing target concentrations and increasing washing stringency to increase selection pressure from round 1 to round 4 (Binz et al. 2004, loc. cit.). The number of reverse transcription (RT)-PCR cycles after each selection round was continuously reduced, adjusting to the yield due to enrichment of binders. The 12 resulting pools were then subjected to a binder screening.

Selected Clones Bind Specifically to the RBD, S2 and S1-NTD Domains of the Spike Protein of SARS-CoV-2 as Shown by Crude Extract HTRF Individually selected ankyrin repeat proteins specifically binding to the RBD, S2 and S1-NTD domains of the spike protein of SARS-CoV-2 in solution were identified by a Homogeneous Time Resolved Fluorescence (HTRF) assay using crude extracts of ankyrin repeat protein-expressing *Escherichia coli* cells using standard protocols. Ankyrin repeat protein clones selected by ribosome display were cloned into a derivative of the pQE30 (Qiagen) expression vector, transformed into *E. coli* XL1-Blue (Stratagene), plated on LB-agar (containing 1% glucose and 50 μg/ml ampicillin) and then incubated overnight at 37° C. Single colonies were picked into a 96 well plate (each clone in a single well) containing 165 μl growth medium (LB containing 1% glucose and 50 μg/ml ampicillin) and incubated overnight at 37° C., shaking at 800 rpm. 150 μl of fresh LB medium containing 50 μg/ml ampicillin was inoculated with 8.5 μl of the overnight culture in a fresh 96-deep-well plate. After incubation for 120 minutes at 37° C. and 850 rpm, expression was induced with IPTG (0.5 mM final concentration) and continued for 6 hours. Cells were harvested by centrifugation of the plates, supernatant was discarded and the pellets were frozen at −20° C. overnight before resuspension in 8.5 μl μl B-PERII (Thermo Scientific) and incubation for one hour at room temperature with shaking (600 rpm). Then, 160 μl PBS was added and cell debris was removed by centrifugation (3220 g for 15 min).

The extract of each lysed clone was applied as a 1:200 dilution (final concentration) in PBSTB (PBS supplemented with 0.1% Tween 20® and 0.2% (w/v) BSA, pH 7.4) together with 20 nM (final concentration) biotinylated spike protein domain, 1:400 (final concentration) of anti-6His-D2 HTRF antibody—FRET acceptor conjugate (Cisbio) and 1:400 (final concentration) of anti-strep-Tb antibody FRET donor conjugate (Cisbio, France) to a well of a 384-well plate and incubated for 120 minutes at 4° C. The HTRF was read-out on a Tecan M1000 using a 340 nm excitation wavelength and a 620±10 nm emission filter for background fluorescence detection and a 665±10 nm emission filter to detect the fluorescence signal for specific binding.

The extract of each lysed clone was tested for binding to the biotinylated spike protein domains, in order to assess specific binding to the spike protein.

Further Analysis and Selection of Binding Proteins

A total of 909 binders and inhibitors were identified. Based on binding profiles, 360 candidates were selected to be expressed in 96-well format and purified to homogeneity in parallel to DNA sequencing. Candidates were characterized biophysically by size exclusion chromatography, Sypro-Orange thermal stability assessment (see Niesen et al., *Nat Protoc* 2, 2212-2221, (2007)), ProteOn surface plasmon resonance (SPR) target affinity assessment, ELISA, hACE2-competition HTRF experiments, SDS-PAGE, and/or SARS-CoV-2 pseudotype virus inhibition assay. Based on these data, 11 candidates (SEQ ID NOs: 1 to 11), binding to the RBD, S1-NTD or the S2 domain, were chosen for further analysis. This analysis also included 31 combinations in multi-domain formats (SEQ ID NOs: 12 to 42), exploring novel modes of action, determining inhibition potency, epitope and target diversity, sequence diversity, and/or biophysical properties. Multi-domain constructs were prepared using Gibson assembly as described previously (see Binz, H. K. et al. *MAbs* 9, 1262-1269, (2017)). Binding proteins of the invention were expressed with a His-tag (SEQ ID NO: 46) at their N-terminus for ease of purification or detection and tested in this His-tagged form in the experiments described below.

Engineering of Additional Binding Proteins

In further development of the initially identified binding proteins, binding domains with improved properties, such as increased affinity to and/or reduced off-rate from target protein or improved pharmacokinetic characteristics in mouse, were generated using various methods. In one approach, an initially identified binding protein (the "parental" binding protein) was selected as a suitable starting point for affinity maturation. The affinity maturation procedure entailed saturation mutagenesis of each randomized position of the ankyrin repeat domain used as a starting point. Sequences generated by the affinity maturation procedure were screened for lower off-rates by competition HTRF. Beneficial mutations identified thereby were combined in binding proteins by protein engineering. The binding properties of affinity matured and engineered binding proteins were validated by surface plasmon resonance (SPR). In another approach, certain amino acid residues in the N-terminal and/or C-terminal capping modules of the ankyrin repeat domain were altered in order to achieve improved pharmacokinetic properties, including a prolonged terminal half-life, of the ankyrin repeat domain and of proteins comprising the ankyrin repeat domain. Such altered amino acid residues were mostly surface exposed residues (see, e.g., PCT/EP2020/085855).

In one example, ankyrin repeat domains with binding specificity for the S1-NTD domain of the SARS-CoV-2 spike protein, namely vS07_08F10v27 (SEQ ID NO: 76) and vS07_08F10v47 (SEQ ID NO: 85), were generated by introducing a number of mutations in ankyrin repeat domain vS07_08F10 (SEQ ID NO: 9), in order to reduce hydrophobicity and/or increase binding affinity to and/or reduce off-rate from its target. Reduction of hydrophobicity (e.g. by altering residues in the N-terminal and C-terminal capping modules) reduced the amount of any multimerization detected by SEC, reduced viscosity and/or improved the pharmacokinetic properties in mouse. Several mutated residues were identified in an affinity maturation process using a single site mutagenesis approach on "parental" binding protein, whereby potential binding residues were randomized to all 20 amino acids by PCR, using degenerated primers. Individual variants were tested for an improved off-rate by using a competitive HTRF screening. Some individual mutations increased the HTRF signal at least up to 2 to 3-fold. As examples, mutations found in vS07_08F10v47 (SEQ ID NO: 85) include the following:

IR1_V11T: In the first internal repeat module, Valine at position 11 was mutated to Threonine based on a 2 to 3-fold higher signal in a HTRF competition assay indicating an improved off-rate;

IR2_S3K: In the second internal repeat module, Serine at position 3 was mutated to Lysine based on a 1.5 to 2-fold higher signal in a HTRF competition assay indicating an improved off-rate;

IR2_I4V: In the second internal repeat module, Isoleucine at position 4 was mutated to Valine based on a 1.5 to 2-fold higher signal in a HTRF competition assay indicating an improved off-rate, and reduced multimerization of the protein compared to parental protein;

IR2_R14Q: In the second internal repeat module, Arginine at position 14 was mutated to Glutamine based on a >3-fold higher signal in a HTRF competition assay indicating an improved off-rate;

IR2_V15S: In the second internal repeat module, Valine at position 15 was mutated to Serine based on a 1.5 to 2-fold higher signal in a HTRF competition assay indicating an improved off-rate;

C_W3V: In the C-terminal capping module, Tryptophan at position 3 was mutated to Valine based on a 1.2 to 1.5-fold higher signal in a HTRF competition assay indicating an improved off-rate, and reduced multimerization of the protein compared to parental protein;

C_14V: In the C-terminal capping module, Isoleucine at position 4 was mutated to Valine based on a 2 to 3-fold higher signal in a HTRF competition assay indicating an improved off-rate; and C_16V: In the C-terminal capping module, Isoleucine at position 6 was mutated to Valine based on a 2 to 3-fold higher signal in a HTRF competition assay indicating an improved off-rate.

In another example, an ankyrin repeat domain with binding specificity for the S2 domain of the SARS-CoV-2 spike protein having improved properties, namely the ankyrin repeat domain of SEQ ID NO: 77, was generated by introducing a number of mutations in ankyrin repeat domain vS07_14G03 (SEQ ID NO: 10).

Engineered binding proteins, such as SEQ ID NOs: 76, 77 and 85, were characterized biophysically similarly as described above for SEQ ID NOs: 1 to 11. Furthermore, combinations in multi-domain formats comprising one or more of such engineered binding domains were generated (e.g. SEQ ID NOs: 75, 84, 87 and 88), exploring novel modes of action, determining inhibition potency, epitope and target diversity, sequence diversity, and/or biophysical properties, similarly as described above for SEQ ID NOs: 12 to 42.

Example 2: SPR Binding Assays

Surface plasmon resonance (SPR) assays were used to determine the binding affinity of the binding proteins of the invention to the spike protein of SARS-CoV-2.

All SPR data were generated using a Bio-Rad ProteOn XPR36 instrument with PBS-T (0.005% Tween20) as running buffer. A new neutravidin sensor chip (NLC) was air-initialized and conditioned according to Bio-Rad manual.

Mono-domain DARPin proteins: In-house chemically biotinylated (via lysines) SARS-CoV-2 Spike Protein (Sino Biologics, cat. 40589-V08B1, Lot MF14MA0701) was captured to ~3400 RUs (30 ug/ml, 30 ul/min, 300 s). Two buffer injections (100 uV/min, 60 s) followed by two 12.5 mM NaOH regeneration steps (100 uV/min, 18 s) were applied before the first injections. Mono-domain DARPin proteins were injected (at 50/16.7/5.6/1.9/0.6 nM (or at 16.7/5.6/1.9/0.6 nM for SEQ ID NO: 9 and 10)) for 180 s at 100 ul/min for association and dissociation was recorded for 3600 s (at 100 ul/min). The ligand was regenerated with a 12.5 mM NaOH pulse (100 ul/min, 18 s). The data was double referenced against the empty surface and a buffer injection and fitted according to the 1:1 Langmuir model.

Multi-domain DARPin proteins: In-house chemically biotinylated (via lysines) SARS-CoV-2 (COVID-19) S protein RBD (cat. SPD-C5255, lot. BV3539b-203FF1-203K) was captured to ~1000 RUs (775 ng/ml, 30 uV/min, 300 s). Two buffer injections (100 ul/min, 60 s) followed by two 12.5 mM NaOH regeneration steps (100 ul/min, 18 s) were applied before the first injections. One single concentration of 25 nM of each multi-domain DARPin construct (including, e.g. ALE033, ALE030, ALE038, ALE049, ALE058) was injected for 180 s at 100 ul/min for association and dissociation was recorded for 36000 s (at 100 ul/min). The data was double referenced against the empty surface and a buffer injection. Due to avidity gain, no significant dissociation can be recorded during the measured time.

Exemplary results of SPR assays are shown in FIGS. 6, 9*a-c*, 15*a*, 16 and 17 and in Table 4. See also Example 4.

Ankyrin repeat domains according to SEQ ID Nos 1-11 were tested for their binding affinity to specific coronavirus spike protein domains using SPR (multi trace, unless indicated). In addition, other biophysical and functional properties were also tested, using methods described herein in the Examples, such as size exclusion chromatography (SEC), thermal stability measurements (Tm), and SARS-CoV-2 VSV pseudovirus neutralization assays.

Figure 9A:
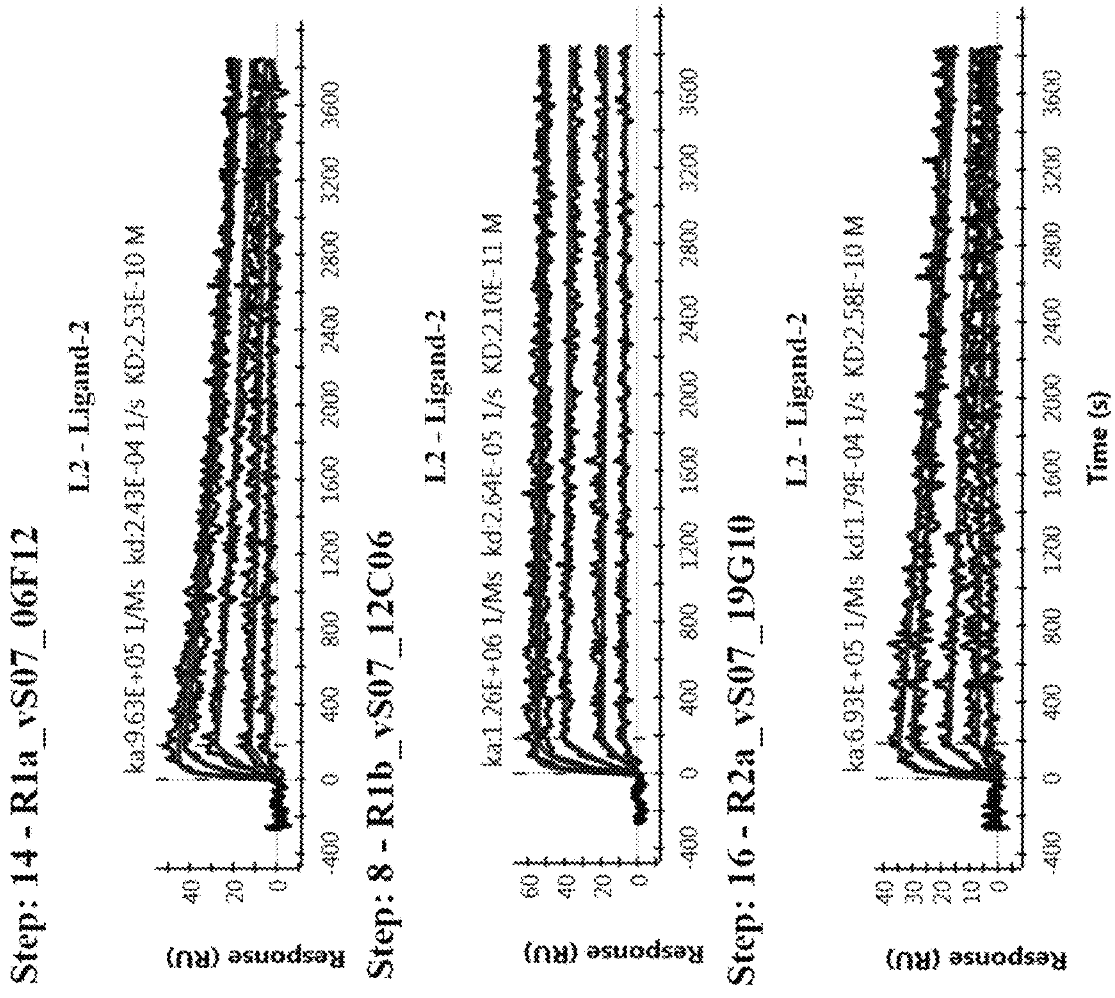
FIGS. 9*a-c*: SPR (surface plasmon resonance) trace of recombinant binding proteins comprising a single ankyrin repeat domain that binds to the spike protein. Four or five concentration SPR fitted curves confirm the high binding affinity of these mono-domain, mono-paratopic DARPin® binding proteins (e.g. in the double-digit pM range).
Figure 9B:
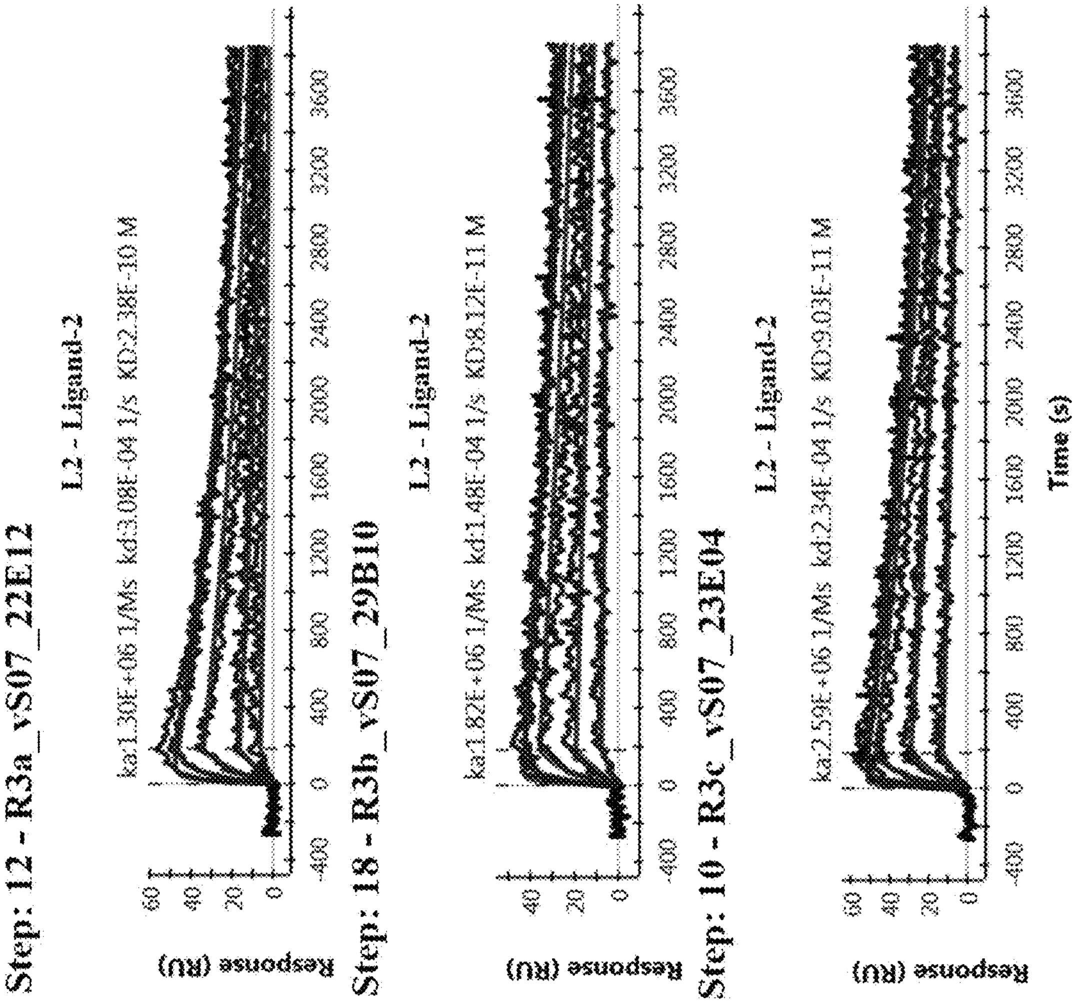
Figure 9C:
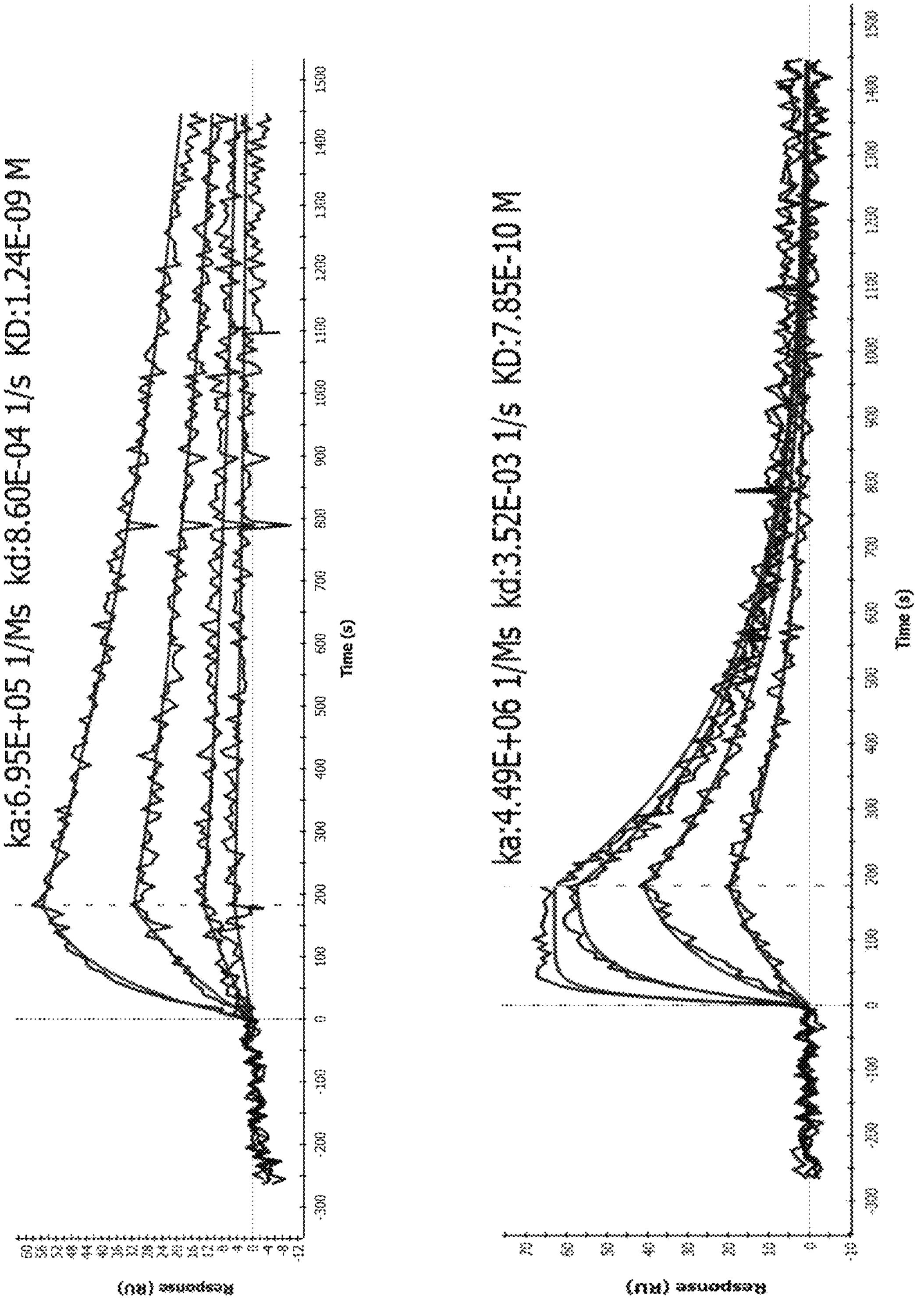
Figure 10:
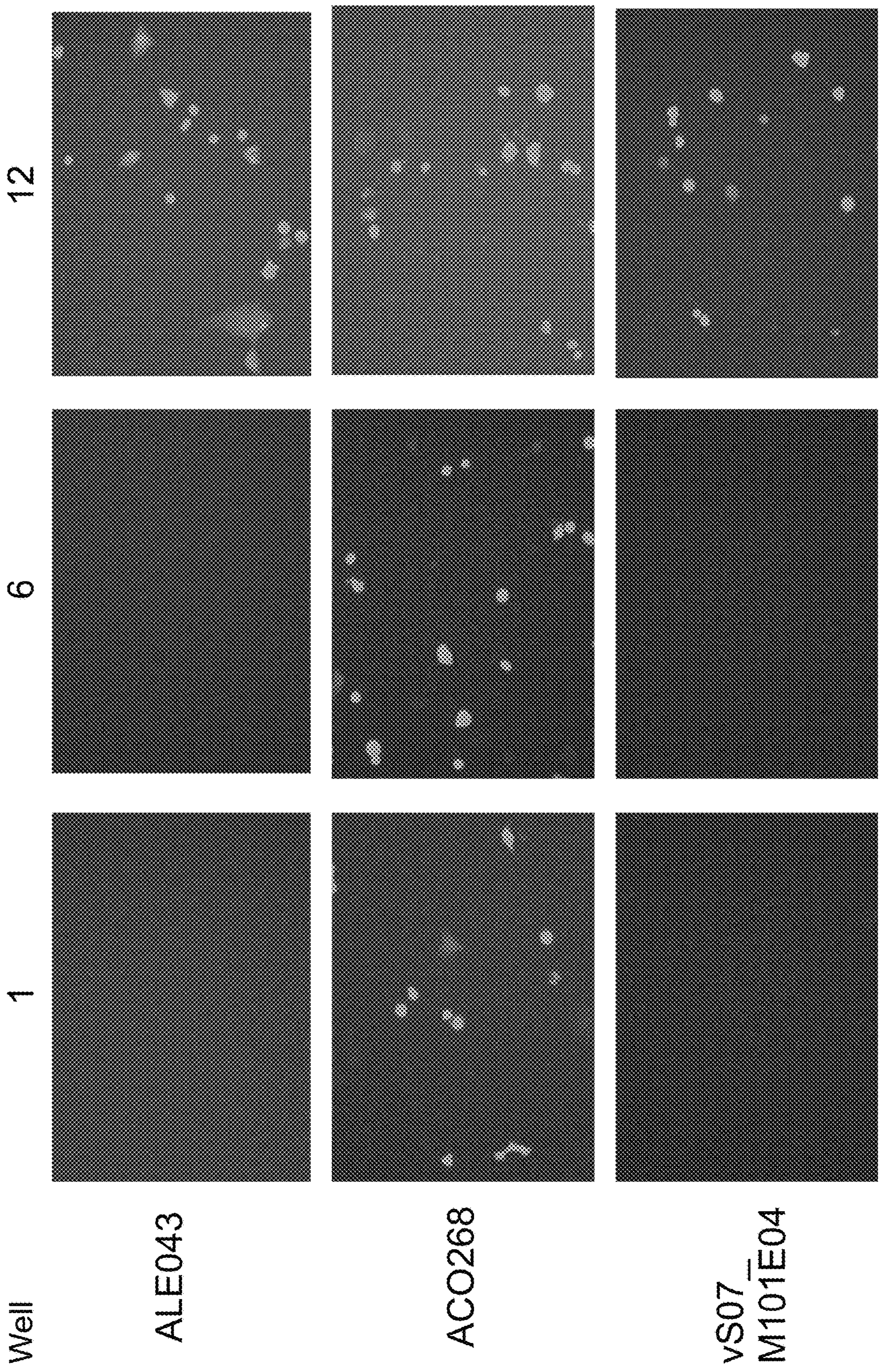
FIG. 10: Fluorescence microscopy image showing GFP positive Vero E06 cells which were infected with the GFP-labeled VSV pseudotype SARS-CoV-2 virus. DARPin® constructs ALE043 (SEQ ID NO: 25) and vS07_M101E04 do not show any infected cells in well 1 (at 100 nM concentration) and well 6 (at 3.125 nM) while there is infection of the Vero E06 cells with the GFP-labeled VSV pseudotype SARS-CoV-2 virus visible in wells 1 and 6 for the isotype negative control (his-tagged MP0250). At lower DARPin® protein concentrations in well 12 (0.049 nM) infected Vero E06 cells (GFP positive) are visible for all constructs.

Results are provided in FIGS. 9*a-c* and in Tables 4a and 4b below:

TABLE 4a

| SEQ ID NO | bio-S ecto Sino (SEQ ID NO: 44) $K_D$ [M] |
|---|---|
| 1 | 2.6E−10 |
| 2 | 2.5E−10 |
| 3 | 2.1E−11 |
| 4 | 2.4E−10 |
| 5 | 9.0E−11 |
| 6 | 8.1E−11 |
| 7 | 1.4E−08 * |
| 8 | 2.3E−08 * |

* single trace

TABLE 4b

| SEQ ID NO | SEC | Tm [° C.] | VSV-SARS-CoV-2 $IC_{50}$ [$10^{-9}$ M] |
|---|---|---|---|
| 3 | Monomer | >85° C. | <2 |
| 5 | Monomer | >85° C. | <2 |
| 6 | Monomer | >85° C. | <2 |
| 9 | Monomer | >85° C. | |
| 10 | Monomer | | <100 |

SEQ ID NOs: 1 to 8 were shown by SPR (single trace) to bind to the RBD domain or the S1 domain of the spike protein with similar affinities as indicated in Table 4a, using the bio-RBD Fc Acro (SEQ ID NO: 45) and the bio-S1 Acro (SEQ ID NO: 43) as target materials. SEQ ID NO: 9 was shown to bind to the S1 domain of the spike protein with a $K_D$ of 2.0E-08 M (single trace), using the bio-S1 Acro (SEQ ID NO: 43) as target material. SEQ ID NO: 9 and SEQ ID NO: 10 were shown to bind to the ecto-domain of the spike protein with a $K_D$ of 1.2E-09 M and 7.9E-10 M, respectively, using the S ecto U (SEQ ID NO: 61) as target material (see FIG. 9*c*). SEQ ID NO: 76 was shown to bind to the S1 domain or the ecto-domain of the spike protein with about the same $K_D$ as observed for SEQ ID NO: 9, while SEQ ID NO: 85 was found to bind to the S1 domain or the ecto-domain of the spike protein with an even higher binding affinity (i.e. a lower $K_D$) than SEQ ID NO: 9 or SEQ ID NO: 76. SEQ ID NOs: 10, 11 and 77 were shown to bind to the S2 domain of the spike protein, e.g. by HTRF assay. Table 4b shows that each of SEQ ID NOs: 3, 5, 6, 9 and 10 was monomeric in size exclusion chromatography. Furthermore, high thermal stability (>85° C.) and $IC_{50}$ values in the nanomolar range (e.g. <2 nM) when tested against SARS-CoV-2 VSV pseudovirus are indicated for several of the SEQ ID Nos.

Figure 15A:
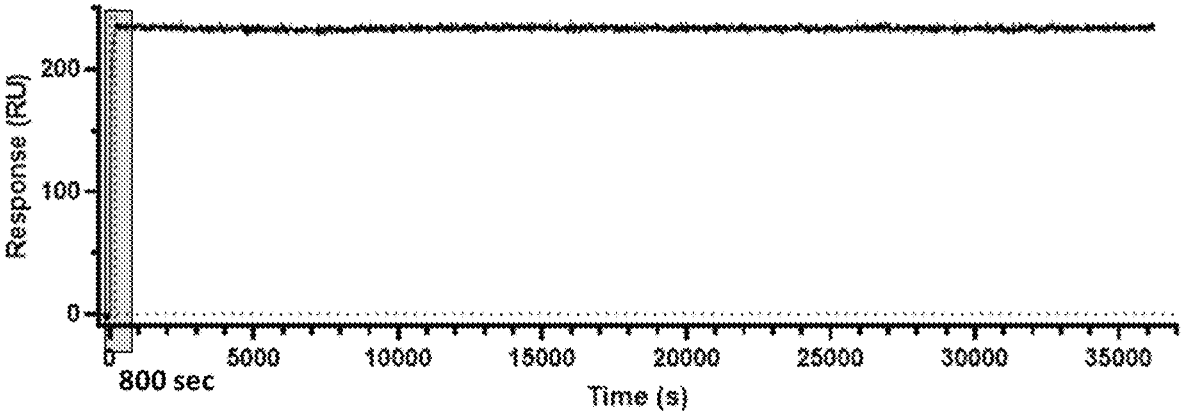
FIGS. 15*a-b*: Characterization of ALE033 (see Table 5, sample 3).
Figure 15B:
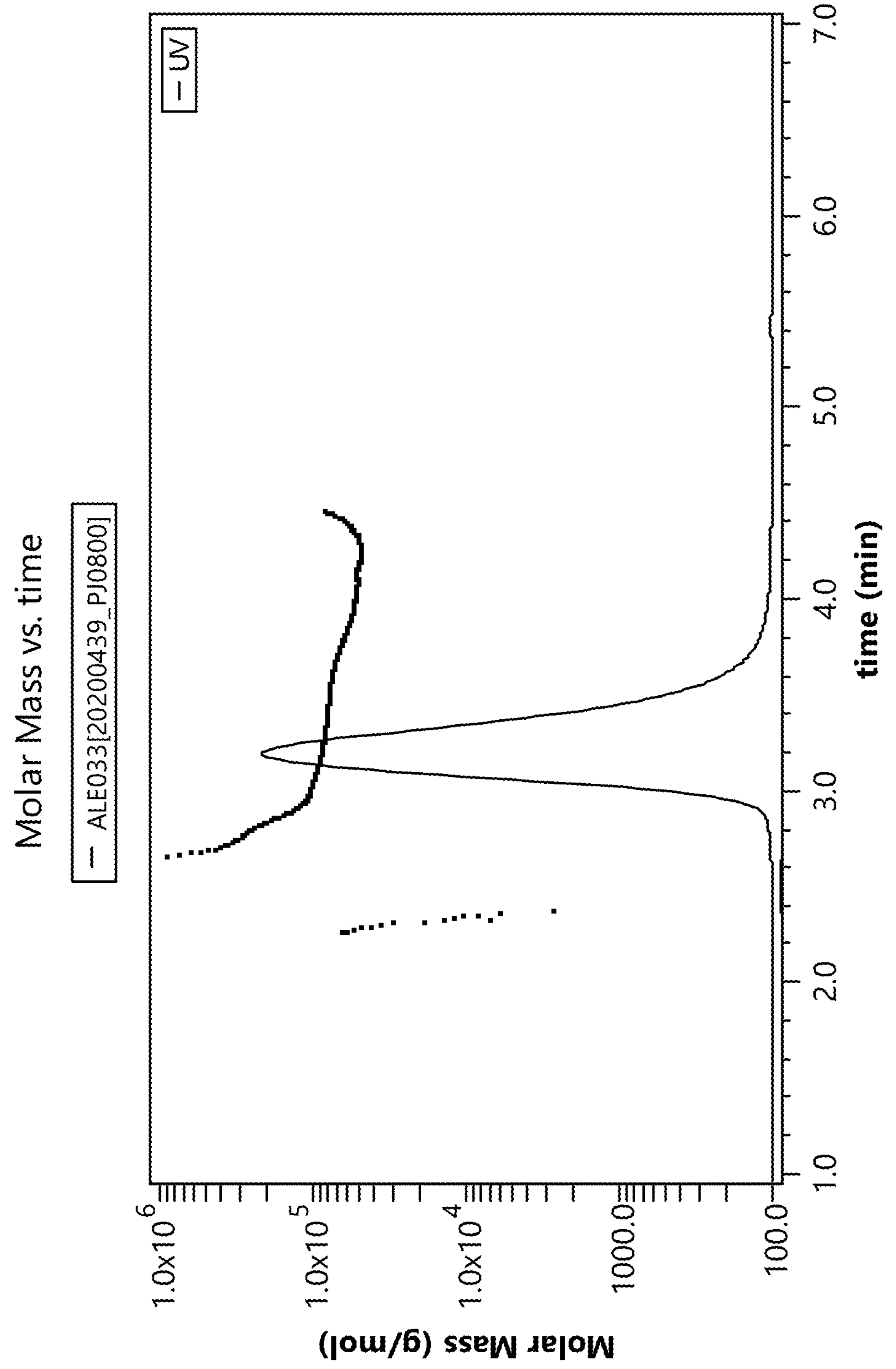
Figure 16:
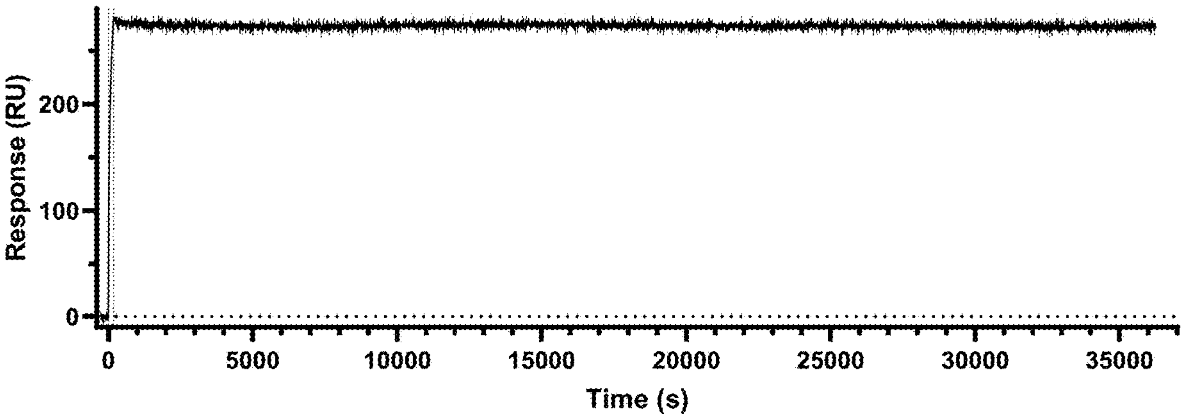
FIG. 16: SPR (surface plasmon resonance) trace for ALE030 (see Table 5, sample 1).
Figure 17:
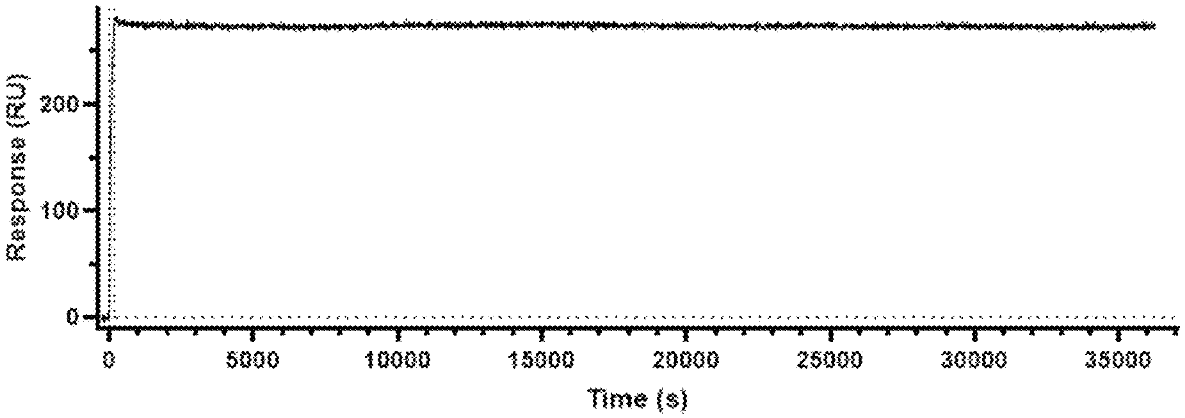
FIG. 17: SPR (surface plasmon resonance) trace for ALE038 (see Table 5, sample 7).
Figure 18A:
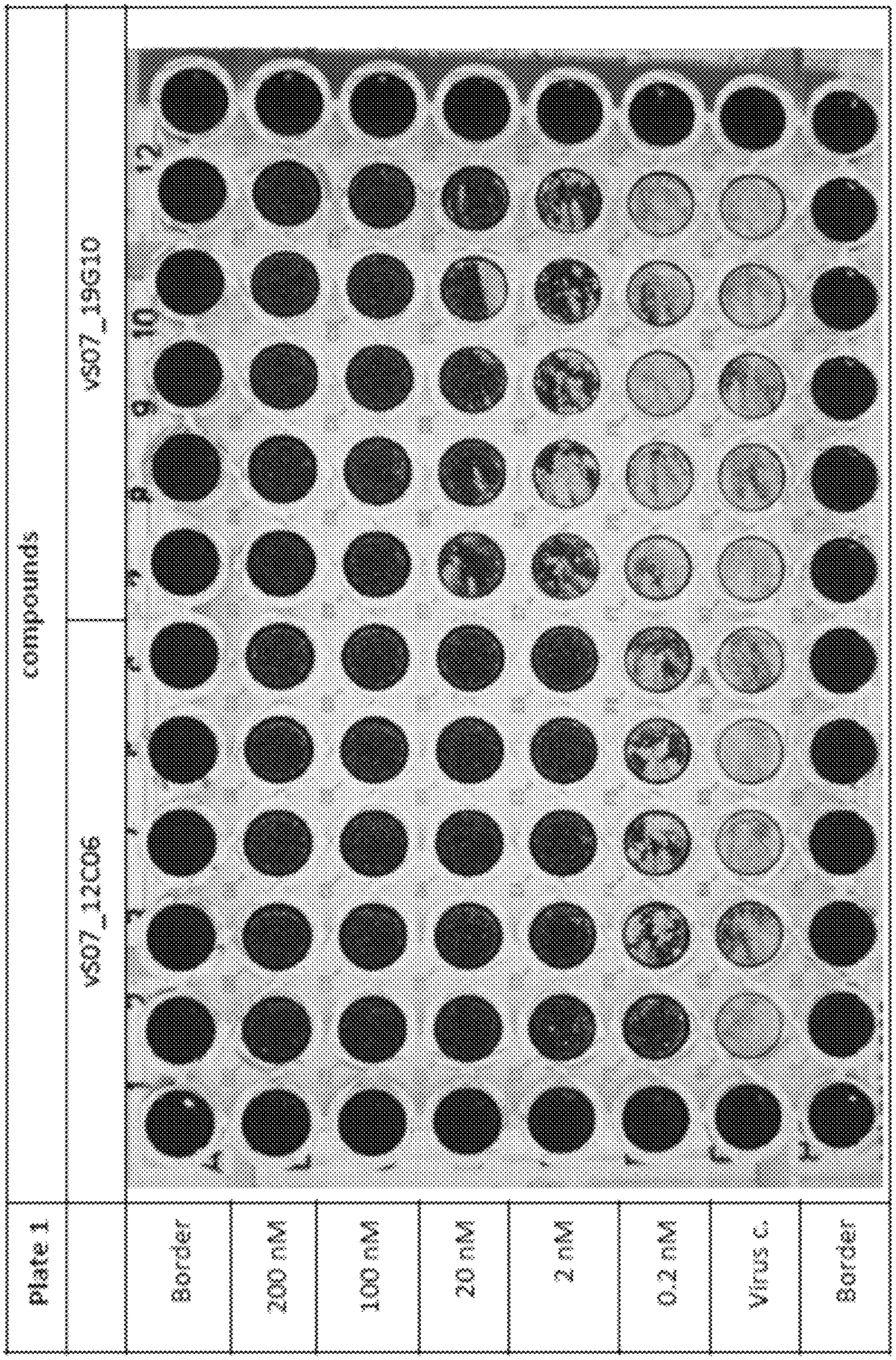
FIGS. 18*a-d*: Photographs of the test plates obtained from Example 5.
Figure 18B:
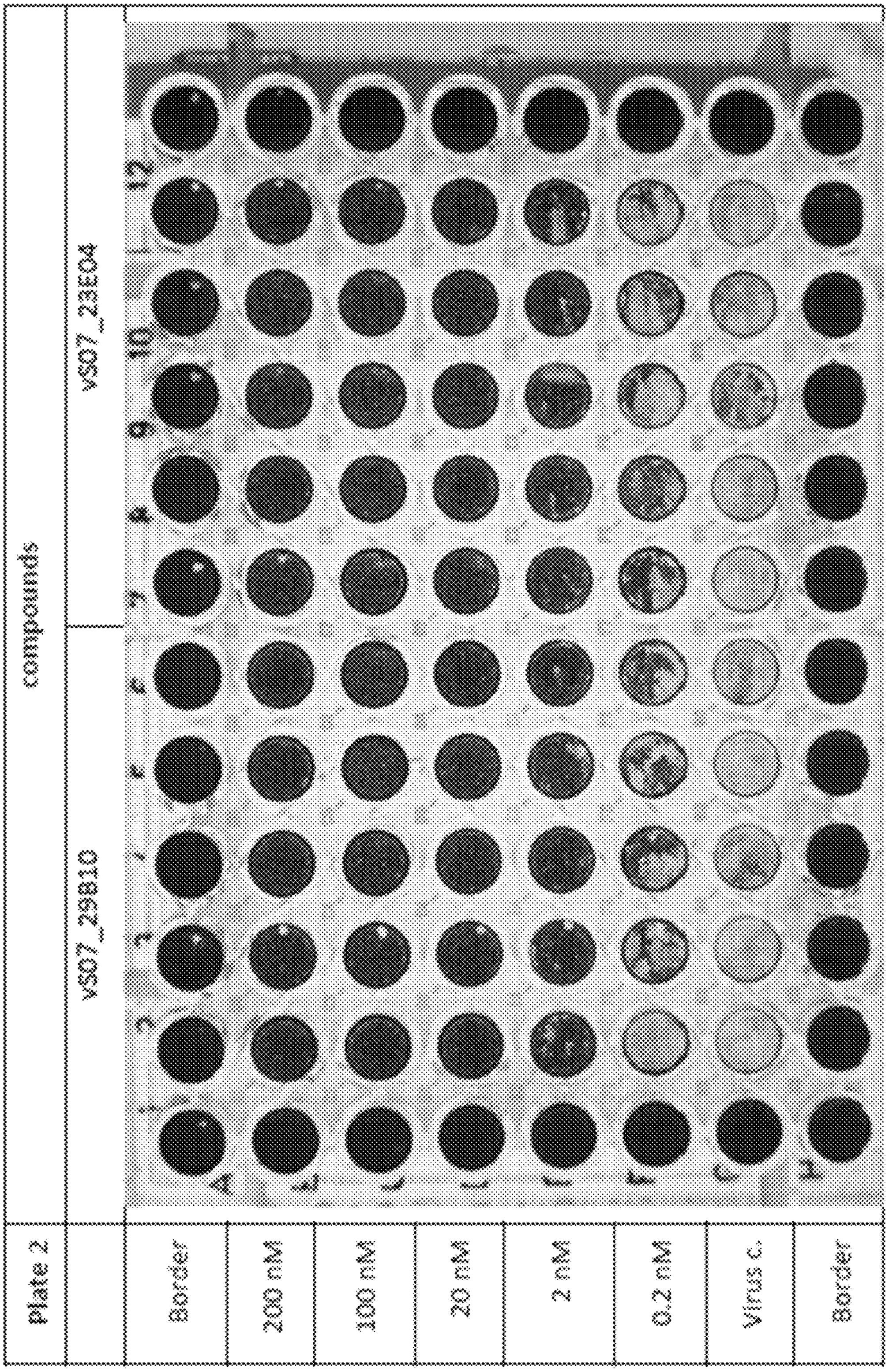
Figure 18C:
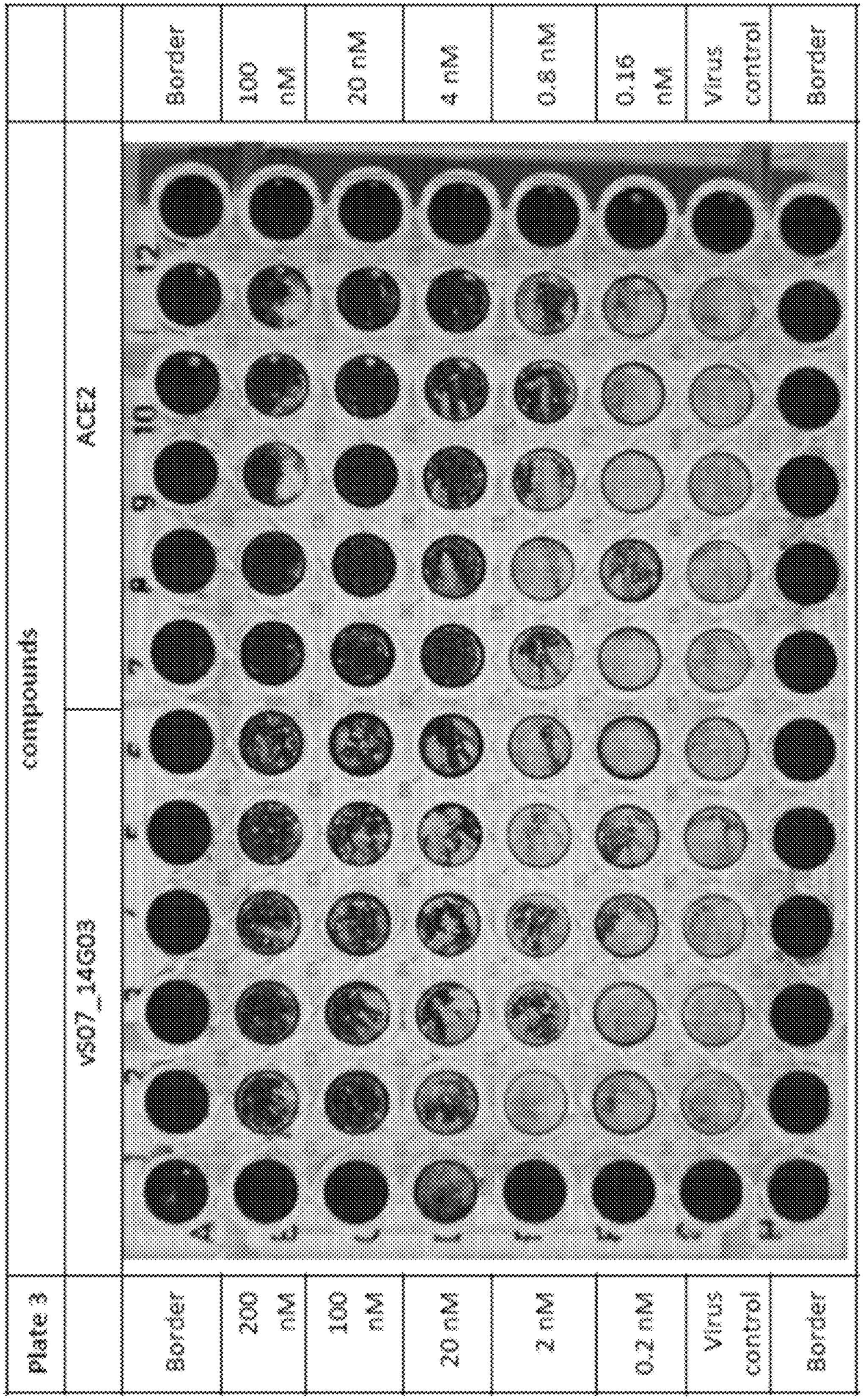
Figure 18D:
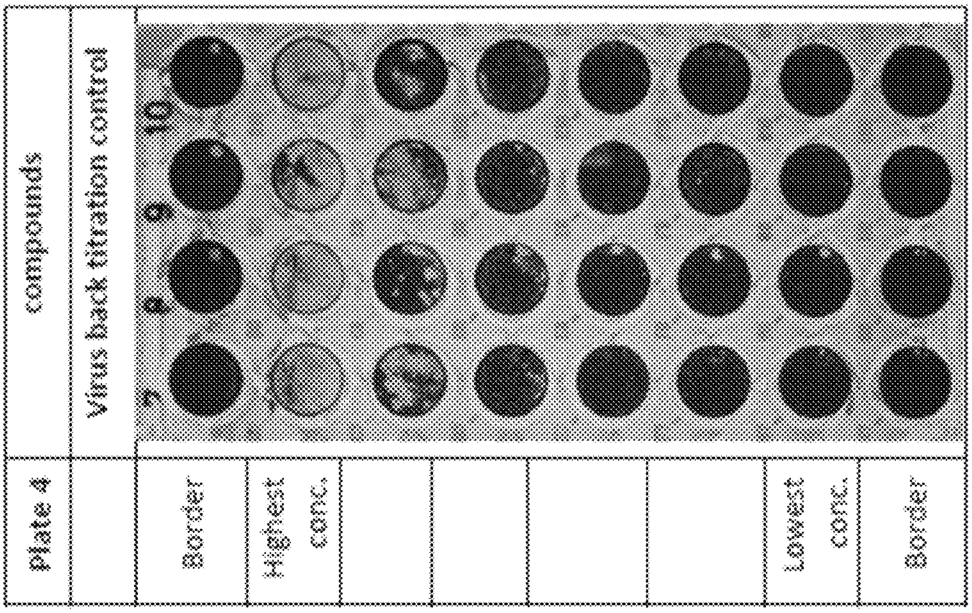

For the multi-domain DARPin proteins, no significant dissociation could be recorded during the measured time due to avidity gain (see, e.g., FIGS. 15*a*, 16 and 17). The apparent affinity of the multi-domain proteins (including, e.g., of ALE049 and ALE058) was beyond the limit of SPR, indicating sub-pM target affinity (data not shown).

Example 3: Functional Screening

This Example describes functional screening of mono-domain and multi domain proteins using the SARS-CoV-2 VSV pseudotype virus assay. The results of this assay are provided in FIGS. 5 to 8.

Infection inhibition was assessed using a vesicular stomatitis virus (VSV) pseudovirus assay (psVSV), where the glycoprotein of VSV was replaced by the Wuhan variant of the SARS-CoV-2 spike glycoprotein tagged with an enhanced green fluorescent protein (EGFP) and firefly luciferase (LUC). Inhibition of infection following addition of 1 nM, 10 nM, or 100 nM of candidate was measured by simple quantification of EGFP and LUC activity (see Torriani, G. et al., *Virology* 531, 57-68 (2019)).

Figure 5:
FIG. 5: SARS-CoV-2 VSV pseudotype virus inhibition at 100 nM of various recombinant binding proteins comprising a single ankyrin repeat domain that binds to the spike protein (mono-domain and mono-paratopic DARPin® binding proteins). Shorter bars are indicative of stronger virus inhibition.
Figure 6:
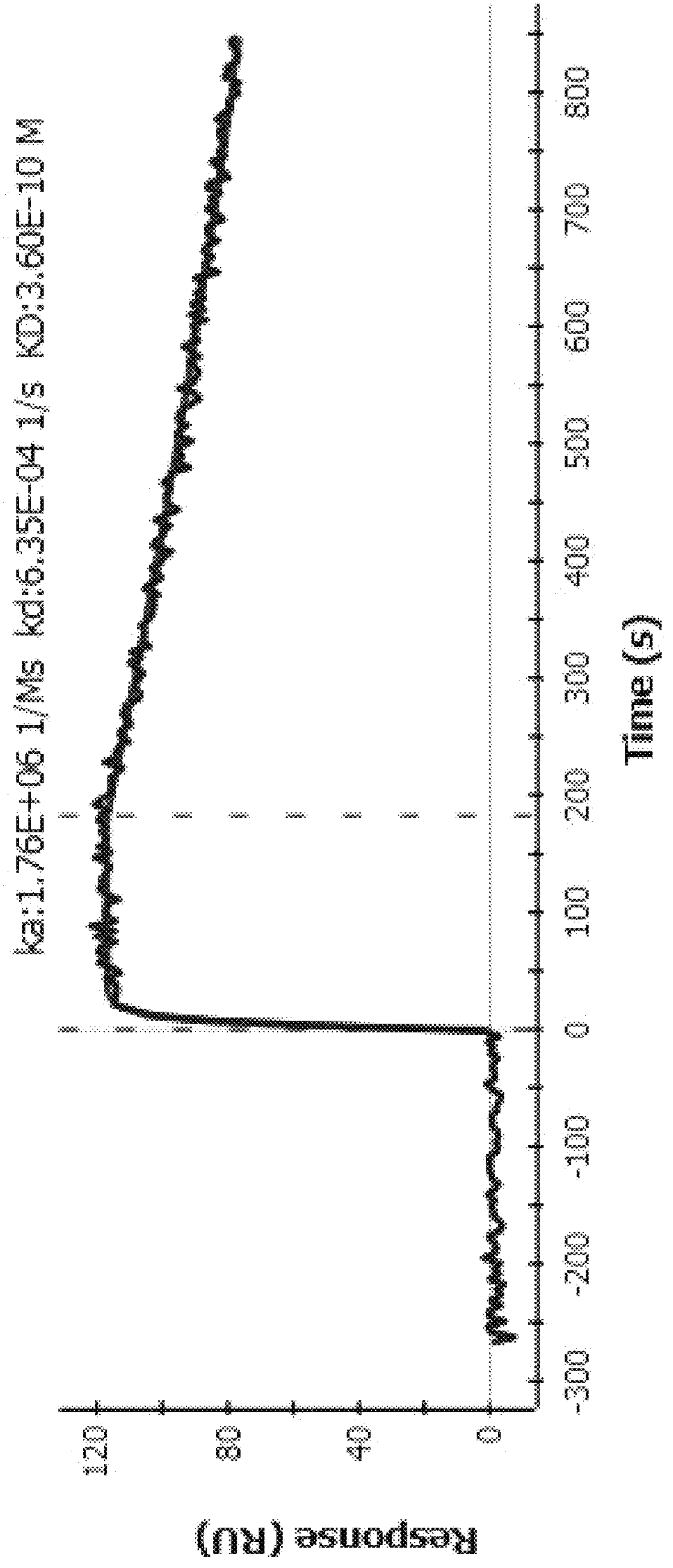
FIG. 6: Representative SPR (surface plasmon resonance) trace of a recombinant binding protein comprising a single ankyrin repeat domain that binds to the spike protein (mono-domain and mono-paratopic DARPin® binding protein).
Figure 7:
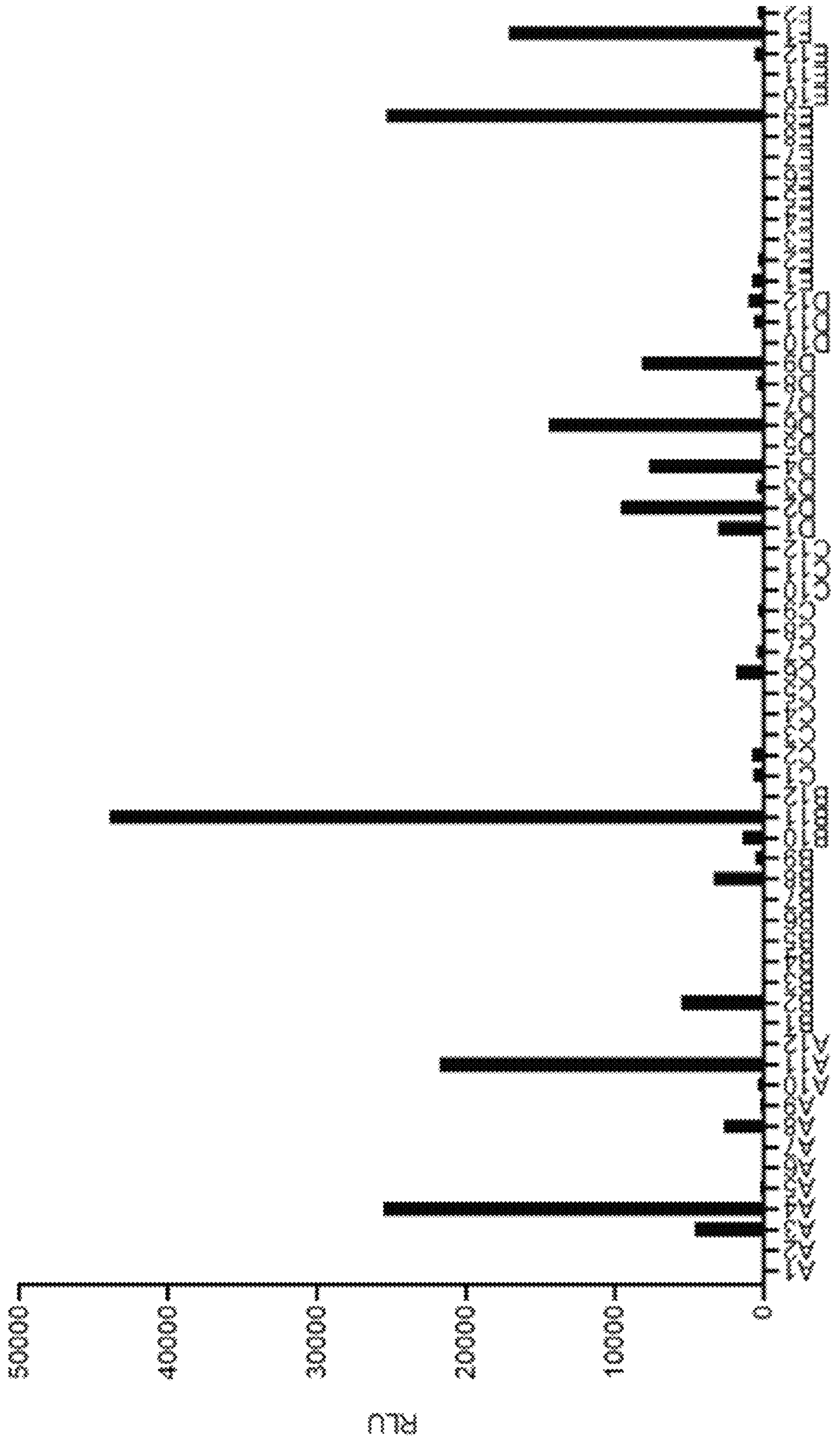
FIG. 7: SARS-CoV-2 VSV pseudotype virus inhibition at 100 nM of various recombinant binding proteins comprising three ankyrin repeat domains that bind to the spike protein (multi-domain and multi-paratopic DARPin® binding proteins). Shorter bars are indicative of stronger virus inhibition.
Figure 8:
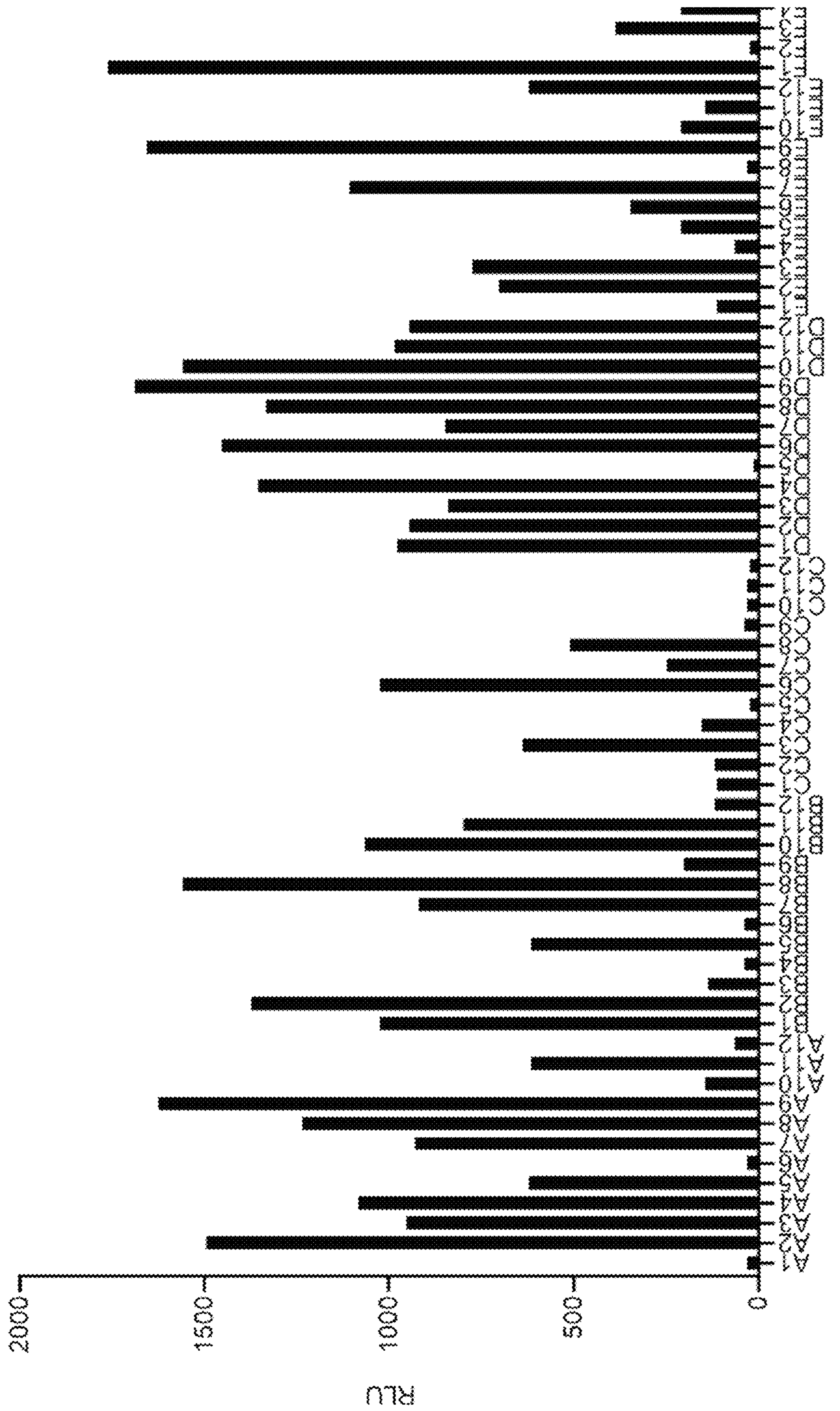
FIG. 8: SARS-CoV-2 VSV pseudotype virus inhibition at 1 nM of various recombinant binding proteins comprising three ankyrin repeat domains that bind to the spike protein (multi-domain and multi-paratopic DARPin® binding proteins). Shorter bars are indicative of stronger virus inhibition.

FIGS. 5 and 7 show pseudotype SARS-CoV-2 virus inhibition at 100 nM of various recombinant binding proteins that bind to a single site on the spike protein (mono-domain DARPin® proteins) and three sites on the spike protein (multi-domain DARPin® proteins), respectively. Shorter bars are indicative of stronger virus inhibition. FIG. 8 repeats FIG. 7 but at 1 nM. FIG. 6 shows a representative SPR trace of a mono-domain recombinant binding protein. This data shows that the Applicant was able to rapidly establish the structures of multi-domain DARPin® proteins having sub-nanomolar antiviral activity. Further rational design of the recombinant binding proteins further increased potency.

Example 4: Neutralization Assay Using SARS-CoV-2 VSV Pseudovirus (PsV nCoV)

Cells

Vero E6, plated in 9 Costar 3610, clear bottom, white plate

Pseudo SARS-CoV-2 (PsV nCoV)

2000 IU/well (25 μL)

80'000 IU/mL=8*$10^4$ IU/mL

4000 IU/well made 1.6*$10^5$ IU/mL

Per plate 100*35 μL. Prepared 4 mL of virus×8 plates=32 mL.

Took C15 at about 1*$10^6$ IU/mL 6 ml stock into 26 mL medium 2% FCS (fetal calf serum). Total 32 mL Recombinant Binding Proteins

TABLE 5

| Samples | | | | | | | | |
|---|---|---|---|---|---|---|---|---|
| Sample | Sample | 5 Domain Multi-Specific DARPin ® Designs | | | | | Stock | Vol |
| no. | name | 1 | 2 | 3 | 4 | 5 | (μM) | (μL) |
| 1 | ALE030 | H | H | R3b | R2a | R1b | 20 | 100 |
| 2 | ALE031 | H | H | R3a | R1a | R2a | 20 | 100 |
| 3 | ALE033 | H | H | R3b | R1b | R3b | 20 | 100 |
| 4 | ALE034 | H | H | RN1 | R1b | R3b | 20 | 100 |
| 5 | ALE035 | H | H | RN2 | R3a | R2a | 20 | 100 |
| 6 | ALE037 | H | H | R3a | R2a | RN2 | 20 | 100 |
| 7 | ALE038 | H | H | R1b | R3b | S1a | 20 | 100 |
| 8 | ALE039 | H | H | S1a | R1b | R3b | 20 | 100 |
| 9 | ALE040 | H | H | R2a | R3b | S1a | 20 | 100 |
| 10 | ALE041 | H | H | S1a | R3b | R2a | 20 | 100 |
| 11 | ALE042 | H | H | R3b | S1a | S2a | 20 | 100 |
| 12 | ALE043 | H | H | R1b | S1a | S2b | 20 | 100 |
| 13 | ALE044 | H | H | S2a | S1a | R3b | 20 | 100 |
| 14 | ALE045 | H | H | S2b | S1a | R1b | 20 | 100 |
| 15* | ACO268 | | | | | | 167 | |
| 16** | vS07_M101E04 | | | | | | 10 | 50 |

*negative control;
**positive control

Human Serum Albumin

A 3.0 mM stock solution of human serum albumin (HSA) was used to prepare a 10 μM solution of HSA.

The medium for this solution comprised DMEM (Dulbecco's Modified Eagle Medium) 2% FCS (fetal calf serum) and 20 μM HEPES buffer solution (4-(2-hydroxyethyl)-1-piperazineethanesulfonic acid).

Sample Dilutions 2-fold dilutions were prepared. Each dilution was mixed with one volume (PsV nCoV).

Samples 1-14: Stock at 20 μM

Prepared 300 μL (quadruplicates, 4×70 μL) at 100 nM

Dilution 1: /1/10:

Took 15 μL of the stock 20 μM+135 μL PBS Final conc. 2 μM

Dilution 2: 1/20:

Took 15 μL of the dilution 1+285 μL de milieu DMEM 2% FCS, with 20 μM HSA.

Final conc. 100 nM

Negative Control:

Dilution 1 neg control.

Dilution 1: /1/16.5:

Took 10 μL of the stock 167 μM+157 μL PBS Final conc. 10 μM

Dilution 2: 1/10:

Took 15 μL of the stock 10 μM+135 μL PBS Final conc. 1 μM

Dilution 3: /1/10:

Took 30 μL of the dilution 2+270 μL de milieu DMEM 2% FCS, with 20 μM HSA.

Positive Control:

Prepared 300 μL (quadruplicates, 4×70 μL) at 100 nM

Dilution 1: /1/10:

Took 15 μL of the stock 10 μM+135 μL PBS Final conc. 1 μM

Dilution 2: 1/10:

Took 30 μL of the dilution 1+270 μL de milieu DMEM 2% FCS, with 20 μM HSA.

Final conc. 100 nM

Prepared

In a V-bottom plate

Prepared an initial 1/10 dilution of the samples. Volume needed 4×70 μl=280 μl. Prepared 300 μl media containing 2% FCS and 10 mM HEPES and Distributed 70 μl in the quadruplicate samples Two-fold dilutions carried out in the V-bottom plate Method & Results One volume (35 μl) of PsV nCOV was added to each well before incubation for one hour at 37° C. The cells were then infected with 50 μl/well and incubated again 37° C. for 90 minutes. The inoculum was then removed, and 150 μl medium 2% FCS was added before a final incubation at 37° C. for 16 hours. After the final incubation period, the assay was stopped and infected cells (EGFP+) were counted at the appropriate dilution using an inverted fluorescence microscope. Fixation of the cells was not required. A luciferase assay was then carried out. Part of the cell media was removed (100 μl out of the 150 μl) and 50 μl of Glow (PROMEGA) was added to each well. The results were read using a Berthold® TriStar LB941 luminometer for approximately 1 sec. The data was analysed using the software Graph Pad Prism 7, and the results are provided in Table 6:

TABLE 6

| Sample no. | Sample name | Stock (μM) | $IC_{50}$ (nM) |
|---|---|---|---|
| 1 | ALE030 | 20 | 0.11950 |
| 2 | ALE031 | 20 | 0.07529 |
| 3 | ALE033 | 20 | 0.12470 |
| 4 | ALE034 | 20 | 0.24070 |
| 5 | ALE035 | 20 | 0.23770 |
| 6 | ALE037 | 20 | 0.26320 |
| 7 | ALE038 | 20 | 0.26380 |
| 8 | ALE039 | 20 | 0.27920 |
| 9 | ALE040 | 20 | 0.41750 |
| 10 | ALE041 | 20 | 0.47560 |
| 11 | ALE042 | 20 | 0.09803 |
| 12 | ALE043 | 20 | 1.26700 |
| 13 | ALE044 | 20 | 0.14710 |
| 14 | ALE045 | 20 | 0.69270 |
| 15 | ACO268 | 167 | >>250.0000 |
| 16 | vS07_M101E04 | 10 | 0.35780 |

Samples 1-14 have been found to be potent inhibitors of pseudo-SARS-CoV-2, showing an $IC_{50}$ of less 1.5 nM, and in most cases of less than 0.7 nM. Samples 2 and 11 were particularly potent, with an $IC_{50}$ of less than 0.1 nM. FIG. 5 shows fluorescence microscopy images showing GFP positive Vero E06 cells which were infected with the GFP-labeled VSV pseudotype SARS-CoV-2 virus. ALE043 in FIG. 5 corresponds to sample no. 12 in Table 6 above. ACO268 and vS07_M101E04 are the negative and positive controls respectively.

Figure 11:
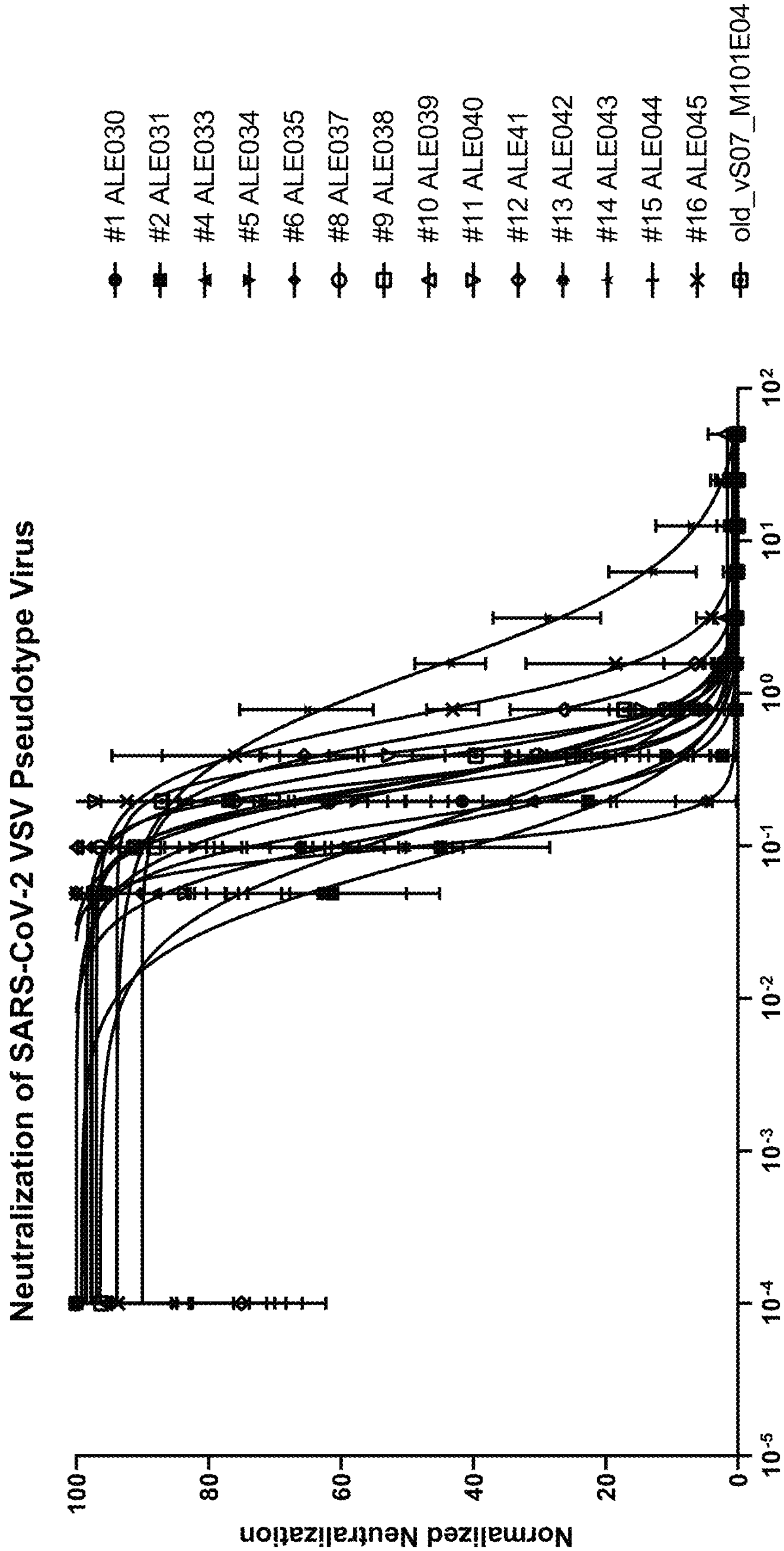
FIG. 11: Neutralization of VSV pseudotype SARS-CoV-2 virus by multi-domain DARPin® binding proteins. The names of the tested constructs (ALE030, ALE031, etc.) are indicated in the Figure.

FIG. 11 shows neutralization of SARS-CoV-2 VSV pseudotype virus.

Figure 12:
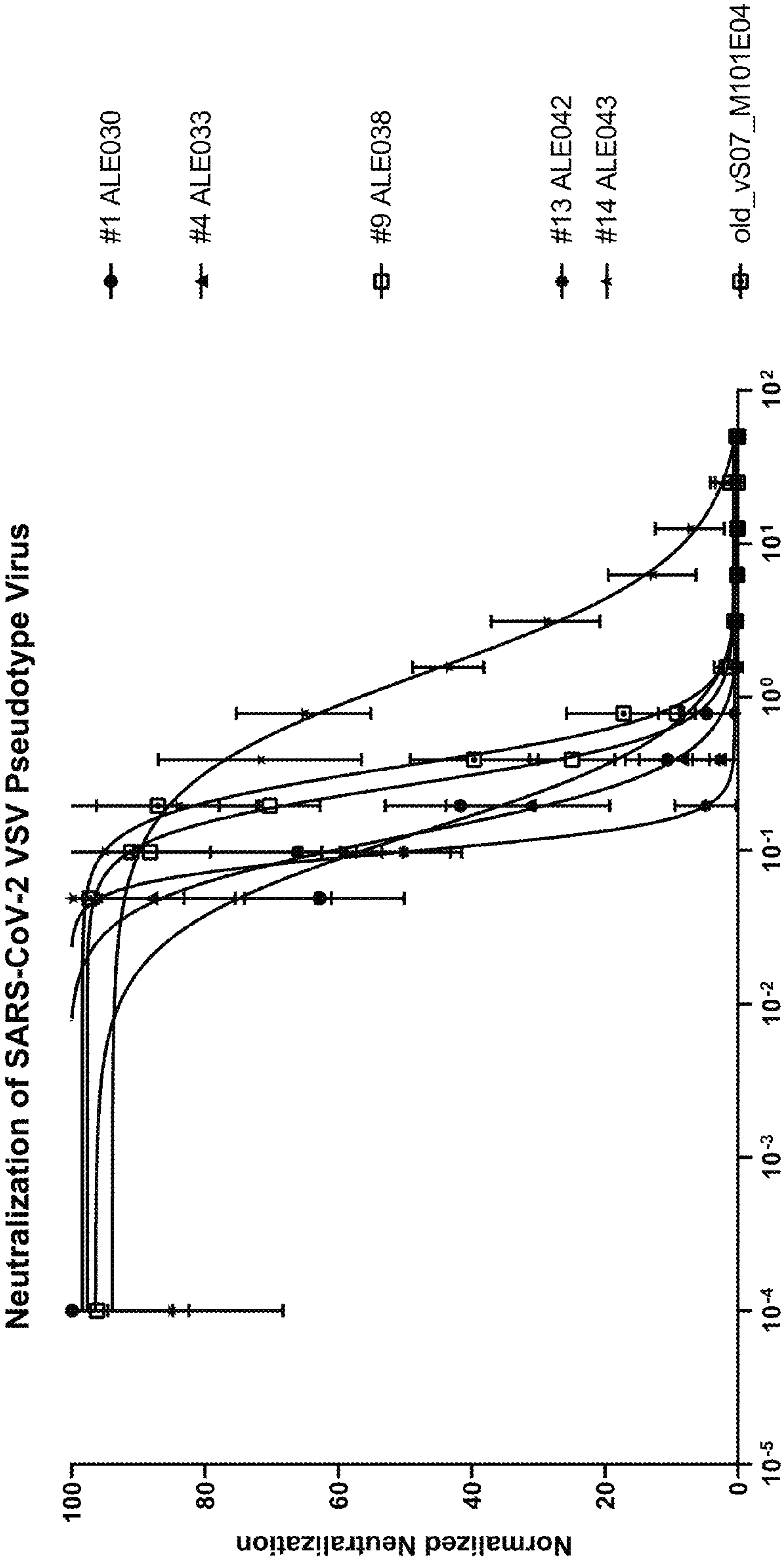
FIG. 12: Neutralization of VSV pseudotype SARS-CoV-2 virus by multi-domain DARPin® binding proteins. The names of the tested constructs (ALE030, ALE033, etc.) are indicated in the Figure.

FIG. 12 shows neutralization of SARS-CoV-2 VSV pseudotype virus for samples 1 (ALE030), 4 (ALE033), 9 (ALE038), 13 (ALE042) and 14 (ALE043). The positive control is also included (vS07_M101E04).

In FIGS. 11 and 12, titration of candidates was from 50 nM-50 pM (2-fold dilutions). The presence of 10 μM of HSA did not seem to influence the assay (see the control M101E04 without HSA-binders). The results demonstrate that half-life extended multi-domain constructs are potent inhibitors of PsV nCoV, with $IC_{50}$ values around 100 μM.

Example 5: Virus Neutralization Activity; Microtitration Assay of DARPIn® Proteins (Open Cell System)

In this example, samples were tested against SARS-CoV-2 virus samples (i.e. not pseudovirus). Samples of the compounds set out in Table 8 below were prepared in dilutions of 100 nM, 20 nM, 4 nM, 0.8 nM, 0.16 nM, 0.032 nM and 0.0064 nM.

TABLE 8

| Sample no. | Sample name | Stock (μM) | $IC_{50}$ (nM) |
|---|---|---|---|
| 1 | ALE030 | 20 | 0.11950 |
| 3 | ALE033 | 20 | 0.12470 |
| 4 | ALE034 | 20 | 0.24070 |
| 5 | ALE035 | 20 | 0.23770 |
| 6 | ALE037 | 20 | 0.26320 |
| 7 | ALE038 | 20 | 0.26380 |
| 8 | ALE039 | 20 | 0.27920 |
| 9 | ALE040 | 20 | 0.41750 |
| 10 | ALE041 | 20 | 0.47560 |
| 11 | ALE042 | 20 | 0.09803 |
| 12 | ALE043 | 20 | 1.26700 |
| 13 | ALE044 | 20 | 0.14710 |
| 14 | ALE045 | 20 | 0.69270 |

The following control samples were also prepared:

Antibody positive serum (from a patient): 1:100, 1:500, 1:2500, 1:625, . . .

Antibody negative serum: 1:100, 1:500, 1:2500, 1:625, . . .

Negative control DARPin protein: ACO268, a HSA-binding DARPin protein

ACE2

Virus back titration

Medium: MEM, 2% FCS, L-Glut, NEAA, Neo, Pen Add: 10 μM HSA (Human Serum Albumin) dilute stock 1:300

Figure 13:
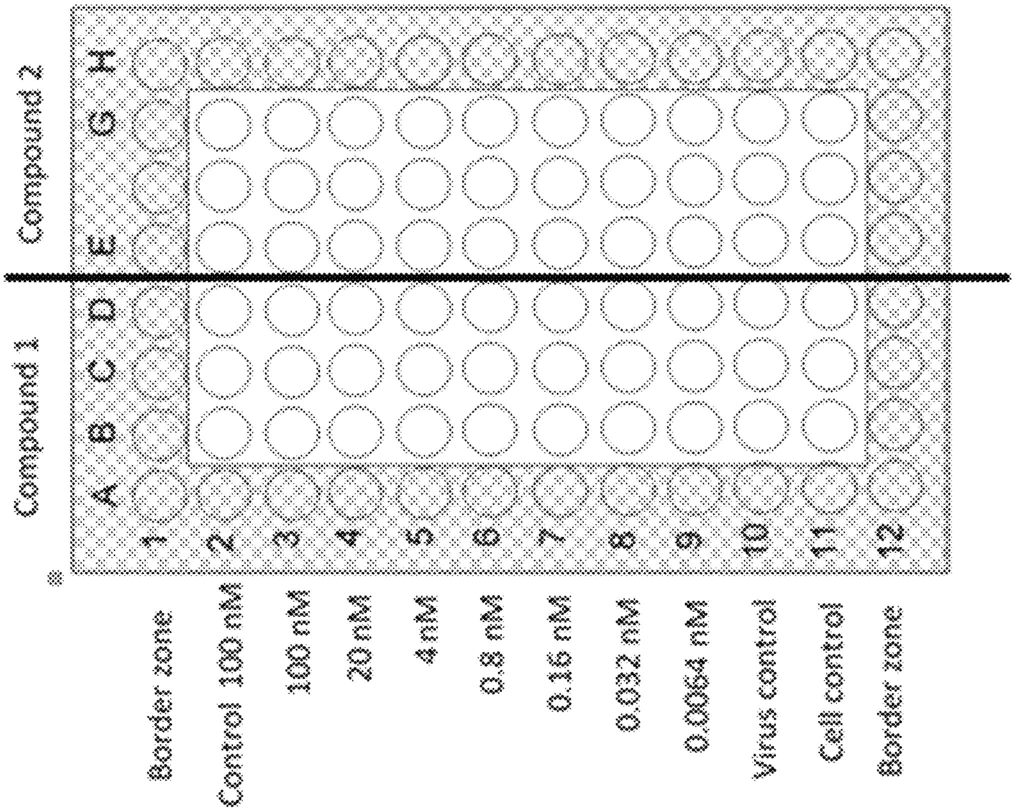
FIG. 13: A map of the test plates used in Example 4 with border zones around the edge and triplicate wells for each dilution value from 0.0064 to 100 nm, and control wells.
Figure 14A:
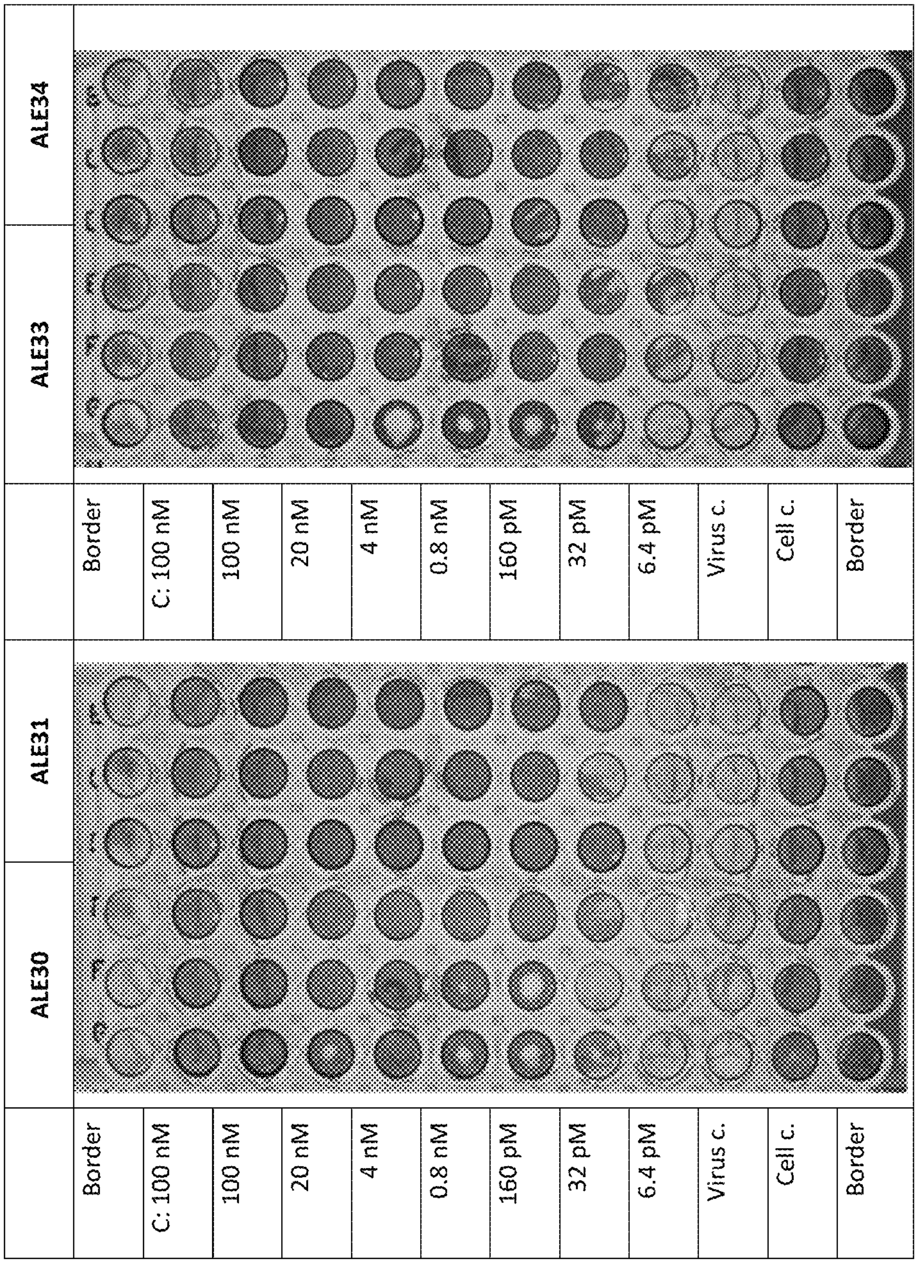
FIGS. 14*a-f*: Photographs of the test plates obtained from Example 4.
Figure 14B:
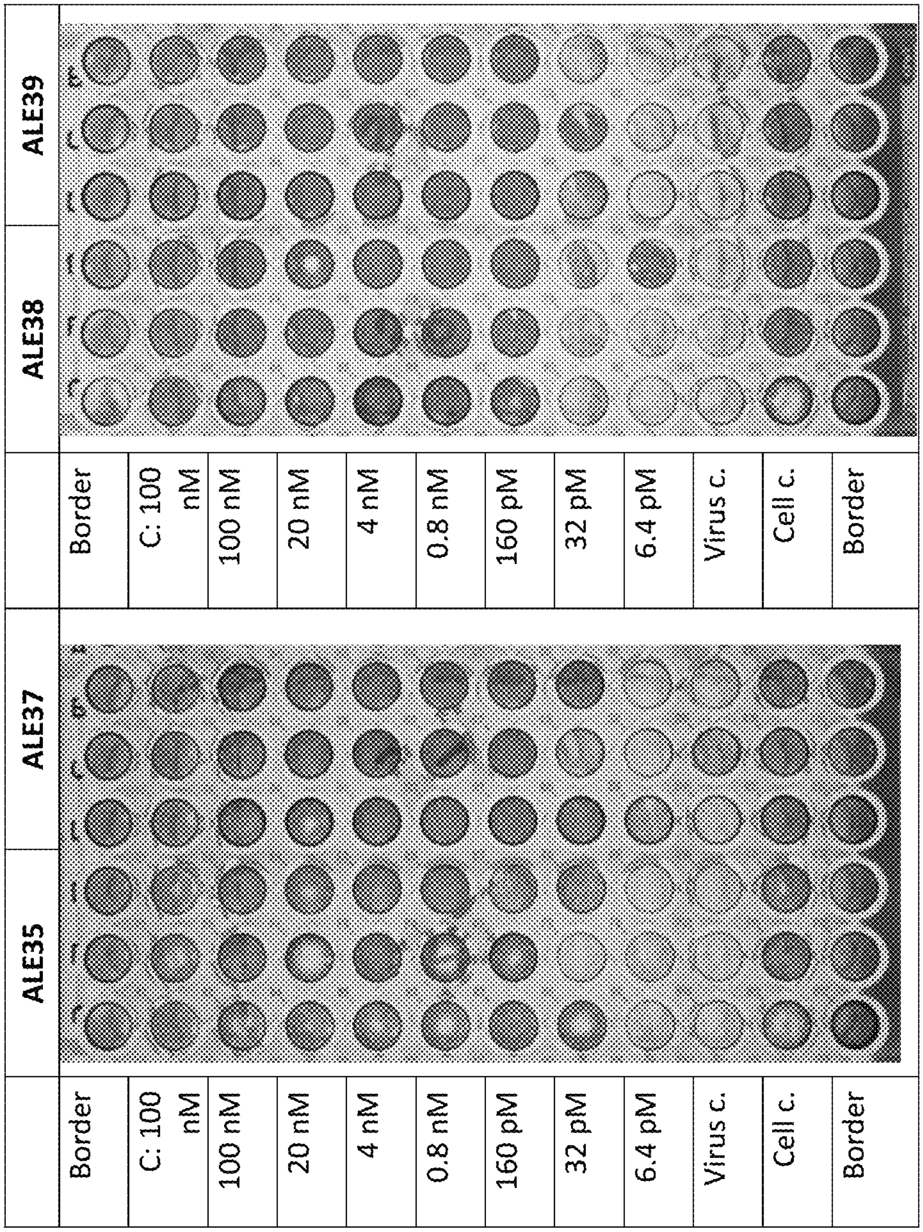
Figure 14C:
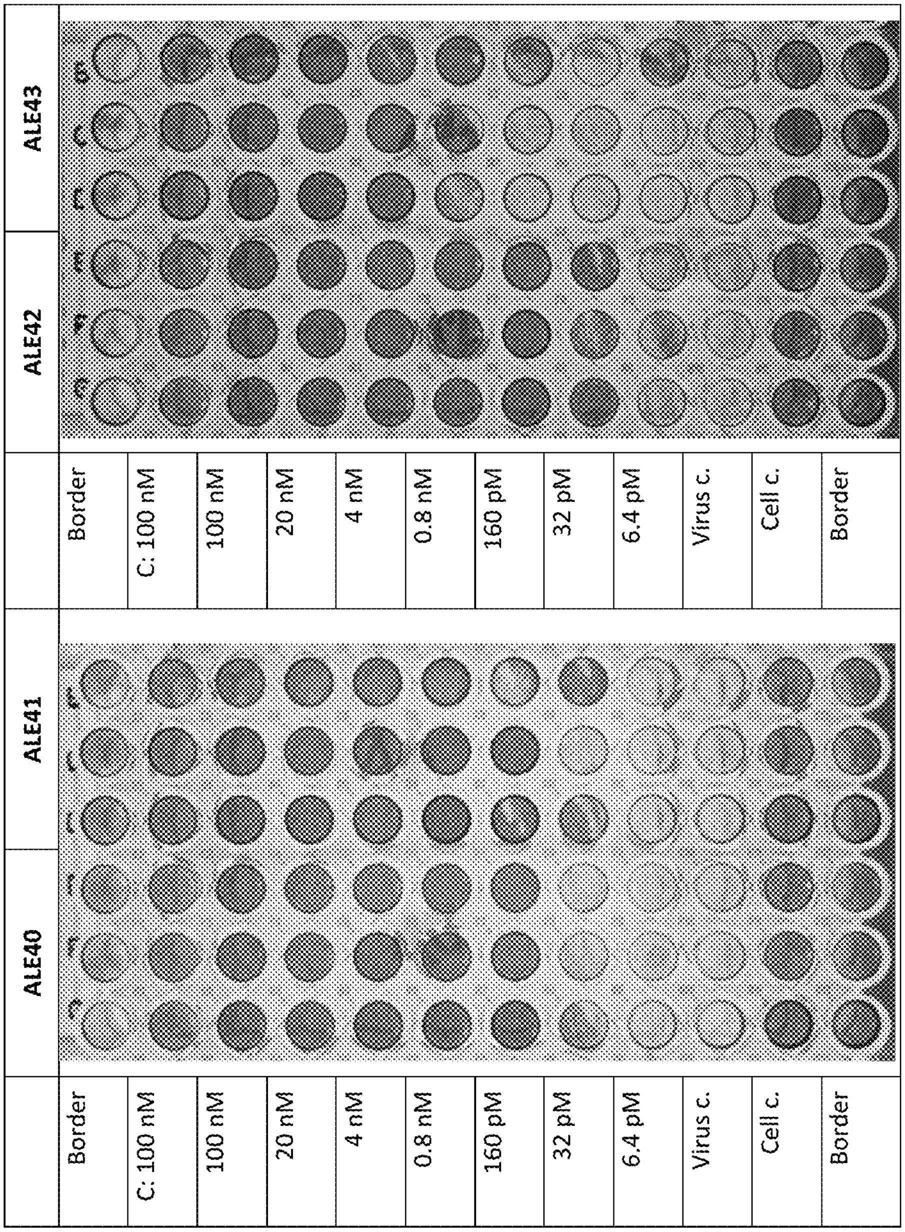
Figure 14D:
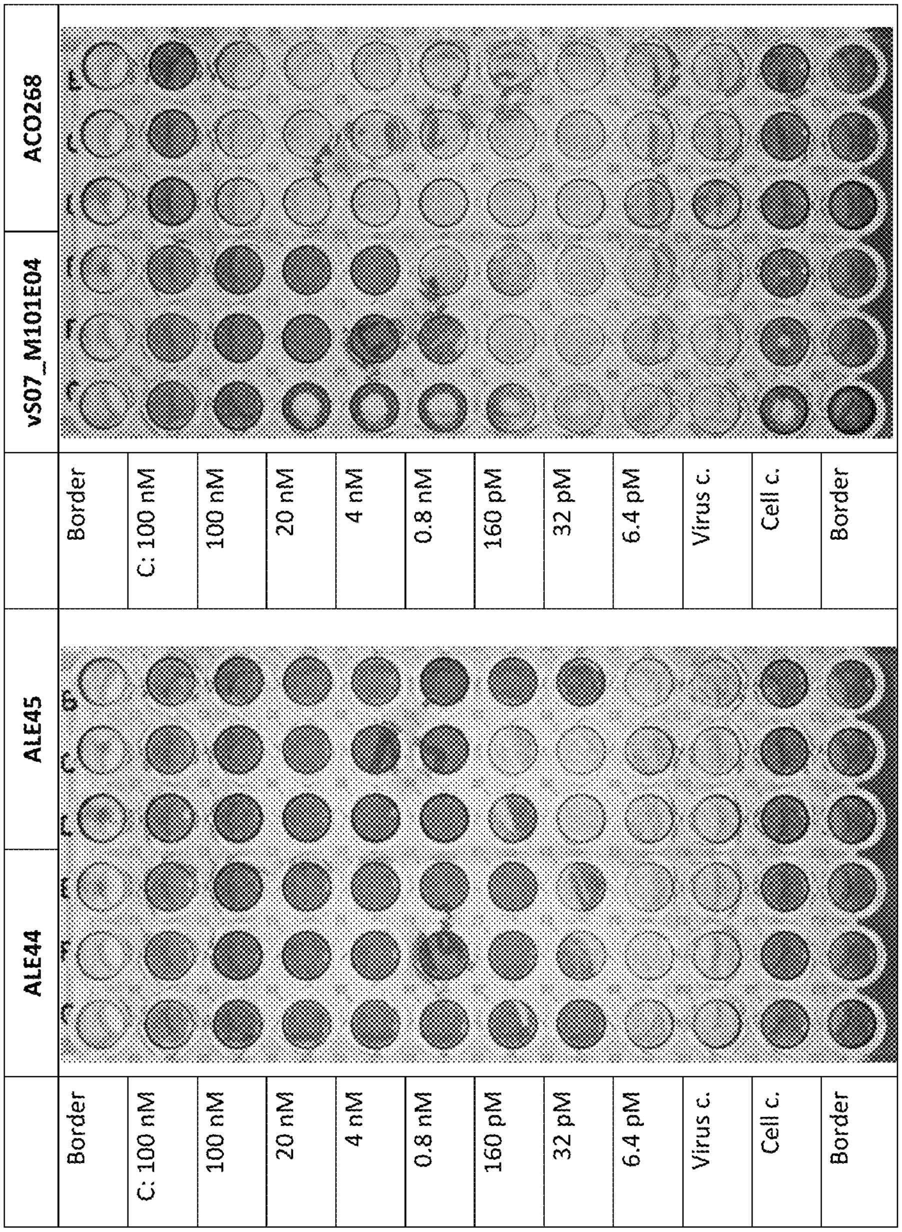
Figure 14E:
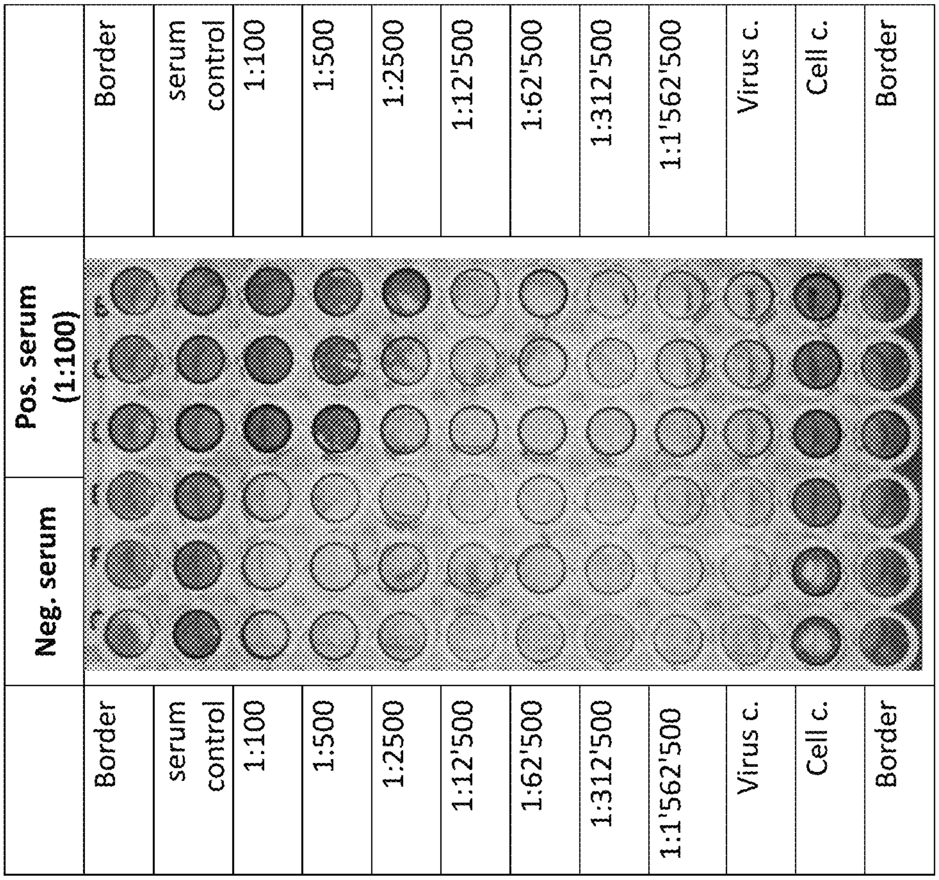
Figure 14F:
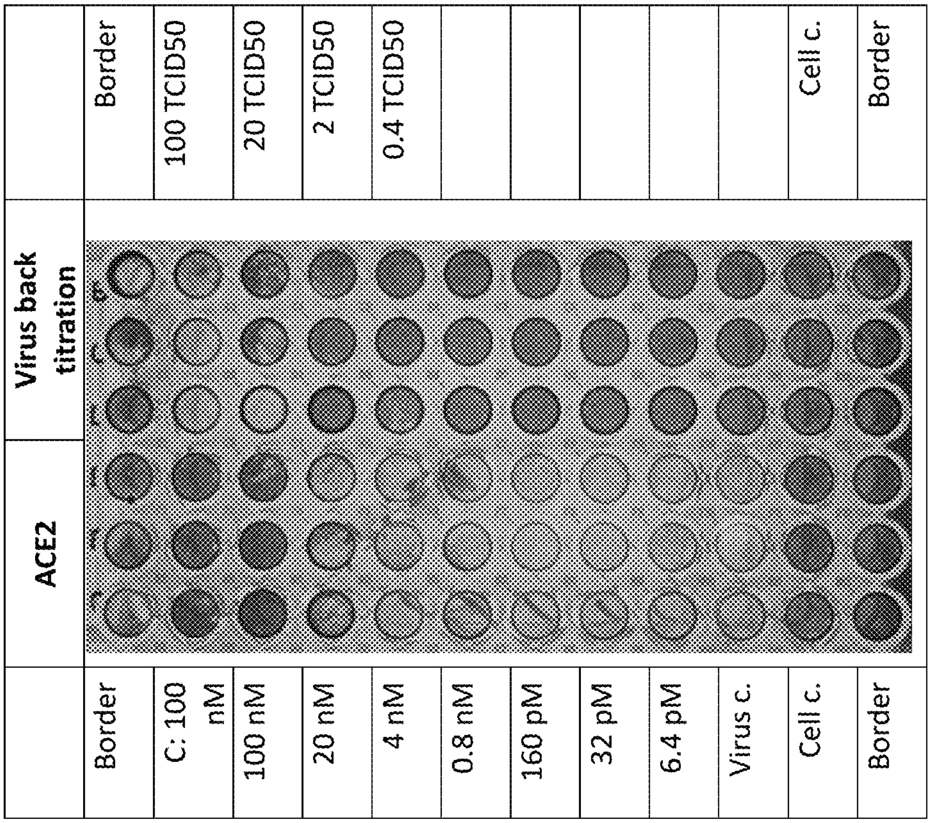

The day before the assay was carried out, a 96-well plate was prepared with confluent VeroE6 cells (open system) per two compounds to be tested. All tests were carried out in triplicate. FIG. 13 shows a map of the test plates, with border zones around the edge and triplicate wells for each dilution value from 0.0064 to 100 nm, and control wells.

The samples were diluted to 100 nM in 1 ml medium containing 2% FCS (fetal calf serum) and 10 μM HSA (human serum albumin). 100 μl medium containing 2% FCS and 10 μM HSA was added to all wells in lines 4-11. 100 μl of diluted test compound or control (100 nM) was added to line 2, and 125 μl was added to line 3. Starting from line 3, the serum was serially diluted 1:5, by mixing 25 μl of the upper row with the lower row (each time, the wells were thoroughly mixed by transferring the liquid up and down the pipette 5 times) until line 10.

6 ml of virus suspension was prepared per plate with 1000 TCID50/ml in MEM, 2% FCS, 10 μM HSA (TCID50 is the 50% tissue culture infective dose). 100 μl virus suspension (100 TCID50) was added to each well of line 3-10. The plates were incubated for 1 h at 37° C. The medium was then removed from the 96 well plate containing VeroE6 cells. 200 μl of the test compound/virus mixture was transferred to the 96 well plate with cells, and the plates were incubated for 3 days at 37° C. CPE was then determined by microscope and crystal violet staining.

The results of Example 4 are shown in FIGS. **14*a* to 14*f***. Blue colored cells indicate 100% activity; colorless cells indicate no activity. As clearly demonstrated, there was almost complete protection of the cells down to 32 μM showing that the recombinant binding proteins of the present invention are very potent inhibitors of coronavirus spike protein, and specifically SARS-CoV-2 spike protein.

Example 6: Virus Neutralization Activity; Microtitration Assay of DARPIn® Proteins (Open Cell System)

In this example, ankyrin repeat binding domains were tested against SARS-CoV-2 virus. Samples of the ankyrin repeat binding domains set out in Table 9 below were prepared in dilutions of 200 nM, 100 nM, 20 nM, 2 nM and 0.2 nM.

TABLE 9

| SEQ ID NO | Sample name |
|---|---|
| 3 | vS07_12C06 |
| 1 | vS07_19G10 |
| 6 | vS07_29E310 |
| 5 | vS07_23E04 |
| 10 | vS07_14G03 |

The following control samples were also prepared:

ACE2 100 nM, 20 nM, 4 nM, 0.8 nM, 0.16 nM

Virus back titration

Material used: Biotinylated human ACE-2 Fc, Acro Biosystems (cat #AC2-H82F9) Medium: MEM, 2% FCS, L-Glut, NEAA, Neo, Pen Add: 10 µM HSA (Human Serum Albumin) dilute stock 1:300

The day before the assay was carried out, a 96-well plate was prepared with confluent VeroE6 cells (open system) per two compounds to be tested. All tests were carried out in quintuplicate. As per FIG. 13 each 96-well plate included a border zone, and then rows of differing concentration wells, from 200 nm through 0.2 nM.

The samples were diluted to 200 nM in 1 ml medium containing 2% FCS (fetal calf serum) and 10 µM HSA (human serum albumin). 100 µl medium containing 2% FCS and 10 µM HSA was added to all wells. The ACE2 control wells were prepared in an analogous fashion, using the indicated concentrations of ACE2.

10 ml of virus suspension was prepared per plate with 1000 TCID50/ml in MEM, 2% FCS, 10 µM HSA. 100 µl virus suspension (100 TCID50) was added to each well, except for the wells at the edges of the plates (i.e. the border wells). The plates were sealed and incubated for 1 h at 37° C. The medium was then removed from the 96 well plate containing VeroE6 cells. 200 µl of the test compound/virus mixture was transferred to the 96 well plate with cells, and the plates were sealed and incubated for 2-3 days at 37° C. CPE was then determined by microscope or methyl blue staining.

The results of Example 5 are shown in FIGS. 18*a* to 18*d*. Blue colored cells indicate 100% activity; colorless cells indicate no activity. As clearly demonstrated, there was complete or almost complete protection of the cells down to 20 nM or even below, showing that the recombinant binding proteins of the present invention are very potent inhibitors of coronavirus spike protein, and specifically SARS-CoV-2 spike protein. Specifically, full protection was observed for vS07_12C06 down to 2 nM, for vS07_29B10 and vS07_23E04 down to 20 nM, and for vS07_19G10 down to 100 nM (with almost full protection at 20 nM). For vS07_14G03, partial protection was observed between 2 and 200 nM.

Figure 19:
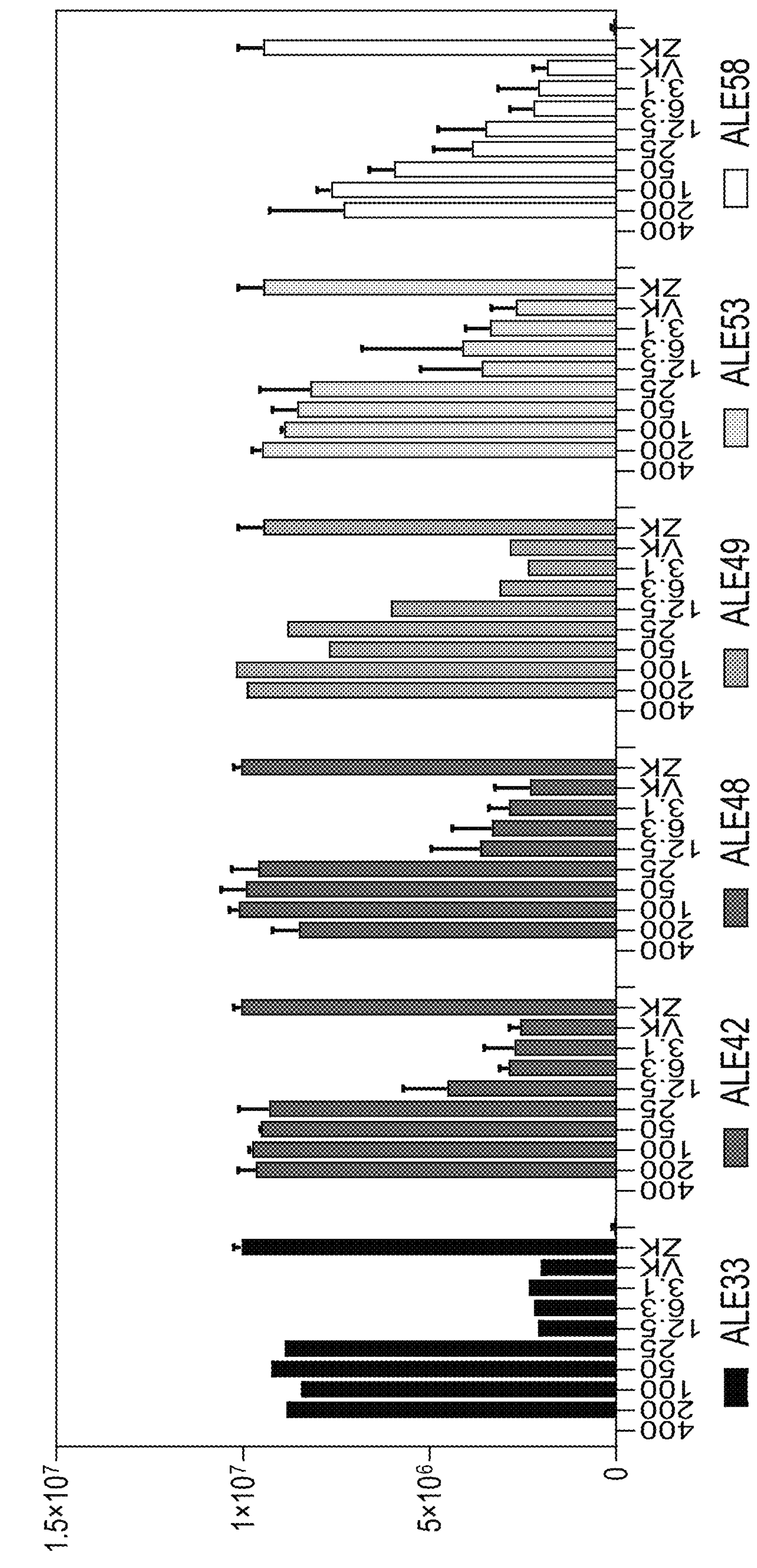
FIG. 19: Cell protection as measured with CellTiter-Glo® luminescent cell viability assay (Promega), see Example 7.

Example 7: Virus Neutralization Activity; Titration of DARPIn® Proteins in a Low Concentration Range In order to further investigate the ability of recombinant binding proteins of the invention to inhibit the infection of cells with live SARS-CoV-2, two distinct assays were performed measuring cell viability of Vero E06 cells with i) CellTiter-Glo® from Promega and ii) crystal violet staining. The samples tested are listed in Table 10, and the results are shown in FIG. 19.

TABLE 10

| SEQ ID NO | Sample name |
|---|---|
| 15 | ALE033 |
| 24 | ALE042 |
| 30 | ALE048 |
| 31 | ALE049 |
| 35 | ALE053 |
| 39 | ALE058 |

All samples were provided in 20 µM stock and were initially diluted to 800 µM, 400 µM, 200 µM, 100 µM, 50 µM, 25 µM, 12.5 µM, 6.25 µM, and 3.125 µM in 2% FCS medium containing 10 µM HSA, then further diluted 1:2 with the virus suspension.

Preparation

- 96-well plates with 80% confluent VeroE6 cells (open system) per two compounds were prepared the day before testing (compounds are tested in triplicates)
- Compounds were diluted to 800 µM in 1 ml MEM medium containing 2% FCS and 10 µM HSA.
- All compounds were serially diluted 1:2 by mixing 100 µl diluted compound in 100 µl MEM medium containing 2% FCS and 10 µM HSA.
- Border wells were kept free (only cells and medium) to avoid border effects in test
- To identify unspecific effects of compounds on cells a control line with only compound and cells was foreseen (control; line 2)
- From line 3 to 9 the compounds were serially diluted 1:2 from 200 µM to 3.125 µM
- In line 10 and 11 MEM medium containing 2% FCS and 10 µM HSA was added for the virus control and cell control Test Procedure The plate layout was similar to the layout as shown in FIG. 13, but with the compound concentrations indicated above

- Virus suspension (10 ml per plate) with 1000 TCID50/ml of SARS-CoV-2 (2019-nCoV/IDF0372/2020) in MEM medium containing 2% FCS and 10 µM HSA
- 100 µl of virus suspension (100 TCID50) was added to each well of line 3-10, medium was added to all other wells
- The plates were incubated for 1 hour at 37° C.
- From the 96 well plates containing the 80% confluent VeroE6 cells medium was removed and 200 µl of the test compound/virus mixture added to the 96 well plate with cells
- Cultures were incubated 3 days at 37° C.
- For analysis of virus genome copies by qPCR: 100 µl supernatant was inactivated in 400 µl AVL buffer+400 µl 100% EtOH→Inactivated supernatant was sluiced out of the BSL3 lab
- To determine cell viability: 100 ul CellTiter-Glo® (Promega) substrate was prepared and added according to the manufacturers protocol, plates were shaken for 2 min and fluorescence red analysed in a GloMax® (Promega).

Results

The results of testing by CellTiter-Glo® luminescent viability assay are provided in FIG. 19. VK: viral control;

ZK: cell control. Full protection of Vero E06 cells was observed at approximately 25 pM of test compound. Complete protection of cells was observed down to 25 pM for ALE033, ALE042 and ALE048. Protection was somewhat less efficient for ALE049, ALE053 and ALE058, but at least partial protection of cells was observed at 25 pM also for these compounds. In conclusion, multi-domain binding proteins of the invention are capable of inhibiting infection of cells by SARS-CoV-2 at picomolar concentrations.

Example 8: Further Characterization of Multi-Specific Binding Proteins Comprising SEQ ID NO: 31 (ALE049) or SEQ ID NO: 39 (ALE058)

Further characterization of multi-specific binding proteins comprising the amino acid sequence of SEQ ID NO: 31 or SEQ ID NO: 39 included SDS-PAGE (result: fully intact size without degradation; data not shown), mass spectrometry (result: expected molecular weight; data not shown), size exclusion chromatography coupled to static light scattering, circular dichroism, storage stability (result: stable at 60° C. for 1 week; data not shown), serum stability (result: stable at 37° C. in serum for one week; data not shown), surface plasmon resonance, SARS-CoV-2 pseudotype virus inhibition assay, live virus inhibition assay, mouse pharmacokinetic analysis (see Example 9), and hamster efficacy model (see Example 10).

Experimental Methods and Results

Circular Dichroism

Circular dichroism measurement was performed with a Jasco J-815 using a 1 cm pathlength cuvette (Hellma) with the monitor sensor inserted in the cuvette. The MRE at 222 nm was followed over a temperature ramp from 20° C. to 90° C. (heating and cooling). Spectra from 190-250 nm were taken before and after the variable temperature measurement at 20° C. The protein was measured at 0.25 μM in PBS.

Surface Plasmon Resonance Affinity Determination

SPR assays were used to determine the binding affinity of the multi-specific binding proteins to the spike protein of SARS-CoV-2. SPR experiments were performed as described in Example 2.

SARS-CoV-2 VSV Pseudotype Virus Assay

The binding proteins were assessed for inhibition potency in a SARS-CoV-2 VSV pseudotype virus assay. This assay was performed as described in detail, e.g., in Examples 3 and 4.

SARS-CoV-2 Live Virus Assay

The binding proteins were assessed for inhibition potency in a SARS-CoV-2 virus assay, similar as described in Example 5. In brief, the binding proteins were prepared in dilutions of 100 nM, 20 nM, 4 nM, 0.8 nM, 0.16 nM, 0.032 nM and 0.0064 nM in 96-well plates as described below, using the following medium: MEM, 2% FCS, L-Glut, NEAA, Neo, Pen; with addition of 10 μM HSA (Human Serum Albumin) (dilute stock 1:300). All tests were carried out in triplicates. The day before the assay was carried out, a 96-well plate was prepared with confluent VeroE6 cells (open system) per two compounds to be tested. The test plate was designed similar as shown in FIG. 13, with border zones around the edge and triplicate wells for each final dilution value from 0.0032 nM to 50 nM, and control wells. Samples were diluted to 100 nM in 1 ml medium containing 2% FCS (fetal calf serum) and 10 μM HSA (human serum albumin) (see above). 100 μl medium containing 2% FCS and 10 μM HSA was added to all wells in lines 4-11. 100 μl of diluted test compound or control (100 nM) was added to line 2, and 125 μl was added to line 3. Starting from line 3, the serum was serially diluted 1:5, by mixing 25 μl of the upper row with the lower row (each time, the wells were thoroughly mixed by transferring the liquid up and down the pipette 5 times) until line 10. 6 ml of virus suspension was prepared per plate with 1'000 TCID50/ml in MEM, 2% FCS, 10 μM HSA. 100 μl virus suspension (100 TCID50) was added to each well of lanes 3-10. The plates were incubated for 1 h at 37° C. The medium was then removed from the 96 well plate containing VeroE6 cells. 200 μl of the test compound/virus mixture was transferred to the 96 well plate with cells, and the plates were incubated for 3 days at 37° C. Cytopathic effect was then determined either by microscope and crystal violet staining, where blue colored cells indicate 100% activity and colorless cells indicate no activity (see FIG. 20), or, alternatively, using a CellTiter-Glo® luminescent cell viability assay (Promega; see FIGS. 21*a-c*). For the latter, 1'000, 10'000, or 100'000 TCID50 were used.

Figure 20:
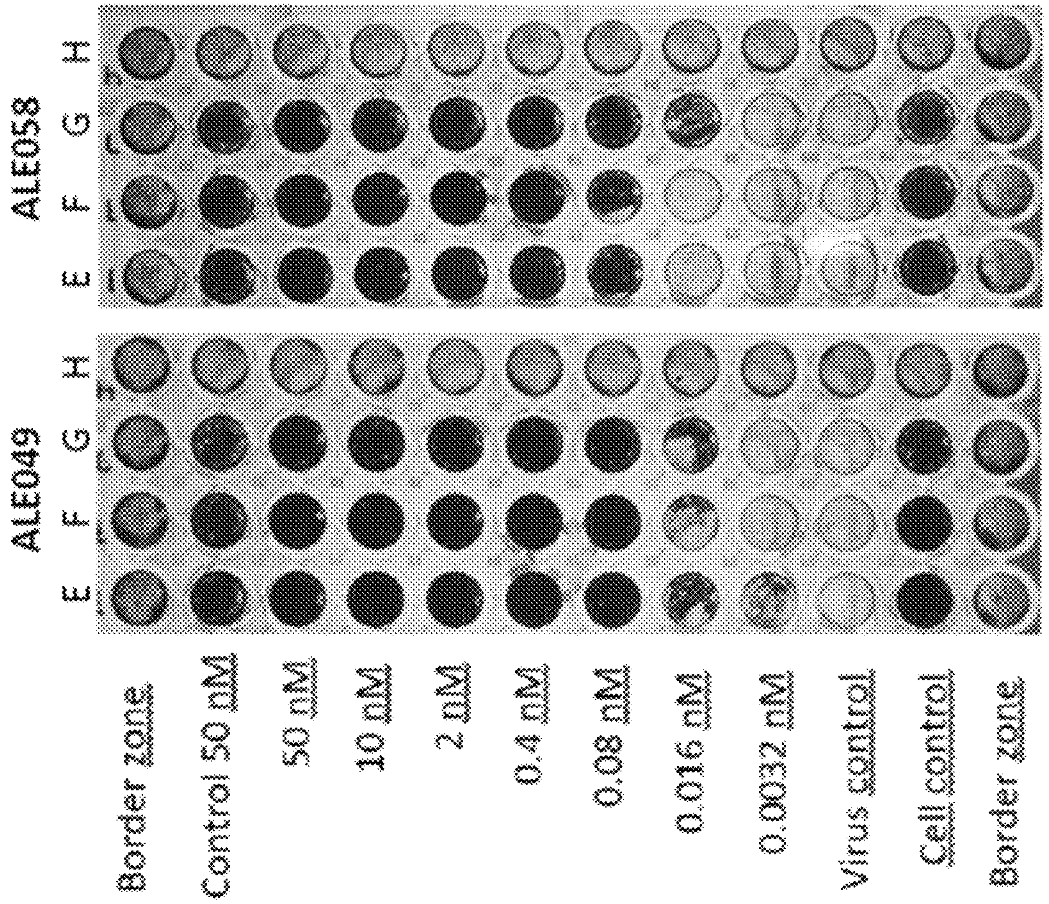
FIG. 20: Photographs of the test plates obtained following violet crystal staining, see Example 8.
Figure 21A:
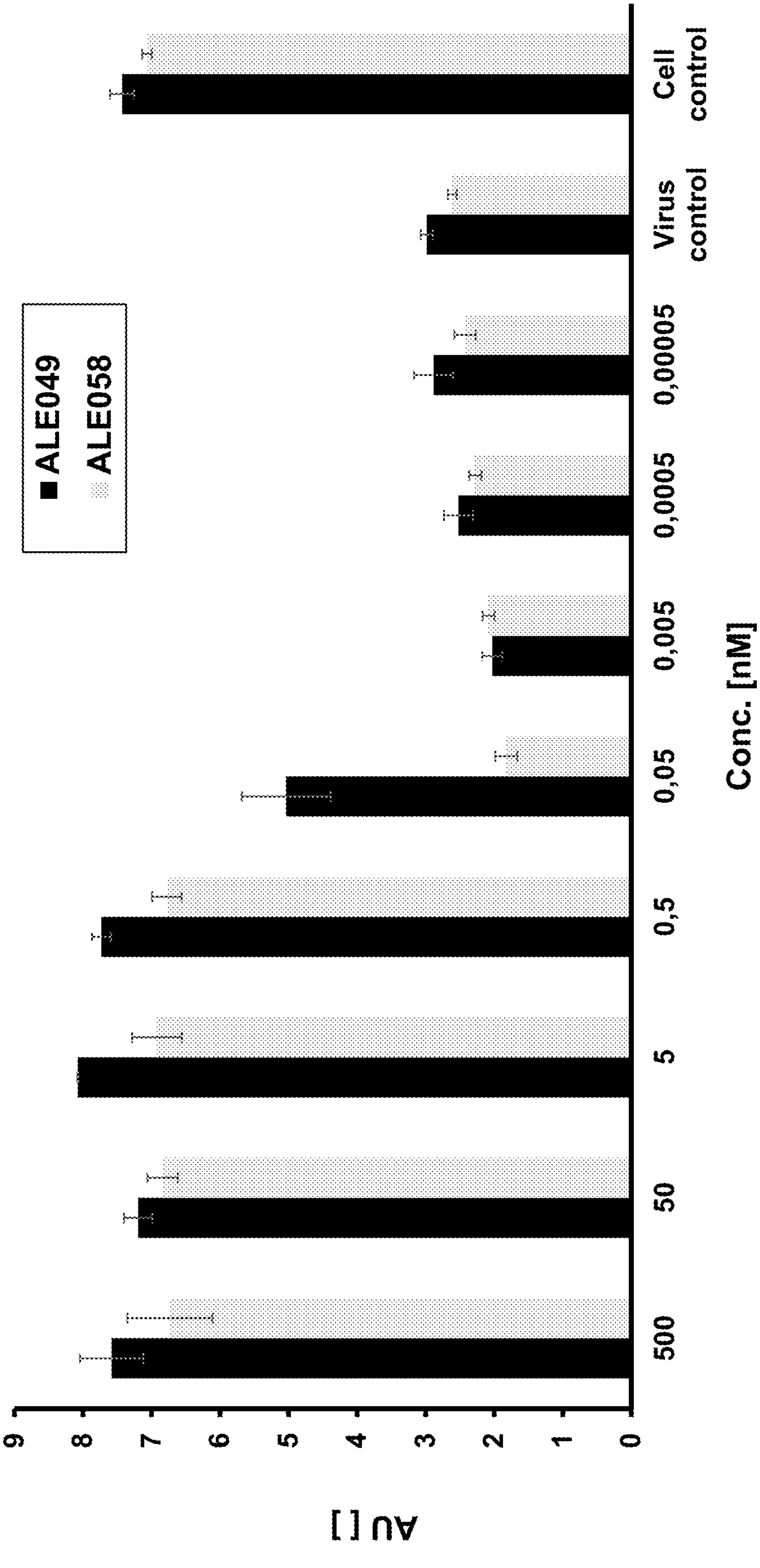
FIG. 21*a-c*: Cell protection as measured with CellTiter-Glo® luminescent cell viability assay (Promega), see Example 8.
Figure 21B:
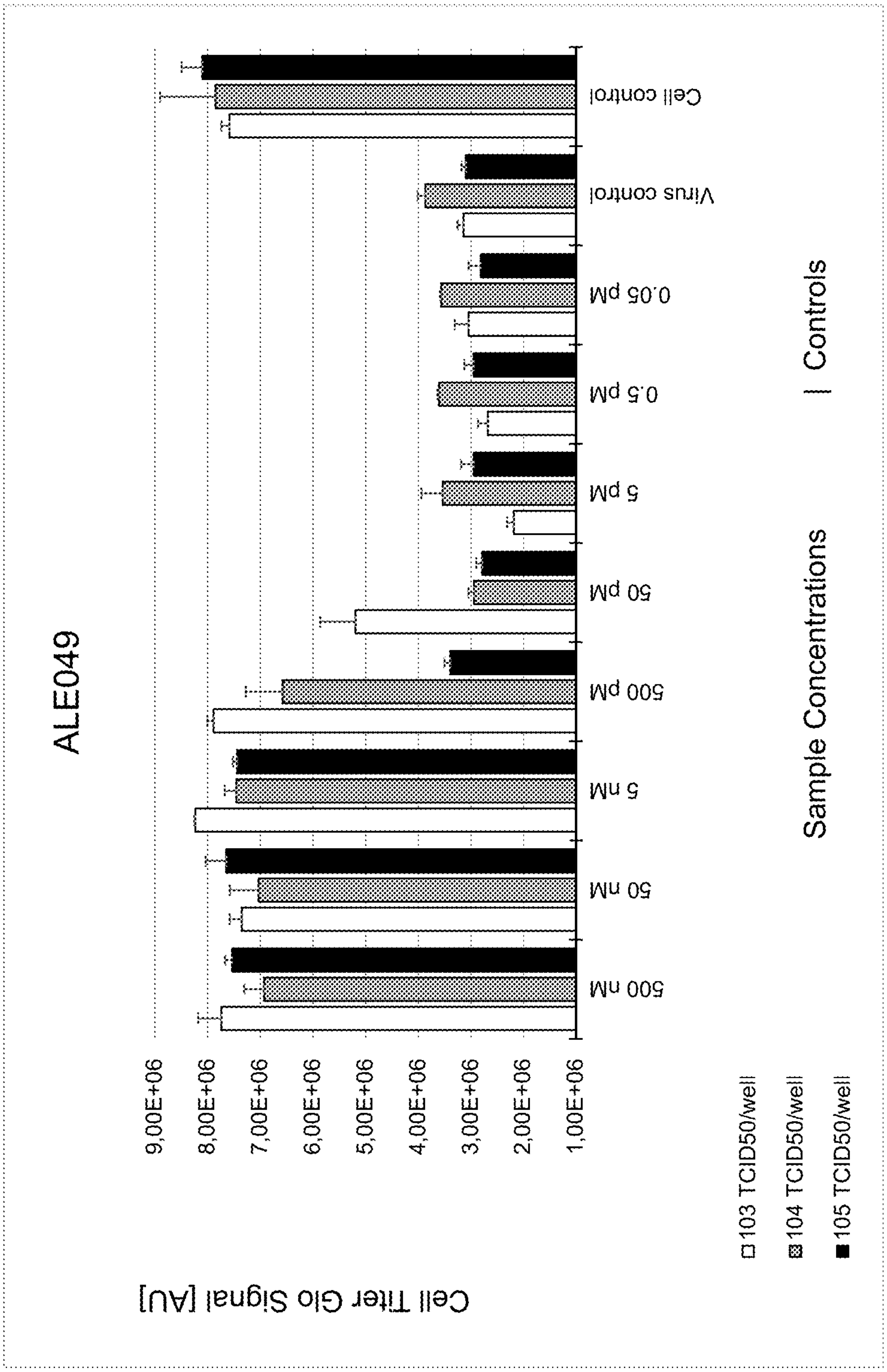
Figure 21C:
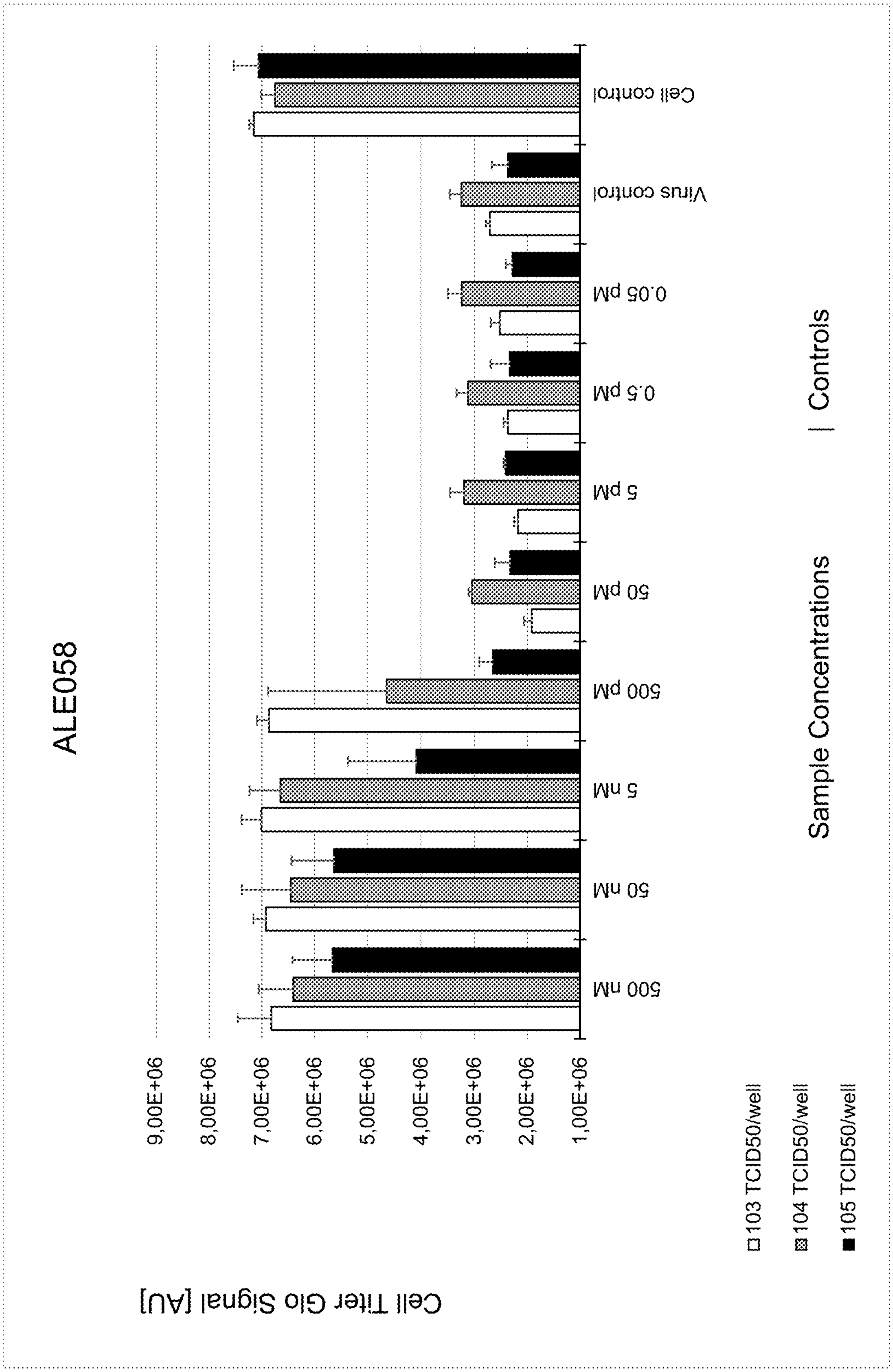

As clearly demonstrated in FIG. 20, there was complete or almost complete protection of the cells down to 0.08 nM for both ALE049 and ALE058, showing that the recombinant binding proteins of the present invention are very potent inhibitors of coronavirus spike protein, and specifically SARS-CoV-2 spike protein, and of infection of cells by a coronavirus, and specifically by SARS-CoV-2. Corresponding results are shown in FIGS. 21*a-c*, which also demonstrate potent inhibition for both ALE049 and ALE058. The exact concentration of the recombinant binding proteins required to achieve efficient inhibition in these assays was dependent on the viral load used. For both ALE049 and ALE058, potent inhibition of SARS-CoV-2 was observed in the picomolar range, for ALE049 down to 50 μM. $IC_{50}$ values for ALE049 and ALE058 are shown in Table 11 below. These values of virus inhibition represent the strongest SARS-CoV-2 inhibition reported to date.

Molecular Model of Drug Candidates

Figures 22A, 22B:
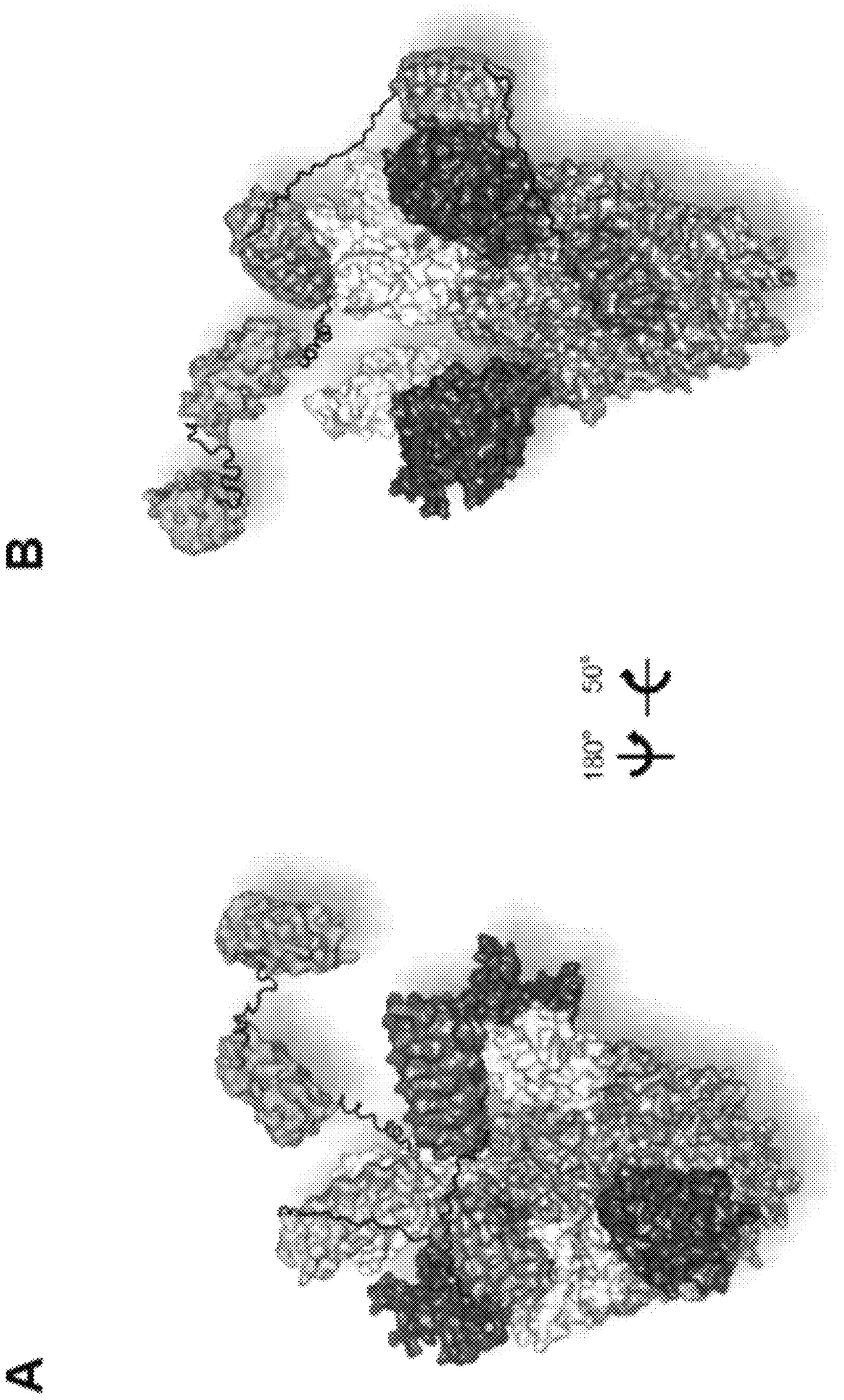
FIGS. 22*a-b*: (A) Molecular model of ALE049 (yellow: HSA-binding domains; cyan, blue and magenta: RBD-binding domains) bound to the spike ectodomain (gray) of SARS-CoV-2. (B) Molecular model of ALE058 (yellow: HSA-binding domains; blue: RBD-binding domain; green: S1-NTD-binding domain; red: S2-binding domain) bound to the spike ectodomain (grey) of SARS-CoV-2.

A molecular model for ALE049 (FIG. 22A) was built based on cryogenic electron microscopy data (data not shown). In the first step, a model structure of binding domain #2 was generated. The consensus designed ankyrin repeat domain PDB:2xee was used as template. Mutations were introduced with RosettaRemodel with fixed backbone, and the structure was refined with RosettaRelax. Forty refined structures were clustered using RosettaCluster with 0.3 Å radius, and the lowest-energy model from the largest cluster served as the final model. This model was then used for fitting domain #2 into the observed electron density generated from the complex structure of the spike protein and domain #2, resulting in a PDB file with the coordinates of the trimer of domain #2:RBD. This trimeric model was used as an input structure for the conceptual modeling of ALE049 bound to the spike ectodomain as shown in FIG. 22A. Similarly, a molecular model was also built for ALE058 (FIG. 22B). This model for ALE058 is based on the cryogenic electron microscopy data as well as a schematic structural prediction for the S2 binding domain.

Multi-specific binding proteins comprising the amino acid sequence of SEQ ID NO: 31 (ALE049) or SEQ ID NO: 39 (ALE058) each comprise combinations of 3 SARS-CoV-2 spike protein binders fused C-terminally to 2 clinically validated serum albumin-binding domains for systemic half-life extension. The resulting 5-domain proteins were expressed, purified and characterized in detail regarding biophysical properties, target affinity, and virus inhibition. The multi-specific binding proteins were expressed in soluble form at high levels in the cytoplasm of *E. coli*. Purified proteins are monomeric and exhibit high thermal stability (Tm>88° C.) and reversible unfolding as assessed by circular dichroism, and high stability in accelerated storage stability assays at 60° C. (data not shown). Their apparent affinity is beyond the limit of SPR, indicating sub-pM target affinity (data not shown). In psVSV assays, the multi-specific binding proteins inhibited viral entry with $IC_{50}$ values ranging from 3 pM to 138 pM or 0.24 ng/ml to 11.04 ng/ml (see Table 11, FIG. 23). The psVSV assay results correlated well to live virus assay results, where infection inhibition was observed with concentrations of 25 pM to 100 pM or 2 ng/ml to 8 ng/ml (see Table 11, FIGS. 21*a-c*).

TABLE 11

| Name | SEC | Tm [° C.] (CD) | $IC_{50}$ psVSV [$10^{-12}$M] | $IC_{50}$ LV* [$10^{-12}$M] |
|---|---|---|---|---|
| ALE049 | Monomer | >88° C. | 46-138 | 25 |
| ALE058 | Monomer | >88° C. | 3-99 | 100 |

*LV: Live virus cytopathic effect assay

Figure 23:
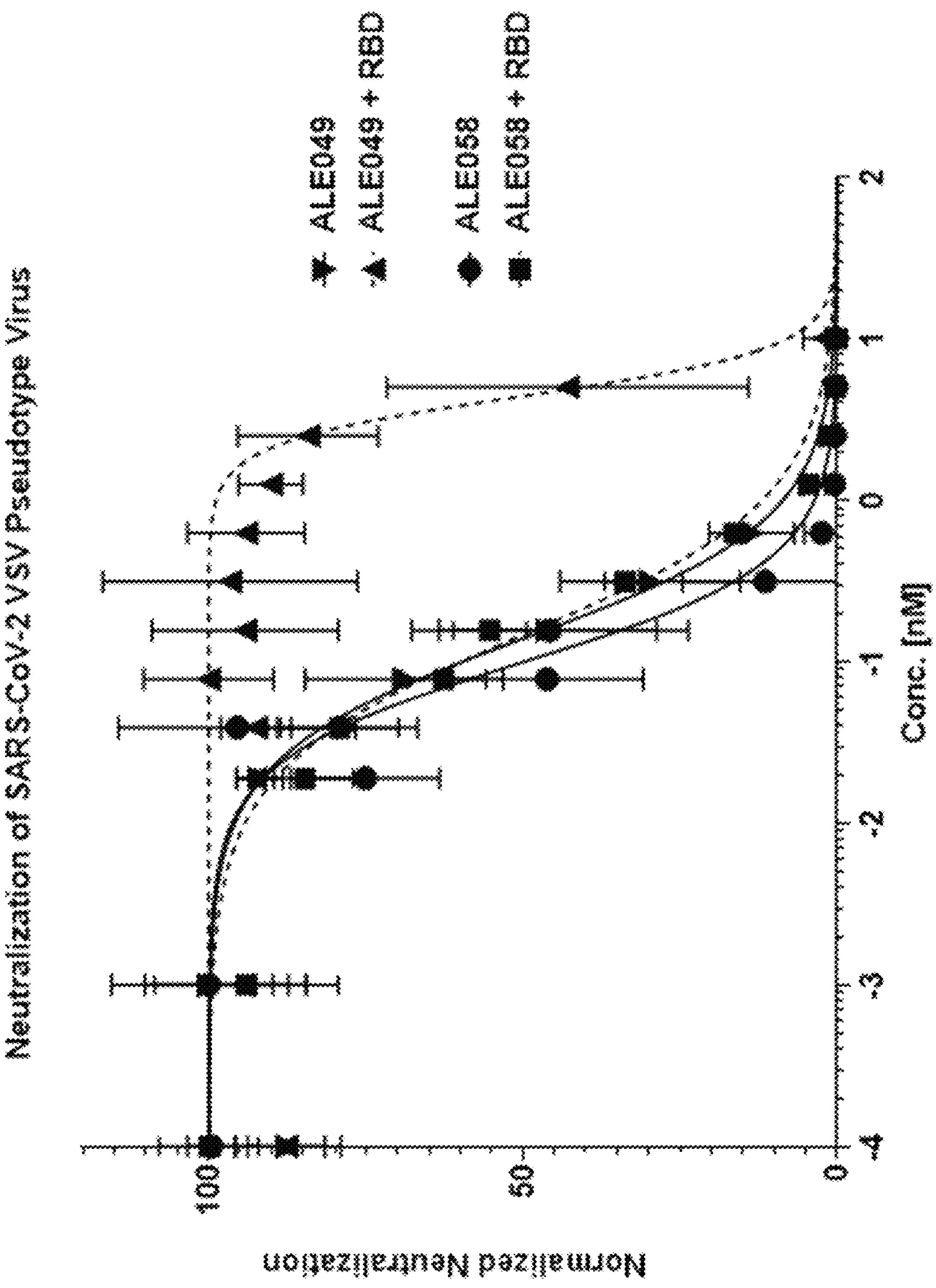
FIG. 23: Neutralization of SARS-CoV-2 VSV pseudotype virus with multi-specific binding proteins ALE049 and ALE058, see Example 8.

FIG. 23 further shows neutralization of the SARS-CoV-2 VSV pseudovirus by the recombinant binding proteins of the invention tested in the presence of the RBD domain of the spike protein. FIG. 23 shows that the RBD domain competes strongly with ALE049, which contains three RBD binding domains, but not with ALE058, which contains one RBD binding domain, one S1-NTD binding domain and one S2 binding domain. ALE049 lost potency when competing with the isolated RBD-domain, while competition of the single RBD-binder in ALE058 had no significant impact on the potency of ALE058. Without wishing to be bound by theory, this data appears to confirm that ALE049 and ALE058 inhibit SARS-CoV-2 by different modes of action. While ALE049 seems to rely strongly on the neutralization of the RBD/ACE-2 interaction, ALE058 seems to show multi-mode binding and a diversified mode of action, which beyond the neutralization of the RBD/ACE-2 interaction also utilizes an independent neutralization potency of the S1-NTD-S2 arm of the molecule. Thus, based on the data shown in FIG. 23, ALE049 and ALE058 appear to have different modes of action, consistent with the molecular models of the two molecules shown in FIG. 22.

Such high potency as observed for the binding proteins of the invention is key for the use in SARS-CoV-2 treatment and prophylaxis where very low virus titers at infection initiation are envisioned. Importantly, several spike protein variants of the most abundant SARS-CoV-2 serotypes were blocked with high potency by the multi-specific binding proteins (see Table 12), indicating robustness against viral escape and potential of use in prophylactic treatment in the current pandemic and potentially also future pandemics. In mouse experiments, no adverse events were observed up to the highest dose (50 mg/kg, i.v.) tested.

TABLE 12

| | Potency of inhibition of SARS-CoV-2 spike protein variants ($IC_{50}$, [$10^{-12}$M]) | | | | |
|---|---|---|---|---|---|
| | wt | G476S | V483A | D614G | D614G × Q675H |
| ALE049 | 16.53 | 27.08 | 27.48 | 11.77 | 12.11 |
| ALE058 | 5.48 | 14.46 | 32.40 | 4.64 | 22.44 |

Example 9: Pharmacokinetic Analysis of Multi-Specific Binding Proteins of the Invention in Mice A pharmacokinetic (PK) study was conducted to assess the PK characteristics of multi-specific recombinant binding proteins of the invention in mice. Such PK characteristics are useful for dose predictions of multi-specific binding proteins of the invention in animal pharmacodynamic studies, in toxicology studies or in human clinical trials.

The investigated multi-specific binding proteins of the invention comprise—from N-terminus to C-terminus—two HSA-specific binding domains followed by three spike protein-specific binding domains (see Table 2). The HSA-specific binding domains are cross-reactive to serum albumin of the mouse.

For this PK study, naive female BALB/c mice received a single intravenous bolus injection at a target dose level of 1 mg/kg of the compounds. Blood samples were collected at several time points between 5 min and 165 h after compound administration. Serum concentrations were determined with ELISA-based analytical methods.

From 6 h onwards the concentration-time profiles indicate a slow and steady decrease of the serum concentrations resembling roughly mono-exponential declines until 165 h, the last sampling time point. From the concentration time profiles pharmacokinetic parameters were determined using non-compartmental analysis.

The following multi-specific binding proteins were tested in this example:

TABLE 13

| SEQ ID NO | Sample name |
|---|---|
| 15 | ALE033 |
| 30 | ALE048 |
| 31 | ALE049 |

In Vivo Animal Experiments

The test items were administered to healthy female BALB/c mice (6 mice per test item) as a single intravenous bolus injection into the tail vein. The target dose level was 1 mg/kg. For the study of each compound, the 6 mice were split into 2 groups with equal numbers of animals. For pharmacokinetic investigations, serum samples, 4 from each mouse, were collected from the saphenous vein at time points 5 min, 6 h, 24 h, 48 h, 72 h, 96 h and 165 h. The assignment of the individual animals to the respective sampling time points was according to a predetermined scheme. Blood was kept at room temperature for approx. 30 min to allow clotting followed by centrifugation (5 min/12000 g/4° C.). Afterwards serum was frozen and stored at −20° C. pending analyses. No major issues and no drug-related adverse effects were reported for the in vivo experiment.

ELISA Method

Figure 24:
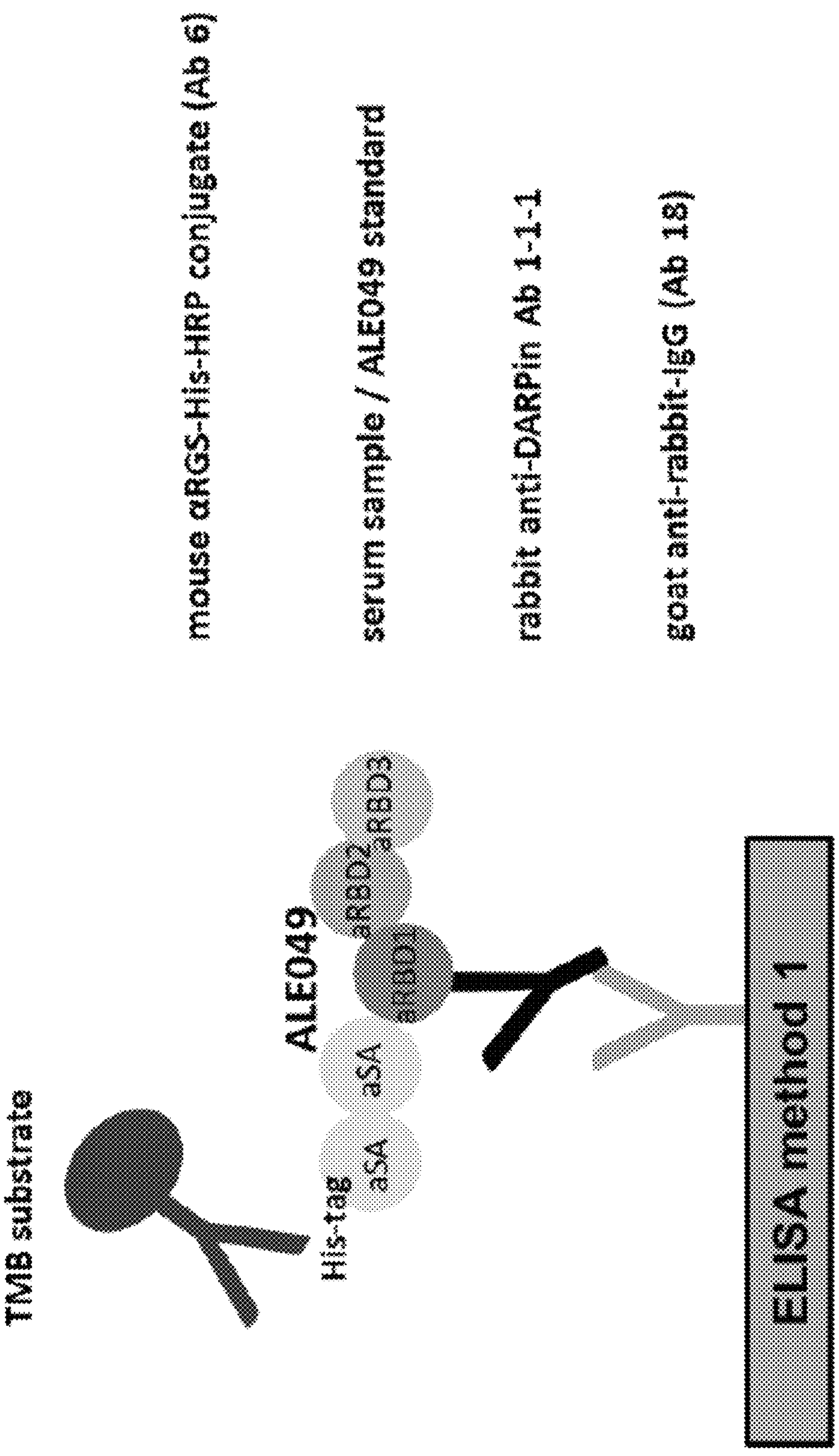
FIG. 24: ELISA method as used in Example 9.

An ELISA method (see FIG. 24) was used for measuring serum concentrations of the multi-specific binding proteins making use of a common epitope of DARPin® moieties recognized by the anti-DARPin® antibody 1-1-1 for capturing and of the N-terminal His-tag, which is present in the tested binding proteins, to facilitate detection. The ELISA setup scheme illustrated in FIG. 24 (showing ALE049 as a binding protein example) uses monoclonal goat anti-rabbit-IgG immobilized on the ELISA plate, which binds rabbit anti-DARPin® antibody 1-1-1, capturing the multi-specific binding proteins via DARPin® scaffold epitopes in serum sample. The captured DARPin® molecule is detected using mouse anti-RGS-His-IgG-HRP conjugate. aSA: anti serum albumin, aRBD: anti receptor binding domain (RBD)

Test Procedure

One hundred μL per well of 10 nmol/L polyclonal goat anti-rabbit IgG antibody (Ab18) in PBS was coated onto a NUNC Maxisorb ELISA plate overnight at 4° C. After washing with 300 μL PBST (PBS supplemented with 0.1% Tween20) per well five times, the wells were blocked with 300 μL PBST supplemented with 0.25% Casein (PBST-C) for 1 h at room temperature (RT) on a Heidolph Titramax 1000 shaker (450 rpm). Plates were washed as described above. One hundred μL per well of 5 nmol/L rabbit anti-DARPin® 1-1-1 antibody in PBST-C was added and the plates were incubated at RT (22° C.) with orbital shaking (450 rpm) for 1 h. Plates were washed as described above.

One hundred μL per well of diluted serum samples (1-20-1:312500, in 1:5 dilution steps), multi-specific binding protein quality control samples (100, 10 and 1 nmol/L) or multi-specific binding protein standard curve samples (0 and 50-0.001 nmol/L in 1:3 dilution steps) diluted in PBST-C (supplemented with naive mouse serum to result in a final serum concentration of 1% (initial 1:20 dilution final serum concentration of 5%)) were applied for 2 h, at RT, shaking at 450 rpm. Plates were washed as described above.

Wells were then incubated with 100 μL murine anti-RGS-His-HRP IgG (Ab06) 1:2000 in PBST-C and incubated for 1 h, at RT, 450 rpm. Plates were washed as described above. The ELISA was developed using 100 μL per well TMB substrate solution for 5 minutes and stopped by the addition of 100 μL per well 1 mol/L $H_2SO_4$. The difference between the absorbance at 450 nm and the absorbance at 620 nm was calculated. Samples were measured in duplicate on two different plates.

Quality control samples of known concentrations were included in the measurements in order to monitor the performance of the assay.

Pharmacokinetic data analysis was performed using Phoenix WinNonlin™ 8.0 program from Certara. Calculation of the pharmacokinetic parameters of the study based on the mean concentration-time data of the animals dosed via intravenous bolus injection was performed with non-compartmental analysis (NCA model 200-202, IV bolus, linear trapezoidal linear interpolation).

The calculated pharmacokinetic parameters included at least the following: AUCinf_pred, AUClast, AUC_% extrapol, AUC_% Back_Ext_red, Cmax, Tmax, CI_pred, Vss_pred, t½ (HL_Lambda_z)

Figure 25:
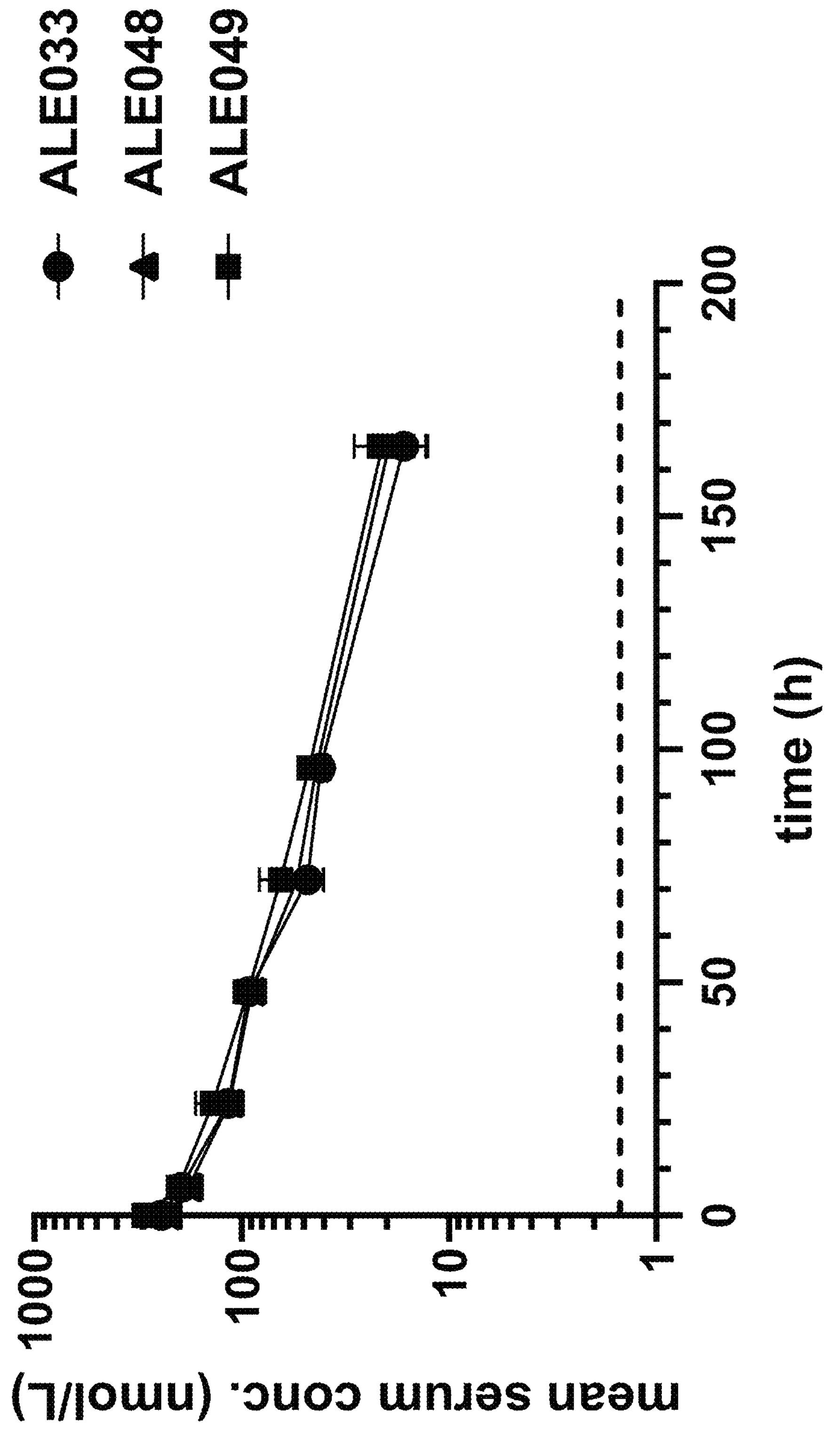
FIG. 25: Mean serum concentration data for ALE033, ALE048 and ALE049, see Example 9.

The results are shown in Table 14 and FIG. 25:

TABLE 14

| Parameter | Unit | ALE033 | ALE048 | ALE049 |
|---|---|---|---|---|
| AUCINF_pred | h*(nmol/L) | 12428 | 12768 | 14329 |
| AUClast | h*(nmol/L) | 11439 | 11461 | 12949 |
| Cmax | nmol/L | 244 | 230 | 291 |
| Tmax | h | 0.083 | 0.083 | 0.083 |
| CI_pred | L/(h*kg) | 0.00094 | 0.00091 | 0.00081 |
| Vss_pred | L/kg | 0.058 | 0.063 | 0.055 |
| HL_Lambda_z | h | 45.8 | 50.8 | 49.6 |
| AUC_%Extrap_pred | (%) | 8 | 10 | 10 |
| AUC_%Back_Ext_pred | (%) | 0 | 0 | 0 |

Results and Conclusions

In the mono-exponential elimination phases, serum concentrations of ALE033, ALE048 and ALE049 declined with half-life values of 45.8 h, 50.8 h and 49.6 h, respectively. Clearance of ALE033, ALE048 and ALE049 was determined to be 0.00094, 0.00091 and 0.00081 L/(h*kg), respectively, and volume of distribution (Vss) of ALE033, ALE048 and ALE049 was calculated to be 0.058, 0.063 and 0.055 L/kg, respectively. The values determined for Vss indicate that ALE033, ALE048 and ALE049 are largely confined to the systemic circulation of the animals, similarly to monoclonal antibodies.

In conclusion, following intravenous administration at a dose level of 1 mg/kg the three tested multi-specific binding proteins of the invention display a systemic half-life in the range of the half-life of albumin in mice. Considering the half-life of albumin in mouse and human as well as previous data (Binz et al., *MAbs* 9, 1262-1269 (2017)), the terminal half-life of ALE049 in humans is expected to extrapolate to around 3 weeks. The terminal half-lives of ALE033 and ALE048 in humans are expected to extrapolate similarly.

Example 10: SARS-CoV-2 Inhibition Efficacy Experiments in Syrian Hamster

The efficacy of ALE049 was further assessed in a Syrian hamster model of preventive treatment of SARS-CoV-2 infection.

Syrian hamsters were divided into 4 groups of 6 female animals each. The groups were treated with of 16 μg, 160 μg, or 1600 μg of multi-specific binding protein having the amino acid sequence of SEQ ID NO: 31 or with placebo in a blinded manner. Treatment injection (i.p., intraperitoneal) was done 24 h prior (Day −1) to intranasal infection (Day 0) of the animals with $5\times10^4$ TCID50 (in 100 μl) of SARS-CoV-2 (BetaCoV/Munich/BavPat1/2020). At Day −2, body weight was measured, blood was taken, and the first throat swab performed. Animals were euthanized on Day 4 and tissue was taken and gross pathology was performed. Throat swabs were collected daily in virus transport medium, aliquoted and stored. At the time of necropsy, gross pathology was performed. Lung lobes were inspected and an estimation of the percentage of affected lung tissue from the dorsal view was performed. Left lung lobes and nasal turbinates were preserved in 10% neutral buffered formalin for histopathology. The right side of these tissues was homogenised and subjected to Taqman PCR and virus titration. Additionally, other organs were collected. Tissue samples were frozen for virological analysis, weighed, homogenized in infection medium and centrifuged briefly before titration. Histopathology was performed on lung and nasal turbinates for all animals. After fixation with 10% formalin, sections from left lung and left nasal turbinate were embedded in paraffin and the tissue sections were stained by H&E for histological examination. For virological analyses, quadruplicate 10-fold serial dilutions were used to determine the virus titers in confluent layers of Vero E6. To this end, serial dilutions of the samples (throat swabs and tissue homogenates) were made and incubated on Vero E6 monolayers for 1 h at 37° C. Vero E6 monolayers were washed and incubated for 4-6 days at 37° C. after which plates were scored WST8. Viral titers (TCID50) were calculated using the method of Spearman-Karber. Readout included observation of body weight, lung lesions, virus titers, and histopathology.

Histopathology

After fixation with 10% neutral-buffered formalin, sections of the left lung, left nasal turbinate and trachea were embedded in paraffin. The tissue sections were stained with hematoxylin and eosin (H&E) for histopathological evaluation. Semi-quantitative scores of 0, 1, 2 or 3 were given when the extent of alveolitis and alveolar damage were estimated at 0%; 1-25%; 26-50% or >50%, respectively. The cumulative score for the extent and severity of inflammation of the lung provided the total score of alveolitis per animal (see Table 15, column "SUM of extent+severity"). For the severity of alveolitis, bronchiolitis, and bronchitis, semi-quantitative scores of 0, 1, 2 or 3 were given when no, few, moderate numbers or many inflammatory cells were present, respectively. For the presence of alveolar edema, alveolar hemorrhage, and type II pneumocyte hyperplasia, scores of 0 or 1 were given upon their absence or presence, respectively. In Table 16, the presence of alveolar edema, alveolar hemorrhage, and type II pneumocyte hyperplasia is indicated by "yes" and "no" instead of the numerical score.

Figure 26A:
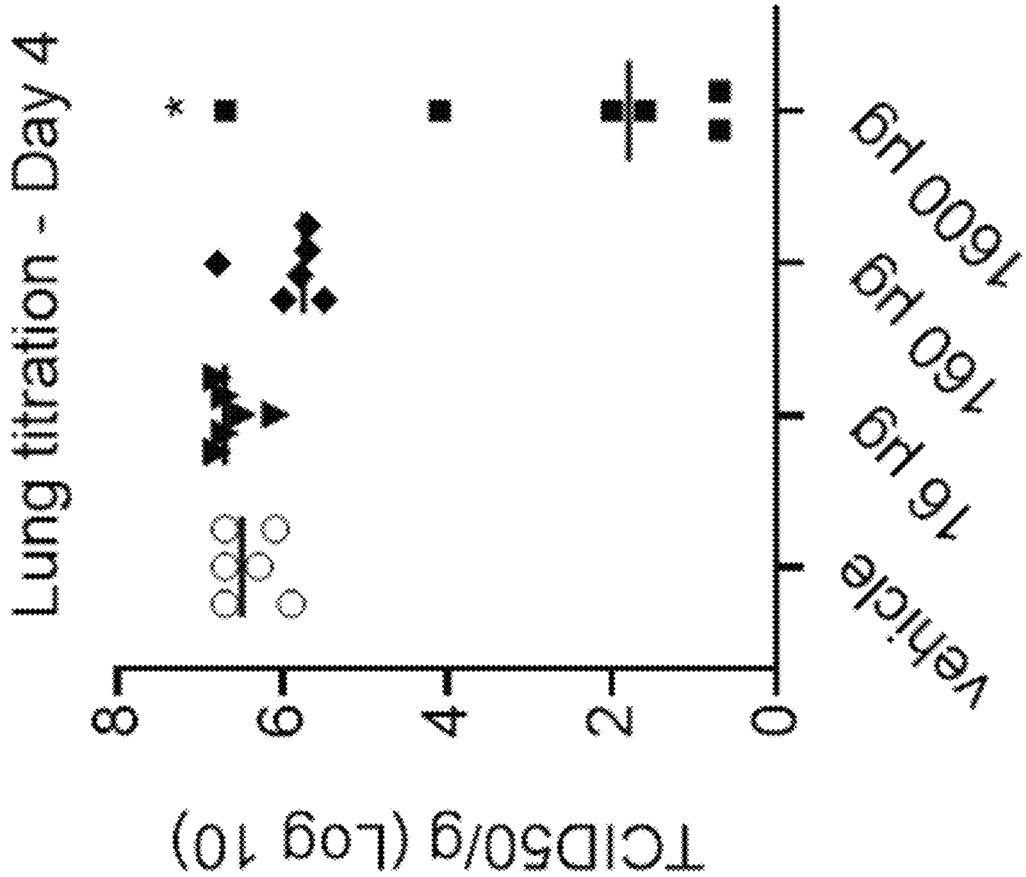
FIGS. 26*a-e*: Efficacy of ALE049 in treating SARS-CoV-2 infection in a preventative Syrian gold hamster model, see Example 10.
Figure 26B:
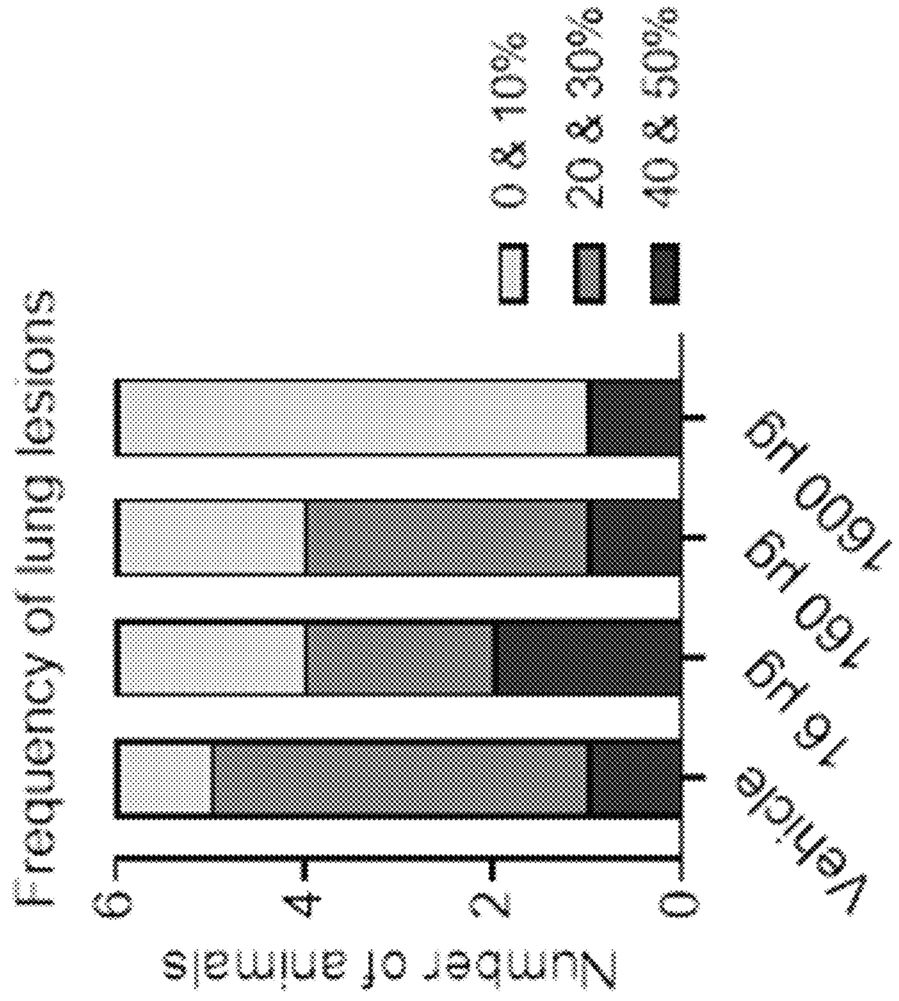
Figure 26C:
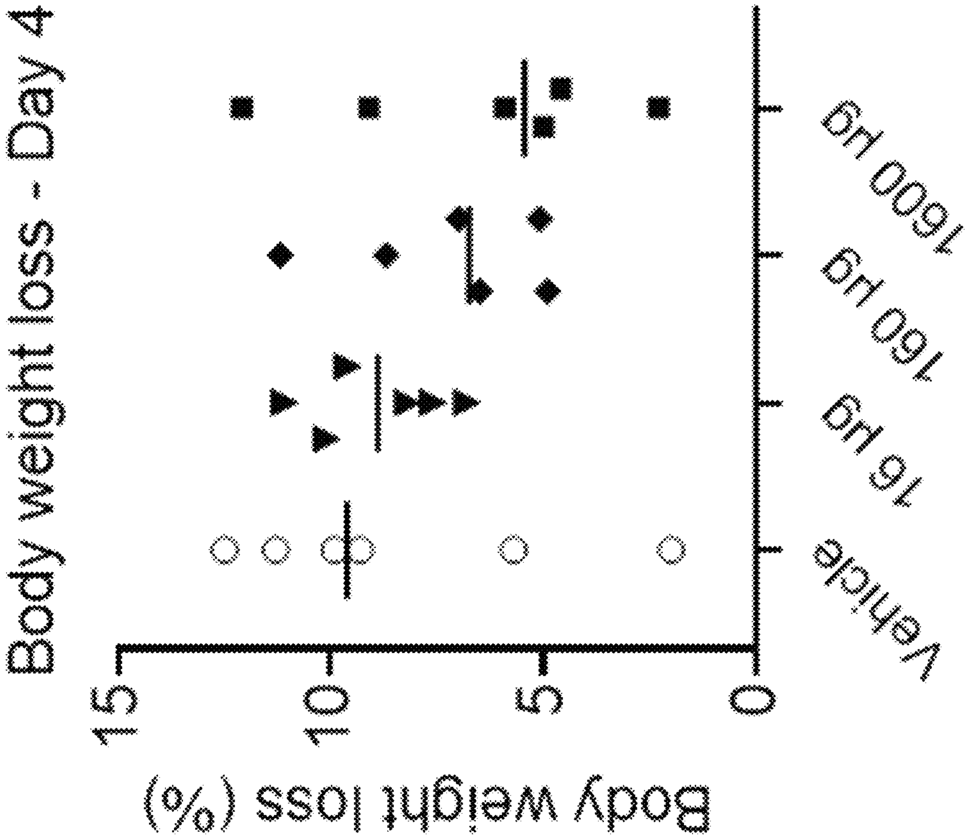
Figure 26D:
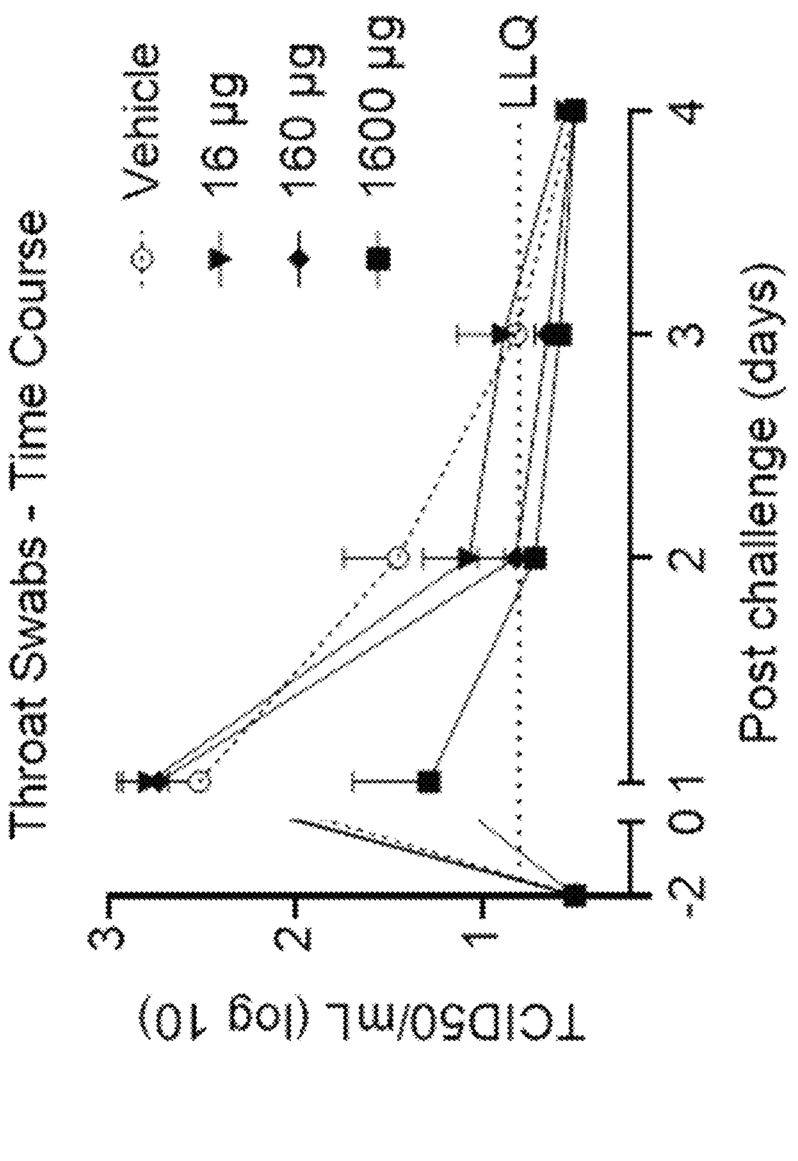
Figure 26E:
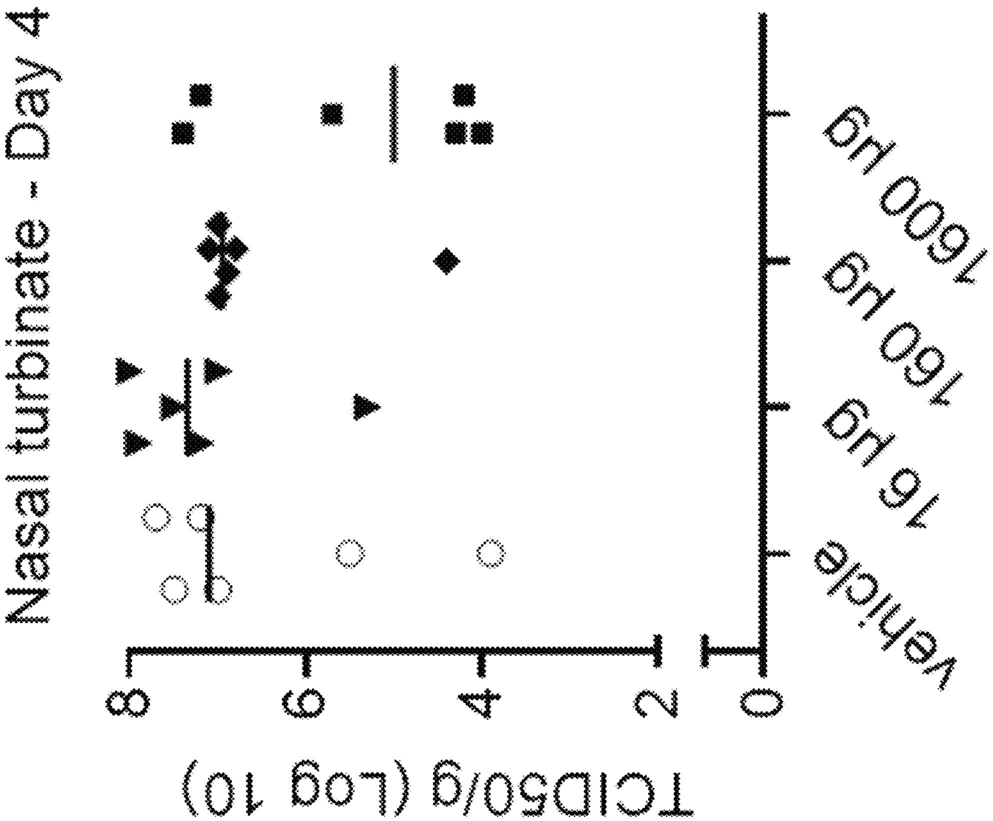
Figure 27:
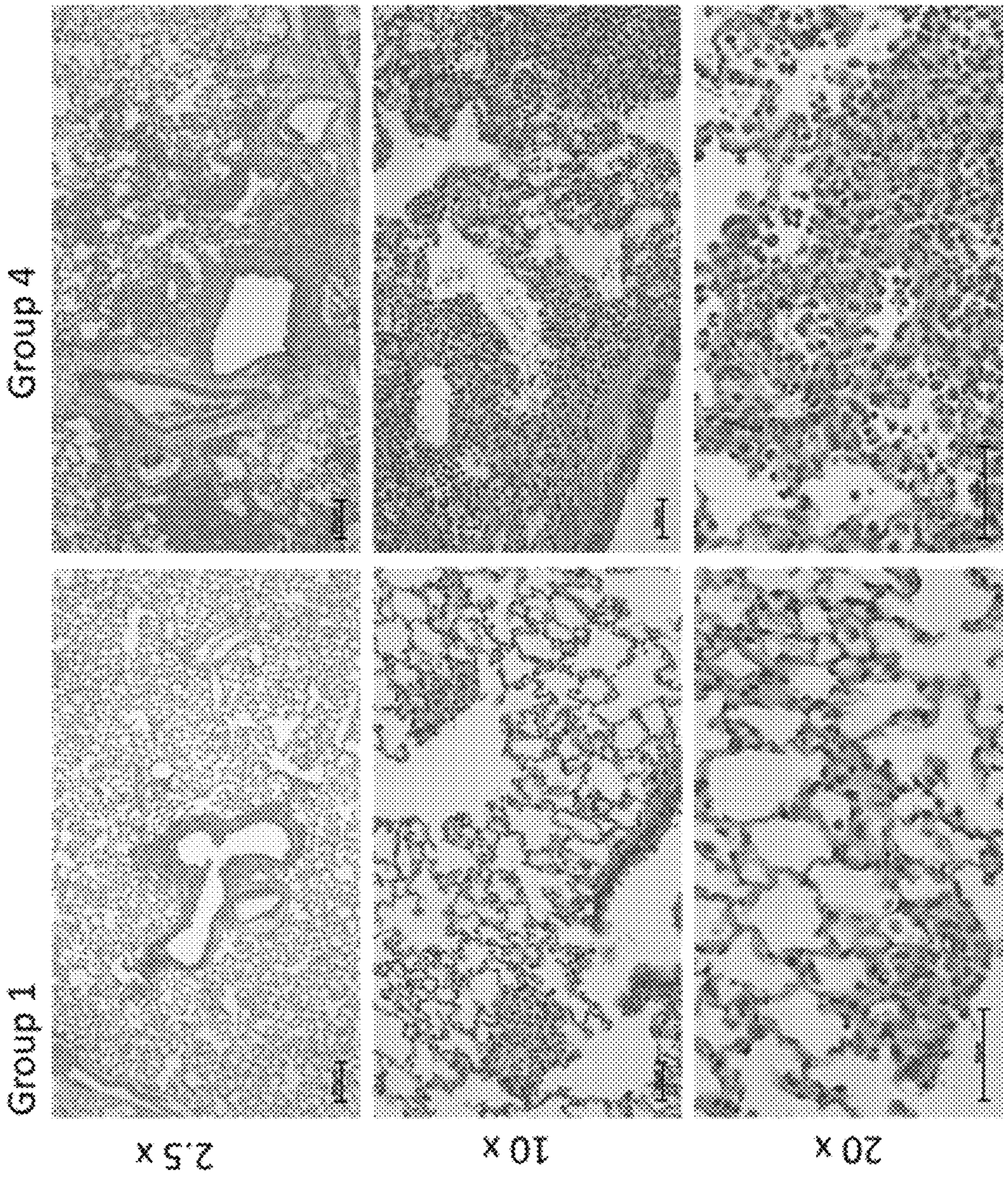
FIG. 27: Representative histopathology microscopic pictures of hamster lung tissue taken at day 4. Left panel: healthy hamster lung tissue of an animal treated with 1600 μg ALE049 (group 1); right panel: diseased lung tissue of an animal which received the placebo injection (group 4).

Readout included observation of body weight, lung lesions, virus titers, and histopathology. At the 1600 μg dose, ALE049 exhibited significant reduction of the viral titers in the lung (FIG. 26*a*). While the model exhibited high inter-animal variability, trends to a dose-dependent reduction of virus titers (FIG. 26*a*), dose-dependent reduction of macroscopically determined lung lesions (FIG. 26*b*), and dose-dependent reduction of body weight loss (FIG. 26*c*) were observed, indicating both the 160 μg as well as the 1600 μg dose exhibited anti-viral activity. Virus titers in the throat swabs further showed that the 1600 μg dose, and to a lesser extent the 160 μg dose, inhibited the virus titers and/or accelerated the reduction of virus titers in the throat during the four day post-infection time period (FIG. 26*d*). Virus titers in nasal turbinates (FIG. 26*e*) and histopathology data (Tables 15 and 16, FIG. 27) confirmed that the 1600 μg dose had the strongest anti-viral protective effects. Based on these encouraging initial findings further animal experiments are ongoing.

TABLE 15

Histopathology results (a)

| Animal no. | Group no. | Compound | Dose | Extent of alveolitis/ alveolar damage | Severity of alveolitis | SUM of extent + severity | Severity of bronchitis | Severity of bronchiolitis |
|---|---|---|---|---|---|---|---|---|
| 1 | 1 | ALE049 | 1600 μg | 1 | 1 | 2 | 2 | 1 |
| 2 | | | | 0 | 0 | 0 | 1 | 1 |
| 3 | | | | 1 | 2 | 3 | 3 | 1 |
| 4 | | | | 1 | 1 | 2 | 3 | 1 |
| 5 | | | | 1 | 1 | 2 | 2 | 1 |
| 6 | | | | 0 | 0 | 0 | 1 | 1 |
| 7 | 2 | ALE049 | 160 μg | 1 | 3 | 4 | 3 | 2 |
| 8 | | | | 2 | 3 | 5 | 3 | 3 |
| 9 | | | | 2 | 3 | 5 | 3 | 3 |
| 10 | | | | 2 | 3 | 5 | 3 | 3 |
| 11 | | | | 2 | 3 | 5 | 2 | 3 |
| 12 | | | | 2 | 3 | 5 | 3 | 3 |
| 13 | 3 | ALE049 | 16 μg | 2 | 3 | 5 | 3 | 3 |
| 14 | | | | 2 | 3 | 5 | 3 | 3 |
| 15 | | | | 3 | 3 | 6 | 3 | 3 |
| 16 | | | | 2 | 3 | 5 | 3 | 3 |
| 17 | | | | 1 | 3 | 4 | 3 | 2 |
| 18 | | | | 3 | 3 | 6 | 3 | 3 |
| 19 | 4 | Placebo | N/A | 2 | 3 | 5 | 3 | 3 |
| 20 | | | | 2 | 3 | 5 | 3 | 3 |
| 21 | | | | 2 | 3 | 5 | 3 | 3 |
| 22 | | | | 2 | 3 | 5 | 3 | 3 |
| 23 | | | | 2 | 3 | 5 | 3 | 3 |
| 24 | | | | 2 | 3 | 5 | 3 | 3 |

TABLE 16

Histopathology reuslts (2)

| Animal no. | Group no. | Compound | Dose | Alveolar edema presence | Alveolar hemorrhage presence | Type II pneumocyte hyperplasia presence |
|---|---|---|---|---|---|---|
| 1 | 1 | ALE049 | 1600 μg | no | no | no |
| 2 | | | | no | no | no |
| 3 | | | | no | no | yes |
| 4 | | | | no | no | yes |
| 5 | | | | no | no | yes |
| 6 | | | | no | no | no |
| 7 | 2 | ALE049 | 160 μg | yes | yes | yes |
| 8 | | | | yes | yes | yes |
| 9 | | | | yes | yes | yes |
| 10 | | | | yes | yes | yes |
| 11 | | | | yes | yes | yes |
| 12 | | | | yes | yes | yes |
| 13 | 3 | ALE049 | 16 μg | yes | yes | yes |
| 14 | | | | yes | yes | yes |
| 15 | | | | yes | yes | yes |
| 16 | | | | yes | yes | yes |
| 17 | | | | yes | yes | yes |
| 18 | | | | yes | yes | yes |
| 19 | 4 | Placebo | N/A | yes | yes | yes |
| 20 | | | | yes | yes | yes |
| 21 | | | | yes | yes | yes |
| 22 | | | | yes | yes | yes |
| 23 | | | | yes | yes | yes |
| 24 | | | | yes | yes | yes |

Example 11: SARS-CoV-2 Variant Inhibition Efficacy Experiments

The efficacy of ALE049 (SEQ ID NO: 31) and ALE109 (SEQ ID NO: 75) was assessed against SARS-CoV-2 variants B.1.1.7 (the "UK variant") and B.1.351 (the "South African variant"), as well as against SARS-CoV-2 variants having single mutations in the spike protein.

The spike protein of SARS-CoV-2 mediates cell entry through binding to the human ACE2 receptor. SARS-CoV-2 is also capable of infecting non-primate hosts, such as felines and minks (Oude Munnink et al., 2021, *Science* 371, 172-177). The promiscuity of a multi-host lifestyle is often an indicator of early, still sub-optimal adaptation of the virus to its new host. This suggests inherent dynamic plasticity and potential for further human adaptation. The receptor-binding domain (RBD) in the spike protein forms the interface with ACE2. Site mutagenesis scanning and structure analysis revealed amino acid residues important for this interaction, such as L455, F456, A475, F486, F490 and Q493 (Yan et al., 2020, *Science* 367, 1444-1448; Yi et al., 2020, *Cell Mol Immunol* 17, 621-630). Notably, single amino acid substitutions N439R, L452K, N470T, E484P, Q498Y and N501T have been shown to increase the affinity for human ACE2 (Yi et al., 2020, loc. cit.). Consistent with these experimental findings, mutation N439K and mutation N501Y appeared in rapidly spreading SARS-CoV2 spike variants in association with facilitated receptor binding and increased transmissibility (Thomson et al., 2021, *Cell*, https//doi.org/10.1016/j.cell.2021.01.037). The RBD domain is also immunogenic, and among other residues, K444, E484, and F486 have been shown to be important for the binding of neutralizing antibodies (Ku et al., 2021, *Nat Commun* 12, 469).

Figure 28:
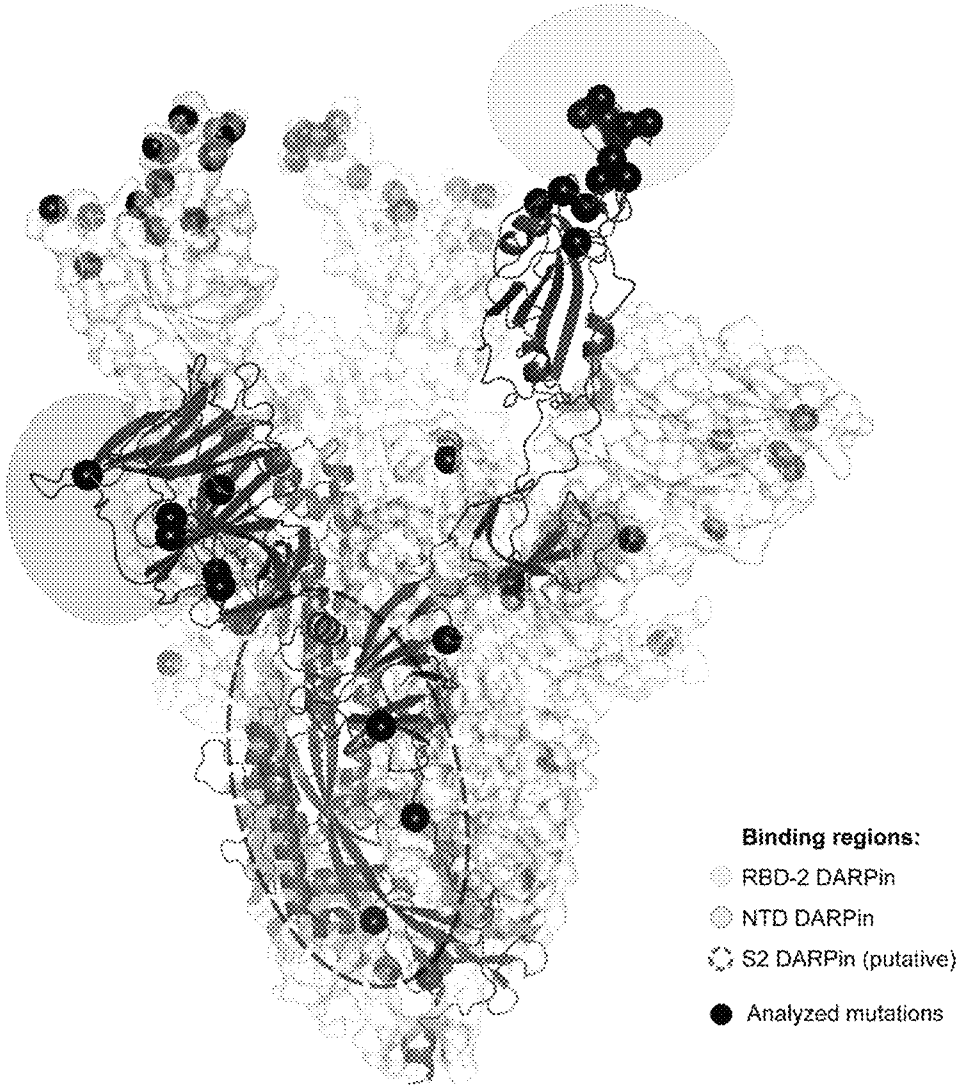
FIG. 28: Structural visualization of mutations of the SARS-CoV-2 spike protein evaluated in Examples 11 and 12. A) Representation of the full trimeric SARS-CoV-2 spike protein with all residues analyzed in the Pseudovirus neutralization assay visualized as blue spheres. Binding regions for the individual DARPin® domains incorporated in ALE049 and ALE109 are colored in blue (RBD), green (NTD) and red (S2); B) monomeric spike protein structure representing the variant first identified in the UK B.1.1.7 (del69-70, del145, N501Y, A570D, D614G, P681H, T716I, S982A, D1118H); C) monomeric spike protein structure representing the variant first identified in South Africa B.1.351 (D80A, D215G, E484K, N501Y, A701V). The PDB file 6xcn was used for generating the figures with PyMol version 2.1.1 (Schrödinger, LLC). In order to visualize all mutations, the loops 518-520, 676-689, 811-813 and the regions of the NTD domain missing in the cryo-EM structure, were modelled with MODELLER included in the BIOVIA Discovery Studio software using the PDB file 6zge as template for the NTD domain (BIOVIA, Dassault Systbmes, BIOVIA Discovery Studio 2021).
Figure 28:
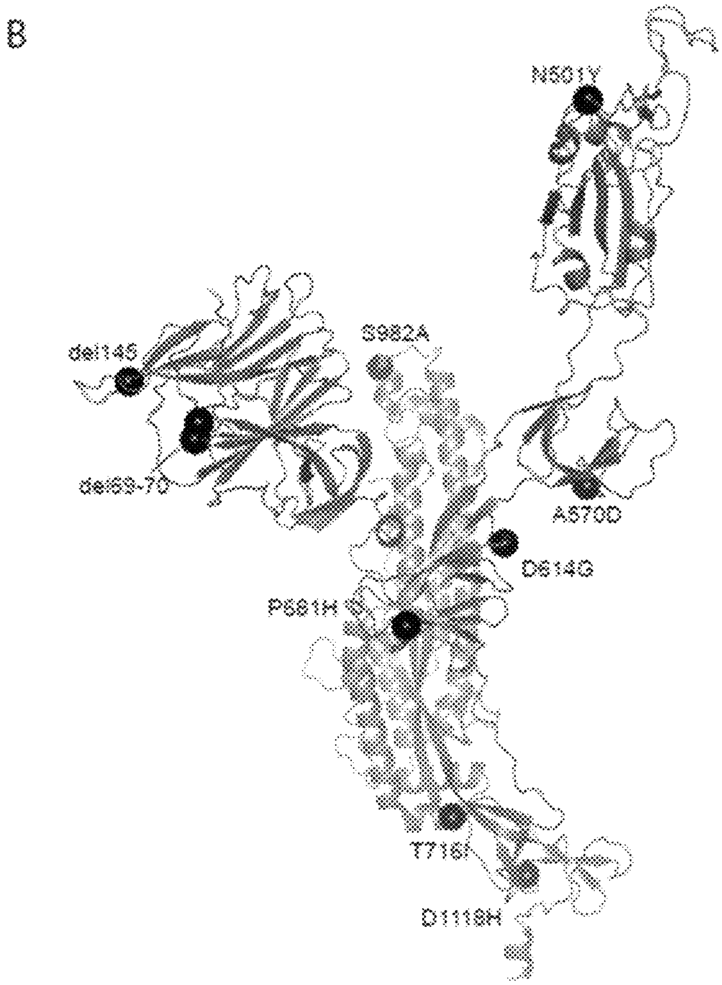
Figure 28:
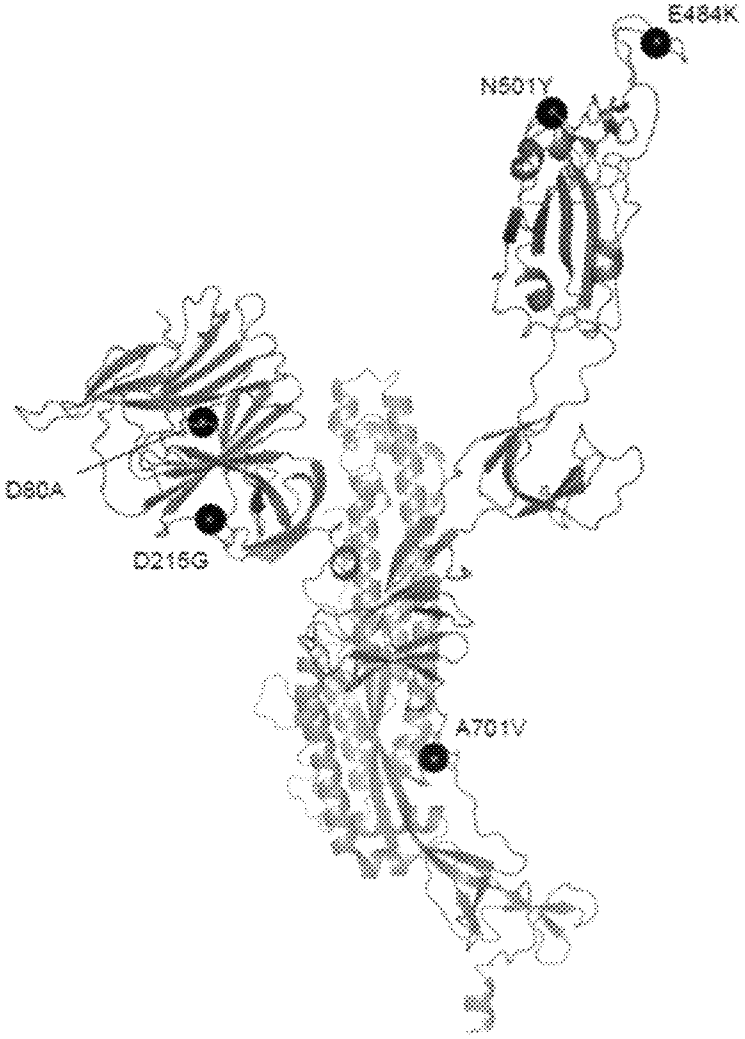

In this example, we analyzed the impact of selected mutations of the spike protein on the neutralization capacity of ALE049 and ALE109 (FIG. 28).

Generation of His-Tagged Mono-Valent RBD Binders, ALE049, ALE109 and the Domain Knockout Variants of ALE109

Ankyrin repeat protein constructs selected and cloned as described in Example 1 and in Walser et al., 2020 (bioRxiv preprint doi: https://doi.org/10.1101/2020.08.25.256339) were transformed in *E. coli* BL21 cells, plated on LB-agar (containing 1% glucose and 50 μg/ml ampicillin) and then incubated overnight at 37° C. For each construct, a single colony was picked into TB medium (containing 1% glucose and 50 μg/ml ampicillin) and incubated overnight at 37° C., shaking at 230 rpm. Fresh TB medium (containing 50 μg/ml ampicillin) was inoculated with 1:20 of overnight culture and incubated at 37° C. at 230 rpm. At OD600=1.1 the culture was induced by addition of IPTG (0.5 mM final concentration) and incubated for further 5 h at 37° C. 230 rpm. Harvest was done by centrifugation (10 min 5000×g). After cell disruption by sonication primary recovery was done by heat treatment for 30 min at 62.5° C. and subsequent centrifugation (15 min, 12000×g). 20 mM Imidazole and 1% Triton X-100 was added to the supernatant and the 0.22 μm centrifuged supernatant was further purified by immobilized metal affinity chromatography (HisTrap FF crude, Cytiva, Sweden) using the N-terminal His-tag including a wash step with 1% Triton X-100 and a step elution with 250 mM Imidazole. In a subsequent step, the elution fraction of the IMAC step was applied on a size exclusion chromatography (Superdex 200, Cytiva, Sweden) and fractions of interest were pooled and concentrated. Finally, the concentrated sample was filtered through a 0.22 μm Mustang E filter for Endotoxin removal and sterile filtration and quality controlled.

Generation of Monoclonal Reference Antibodies, RA1 and RA2

Publicly available sequences of variable domains from monoclonal antibodies RA1 and RA2 (the U.S. Food and Drug Administration issued an emergency use authorization for RA1 and RA2 to be administered as a cocktail for the treatment of COVID-19) were used to synthetize the corresponding cDNA fragments and cloned into a proprietary expression vector at Evitria AG (Switzerland). Generated vectors containing the constant immunoglobulin hIgG1 chain or kappa light chain were used for transfection in Chinese hamster ovary cells by Evitria. Sterile filtered cell supernatants were purified via affinity purification with HiTrap MabSelect column followed by a size exclusion chromatography using HiLoad 26/600 Superdex 200 column in PBS pH7.4. Selected fractions were pooled and quality controlled (by SDS-PAGE, size exclusion chromatography and endotoxin measurement) before use in assays.

VSV-SARS-CoV-2 Pseudotype Mutation-Vector Generation

Plasmid pCAGGS encoding the spike protein of SARS-CoV-2 (Walser et al., 2020, loc. cit.) was used as template for generation of single and multiple spike protein mutants. Forward and reverse complementary primers encoding the mutation were synthesized by Microsynth (Balgach, Switzerland). High-fidelity Phusion polymerase (New England Biolabs, USA) was used for all DNA amplification.

Single mutations of the spike protein were generated via two PCR fragments of the spike ORF using high-fidelity Phusion polymerase (New England Biolabs, USA). The first fragment was generated via a generic forward primer (pCAGGS-5) annealing upstream of the spike ORF and the specific reverse primer encoding the mutation. The second fragment was generated using the specific forward primer encoding the mutation and a reverse primer (rbglobpA-R). The two fragments were gel-purified and used as input for an assembly PCR without addition of flanking primers.

For multi-mutation spike proteins, a complementary pair of primers (forward and reverse) encoding each mutation was designed. Fragment 1 was generated with forward primer pCAGGS-5 and reverse primer encoding mutation 1. Fragment 2 was generated using forward primer encoding mutation 1 and reverse primer encoding mutation 2. All subsequent fragments were generated analogously. DNA fragments were gel-purified and mixed in equimolar amounts. This mix was used for re-assembly of the full spike ORF using outer primers pCAGGS-5 and rbglobpA-R.

For both single as well as multi-mutation spike protein, the full-length spike ORF was isolated from an agarose gel, digested by restriction enzymes NheI/EcoRI and inserted into the pCAGGS vector backbone. The correct sequence was verified via sequencing the whole ORF of the spike protein by Microsynth (Baigach, Switzerland).

VSV-SARS-CoV-2 Pseudotype Neutralization Assay for Mutational Analyses and ALE109 Domain Knock The pseudotype viral system was based on the recombinant VSV*ΔG-Luc vector in which the glycoprotein gene (G) had been deleted and replaced with genes encoding green fluorescent protein and luciferase (Berger Rentsch and Zimmer, PLoS One. 2011; 6(10):e25858). Pseudoviruses were generated as reported previously (Torriani et al., Virology. 2019 May; 531:57-68; Torriani et al., J Virol. 2019 Mar. 5; 93(6):e01744-18). For the neutralization assay, an initial dilution of the compounds was followed by three-fold dilutions in quadruplicates in DMEM-2% [vol/vol] FCS supplemented with 20 μM human serum albumin (CSL Behring).

The mixture was mixed with an equal volume of DMEM-2% FCS containing 250 IU per well of SARS-CoV-2 pseudoviruses and incubated for 90 min at 37° C. The mix was inoculated onto Vero E6 cells in a clear bottom white walled 96-well plate during 90 min at 37° C. The inoculum was removed and fresh medium added, and cells further incubated at 37° C. for 16 h. Cells were lysed according to the ONE-Glo™ luciferase assay system (Promega, Madison, US) and light emission was recorded using a BertholdD TriStar LB941 luminometer. The raw data (relative light unit values) were exported to GraphPad Prism v8.01, and the % neutralization values were normalized to the untreated PsV signal. $IC_{50}$ with 95% confidence interval were estimated by model of nonlinear regression fit with settings for log (inhibitor) vs normalized response curves.

Cells and Viruses

Vero E6 cells were passaged in Minimum Essential Medium (MEM) (Cat N° M3303) containing 10% fetal bovine serum (FBS) and supplements (2 mM L-Glutamine, 1% Non-essential amino acids, 100 U/ml Penicillin, 100 μg/ml Streptomycin, 0.06% Sodium bicarbonate, all from Bioswisstec, Schaffhausen, Switzerland) at 37° C., >85% humidity and 5% $CO_2$. SARS-CoV-2 (2019-nCoV/IDF0372/2020) was propagated in Vero E6 cells in MEM containing 2% FBS and supplements (2%-FBS-MEM) at 37° C., >85% humidity and 5% $CO_2$. Viral titer was determined by standard plaque assay as described elsewhere.

Virus Neutralization of Authentic SARS-CoV-2 Determined by CellTiter-Glo and Real-Time RT-PCR Virus neutralization capacity of mono-domain and multi-domain ankyrin repeat binding proteins was determined for 100 TCID50 SARS-CoV-2 by measuring ATP levels of protected cells in a cell viability assay. DARPin® proteins were serially diluted 1:4 from 40 nM to 2.4 μM (in triplicates) in 100 μl cell culture medium (2%-FBS-MEM) enriched with 10 μM HSA in 96 well plates. The diluted DARPin® proteins were mixed with 100 TCID50 SARS-CoV-2 in 100 μl 2%-FBS-MEM+HSA and incubated for 1 h at 37° C. DARPin® protein/virus mixtures (200 pl) were transferred onto 80% confluent Vero E6 cells. The controls consisted of Vero E6 cells exposed to virus suspension only, to determine maximal cytopathic effect and of cells incubated with medium only, to determine baseline state of cells. The plates were incubated for 3 days at 37° C., >85% humidity and 5% $CO_2$. Cell viability was determined by removing 100 μl supernatant from all wells and adding 100 μl CellTiter-Glo reagent as described in the manufacturers protocol (CellTiter-Glo® Luminescent Cell Viability Assay, Promega, Madison, USA). Luminescence was read after 2 minutes shaking on an orbital shaker, transferring the mixture to an opaque-walled plate and 10 min incubation at room temperature using the GloMax instrument (Promega). To determine inhibition of virus replication, the previously removed supernatant (100 μl) was inactivated in 400 μl AVL-buffer (Qiagen, Hilden, Germany) and 400 μl 100% Ethanol and extracted and eluted in 100 μl using the MagNAPure 96 system (Roche, Basel, Switzerland). Viral RNA was quantified by real-time RT-PCR targeting the E gene (Ref. Eurosurveillance|Detection of 2019 novel coronavirus (2019-nCoV) by real-time RT-PCR) using 5 μl RNA and 45 μl TaqMan Fast Virus 1-Step Master Mix (Life Technologies, Zug, Switzerland). Viral genome equivalents (ge) were calculated using a regression analysis and an internal standard.

The results of the neutralization tests with multi-specific DARPin® molecules ALE049 and ALE109 or reference antibodies 1 or 2 (RA1 and RA2 respectively) are shown in Table 17. Table 18 shows the activity of the three spike protein-binding domains of ALE049 (SEQ ID NO: 31) as individual binders against spike protein variants.

TABLE 17

Efficacy Results

| Variants | Rational | VSV Pseudotype Neutralization Assay $IC_{50}$ [ng/mL] | | | |
|---|---|---|---|---|---|
| | | ALE049 | ALE109 | RA1 | RA2 |
| wild type | (Wuhan) | 1.0 | 3.1 | 3.9 | 6.1 |
| B.1.351 | (SA, Δ5)* | 3.0 | 2.4 | 19 | 6.2 |
| B.1.1.7 | (UK, Δ9)** | 1.7 | 70 | 2.4 | 3.5 |
| Individual Mutations | Residues in variants | | | | |
| N501Y | in UK, SA, BRA variants. increases RBD/ACE2 interaction[1] | 0.5 | 1.4 | 4.3 | 5.8 |
| E484K | in SA, BRA variants; increases RBD/ACE2 interaction[1] | 2.7 | 1.8 | 17 | 5.8 |
| K417E | residue mutated to N/T in SA, BRA variants | 0.5 | 1.2 | >100 | 1.5 |
| Y453F | key residue evolved in Danish mink farms variants | 3.2 | 2.0 | >100 | 12 |
| Individual Mutations | Highly frequent mutations | | | | |
| D614G | Wide global spread | 2.4 | 2.8 | n.d. | n.d. |
| S477N | Wide global spread | 1.9 | 0.8 | n.d. | n.d. |
| N439K | Widespread in Northern America, UK; increases RBD/ACE2 interaction[1] | 1.3 | 2.5 | 2.8 | 30 |
| A222V | Wide European spread | 2.2 | 3.1 | 7.0 | 2.9 |
| Individual Mutations | Within RBD epitope of DARPin ® binder or reported resistance mutation for other therapeutics | | | | |
| G446V | | 1.7 | 1.0 | 1.5 | >100 |
| G476S | | 1.5 | 3.1 | n.d. | n.d. |

TABLE 17-continued

| Efficacy Results | | | | | |
|---|---|---|---|---|---|
| | | VSV Pseudotype Neutralization Assay $IC_{50}$ [ng/mL] | | | |
| Variants | Rational | ALE049 | ALE109 | RA1 | RA2 |
| T478I | | 2.7 | 2.8 | 4.0 | 7.0 |
| P479S | | 2.1 | 1.5 | 3.7 | 9.8 |
| V483A | | 2.3 | 1.9 | n.d. | n.d. |
| F486V | key residue for DARPin ® RBD binder[2]; reduces RBD/ACE2 interaction[1] | >100 | 7.7 | >100 | 4.4 |
| Q493K | | 7.9 | 2.4 | >100 | 10 |
| F490S | Reduces RBD/ACE2 interaction[1] | 3.8 | 1.6 | 3.1 | 9.2 |

n.d.: not determined

*Mutations (SA): D80A, D215G, E484K, N501Y, A701V

**Mutations (UK): del69-70, del145, N501Y, A570D, D614G, P681H, T716I, S982A, D1118H

[1]Influence of residue mutations on spike protein binding to human ACE2 (Yi et aL, 2020, loc. cit.)

[2]Predicted interaction residue for DARPin ® RBD binder (Walser et aL, 2020, https://doLorg/10.1101/2020.08.25.256339)

TABLE 18

| Efficacy of RBD domains of ALE049 | | | | | |
|---|---|---|---|---|---|
| | | VSV Pseudotype Neutralization Assay $IC_{50}$ [ng/mL] | | | |
| | | | Mono-valent RBD Binders in ALE049 | | |
| Variants | Rational | ALE049 | R3b | R1b | R3c |
| wild type | (Wuhan) | 1.0 | 7.2 | 2.1 | 13.3 |
| B.1.351 | (SA, Δ5)* | 3.0 | 76 | 26 | >100 |
| B.1.1.7 | (UK, Δ9)** | 1.7 | 4.6 | 5.4 | 11.7 |
| Individual Mutations | Residues in variants | | | | |
| N501Y | in UK, SA, BRA variants; increases RBD/ACE2 interaction[1] | 0.5 | 9.1 | 4.8 | 27.8 |
| E484K | in SA, BRA variants; increases RBD/ACE2 interaction[1] | 2.7 | 64.2 | 10.2 | >100 |
| K417E | residue mutated to NIT in SA, BRA variants | 0.5 | 1.8 | 1.0 | 3.6 |
| Y453F | key residue evolved in Danish mink farms variants | 3.2 | 10.9 | 5.9 | 3.3 |
| Individual Mutations | Highly frequent mutations | | | | |
| D614G | Wide global spread | 2.4 | 11.9 | 6.2 | 23 |
| S477N | Wide global spread | 1.9 | 3.0 | 2.0 | 9.0 |
| N439K | Widespread in Northern America, UK; increases RBD/ACE2 interaction[1] | 1.3 | 7.3 | 5.3 | 12.9 |
| A222V | Wide European spread | 2.2 | 3.3 | 4.6 | 19.5 |
| Individual Mutations | Within RBD epitope of DARPin ® binder or reported resistance mutation for other therapeutics | | | | |
| G446V | | 1.7 | 0.7 | 1.8 | 2.3 |
| G476S | | 1.5 | 2.3 | 3.7 | 29 |
| T478I | | 2.7 | 11.2 | 3.1 | 16.7 |
| P479S | | 2.1 | 7.2 | 2.3 | 27.6 |
| V483A | | 2.3 | 21.8 | 8.4 | 21.3 |
| F486V | key residue for DARPin ® RBD binder[2]; reduces RBD/ACE2 interaction[1] | >100 | >100 | >100 | >100 |
| Q493K | | 7.9 | 30 | 28.2 | 45.8 |
| F490S | Reduces RBD/ACE2 interaction[1] | 3.8 | 2.3 | 1.7 | 8.1 |

n.d.: not determined

*Mutations (SA): D80A, D215G, E484K, N501Y, A701V

**Mutations (UK): del69-70, del145, N501Y, A570D, D614G, P681H, T716I, S982A, D1118H

[1]Influence of residue mutations on spike protein binding to human ACE2 (Yi et al. 2020, loc. cit.)

[2]Predicted interaction residue for DARPin ® RBD binder (Walser et al. 2020)

These results show that ALE049 can neutralize variants B.1.1.7 and B.1.351 as efficiently as the wild-type form with $IC_{50}$ values in the low single-digit ng/mL range. ALE109 neutralized the B.1.351 variant equally efficiently as the wild-type form, with $IC_{50}$ values in the low single-digit ng/mL range. A slight potency loss was observed for ALE109 against the UK variant B.1.1.7 (IC50 value of 70 ng/ml). Nevertheless, the potency of ALE109 against the UK variant B.1.1.7 was within the therapeutic range. It is interesting to note that the RBD binder of ALE109 (i.e. Rib) retained the same neutralization ability for B.1.1.7 as for the wild-type. The observed slight potency drop observed for ALE109 may be caused by the exposed mutations in the S2 domain (potentially P681H and T716I) alone or in combination with the NTD mutations. The structural determinants responsible for this slight potency drop are currently under investigation. Taken together, the results showed that both tested multi-specific binding proteins, ALE049 and ALE109, potently neutralized the wild-type form with $IC_{50}$ values in the low single-digit ng/mL range and neutralized the variants B.1.1.7 (UK) and B.1.351 (SA) with $IC_{50}$ values in the therapeutic range (i.e., low single-digit to double-digit ng/mL range).

Both multi-specific DARPin® molecules ALE049 and ALE109 also protected well against all individual mutations tested, with the notable exception of F486V for ALE049 and all three mono-valent DARPin® RBD binders. As F486 is a critical residue for ACE2 binding, the selective pressure on the virus favors its conservation, thus maintaining an important anchoring element for the binding of ALE049. The major impact of this mutation on ALE049 is not surprising, as previous structural analysis identified F486 as a core interacting residue for the three related but different RBD binders in ALE049 (Walser et al. 2020, loc. cit.). Consequently, the mutation F486V destabilizes the binding of the ALE049 molecule to the spike protein. Taken together, our analysis confirms that multi-specific DARPin® molecules of the invention remain highly potent against spike proteins carrying the most frequently observed mutations, and mutations known to impact the binding of neutralizing antibodies, as expected from the multi-specific design of the DARPin® molecules.

FIG. 29 shows the neutralization potency of single domain knock-out (k.o.) constructs of ALE109 against the wild type form of SARS-CoV-2. These experiments determined the contribution of each of the three spike protein-binding DARPin® domains of ALE109 to the neutralization activity against SARS-CoV-2. No potency loss compared to ALE109 was observed for the NTD knock out construct while some potency loss was observed for the RBD and S2 knock-out constructs. Without wishing to be bound by theory, the NTD binding domain of ALE109 is believed to play a significant role in the neutralization activity of ALE109 against mutated forms or variants of SARS-CoV-2, e.g., by providing increased binding avidity to mutated spike protein.

Example 12: Viral Passaging of SARS-CoV-2

Previous studies have shown that viral escape mutants may rapidly appear under selective pressure of a therapy (Ku et al., 2021, loc. cit.; Andreano et al., 2020, DOI:10.1101/2020.12.28.424451). We used a viral passaging model adapted from Baum et al., Science 369, 1014-1018 (2020), to estimate the risk of viral escape from therapeutic pressure of multi-specific DARPin® proteins ALE049 and ALE109 and of a cocktail of reference antibodies RA1 and RA2, in comparison to the mono-valent DARPin® binder R1b (SEQ ID NO: 3) and to the monoclonal antibodies S309, RA1 and RA2 applied as single molecules. S309 is an antibody that was isolated from a patient who recovered from severe acute respiratory syndrome (SARS) in 2003 and has been shown to be effective against SARS-CoV-2 infection in cells and in animal models (Pinto et al., Nature, Vol 583, p. 290-295, 9 Jul. 2020). S309 was prepared in the same manner as RA1 and RA2 (see Example 11 above).

Figure 30:
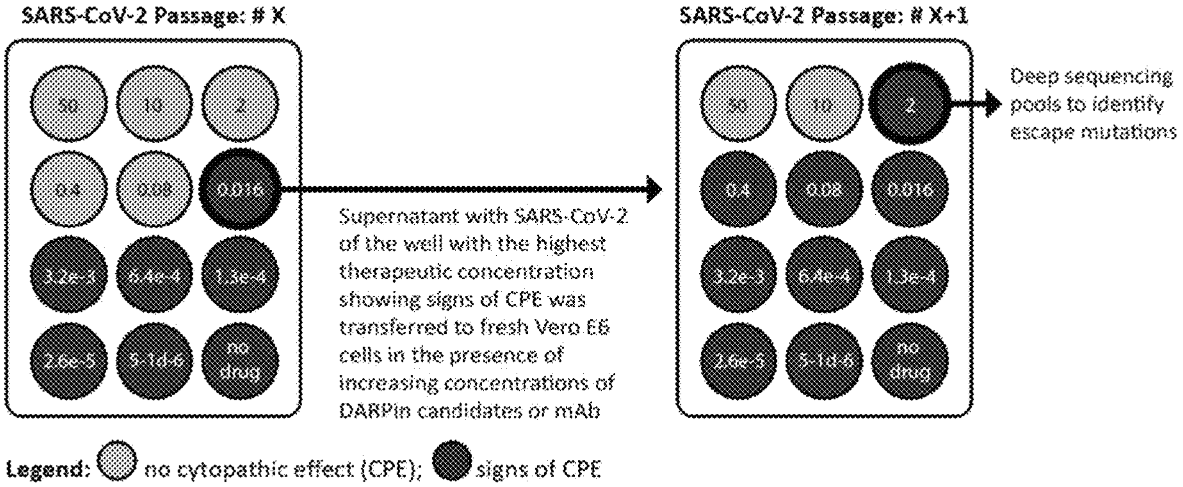
FIG. 30: Schematic representation of the procedure of Example 12.

Experimental Protocol:

1:5 serial dilutions of DARPin® proteins and monoclonal antibodies from 100 μg/ml to 0.032 μg/ml were prepared in Minimum Essential Medium (MEM) containing 2% FBS, supplements and 10 μM human serum albumin (HSA; CSL Behring, Switzerland; 2%-FBS-MEM+HSA). 500 ul of virus suspension containing $1.5\times10^6$ plaque forming units (pfu) SARS-CoV-2 (a French isolate with the following differences compared to wild-type: V367F; E990A) in 2%-FBS-MEM+HSA were mixed with 500 μl of serially diluted DARPin® proteins or monoclonal antibodies and subsequently incubated for 1 hour at 37° C. The mixtures were then transferred to 80% confluent Vero E6 cells in 12 well plates and incubated for 4 days at 37° C., >85% humidity and 5% $CO_2$. Each culture well was assessed for cytopathic effect (CPE) by microscopy. Supernatant was removed from wells with the highest DARPin® protein or antibody concentrations showing significant CPE (>20%) and used for total RNA extraction and further passaging. For subsequent rounds of passaging, remaining 900 μl supernatant of selected wells was diluted to 4 ml in 2%-FCS-MEM+HSA and thereof 500 μl mixed with serial dilutions of DARPin® proteins or antibodies, incubated and the mixture transferred to 12 well plate with fresh Vero E6 cells as described above. Cell culture wells were assessed for CPE again after 4 days and the supernatant of wells with highest DARPin® protein or antibody concentrations with evident viral replication (CPE) harvested and used for additional passages (see FIG. 30). A total of 4 passages were performed this way.

Results:

Resistant escape variants were selected by passaging the supernatant of cultures showing significant virus-induced cytopathic effect under the greatest selective pressure onto fresh cells while maintaining the selective pressure of increasing concentrations of antiviral proteins. FIG. 31 shows the results obtained after the first to fourth incubation cycles (passages #1 to #4). After the first incubation cycle of four days (passage #1) the mono-valent DARPin® binder Rb1 and the multi-specific DARPin® proteins ALE049 and ALE109, as well as the monoclonal antibody RA1 and the cocktail of the two monoclonal antibodies RA1 and RA2 conferred protection at the same concentrations of 0.4 μg/mL. The monoclonal antibody S309 was less efficient, requiring higher concentration (10 μg/mL) for protection and the monoclonal antibody RA2 as a single molecule was not protective up the highest concentration tested of 50 μg/mL. Under continuous selective pressure through passage 2 to 4, the monovalent DARPin® binder Rb1, and the individual monoclonal antibodies RA2 and RA1 lost the capacity to protect cells from virus-induced cytopathic effect, which manifested in complete CPE up to the highest selective pressure tested. In contrast, the two multi-specific DARPin® proteins ALE049 and ALE109, as single molecules or as a mixture, and the cocktail of two monoclonal antibodies (RA1 and RA2) remained effective and protected cells from CPE throughout the 4 passages.

The multi-specific DARPin® proteins ALE049 and ALE109 as single agents prevented the selection of escape mutants at concentrations of 2 μg/mL and 10 μg/mL, respectively, after 4 passages, while the combination of the two multi-specific DARPin® proteins ALE049 and ALE109 retained effectiveness even at a low concentration of 0.08 μg/mL. The antibody cocktail RA1 & RA2 prevented the selection of escape mutants at a concentration of 0.4 μg/mL after passage 4.

Example 13: Comparison of Several Multi-Specific Binding Proteins in a Neutralization Assay Using SARS-CoV-2 VSV Pseudovirus (PsV nCoV)

Several multi-specific binding proteins of the invention were compared in a neutralization assay using SARS-CoV-2 VSV pseudovirus (PsV nCoV). The neutralization assay was performed similar as described in Example 4 above. The tested multi-specific binding proteins included ALE049, ALE058, ALE109, ALE126, ALE129 and ALE133. ALE049, ALE058 and ALE109 have been described above. ALE126, ALE129 and ALE133 comprise a further engineered S1-NTD binding domain (vS07_08F10v47; SEQ ID NO: 85) as compared to ALE109, which comprises vS07_08F10v27 (SEQ ID NO: 76). ALE126, ALE129 and ALE133 differ from each other only in the length of the linker that connects the S1-NTD binding domain and the S2 binding domain (SEQ ID NO: 77).

Figure 32:
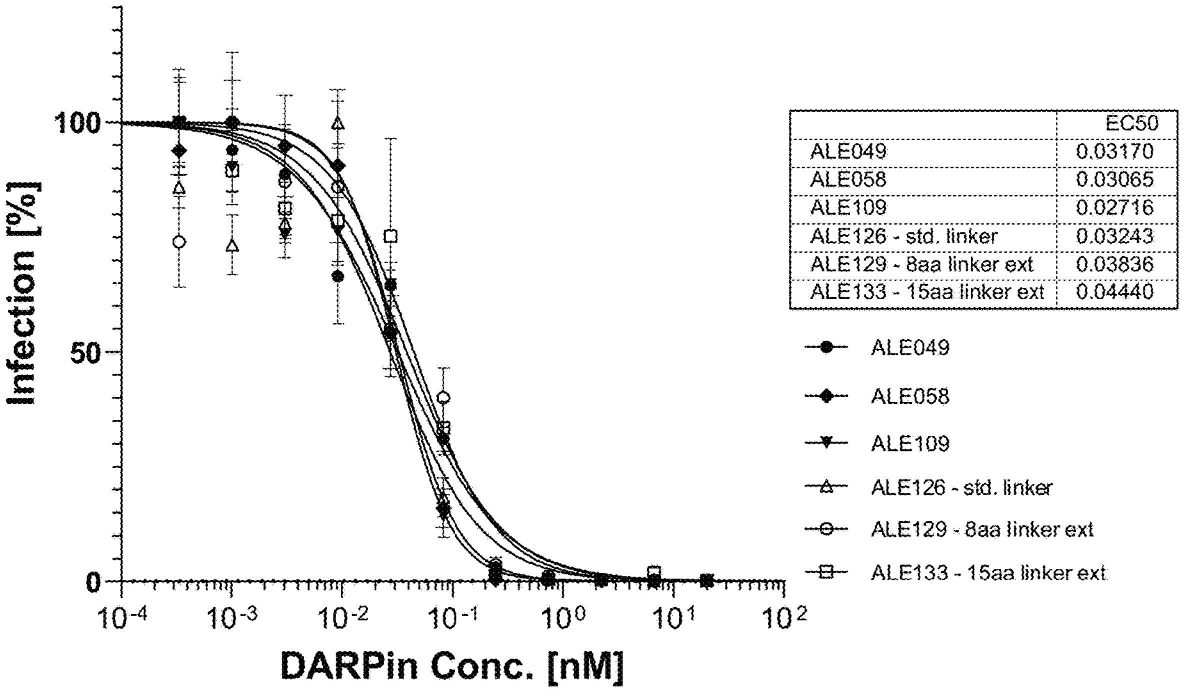
FIG. 32: Neutralization of VSV pseudotype SARS-CoV-2 virus by multi-domain DARPin® binding proteins. The names of the tested constructs (ALE049, ALE058, etc.) are indicated in the Figure.

The results of the PsV nCoV assay are shown in FIG. 32, with EC50 values provided in nM. The experiment demonstrated that all the tested multi-specific binding proteins have overall comparable neutralization potencies in this SARS-CoV-2 VSV pseudovirus neutralization assay. The EC50 values of all tested constructs were in the range of 20 to 50 μM.

Example 14: Pharmacokinetic Analysis of Multi-Specific Binding Proteins of the Invention in Mice Another pharmacokinetic (PK) study was conducted to assess the PK characteristics of several multi-specific recombinant binding proteins of the invention in mice. Such PK characteristics are useful for dose predictions of multi-specific binding proteins of the invention in animal pharmacodynamic studies, in toxicology studies or in human clinical trials.

The PK study was performed essentially as described in Example 9.

The following multi-specific binding proteins were tested in this study:

TABLE 19

| SEQ ID NO | Sample name |
|---|---|
| 39 | ALE058 |
| 75 | ALE109 |
| 87 | ALE126 |
| 88 | ALE129 |
| 84 | ALE133 |

Pharmacokinetic data analysis was performed, as also described in Example 9, using Phoenix WinNonlin™ 8.0 program from Certara. Calculation of the pharmacokinetic parameters of the study based on the mean concentration-time data of the animals dosed via intravenous bolus injection was performed with non-compartmental analysis (NCA model 200-202, IV bolus, linear trapezoidal linear interpolation).

Figure 33:
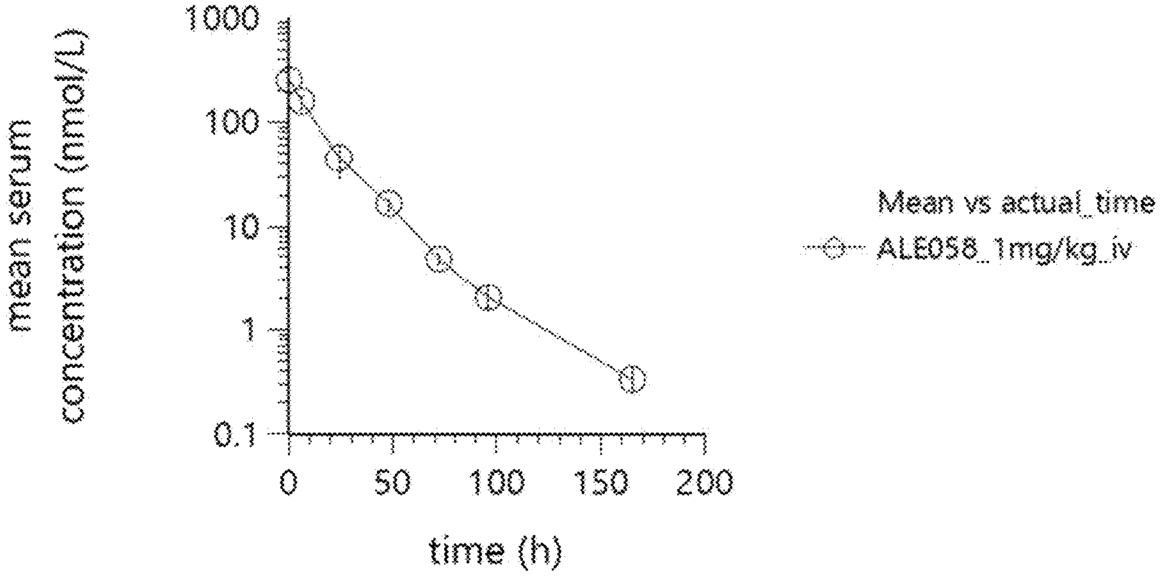
FIG. 33: Mean serum concentration-time profile of ALE058 in BALB/c mice following administration of 1 mg/kg.
Figure 34:
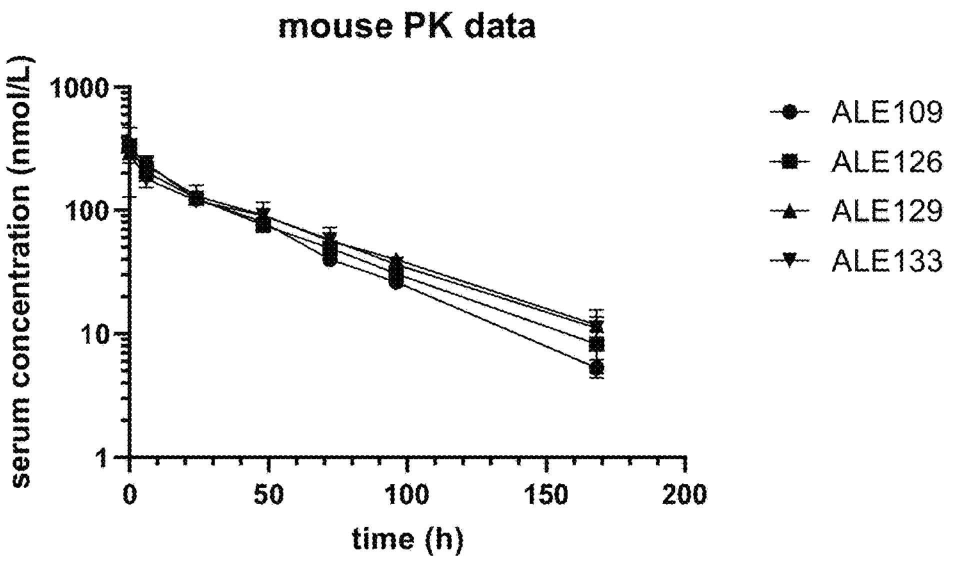
FIG. 34: Mean serum concentration-time profile of ALE109, ALE126, ALE129, and ALE133 in BALB/c mice following administration of 1 mg/kg.

The calculated pharmacokinetic parameters included at least the following: AUCinf_pred, AUClast, AUC_% extrapol, AUC_% Back_Ext_pred, Cmax, Tmax, CI_pred, Vss_pred, t½ (HL_Lambda_z). The results are shown in Table 20 and FIGS. 33 and 34:

TABLE 20

| Parameter | Unit | ALE058 | ALE109 | ALE0126 | ALE129 | ALE133 |
|---|---|---|---|---|---|---|
| AUCINF_pred | h * (nmol/L) | 4261 | 10980 | 11145 | 12986 | 11909 |
| AUClast | h * (nmol/L) | 4253 | 10740 | 10726 | 12281 | 11246 |
| Cmax | nmol/L | 255 | 328 | 337 | 295 | 295 |
| Tmax | h | 0.083 | 0.083 | 0.083 | 0.083 | 0.083 |
| Cl_ pred | L/(h * kg) | 0.00297 | 0.00115 | 0.00114 | 0.00097 | 0.00105 |
| Vss_ pred | L/kg | 0.052 | 0.047 | 0.053 | 0.052 | 0.058 |
| HL_ Lambda_z | h | 20.0 | 31.5 | 36.7 | 41.4 | 41.1 |
| AUC_% Extrap_pred | (%) | 0 | 2 | 4 | 5 | 6 |
| AUC_% Back_Ext_pred | (%) | 1 | 0 | 0 | 0 | 0 |

Results and Conclusions

The results demonstrated that ALE109 has improved pharmacokinetic properties for systemic administration as compared to the precursor molecule ALE058. In the mono-exponential elimination phase of the serum concentration time profile, ALE109 serum concentrations declined with a half-life of 31.5 hours, whereas ALE058 showed a half-life of 20 hours. Moreover, the further engineered binding proteins ALE126, ALE129 and ALE133 displayed even more extended half-lives, when compared to ALE109, i.e. half-lives of 36.7 hours, 41.4 hours and 41.1 hours, respectively.

Example 15: In Vivo Evaluation of Therapeutic Efficacy of Two Multi-Specific Binding Proteins, ALE049 and ALE109, in a Roborovaki Dwarf Hamster Model In this study, a Roborovski dwarf hamster model was used to evaluate the efficacy of two multi-specific binding proteins of the invention as potential antiviral agents against SARS-CoV-2. The Roborovski dwarf hamster model is a valuable non-transgenic rodent model for SARS-CoV-2 research due to its high sensitivity to SARS-CoV-2 infections, as indicated by severe clinical signs (e.g. body weight loss or body temperature drop), viral replication in both the upper and lower respiratory tract and histopathological changes (Trimpert et al., Cell Reports 33, 108488, Dec. 8, 2020).

Thus, the objective of this study was to investigate the therapeutic potential of ALE049 and ALE109 to inhibit or prevent body weight loss, replication of SARS-CoV-2 in the upper and lower respiratory tract and histopathological changes.

The tested binding proteins ALE049 and ALE109 are serum half-life extended with domains that bind to human serum albumin (HSA) (as well as to hamster serum albumin) to support long-acting activity. In vitro data demonstrated potent inhibition of SARS-CoV-2 virus infection in cell culture titration experiments by both binding proteins.

Figure 35:
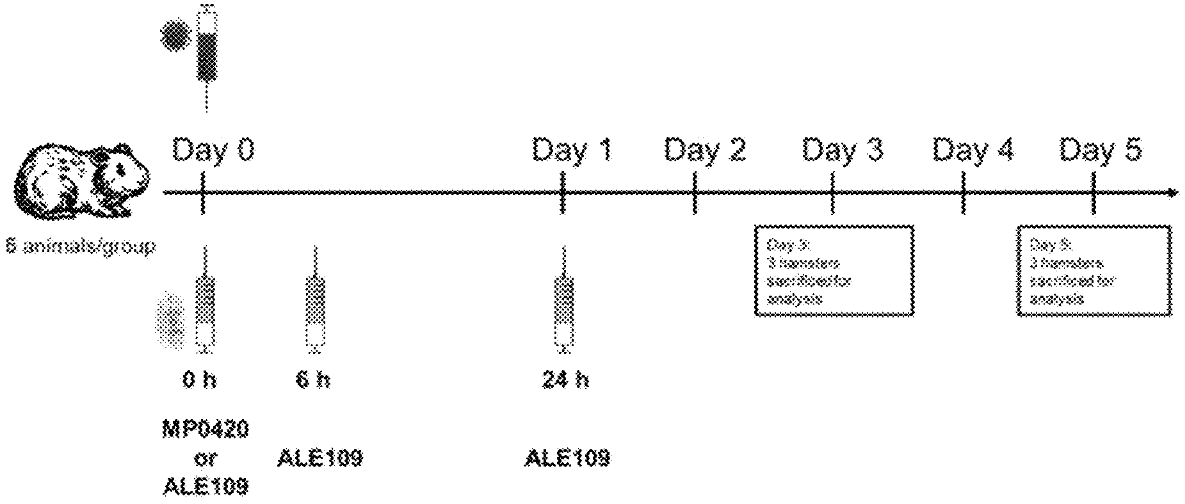
FIG. 35. Schematic study outline. Body weight and temperature were measured daily and swabs, blood and tissues were collected from 3 animals for each group, which were euthanized at day 3 and day 5, respectively.

The study design provided that 5 groups of 6 animals each were used and treatment with tested binding protein was given either at 0, 6 or 24 hours after inoculation with SARS-CoV-2. The study design is illustrated in FIG. 35 (ALE049 is also called MP0420 in this Example). Animals were treated by intraperitoneal (i.p.) administration, which served as a safe and reproducible alternative for intravenous administration. Animals in group 1 were treated with ALE049 at 20 mg/kg at 0 h and animals in groups 2 to 4 were treated with ALE109 at 20 mg/kg at time points 0, 6 or 24 h post-infection, respectively. Animals in the control group (group 5) were treated at time 0 h with a placebo (i.e. vehicle of tested proteins only). Infection with SARS-CoV-2 was performed via the intranasal (i.n.) route, for which the dose and route of infection were based on results from earlier (model development) studies. Animals were weighed and temperatures were measured daily. Three animals for each group were euthanized on day 3 and 5 post-infection, respectively, to perform necropsy. Viral load in lung and throat tissue was determined by qPCR or virus titration and counting the plaque forming units (PFUs). Histopathological changes in selected tissues were assessed after euthanasia.

Materials

Formulation buffer and all test and control item formulations were prepared on the day of administration and were aliquoted into appropriate volumes for each group and stored at 4° C. until administration. The volume of the test/control item administered was 100 μL per animal and adjusted to the animal's body weight measured on the administration day. The infection material was SARS-CoV-2, strain BetaCoV/Germany/BavPat1/2020.

Animals

Roborovski dwarf hamsters (*Phodopus roborovskii*), age 6-9 weeks, with a body weight range at the start of the study on day −2 of 20-25 gram, were used.

Procedures

Anaesthesia and Analgesia

For infections and prior to euthanasia, animals were anesthetized by the injection of medetomidine, midazolam, and butorphanol at doses of 0.15, 2.0 and 2.5 mg/kg, respectively. Following infection, anaesthesia was antagonized with 0.15 mg/kg atipamezole.

Intraperitoneal Administration

For intraperitoneal administration the animal was fixed by grasping the neck skin and the back skin between thumb and fingers. Subsequently, the hand was turned over so that the animal rests with its back in the palm of the hand. The head of the animal was kept downwards to prevent injection/damage in/of the organs and the needle was inserted left of the median line in the groin area, between the 4th and the 5th mammary gland/nipple. Finally, the needle was removed in a smooth motion.

Intranasal Administration

For intranasal administration the animals were held on their back and the inoculum (20 μl) was equally divided over both nostrils using a pipette. Animals were held on their back until the complete inoculum was inhaled after which they were placed back in the cage to recover.

Sampling for Histology

Histopathological analysis from selected tissues was performed for all animals euthanized at experimental or humane endpoints (i.e. day 2, 5 and 7). After fixation with 4% formalin for a minimum of 48 hours, sections from lung and throat were embedded in paraffin and the tissue sections were stained for histological examination.

End-Point Serum Samples

Serum samples on day 2, 5 and 7 post-infection were collected during euthanasia and immediately transferred to appropriate tubes containing a clot activator.

Virological Analysis

Detection of Viral RNA

RNA was extracted from nasal washes and tracheal swabs with the RTP DNA/RNA Virus Mini Kit (Stratec, Birkenfeld, Germany) according to the manufacturer's instructions. The innuPREP Virus DNA/RNA Kit (Analytic Jena, Jena, Germany) was used for RNA extractions from tissue samples. Viral RNA was quantified using a one-step RT qPCR reaction with the NEB Luna Universal Probe One-Step RT-qPCR (New England Biolabs, Ipswich, Mass., USA) and the 2019-nCoV RT-qPCR primers and probe (E_Sarbeco) on a StepOnePlus RealTime PCR System (Thermo Fisher Scientific, Waltham, Mass., USA) according to the manufacturer's instructions. Viral RNA copies were then normalized to cellular RPL18 as previously described. Standard curves for absolute quantification were generated from serial dilutions of SARS-CoV-2 RNA obtained from a full-length virus genome cloned as a bacterial artificial chromosome and propagated in *E. coli.*

Detection of Replication Competent Virus

Duplicate 10-fold serial dilutions were used to determine the virus titers in confluent layers of Vero E6 cells (SARS-CoV-2 titration on Vero E6 cells). To this end, serial dilutions of the samples (lung tissue homogenates) were made and incubated on Vero E6 monolayers for 2 hours at 37 degrees. Cells were washed and overlaid with semi-solid cell culture medium containing 1.5% Avicel and incubated for 48 h at 37 degrees after which plates were fixed with 4% formalin and stained with 0.75% crystal violet for plaque counting.

Histopathology

Histopathological analysis from selected tissues was performed for all animals euthanized due to reaching an experimental or humane endpoint. After fixation with 4% formalin for 48 hours, sections from lungs were embedded in paraffin and the tissue sections were stained for histological examination.

Results

The aim of this study was to assess the therapeutic potential of binding proteins ALE049 and ALE109 in a COVID-19 Roborovski dwarf hamster model. For this assessment, the hamsters were treated therapeutically with 20 mg/kg of binding protein at 0, 6 or 24 hours after the SARS-CoV-2 intranasal challenge with 105 PFUs per animal.

All 24 animals, treated with a binding protein of the invention at either 0, 6 or 24 hours post-infection, survived until the day of sacrifice (i.e. day 3 or 5), while 5 out of 6 animals from the placebo group had to be taken out of the study prior to the study endpoints by day 3 due to severe clinical symptoms and body weight loss. Average of body weights was determined in each of the five study groups. The placebo group showed a steady decrease in body weight until the timepoint at day 3. After this timepoint only one animal from the placebo group could be taken forward to day 5 for further evaluation. All test protein-treated groups demonstrated no or only minor body weight losses. When comparing the various timepoints for treatment or when comparing ALE049 with ALE109, no significant differences were observed in terms of clinical symptoms or body weight loss (see FIG. 36). Generally, there seemed to be some variation in the response of the individual animals to either the viral infection or the treatment which led to a relatively wide spread in body weight loss.

Measurement of viral titers in lung by live virus titration of lung homogenate and plaque counting demonstrated that, already at day 3, a reduction in the live virus could be observed (FIG. 37A). This was especially pronounced for the timepoint where the treatment was initiated directly after the viral challenge (0 h timepoint). Still, also the treatment injections with ALE109 administered at 6 h or 24 h after the viral challenge showed a considerable reduction in the load of infectious virus already at day 3. This effect seemed to be even more pronounced for the 3 animals remaining at day 5 where only 5 out of 12 binding protein-treated animals had detectable infectious virus remaining in the lung homogenates (FIG. 37B). Reduction of viral RNA genome copies as detected by qPCR seemed to be considerable slower than the elimination of infectious virus. At day 3, only 1 out of 3 animals for each of the 0 h time points showed a reduction of viral RNA in the lungs (FIG. 37C). On viral genome level, more pronounced differences between the binding protein-treated groups and the placebo group occurred only at day 5 post infection, where again a trend for better reduction of viral genomic RNA could be observed for the earlier time points of the treatment (FIG. 37D). When comparing ALE049 and ALE109 at the 0 h time point, a trend for better virus elimination could be observed for ALE049.

The histopathological assessment for various parameters in different tissues was scored with a ranking from 0 (no obvious histopathological signs) to 4 (most severe histopathological signs). All scores were averaged for the different treatment groups and categorized into four sets: i) inflammation, ii) blood vessels, iii) alveoli, and iv) bronchi. The sum graphs for all the averaged parameters are provided in FIGS. 38A to 38D. Generally, in all four categories, clear differences were observed between the binding protein-treated hamsters and the placebo-treated hamsters. According to the histopathological assessment, all binding protein treatments had strongest effects on the reduction of tissue damage in bronchi (FIG. 38D), alveoli (FIG. 38C) and blood vessels (FIG. 38B) and lowest impact on the reduction of inflammatory cells (FIG. 38A), when compared to the placebo group. The group treated with ALE109 at the timepoint 6 h after viral infection indicated the lowest reduction of inflammation and tissue damage amongst all binding protein-treated groups.

CONCLUSIONS

At viral inoculation of 105 PFUs, the Roborovsky dwarf hamster model is a well-suited COVID-19 disease model, in which non-treated animals generally develop strong clinical symptoms reaching criteria for euthanasia. The therapeutic treatment of the animals with either ALE049 at 0 hours after the viral challenge or ALE109 at 0, 6 or 24 hours after the viral challenge, led to significant reductions of severe clinical symptoms, comparable for all binding protein treatment groups, such that none of the 24 binding protein-treated animals reached euthanasia criteria prior to the official sacrifice time points at day 3 or 5, while for the 6 placebo-treated animals, 2 animals at day 2 and another 3 animals at day 3 developed strong clinical symptoms and had to be taken out of the study, with only one placebo-treated animal remaining on study until day 5.

In terms of viral load for infectious virus or viral genome copies, a clear reduction was observed for all binding protein treatment groups. This reduction increased from day 3 to day 5 and the treatment groups where the therapy was given earlier seemed to respond with a more pronounced reduction. When comparing ALE049 with ALE109, administered at 0 h, the ALE049 treatment group responded slightly better, with respect to the rather low number of animals per treatment group.

Histopathological findings in the lungs showed a clear reduction of pathological scores for all binding protein treatment groups when compared to the placebo group. These findings seem to be independent of the therapeutic regimens tested in this study.

In conclusion, both ALE049 and ALE109 demonstrated therapeutic potential against SARS-CoV-2 infections, using a Roborovsky dwarf hamster model.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize or be able to ascertain using no more than routine experimentation, many equivalents to the specific embodiments of the invention described herein. Such equivalents are intended to be encompassed by the following claims.

The invention claimed is:

1. A recombinant binding protein comprising an amino acid sequence wherein the amino acid sequence is selected from the group consisting of SEQ ID NOs 1 to 11, 76, 77 and 85.

2. A nucleic acid encoding a recombinant binding protein according to claim 1.

3. A pharmaceutical composition comprising the binding protein of claim 1 and a pharmaceutically acceptable carrier or excipient.

4. A recombinant binding protein comprising a first ankyrin repeat domain, wherein said first ankyrin repeat domain comprises a first amino acid sequence, wherein the first amino acid sequence is selected from the group consisting of SEQ ID NOs 1 to 11, 76, 77 and 85.

5. The recombinant binding protein according to claim 4 further comprising a second ankyrin repeat domain, wherein said second ankyrin repeat domain comprises a second amino acid sequence, wherein the second amino acid sequence is selected from the group consisting of SEQ ID NOs 1 to 11, 76, 77 and 85.

6. The recombinant binding protein according to claim 5 further comprising a third ankyrin repeat domain, wherein said third ankyrin repeat domain comprises a third amino acid sequence, wherein the third amino acid sequence is selected from the group consisting of SEQ ID NOs 1 to 11, 76, 77 and 85.

7. The recombinant binding protein according to claim 6, wherein said binding protein comprises a polypeptide, wherein said polypeptide comprises an amino acid sequence, wherein the amino acid sequence is selected from the group consisting of SEQ ID NOs: 68, 69, 79, and 89 to 91.

8. The recombinant binding protein according to claim 4, wherein said binding protein binds to a coronavirus spike protein, wherein said spike protein is SARS-CoV-2 spike protein.

9. The recombinant binding protein according to claim 8, wherein said binding protein binds said coronavirus spike protein with a dissociation constant ($K_D$) of or below about 100 nM.

10. The recombinant binding protein according to claim 4 further comprising at least one serum albumin binding domain.

11. The recombinant binding protein according to claim 10, wherein said serum albumin binding domain comprises an amino acid sequence, wherein the amino acid sequence is selected from the group consisting of SEQ ID NOs: 47-49.

12. A nucleic acid encoding a recombinant binding protein according to claim 7.

13. A pharmaceutical composition comprising the binding protein of claim 7 and a pharmaceutically acceptable carrier or excipient.

14. A recombinant binding protein comprising an amino acid sequence, wherein the amino acid sequence is selected from the group consisting of SEQ ID NOs: 12-42, 75, 84, 87 and 88.

15. The recombinant binding protein according to claim 14, wherein said amino acid sequence is SEQ ID NO: 31.

16. The recombinant binding protein according to claim 14, wherein said amino acid sequence is SEQ ID NO: 75.

17. The recombinant binding protein according to claim 14, wherein said amino acid sequence is SEQ ID NO: 87.

18. The recombinant binding protein according to claim 14, wherein said binding protein binds to a coronavirus spike protein, wherein said spike protein is SARS-CoV-2 spike protein.

19. The recombinant binding protein according to claim 18, wherein said binding protein binds said coronavirus spike protein with a dissociation constant ($K_D$) of or below about 100 nM.

20. A nucleic acid encoding the recombinant binding protein according to claim 14.

21. A pharmaceutical composition comprising the binding protein of claim 14 and a pharmaceutically acceptable carrier or excipient.

* * * * *